(12) United States Patent
Tawfik et al.

(10) Patent No.: US 9,023,631 B2
(45) Date of Patent: *May 5, 2015

(54) PON POLYPEPTIDES, POLYNUCLEOTIDES ENCODING SAME AND COMPOSITIONS AND METHODS UTILIZING SAME

(71) Applicant: Yeda Research and Development Co. Ltd., Rehovot (IL)

(72) Inventors: Dan S. Tawfik, Jerusalem (IL); Amir Aharoni, Tel Aviv (IL); Leonid Gaydukov, Moscow (RU); Joel L. Sussman, Rehovot (IL); Israel Silman, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

This patent is subject to a terminal disclaimer.

(21) Appl. No.: 14/058,334

(22) Filed: Oct. 21, 2013

(65) Prior Publication Data
US 2014/0079682 A1    Mar. 20, 2014

Related U.S. Application Data

(60) Division of application No. 12/723,725, filed on Mar. 15, 2010, now abandoned, which is a continuation of application No. 10/547,771, filed as application No. PCT/IL2004/000216 on Mar. 4, 2004, now Pat. No. 7,786,071.

(60) Provisional application No. 60/512,925, filed on Oct. 22, 2003, provisional application No. 60/451,267, filed on Mar. 4, 2003.

(51) Int. Cl.
*C12N 9/00* (2006.01)
*C12Q 1/34* (2006.01)
*C12N 9/18* (2006.01)
*C12N 9/16* (2006.01)
*A61K 38/00* (2006.01)

(52) U.S. Cl.
CPC . *C12N 9/18* (2013.01); *A61K 38/00* (2013.01); *C12N 9/16* (2013.01)

(58) Field of Classification Search
CPC ............. C12N 9/16; C12Y 301/08001; C12Y 101/01027; C12Y 301/01002; C12Y 301/01081; C12Y 304/21069
See application file for complete search history.

(56) References Cited

U.S. PATENT DOCUMENTS

| 6,046,308 | A | 4/2000 | Gluecksmann |
| 7,786,071 | B2 | 8/2010 | Tawfik et al. |

(Continued)

FOREIGN PATENT DOCUMENTS

| WO | WO 01/90336 | 11/2001 |
| WO | WO 2004/078991 | 9/2004 |

OTHER PUBLICATIONS

Furlong et al., Purification of rabbit and human serum paraoxonase., Biochemistry (1991), vol. 30(42), pp. 10133-10140.*

(Continued)

*Primary Examiner* — Alexander Kim

(57) ABSTRACT

Isolated polynucleotides and polypeptides encoded therefrom are provided. These include mutated PON enzymes with increased, modified or substantially the same substrate specificity as compared to respective wild-type PON. Also provided are kits and methods using these enzymes.

6 Claims, 75 Drawing Sheets
(13 of 75 Drawing Sheet(s) Filed in Color)

(56) References Cited

U.S. PATENT DOCUMENTS

2006/0205933 A1 9/2006 Tawfik et al.
2011/0171197 A1 7/2011 Tawfik et al.

OTHER PUBLICATIONS

Draganov et al., Rabbit serum paraoxonase 3 (PON3) is a high density lipoprotein-associated lactonase and protects low density lipoprotein against oxidation., J Biol Chem. (2000), vol. 275(43), pp. 33435-33442.*
Office Action Dated Nov. 26, 2013 From the Israel Patent Office Re. Application No. 211357 and Its Translation Into English.
Applicant-Initiated Interview Summary Dated Aug. 20, 2013 From the US Patent and Trademark Office Re. U.S. Appl. No. 12/723,725.
Communication Pursuant to Article 94(3) EPC Dated Mar. 13, 2009 From the European Patent Office Re.: Application No. 04717208.5.
Communication Pursuant to Article 94(3) EPC Dated Jul. 28, 2010 From the European Patent Office Re.: Application No. 04717208.5.
Communication Pursuant to Article 94(3) EPC Dated Mar. 31, 2008 From the European Patent Office Re.: Application No. 04717208.5.
European Search Report and the European Search Opinion Dated May 25, 2012 From the European Patent Office Re. Application No. 10183160.0.
Notice of Allowance Dated Dec. 15, 2009 From the US Patent and Trademark Office Re.: U.S. Appl. No. 10/547,771.
Official Action Dated Apr. 3, 2008 From the US Patent and Trademark Office Re.: U.S. Appl. No. 10/547,771.
Official Action Dated Jun. 10, 2011 From the US Patent and Trademark Office Re. U.S. Appl. No. 12/723,725.
Official Action Dated Oct. 11, 2011 From the US Patent and Trademark Office Re. U.S. Appl. No. 12/723,725.
Official Action Dated Aug. 17, 2009 From the US Patent and Trademark Office Re.: U.S. Appl. No. 10/547,771.
Official Action Dated May 20, 2013 From the US Patent and Trademark Office Re. U.S. Appl. No. 12/723,725.
Official Action Dated Mar. 21, 2011 From the US Patent and Trademark Office Re. U.S. Appl. No. 12/723,725.
Official Action Dated Mar. 22, 2012 From the US Patent and Trademark Office Re. U.S. Appl. No. 12/723,725.
Supplementary European Search Report Dated Jul. 11, 2007 From the European Patent Office Re.: Application No. 04717208.5.
Aharoni et al. "Directed Evolution of Mammalian Paraoxonases PON1 and PON3 for Bacterial Expression and Catalytic Specialization", Proc. Natl. Acad. Sci. USA, XP002438727, 101(2): 482-487, Jan. 13, 2004.
Aharoni et al. "Synthetic Construct Paraoxonase PON1 Variant G1A5 Gene, Partial Cds", Database EMBL [Online], XP002440082, Retrieved From EBI Accession No. EMBL:AY499188, Database Accession No. AY499188, Jan. 19, 2004.
Aharoni et al. "Synthetic Construct Paraoxonase PON1 Variant G1C4 Gene, Partial Cds", Database EMBL [Online], XP002440083, Retrieved From EBI Accession No. EMBL:AY499189, Database Accession No. AY499189, Jan. 19, 2004.
Aharoni et al. "Synthetic Construct Paraoxonase PON1 Variant G2D6 Gene, Partial Cds", Database EMBL [Online], XP002440084, Retrieved From EBI Accesion No. EMBL:AY499190, Database Accession No. AY499190, Jan. 19, 2004.
Aharoni et al. "Synthetic Construct Paraoxonase PON1 Variant G2E6 Gene, Partial Cds", Database EMBL [Online], XP002440085, Retrieved From EBI Accession No. EMBL:AY499191, Database Accession No. AY499191, Jan. 19, 2004.
Aharoni et al. "Synthetic Construct Paraoxonase PON1 Variant G3C9 Gene, Partial Cds", Database EMBL [Online], XP002440087, Retrieved From EBI Accession No. EMBL:AY499193, Database Accession No. AY499193, Jan. 19, 2004.
Aharoni et al. "Synthetic Construct Paraoxonase PON1 Variant G3H8 Gene, Partial Cds", Database EMBL [Online], XP002440086, Retrieved From EBI Accession No. EMBL:AY299192, Database Accession No. AY499192, Jan. 19, 2004.
Aharoni et al. "Synthetic Construct Paraoxonase PON3 Variant G1A7 Gene, Partial Cds", Database EMBL [Online], XP002440088, Retrieved From EBI Accession No. EMBL:AY499194, Database Accession No. AY499194, Jan. 19, 2004.
Aharoni et al. "Synthetic Construct Paraoxonase PON3 Variant G1B11 Gen, Partial Cds", Database EMBL [Online], XP002440089, Retrieved From EBI Accession No. EMBL:AY499195, Database Accession No. AY499195, Jan. 19, 2004.
Aharoni et al. "Synthetic Construct Paraoxonase PON3 Variant G2C2 Gene, Partial Cds", Database EMBL [Online], XP002440090, Retrieved From EBI Accession No. EMBL:AT499196, Database Accession No. AY499196, Jan. 19, 2004.
Aharoni et al. "Synthetic Construct Paraoxonase PON3 Variant G3A5 Gene, Partila Cds", Database EMBL [Online], XP002440091, Retrieved From EBI Accession No. EMBL:AY499197, Database Accession No. AY499197, Jan. 19, 2004.
Aharoni et al. "Synthetic Construct Paraoxonase PON3 Variant G3G3 Gene, Partial Cds", Database EMBL [Online], XP002440092, Retrieved From EBI Accession No. EMBL:AY499198, Database Accession No. AY499198, Jan. 19, 2004.
Aharoni et al. "Synthetic Construct Paraoxonase PON3 Variant G3H9 Gene, Partial Cds", Database EMBL [Online], XP002440093, Retrieved From EBI Accession No. EMBL:AY499199, Database Accession No. AY499199, Jan. 19, 2004.
Bessette et al. "Efficient Folding of Proteins With Multiple Disulfide Bonds in the *Escherichia coli* Cytoplasm", Proc. Natl. Acad. Sci. USA, 96(24): 13703-13708, 1999.
Brushia et al. "Baculovirus-Mediated Expression and Purification of Human Serum Paraoxonase 1A", Journal of Lipid Research, XP002438729, 42(6): 951-958, Jun. 2001.
Guo et al. "Protein Tolerance to Random Amino Acid Change", Proc. Natl. Acad. sci. USA, PNAS, 101(25): 9205-9210, Jun. 22, 2004.
Hammarstroem et al. "Rapid Screening for Improved Solubility of Small Human Proteins Produced as Fusion Proteins in *Escherichia coli*", Protein Science, 11: 313-321, 2002.
Hill et al. "Functional Analysis of Conserved Histidines in ADP-Glucose Pyrophosphorylase From *Escherichia coli*", Biochemical and Biophysical Research Communications, 244: 573-577, 1998.
Josse et al. "Identification of Residues Essential for Human Paraoxonase (PON1) Arylesterase/Organophosphatase Activities", Biochemistry, 38(9): 2816-2825, 1999.
Josse et al. "Oligomeric States of the Detergent-Solubilized Human Serum Paraoxonase (PON1)", The Journal of Biological Chemistry, XP002988260, 277(36): 33386-33397, 2002. Discussion: Detergent-Dependent Interactions—Nonmicellar Solutions.
Josse et al. "The Active Site of Human Paraoxonase (PON1)", Journal of Applied Toxicology, 27: S7-S11, 2001.
Kuo et al. "Calcium Binding by Human and Rabbit Serum Paraoxonases. Structural Stability and Enzymatic Activity", Drug Metabolism and Disposition, 26(7): 653-660, 1998.
Lazar et al. "Transforming Growth Factor Alpha: Mutation of Aspartic Acid 47 and Leucine 48 Results in Differnet Biological Activities", Molecular and Cellular Biology, 8(3): 1247-1252, Mar. 1988.
Mackness et al. "Paraoxonase and Coronary Heart Disease", Atherosclerosis Supplements, XP002438728, 3(4): 49-55, Dec. 2002.
Maxwell et al. "A Simple In Vivo Assay for Increased Protein Solubility", Protein Science, 8: 1908-1911, 1999.
Ng et al. "Paraoxonase-2 Is A Ubiquitously Expressed Protein With Antioxidant Properties and Is Capable of Preventing Cell-Mediated Oxidative Modification of Low Density Lipoprotein", The Journal of Biological Chemistry, 276(48): 44444-44449, Nov. 30, 2001.
Sun et al. "Expression and Stabilization of Galactose Oxidase in *Escherichia coli* by Directed Evolution", Protein Engineering, 14(9): 699-704, 2001.
Wacey et al. "Disentangling the Pertubational Effects of Amino Acid Substitutions in the DNA-Binding Domain of P53", Human Genetics, 104: 15-22, 1999.
Waldo "Genetic Screens and Directed Evolution for Protein Solubility", Current Opinion in Chemical Biology, 7: 33-38, 2003.

* cited by examiner

FIG. 5A

|  | 1 | | | | | 50 |
|---|---|---|---|---|---|---|
| G1A5 | .......... | .GLGLALFDGQ | .KSSFQTRFNV | .HREVTPVELP | .NCNLVKGIDN |
| G1C4 | MAKLTALTLL | GLGLALFDGQ | KSSFQTRFNV | HREVTPVELP | NCNLVKGIDN |
| G2D6 | MAKLLALTLV | GLGLALFDGQ | KSSFQTRFNV | HREVTPVELP | NCNLVKGIDN |
| G2E6 | MAKLTALTLL | GLGLALFDRQ | KSSFQTRFNV | HREVTPVELP | NCNLVKGIET |
| G3C9 | MAKLTALTLL | GMGLALFDGQ | KSSFQTRFNV | HREVTPVELP | NCNLVKGIDN |
| G3H8 | MAKLTAPTLL | GLGLALFDGQ | KSSFQTRFNV | HREVTPVELP | NCNLVKGVDN |
| RabPON1 | MAKLTALTLL | GLGLALFDGQ | KSSFQTRFNV | HREVTPVELP | NCNLVKGIDN |

|  | | | | | | 100 |
|---|---|---|---|---|---|---|
| G1A5 | .GSEDLEILPN | .GLAFISSGLK | .YPGIMSFDPD | .KSGKILLMDL | .NEEDPVVLEL |
| G1C4 | GAEDLEILPN | GLAFISSGLK | YPGIMSFDPD | KSGKILLMDL | NEEDPVVLEL |
| G2D6 | GSEDLEILPN | GLAFISSGLK | YPGIMSFDPD | KSGKILLMDL | NEEDPVVLEL |
| G2E6 | GSEDLEILPN | GLAFISSGLK | YPGIMSFDPD | KSGKILLMDL | NEKEPAVSEL |
| G3C9 | GSEDLEILPN | GLAFISSGLK | YPGIMSFDPD | KSGKILLMDL | NEEDPVVLEL |
| G3H8 | GSEDLEILPN | GLAFISSGLK | YPGIMSFDPD | KSGKILLMDL | NEEDPVVLEL |
| RabPON1 | GSEDLEILPN | GLAFISSGLK | YPGIMSFDPD | KSGKILLMDL | NEEDPVVLEL |

|  | | | | | | 150 |
|---|---|---|---|---|---|---|
| G1A5 | .GITGNTLDIS | .SFNPHGISTF | .TDEDNTVYLL | .VVNHPDSSST | .VEVFKFQEKE |
| G1C4 | GITGSTFDLS | SFNPHGISTF | TDEDNTVYLL | VVNHPDSSST | VEVFKFQEKE |
| G2D6 | GITGNTLDIS | SFNPHGISTF | TDEDNTVYLL | VVNHPDSSST | VEVFKFQEKE |
| G2E6 | EIIGNTLDIS | SFNPHGISTF | TDDDNTVYLL | VVNHPDSSST | VEVFKFQEEE |
| G3C9 | GITGNTLDIS | SFNPHGISTF | TDEDNTVYLL | VVNHPDSSST | VEVFKFQEKE |
| G3H8 | GITGSTFDLS | SFNPHGISTF | TDEDNTVYLL | VVNHPDSSST | VEVFKFQEKE |
| RabPON1 | GITGSTFDLS | SFNPHGISTF | TDEDNIVYLM | VVNHPDSKST | VELFKFQEKE |

Mouse PON1
RatPON1
HumanPON1
Mutation during the shuffling process

| FIG. 5A |
|---|
| FIG. 5B |
| FIG. 5C |

```
         .     160       .     170       .     180       .     190       .     200
G1A5   KSLLHLKTIR HKLLPSVNDI VAVGPEHFYA TNDHYFIDPY LKSWEMHLGL
G1C4   KSLLHLKTIR HKLLPSVNDI VAVGPEHFYA TNDHYFIDPY LKSWEMHLGL
G2D6   RSLLHLKTIR HKLLPSVNDI VAVGPEHFYA TNDHYFADPY LKSWEMHLGL
G2E6   KSLLHLKTIR HKLLPSVNDI VAVGPEHFYA TNDHYFIDPY LKSWEMHLGL
G3C9   KSLLHLKTIR HKLLPSVNDI VAVGPESFYA TNDHYFIDPY LKSWEMHLGL
G3H8   RSLLHLKTIR HKLLPSVNDI VAVGPESFYA TNDHYFADPY LKSWEMHLGL
RabPON1 KSLLHLKTIR HKLLPSVNDI VAVGPEHFYA TNDHYFIDPY LKSWEMHLGL

.     210       .     220       .     230       .     240       .     250
G1A5   AWSFVTYYSP NDVRVVAEGF DFANGINISP DGKYVVYIAEL LAHKIHVYEK
G1C4   AWSFVTYYSP NDVRVVAEGF DFANGINISP DGKYVVYIAEL LAHKIHVYEK
G2D6   AWSFVTYYSP NDVRVVAEGF DFANGINISP DGKYVVYIAEL LAHKIHVYEK
G2E6   AWSFVTYYSP NDVRVVAEGF DFANGINISP DGKYVVYIAEL LAHKIHVYEK
G3C9   AWSFVTYYSP NDVRVVAEGF DFANGINISP DGKYVVYIAEL LAHKIHVYEK
G3H8   AWSFVTYYSP NDVRVVAEGF DFANGINISP DGKYVVYIAEL LAHKIHVYEK
RabPON1 AWSFVTYYSP NDVRVVAEGF DFANGINISP DGKYVVYIAEL LAHKIHVYEK

.     260       .     270       .     280       .     290       .     300
G1A5   HANWTLTPLK SLDFNTLVDN ISVDPVTGDL WVGCHPNGMR IFYYDPENPP
G1C4   HANWTLTPLK SLDFNTLVDN ISVDPVTGDL WVGCHPNGMR IFYYDPKNPP
G2D6   HANWTLTPLK SLDFNTLVDN ISVDPVTGDL WVGCHPNGMR IFYYDPENPP
G2E6   HANWTLTPLR VLSFDFDTLVDN ISVDPVTGDL WVGCHPNGMR IFYDAENPP
G3C9   HANWTLTPLK SLDFDFDTLVDN ISVDPVTGDL WVGCHPNGMR IFYYDPKNPP
G3H8   HANWTLTPLK SLDFNTLVDN ISVDPVTGDL WVGCHPNGMR IFYYDPENPP
RabPON1 HANWTLTPLK SLDFNTLVDN ISVDPVTGDL WVGCHPNGMR IFYYDPKNPP
```

Mouse PON1
RatPON1
HumanPON1
Mutation during the shuffling process

Fig. 13

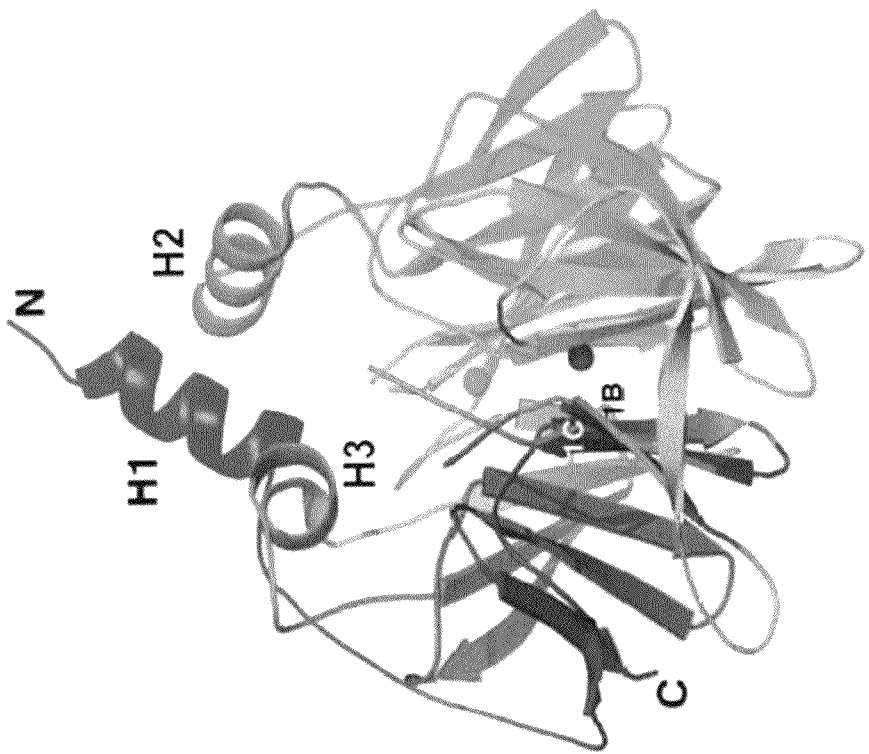
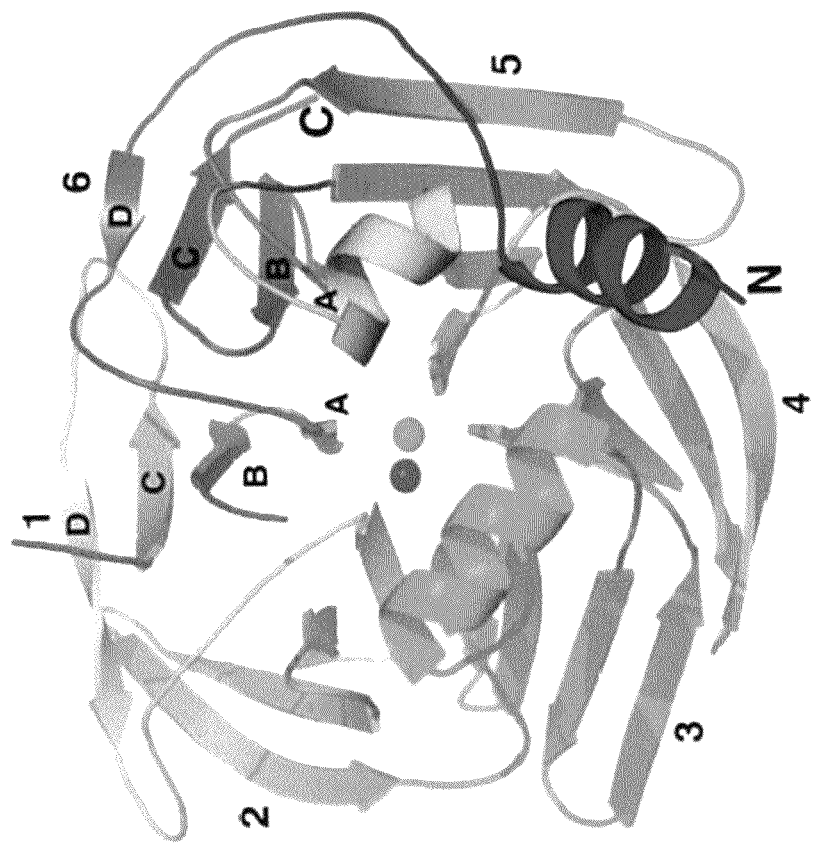
Fig. 15b
Fig. 15a

```
HEADER       ----                                       XX-XXX-XX   xxxx
COMPND
REMARK   3
REMARK   3 REFINEMENT.
REMARK   3   PROGRAM     : REFMAC 5.1.24
REMARK   3   AUTHORS     : MURSHUDOV,VAGIN,DODSON
REMARK   3
REMARK   3    REFINEMENT TARGET : MAXIMUM LIKELIHOOD
REMARK   3
REMARK   3  DATA USED IN REFINEMENT.
REMARK   3   RESOLUTION RANGE HIGH (ANGSTROMS) :   2.20
REMARK   3   RESOLUTION RANGE LOW  (ANGSTROMS) :  20.00
REMARK   3   DATA CUTOFF            (SIGMA(F)) :  NONE
REMARK   3   COMPLETENESS FOR RANGE        (%) :  99.74
REMARK   3   NUMBER OF REFLECTIONS             :  33505
REMARK   3
REMARK   3  FIT TO DATA USED IN REFINEMENT.
REMARK   3   CROSS-VALIDATION METHOD          : THROUGHOUT
REMARK   3   FREE R VALUE TEST SET SELECTION  : RANDOM
REMARK   3   R VALUE     (WORKING + TEST SET) : 0.18666
REMARK   3   R VALUE            (WORKING SET) : 0.18503
REMARK   3   FREE R VALUE                     : 0.21704
REMARK   3   FREE R VALUE TEST SET SIZE   (%) : 5.0
REMARK   3   FREE R VALUE TEST SET COUNT      : 1767
REMARK   3
REMARK   3  FIT IN THE HIGHEST RESOLUTION BIN.
REMARK   3   TOTAL NUMBER OF BINS USED            :     20
REMARK   3   BIN RESOLUTION RANGE HIGH            :  2.200
REMARK   3   BIN RESOLUTION RANGE LOW             :  2.256
REMARK   3   REFLECTION IN BIN     (WORKING SET)  :   2347
REMARK   3   BIN R VALUE           (WORKING SET)  :  0.291
REMARK   3   BIN FREE R VALUE SET COUNT106        :
REMARK   3   BIN FREE R VALUE                     :  0.319
REMARK   3
REMARK   3  NUMBER OF NON-HYDROGEN ATOMS USED IN REFINEMENT.
REMARK   3   ALL ATOMS                :     2756
REMARK   3
REMARK   3  B VALUES.
REMARK   3   FROM WILSON PLOT)          A**2) : NULL
REMARK   3   MEAN B VALUE      (OVERALL, A**2) : 38.485
REMARK   3   OVERALL ANISOTROPIC B VALUE.
REMARK   3    B11 (A**2) :   -0.56
REMARK   3    B22 (A**2) :   -0.56
REMARK   3    B33 (A**2) :    1.13
REMARK   3    B12 (A**20.00   : (
REMARK   3    B13 (A**2) :    0.00
REMARK   3    B23 (A**2) :    0.00
REMARK   3
REMARK   3  ESTIMATED OVERALL COORDINATE ERROR.
REMARK   3   ESU BASED ON R VALUE                       (A):   0.145
REMARK   3   ESU BASED ON FREE R VALUE)                  A):   0.139
REMARK   3   ESU BASED ON MAXIMUM LIKELIHOOD            (A):   0.106
REMARK   3   ESU FOR B VALUES BASED ON MAXIMUM LIKELIHOOD (A**2):   4.256
REMARK   3
REMARK   3 CORRELATION COEFFICIENTS.
REMARK   3   CORRELATION COEFFICIENT FO-FC      :  0.960
REMARK   3   CORRELATION COEFFICIENT FO-FC FREE :  0.947
REMARK   3
REMARK   3  RMS DEVIATIONS FROM IDEAL VALUES        COUNT    RMS   WEIGHT
REMARK   3   BOND LENGTHS REFINED ATOMS       (A):  2705 ; 0.025 ; 0.021
REMARK   3   BOND ANGLES REFINED ATOMS  (DEGREES):  3685 ; 2.048 ; 1.951
```

Fig. 26

```
REMARK   3    TORSION ANGLES, PERIOD 1    (DEGREES):    330 ; 7.737 ; 5.000
REMARK   3    CHIRAL-CENTER RESTRAINTS         (A**3):    417 ; 0.168 ; 0.200
REMARK   3    GENERAL PLANES REFINED ATOMS)        A):   2057 ; 0.009 ; 0.020
REMARK   3    NON-BONDED CONTACTS REFINED ATOMS (A):   1063 ; 0.224 ; 0.200
REMARK   3    H-BOND (X...Y) REFINED ATOMS        (A):    115 ; 0.163 ; 0.200
REMARK   3    POTENTIAL METAL-ION REFINED ATOMS (A):       7 ; 0.131 ; 0.200
REMARK   3    SYMMETRY VDW REFINED ATOMS          (A):     13 ; 0.198 ; 0.200
REMARK   3    SYMMETRY H-BOND REFINED ATOMS       (A):      4 ; 0.102 ; 0.200
REMARK   3
REMARK   3  ISOTROPIC THERMAL FACTOR RESTRAINTS.    COUNT    RMS    WEIGHT
REMARK   3   MAIN-CHAIN BOND REFINED ATOMS  (A**2):   1655 ; 1.091 ; 1.500
REMARK   3   MAIN-CHAIN ANGLE REFINED ATOMS (A**2):   2694 ; 1.872 ; 2.000
REMARK   3   SIDE-CHAIN BOND REFINED ATOMS  (A**2):   1050 ; 3.059 ; 3.000
REMARK   3   SIDE-CHAIN ANGLE REFINED ATOMS (A**2):    991 ; 44.500 ; 521.
REMARK   3
REMARK   3  NCS RESTRAINTS STATISTICS
REMARK   3   NUMBER OF NCS GROUPS : NULL
REMARK   3
REMARK   3
REMARK   3  TLS DETAILS
REMARK   3   NUMBER OF TLS GROUPS  :    1
REMARK   3
REMARK   3   TLS GROUP :     1
REMARK   3    NUMBER OF COMPONENTS GROUP :    1
REMARK   3    COMPONENTS          C SSSEQI   TO   C SSSEQI
REMARK   3    RESIDUE RANGE :         -1               -1
REMARK   3    ORIGIN FOR THE GROUP (A):   8.3288   28.6493   21.4479
REMARK   3    T TENSOR
REMARK   3      T11:    0.0067 T22:    0.1081
REMARK   3      T33:    0.0487 T12:    0.0061
REMARK   3      T13:    0.0168 T23:    0.0414
REMARK   3    L TENSOR
REMARK   3      L11:    3.5916 L22:    2.2014
REMARK   3      L33:    3.4673 L12:    0.6914
REMARK   3      L13:   -1.5993 L23:   -0.1237
REMARK   3    S TENSOR
REMARK   3      S11:   -0.0701 S12:   -0.0679 S13:   -0.2068
REMARK   3      S21:    0.0903 S22:   -0.0402 S23:   -0.1588
REMARK   3      S31:    0.1729 S32:    0.1134 S33:    0.1103
REMARK   3
REMARK   3
REMARK   3  BULK SOLVENT MODELLING.
REMARK   3   METHOD USED : BABINET MODEL WITH MASK
REMARK   3   PARAMETERS FOR MASK CALCULATION
REMARK   3   VDW PROBE RADIUS    :   1.40
REMARK   3   ION PROBE RADIUS    :   0.80
REMARK   3   SHRINKAGE RADIUS    :   0.80
REMARK   3
REMARK   3  OTHER REFINEMENT REMARKS: NULL
REMARK   3
LINK            TYR A  71                 ASP A  80                  gap
CRYST1   98.440   98.440  139.170  90.00  90.00  90.00 P43212
SCALE1     0.010158  0.000000  0.000000        0.00000
SCALE2     0.000000  0.010158  0.000000        0.00000
SCALE3     0.000000  0.000000  0.007185        0.00000
ATOM      1  N   LEU A  16      20.229  -7.374  21.763  1.00 48.03           N
ATOM      2  CA  LEU A  16      21.538  -6.888  21.246  1.00 48.15           C
ATOM      3  CB  LEU A  16      22.372  -8.036  20.623  1.00 48.06           C
ATOM      4  CG  LEU A  16      21.874  -9.103  19.613  1.00 48.10           C
ATOM      5  CD1 LEU A          47.53 1.00  18.185  8.816- 22.390         16 C
ATOM      6  CD2 LEU A  16      22.242 -10.553  20.029  1.00 46.02           C
```

Fig. 26 (Cont.)

| ATOM | 7  | C   | LEU | A | 16 | 21.322 | -5.735 | 20.266 | 1.00 | 48.37 |       |       | C |
|------|----|-----|-----|---|----|--------|--------|--------|------|-------|-------|-------|---|
| ATOM | 8  | O   | LEU | A | 16 | 21.935 | -5     |        | 48.40| 1.00  | 19.197| 694.0 |   |
| ATOM | 9  | N   | PHE | A | 17 | 20.453 | -4.796 | 20.639 | 1.00 | 48.56 |       |       | N |
| ATOM | 10 | CA  | PHE | A | 17 | 20.144 | -3.665 | 19.760 | 1.00 | 49.17 |       |       | C |
| ATOM | 11 | CB  | PHE | A | 17 | 18.662 | -3.649 | 19.324 | 1.00 | 49.00 |       |       | C |
| ATOM | 12 | CG  | PHE | A | 17 | 17.687 | -3.278 | 20.412 | 1.00 | 49.31 |       |       | C |
| ATOM | 13 | CD1 | PHE | A | 17 | 17.171 | -1.970 | 20.497 | 1.00 | 50.66 |       |       | C |
| ATOM | 14 | CE1 | PHE | A | 17 | 16.227 | -1.622 | 21.503 | 1.00 | 51.30 |       |       | C |
| ATOM | 15 | CZ  | PHE | A | 17 | 15.800 | -2.602 | 22.430 | 1.00 | 48.27 |       |       | C |
| ATOM | 16 | CE2 | PHE | A | 17 | 16.308 | -3.892 | 22.338 | 1.00 | 49.43 |       |       | C |
| ATOM | 17 | CD2 | PHE | A | 17 | 17.244 | -4.230 | 21.327 | 1.00 | 48.64 |       |       | C |
| ATOM | 18 | C   | PHE | A | 17 | 20.736 | -2.267 | 20.124 | 1.00 | 49.78 |       |       | C |
| ATOM | 19 | O   | PHE | A | 17 | 20.227 | -1.492 | 20.950 | 1.00 | 48.86 |       |       | O |
| ATOM | 20 | N   | ASP | A | 18 | 21.861 | -2.007 | 19.455 | 1.00 | 50.85 |       |       | N |
| ATOM | 21 | CA  | ASP | A | 18 | 22.558 |        |        | 51.34| 1.00  | 19.411| 0.728-| C |
| ATOM | 22 | CB  | ASP | A | 18 | 23.818 | -0.856 | 18.506 | 1.00 | 51.42 |       |       | C |
| ATOM | 23 | CG  | ASP | A | 18 | 25.093 | -1.310 | 19.264 | 1.00 | 51.79 |       |       | C |
| ATOM | 24 | OD1 | ASP | A | 18 | 25.506 | -0.571 | 20.196 | 1.00 |       |       | 52.10 | O |
| ATOM | 25 | OD2 | ASP | A | 18 | 25.767 | -2.354 | 18.971 | 1.00 | 49.88 |       |       | O |
| ATOM | 26 | C   | ASP | A | 18 | 21.645 | 0.300  | 18.767 | 1.00 | 51.75 |       |       | C |
| ATOM | 27 | O   | ASP | A | 18 | 22.123 | 1.378  | 18.368 | 1.00 | 52.40 |       |       | O |
| ATOM | 28 | N   | ARG | A | 19 | 20.352 | -0.025 | 18.626 | 1.00 | 51.75 |       |       | N |
| ATOM | 29 | CA  | ARG | A | 19 | 19.421 | 0.843  | 17.858 | 1.00 | 51.60 |       |       | C |
| ATOM | 30 | CB  | ARG | A | 19 | 18.166 | 0.079  | 17.386 | 1.00 | 52.00 |       |       | C |
| ATOM | 31 | CG  | ARG | A | 19 | 18.395 | -0.781 | 16.113 | 1.00 | 53.24 |       |       | C |
| ATOM | 32 | CD  | ARG | A | 19 | 19.048 | -0.003 | 14.924 | 1.00 | 54.03 |       |       | C |
| ATOM | 33 | NE  | ARG | A | 19 | 20.422 | -0.455 | 14.632 | 1.00 | 53.37 |       |       | N |
| ATOM | 34 | CZ  | ARG | A | 19 | 21.433 |        |        | 52.80| 1.00  | 14.225| 0.337 | C |
| ATOM | 35 | NH1 | ARG | A | 19 | 21.257 | 1.653  | 14.043 | 1.00 | 50.30 |       |       | N |
| ATOM | 36 | NH2 | ARG | A | 19 | 22.628 | -0.201 | 13.994 | 1.00 | 51.17 |       |       | N |
| ATOM | 37 | C   | ARG | A | 19 | 19.034 | 2.078  | 18.627 |      |       | 50.83 | 1.00  | C |
| ATOM | 38 | O   | ARG | A | 19 | 18.849 | 3.153  | 18.037 | 1.00 | 50.62 |       |       | O |
| ATOM | 39 | N   | GLN | A | 20 | 18.914 | 1.876  | 19.944 | 1.00 | 50.23 |       |       | N |
| ATOM | 40 | CA  | GLN | A | 20 | 18.723 | 2.914  | 20.967 | 1.00 | 49.45 |       |       | C |
| ATOM | 41 | CB  | GLN | A | 20 | 18.600 | 2.261  | 22.355 | 1.00 | 49.61 |       |       | C |
| ATOM | 42 | CG  | GLN | A | 20 | 17.816 | 3.082  | 23.342 | 1.00 | 48.43 |       |       | C |
| ATOM | 43 | CD  | GLN | A | 20 | 16.490 | 3.493  | 22.739 | 1.00 | 50.00 |       |       | C |
| ATOM | 44 | OE1 | GLN | A | 20 | 15.796 | 2.626  | 22.170 | 1.00 | 50.23 |       |       | O |
| ATOM | 45 | NE2 | GLN | A | 20 | 16.141 | 4.808  | 22.813 | 1.00 | 41.99 |       |       | N |
| ATOM | 46 | C   | GLN | A | 20 | 19.835 | 3.976  | 21.023 | 1.00 | 49.06 |       |       | C |
| ATOM | 47 | O   | GLN | A | 20 | 19     |        | 48.53  | 1.00 | 21.172| 5.178 | 546.0 |   |
| ATOM | 48 | N   | LYS | A | 21 | 21.090 | 3.502  | 20.957 | 1.00 | 48.65 |       |       | N |
| ATOM | 49 | CA  | LYS | A | 21 | 22.272 | 4.361  | 20.927 | 1.00 | 47.93 |       |       | C |
| ATOM | 50 | CB  | LYS | A | 21 | 23.565 | 3.555  | 21.137 |      |       | 47.74 | 1.00  | C |
| ATOM | 51 | CG  | LYS | A | 21 | 23.830 | 3.230  | 22.625 | 1.00 | 47.47 |       |       | C |
| ATOM | 52 | CD  | LYS | A | 21 | 24.805 | 2.065  | 22.814 | 1.00 | 46.97 |       |       | C |
| ATOM | 53 | CE  | LYS | A | 21 | 24.621 | 1.374  | 24.183 | 1.00 | 46.00 |       |       | C |
| ATOM | 54 | NZ  | LYS | A | 21 | 24.730 | -0.084 | 24.047 | 1.00 | 39.99 |       |       | N |
| ATOM | 55 | C   | LYS | A | 21 | 22.323 | 5.172  | 19.635 | 1.00 | 47.48 |       |       | C |
| ATOM | 56 | O   | LYS | A | 21 | 22.510 | 6.389  | 19.690 | 1.00 | 47.27 |       |       | O |
| ATOM | 57 | N   | SER | A | 22 | 22.120 | 4.514  | 18.491 | 1.00 | 46.59 |       |       | N |
| ATOM | 58 | CA  | SER | A | 22 | 22.122 | 5.210  | 17.201 | 1.00 | 46.04 |       |       | C |
| ATOM | 59 | CB  | SER | A | 22 | 22.266 | 4.216  | 16.053 | 1.00 | 46.54 |       |       | C |
| ATOM | 60 | OG  | SER | A | 22 |        | 47.25  | 1.00   | 15.301| 4.164| 21.070|       | O |
| ATOM | 61 | C   | SER | A | 22 | 20.895 | 6.120  | 16.966 | 1.00 | 45.39 |       |       | C |
| ATOM | 62 | O   | SER | A | 22 | 20.981 | 7.112  | 16.242 | 1.00 | 45.07 |       |       | O |
| ATOM | 63 | N   | SER | A | 23 | 19.757 | 5.767  | 17     |      |       | 44.20 | 1.00  556.N |
| ATOM | 64 | CA  | SER | A | 23 | 18.571 | 6.608  | 17.481 | 1.00 | 42.87 |       |       | C |
| ATOM | 65 | CB  | SER | A | 23 | 17.354 | 5.764  | 17.813 | 1.00 | 42.54 |       |       | C |
| ATOM | 66 | OG  | SER | A | 23 | 16.206 | 6.541  | 17.796 | 1.00 | 44.03 |       |       | O |
| ATOM | 67 | C   | SER | A | 23 | 18.728 | 7.852  | 18.398 | 1.00 | 42.19 |       |       | C |

Fig. 26 (Cont.)

```
ATOM     68  O   SER A  23      18.415   8.974  18.017  1.00 40.34           O
ATOM     69  N   PHE A  24      19.304   7.640  19.577  1.00 42.24           N
ATOM     70  CA  PHE A  24      19.677   8.734  20.473  1.00 42.54           C
ATOM     71  CB  PHE A  24      20.299   8.171  21.767  1.00 43.00           C
ATOM     72  CG  PHE A  24      20.490   9.211  22.842  1.00 45.48           C
ATOM     73  CD1 PHE A  24           47.44 1.00  23.682   9.575   19.422     C
ATOM     74  CE1 PHE A  24      19.594  10.544  24.675  1.00 47.86           C
ATOM     75  CZ  PHE A  24      20.836  11.182  24.817  1.00 46.62           C
ATOM     76  CE2 PHE A  24      21.904  10.829          46.69 1.00   23.979  C
ATOM     77  CD2 PHE A  24      21.727   9.849  23.002  1.00 46.52           C
ATOM     78  C   PHE A  24      20.678   9.701  19.828  1.00 41.94           C
ATOM     79  O   PHE A  24      20.515  10.913  19.936  1.00 42.08           O
ATOM     80  N   GLN A  25      21.722   9.160  19.188  1.00 40.91           N
ATOM     81  CA  GLN A  25      22.750   9.998  18.587  1.00 41.05           C
ATOM     82  CB  GLN A  25      23.983   9.212  18.146  1.00 40.83           C
ATOM     83  CG  GLN A  25      24.560   8.428  19.327  1.00 44.31           C
ATOM     84  CD  GLN A  25      26.059   8.516  19.471  1.00 46.68           C
ATOM     85  OE1 GLN A  25      26.793   7.859  18.745  1.00 44.53           O
ATOM     86  NE2 GLN A  25           48.05 1.00  20.427   9.324   26.517     N
ATOM     87  C   GLN A  25      22.235  10.922  17.484  1.00 40.09           C
ATOM     88  O   GLN A  25      22.698  12.066  17.363  1.00 39.62           C
ATOM     89  N   THR A  26      21.275  10.430          38.61 1.00   16.708  N
ATOM     90  CA  THR A  26      20.662  11.281  15.720  1.00 37.75           C
ATOM     91  CB  THR A  26      20.251  10.482  14.434  1.00 38.34           C
ATOM     92  OG1 THR A  26      18.866  10.655  14.160  1.00 40          31.O
ATOM     93  CG2 THR A  26      20.353   9.033  14.607  1.00 38.26           C
ATOM     94  C   THR A  26      19.599  12.288  16.289  1.00 36.93           C
ATOM     95  O   THR A  26      19.625  13.461  15.927  1.00 36.82           O
ATOM     96  N   ARG A  27      18.716  11.871  17.207  1.00 35.17           N
ATOM     97  CA  ARG A  27      17.769  12.825  17.814  1.00 34.64           C
ATOM     98  CB  ARG A  27      16.822  12.140  18.811  1.00 33.43           C
ATOM     99  CG  ARG A           34.40 1.00  18.260  10.882   16.145      27 C
ATOM    100  CD  ARG A  27      15.507  10.006  19.341  1.00 34.32           C
ATOM    101  NE  ARG A  27      14.569  10.800  20.161  1.00 34.94           N
ATOM    102  CZ  ARG A  27      14.412  10.675          34.58 1.00   21.484  C
ATOM    103  NH1 ARG A  27      15.095   9.786  22.173  1.00 32.32           N
ATOM    104  NH2 ARG A  27      13.526  11.430  22.122  1.00 34.47           N
ATOM    105  C   ARG A  27      18.476  14.018  18.467  1.00           33.78 C
ATOM    106  O   ARG A  27      18.122  15.169  18.256  1.00 32.49           O
ATOM    107  N   PHE A  28      19.477  13.711  19.268  1.00 33.94           N
ATOM    108  CA  PHE A  28      20.269  14.717  19.973  1.00 35.08           C
ATOM    109  CB  PHE A  28      20.737  14.079  21.309  1.00 35.86           C
ATOM    110  CG  PHE A  28      19.613  13.973  22.310  1.00 37.70           C
ATOM    111  CD1 PHE A  28      19.309  15.040  23.121  1.00 37.60           C
ATOM    112  CE1 PHE A  28      18.224  14.972  24.014  1.00 38.07           C
ATOM    113  CZ  PHE A  28      17.434  13.852  24.060  1.00 33.97           C
ATOM    114  CE2 PHE A  28      17.708  12.779  23.214  1.00 38.17           C
ATOM    115  CD2 PHE A  28      18.779                  39.12 1.00   22.336   12.846  C
ATOM    116  C   PHE A  28      21.437  15.352  19.146  1.00 35.18           C
ATOM    117  O   PHE A  28      22.110  16.280  19.616  1.00 34.98           O
ATOM    118  N   ASN A  29      21.653  14.854  17.925  1                35.26  00.N
ATOM    119  CA  ASN A  29      22.555  15.493  16.973  1.00 36.26           C
ATOM    120  CB  ASN A  29      21.982  16.908  16.672  1.00 35.95           C
ATOM    121  CG  ASN A  29      21.635  17.137  15.185  1.00 37.34           C
ATOM    122  OD1 ASN A  29      21.466  16.201  14.378  1.00 37.30           O
ATOM    123  ND2 ASN A  29      21.529  18.413  14.823  1.00 34.10           N
ATOM    124  C   ASN A  29      23.924  15.584  17.654  1.00 36.07           C
ATOM    125  O   ASN A  29      24.514  16.653  17.751  1.00 37.33           O
ATOM    126  N   VAL A  30      24.423  14.468  18.160  1.00 36.93           N
ATOM    127  CA  VAL A  30      25.428  14.513  19.231  1.00 37.82           C
ATOM    128  CB  VAL A  30      25             38.05 1.00  19.947   13.127    558.C
```

Fig. 26 (Cont.)

```
ATOM    129  CG1  VAL A  30      24.249   12.748   20.690  1.00 35.55           C
ATOM    130  CG2  VAL A  30      25.950   12.105   18.953  1.00 37.94           C
ATOM    131  C    VAL A  30      26.830   15.047   18.829       39.14 1.00      C
ATOM    132  O    VAL A  30      27.593   15.572   19.676  1.00 39.06           O
ATOM    133  N    HIS A  31      27.170   14.938   17.550  1.00 39.88           N
ATOM    134  CA   HIS A  31      28.452   15.469   17.148  1.00 41.80           C
ATOM    135  CB   HIS A  31      29.302   14.400   16.429  1.00 42.41           C
ATOM    136  CG   HIS A  31      29.573   13.175   17.256  1.00 44.50           C
ATOM    137  ND1  HIS A  31      30.397   13.187   18.366  1.00 47.02           N
ATOM    138  CE1  HIS A  31      30.453   11.969   18.891  1.00 47.31           C
ATOM    139  NE2  HIS A  31      29.682   11.170   18.172  1.00 47.94           N
ATOM    140  CD2  HIS A  31      29.119   11.899   17.142  1.00 46.89           C
ATOM    141  C    HIS A  31           42.57 1.00   16.322   16.772   28.364     C
ATOM    142  O    HIS A  31      29.409   17.239   15.923  1.00 42.18           O
ATOM    143  N    ARG A  32      27.163   17.341   16.070  1.00 42.84           N
ATOM    144  CA   ARG A  32      27.066   18.586   15           43.73 1.00  262.C
ATOM    145  CB   ARG A  32      25.608   19.031   14.833  1.00 44.10           C
ATOM    146  CG   ARG A  32      25.670   19.652   13.352  1.00 46.44           C
ATOM    147  CD   ARG A  32      24.440   19.646   12.439  1.00 48.91           C
ATOM    148  NE   ARG A  32      23.627   20.866   12.638  1.00 58.32           N
ATOM    149  CZ   ARG A  32      23.807   22.123   12.090  1.00 58.66           C
ATOM    150  NH1  ARG A  32      24.762   22.401   11.235  1.00 57.63           N
ATOM    151  NH2  ARG A  32      22.984   23.122   12.408  1.00 57.81           N
ATOM    152  C    ARG A  32      27.857   19.769   15.821  1.00 42.89           C
ATOM    153  O    ARG A  32      27.940   20.001   17.035  1.00 41.88           O
ATOM    154  N    GLU A  33           42.73 1.00   14.886   20.498   28.444     N
ATOM    155  CA   GLU A  33      29.270   21.681   15.156  1.00 42.85           C
ATOM    156  CB   GLU A  33      30.759   21.386   14.867  1.00 42.85           C
ATOM    157  CG   GLU A  33      31.455   20.562            46.08 1.00   15.941 C
ATOM    158  CD   GLU A  33      31.795   21.392   17.192  1.00 51.50           C
ATOM    159  OE1  GLU A  33      30.853   21.825   17.908  1.00 52.59           O
ATOM    160  OE2  GLU A  33      33.005   21.626   17.465  1.00 53.12           O
ATOM    161  C    GLU A  33      28.736   22.783   14.251  1.00 41.50           C
ATOM    162  O    GLU A  33      28.503   22.549   13.054  1.00 41.54           O
ATOM    163  N    VAL A  34      28.501   23.965   14.819  1.00 40.12           N
ATOM    164       CA   VAL A  34 27.857   25.046   14.080  1.00 37.78           C
ATOM    165  CB   VAL A  34      27.345   26.176   15.007  1.00 39.12           C
ATOM    166  CG1  VAL A  34      26.163   26.807   14.385  1.00 39.33           C
ATOM    167  CG2  VAL A  34           39.27 1.00   16.359   25.616   26.891     C
ATOM    168  C    VAL A  34      28.730   25.657   13.015  1.00 35.66           C
ATOM    169  O    VAL A  34      29.930   25.905   13.234  1.00 35.36           O
ATOM    170  N    THR A  35      28.160   25.849            33.70 1.00   11.835 N
ATOM    171  CA   THR A  35      28.854   26.681   10.823  1.00 33.15           C
ATOM    172  CB   THR A  35      28.505   26.258    9.342  1.00 32.88           C
ATOM    173  OG1  THR A  35      28.983   24.924    9.125  1.00 32          35.O
ATOM    174  CG2  THR A  35      29.254   27.214    8.238  1.00 27.35           C
ATOM    175  C    THR A  35      28.385   28.108   11.100  1.00 32.81           C
ATOM    176  O    THR A  35      27.185   28.368   10.959  1.00 33.94           O
ATOM    177       N    PRO A  36 29.264   28.986   11.576  1.00 31.78           N
ATOM    178  CA   PRO A  36      28.848   30.369   11.850  1.00 32.49           C
ATOM    179  CB   PRO A  36      30.103   31.049   12.435  1.00 32.26           C
ATOM    180  CG   PRO A              33.26 1.00   12.098   30.137   31.261   36 C
ATOM    181  CD   PRO A  36      30.691   28.738   11.872  1.00 32.51           C
ATOM    182  C    PRO A  36      28.290   31.133   10.586  1.00 32.63           C
ATOM    183  O    PRO A  36      28.753   31               31.81 1.00  9.470 009.O
ATOM    184  N    VAL A  37      27.230   31.878   10.825  1.00 32.30           N
ATOM    185  CA   VAL A  37      26.715   32.821    9.882  1.00 33.56           C
ATOM    186  CB   VAL A  37      25.340   32.318    9.285  1.00           34.80 C
ATOM    187  CG1  VAL A  37      24.754   33.467    8.439  1.00 37.90           C
ATOM    188  CG2  VAL A  37      25.565   31.092    8.368  1.00 33.76           C
ATOM    189  C    VAL A  37      26.565   34.149   10.626  1.00 32.02           C
```

Fig. 26 (Cont.)

```
ATOM    190  O    VAL A   37      25.800  34.253  11.566  1.00 33.52           O
ATOM    191  N    GLU A   38      27.209  35.164  10.152  1.00 32.79           N
ATOM    192  CA   GLU A   38      27.328  36.438  10.862  1.00 35.75           C
ATOM    193  CB   GLU A   38      28.775  36.965  10.746  1.00 35.31           C
ATOM    194  CG   GLU A   38      29.846  36.061  11.355  1.00 36.88           C
ATOM    195  CD   GLU A   38      31.222  36.478  10.861  1.00 45.68           C
ATOM    196  OE1  GLU A   38      31.579          45.43 1.00  11.020  37.677   O
ATOM    197  OE2  GLU A   38      31.966  35.632  10.287  1.00 50.57           O
ATOM    198  C    GLU A   38      26.359  37.540  10.391  1.00 36.81           C
ATOM    199  O    GLU A   38      25.943  37.558   9.212  1              37.04 00.0
ATOM    200  N    LEU A   39      26.018  38.447  11.308  1.00 36.60           N
ATOM    201  CA   LEU A   39      25.169  39.585  10.983  1.00 38.33           C
ATOM    202  CB   LEU A   39      23.812  39.539  11.675  1.00 36.34           C
ATOM    203  CG   LEU A   39      22.842  38.552  11.042  1.00 37.89           C
ATOM    204  CD1  LEU A   39      21.602  38.351  11.873  1.00 38.23           C
ATOM    205  CD2  LEU A   39      22.483  38.792   9.542  1.00 37.73           C
ATOM    206  C    LEU A   39      25.902  40.824  11.395  1.00 40.33           C
ATOM    207  O    LEU A   39      26.716  40.780  12.324  1.00 40.11           O
ATOM    208  N    PRO A   40      25.615  41.952  10.727  1.00 41.55           N
ATOM    209  CA   PRO A   40      26.216          41.09 1.00  11.155  43.239   C
ATOM    210  CB   PRO A   40      26.130  44.132   9.890  1.00 40.23           C
ATOM    211  CG   PRO A   40      24.996  43.474   8.974  1.00 40.72           C
ATOM    212  CD   PRO A   40      24.666  42.104   9.597              40.91 1.00 C
ATOM    213  C    PRO A   40      25.419  43.830  12.353  1.00 41.26           C
ATOM    214  O    PRO A   40      24.152  43.595  12.566  1.00 43.02           O
ATOM    215  N    ASN A   41      26.159  44.527  13.187  1.00 40.27           N
ATOM    216  CA   ASN A   41      25.578  45.252  14.292  1.00 41.60           C
ATOM    217  CB   ASN A   41      24.755  46.423  13.738  1.00 43.44           C
ATOM    218  CG   ASN A   41      24.764  47.671  14.660  1.00 48.67           C
ATOM    219  OD1  ASN A   41      25.799  48.348  14.818  1.00 52.00           O
ATOM    220  ND2  ASN A   41      23.589  48.000  15.235  1.00 50.53           N
ATOM    221  C    ASN A   41      24.751  44.369  15.288  1.00 40.42           C
ATOM    222  O    ASN A   41      23.603          41.11 1.00  15.577  44.639   O
ATOM    223  N    CYS A   42      25.341  43.316  15.810  1.00 38.02           N
ATOM    224  CA   CYS A   42      24.658  42.549  16.827  1.00 37.95           C
ATOM    225  CB   CYS A   42      25.114  41.118  16.739              37.78 1.00 C
ATOM    226  SG   CYS A   42      24.327  40.365  15.308  1.00 43.83           S
ATOM    227  C    CYS A   42      24.969  43.138  18.172  1.00 36.52           C
ATOM    228  O    CYS A   42      26.124  43.367  18.467  1.00 37.85           O
ATOM    229  N    ASN A   43      23.950  43.438  18.971  1.00 35.14           N
ATOM    230  CA   ASN A   43      24.154  43.948  20.336  1.00 33.81           C
ATOM    231  CB   ASN A   43      23.731  45.419  20.461  1.00 34.41           C
ATOM    232  CG   ASN A   43      24.507  46.319  19.522  1.00 34.30           C
ATOM    233  OD1  ASN A   43      23.941  46.939  18.636  1.00 35.48           O
ATOM    234  ND2  ASN A   43      25.818  46.348  19.683  1.00 33.63           N
ATOM    235  C    ASN A   43              33.42 1.00  21.276  43.128  23.318   C
ATOM    236  O    ASN A   43      22.142  42.856  21.003  1.00 31.56           O
ATOM    237  N    LEU A   44      23.938  42.721  22.372  1.00 33.76           N
ATOM    238  CA   LEU A   44      23.228  42.044  23.445              34.03 1.00 C
ATOM    239  CB   LEU A   44      24.192  41.510  24.512  1.00 34.02           C
ATOM    240  CG   LEU A   44      24.999  40.309  23.965  1.00 36.01           C
ATOM    241  CD1  LEU A   44      26.328  40.156  24.781  1.00 35.88           C
ATOM    242  CD2  LEU A   44      24.173  38.985  23.794  1.00 31.36           C
ATOM    243  C    LEU A   44      22.261  43.035  24.045  1.00 33.85           C
ATOM    244  O    LEU A   44      22.566  44.197  24.175  1.00 32.52           O
ATOM    245  N    VAL A   45      21.070  42.559  24.348  1.00 34.08           N
ATOM    246  CA   VAL A   45      20.078  43.421  24.917  1.00 35.36           C
ATOM    247  CB   VAL A   45      18.642  42.852  24.648  1.00 35.04           C
ATOM    248  CG1  VAL A   45              33.42 1.00  25.305  43.709  17.654   C
ATOM    249  CG2  VAL A   45      18.360  42.765  23.119  1.00 34.45           C
ATOM    250  C    VAL A   45      20.330  43.686  26.429  1.00 36.38           C
```

Fig. 26 (Cont.)

```
ATOM    251  O    VAL A  45      20.172  42.801          36.59 1.00  27.287         O
ATOM    252  N    LYS A  46      20.674  44.927  26.752  1.00 37.39                 N
ATOM    253  CA   LYS A  46      20.825  45.345  28.138  1.00 38.09                 C
ATOM    254  CB   LYS A  46      21.018  46.851  28.165  1.00 39.12                 C
ATOM    255  CG   LYS A  46      21.747  47.447  29.352  1.00 43.04                 C
ATOM    256  CD   LYS A  46      22.744  48.499  28.768  1.00 50.53                 C
ATOM    257  CE   LYS A  46      22.939  48.297  27.195  1.00 48.21                 C
ATOM    258  NZ   LYS A  46      24.221  48.860  26.630  1.00 47.64                 N
ATOM    259  C    LYS A  46      19.596  44.982  28.976  1.00 38.22                 C
ATOM    260  O    LYS A  46      18.443  45.368  28.646  1.00 38.43                 O
ATOM    261  N    GLY A          38.07 1.00  30.069  44.257  19.855          47     N
ATOM    262  CA   GLY A  47      18.809  43.881  31.022  1.00 37.70                 C
ATOM    263  C    GLY A  47      18.242  42.474  30.886  1.00 38.75                 C
ATOM    264  O    GLY A  47      17.309  42          40.30 1.00  31.612  102.O
ATOM    265  N    ILE A  48      18.728  41.687  29.929  1.00 37.62                 N
ATOM    266  CA   ILE A  48      18.219  40.321  29.800  1.00 36.52                 C
ATOM    267  CB   ILE A  48      17.646  40.087  28.393  1.00 35.98                 C
ATOM    268  CG1  ILE A  48      16.552  41.132  28.118  1.00 35.58                 C
ATOM    269  CD1  ILE A  48      15.634  40.760  26.954  1.00 37.20                 C
ATOM    270  CG2  ILE A  48      17.184  38.602  28.196  1.00 33.42                 C
ATOM    271  C    ILE A  48      19.351  39.372  30.121  1.00 37.25                 C
ATOM    272  O    ILE A  48      20.344  39.294  29.352  1.00 36.71                 O
ATOM    273  N    ASP A  49      19.271  38.727  31.292  1.00 37.85                 N
ATOM    274  CA   ASP A  49      20.357  37.826  31.686  1.00 39.99                 C
ATOM    275  CB   ASP A  49      21.291  38.460  32.704  1.00 40.77                 C
ATOM    276  CG   ASP A  49      22.022  39.620  32.103  1.00 46.27                 C
ATOM    277  OD1  ASP A  49      23.055          49.10 1.00  31.385  39.404         O
ATOM    278  OD2  ASP A  49      21.560  40.778  32.208  1.00 51.18                 O
ATOM    279  C    ASP A  49      19.925  36.477  32.144  1.00 39.79                 C
ATOM    280  O    ASP A  49      20.786  35.639  32.392  1.00          40.81 O
ATOM    281  N    ASN A  50      18.609  36.278  32.227  1.00 39.81                 N
ATOM    282  CA   ASN A  50      18.017  35.073  32.811  1.00 39.57                 C
ATOM    283  CB   ASN A  50      17.421  35.415  34.179  1.00 40.04                 C
ATOM    284  CG   ASN A  50      18.508  35.538  35.244  1.00 46.75                 C
ATOM    285  OD1  ASN A  50      18.756  34.583  35.962  1.00 52.04                 O
ATOM    286  ND2  ASN A  50      19.226  36.674  35.279  1.00 45.67                 N
ATOM    287  C    ASN A  50      16.977  34.475  31.886  1.00 38.33                 C
ATOM    288  O    ASN A  50      15.993  33.866  32.335  1.00 37.99                 O
ATOM    289  N    GLY A  51      17.180  34.682  30.591  1.00 36.70                 N
ATOM    290  CA   GLY A  51      16.463          35.87 1.00  29.575  33.944         C
ATOM    291  C    GLY A  51      15.481  34.869  28.892  1.00 36.19                 C
ATOM    292  O    GLY A  51      15.095  35.926  29.455  1.00 34.76                 O
ATOM    293  N    SER A  52      15.054  34.415  27.722          33.57 1.00         N
ATOM    294  CA   SER A  52      14.182  35.161  26.838  1.00 35.00                 C
ATOM    295  CB   SER A  52      14.985  36.214  25.995  1.00 34.00                 C
ATOM    296  OG   SER A  52      16.239  35.693  25.541  1.00 33.23                 O
ATOM    297  C    SER A  52      13.563  34.106  25.945  1.00 35.67                 C
ATOM    298  O    SER A  52      13.634  34.219  24.720  1.00 34.71                 O
ATOM    299  N    GLU A  53      13.008  33.050  26.574  1.00 35.64                 N
ATOM    300  CA   GLU A  53      12.706  31.832  25.828  1.00 35.43                 C
ATOM    301  CB   GLU A  53      12.179  30.713  26.749  1.00 37.07                 C
ATOM    302  CG   GLU A  53      12.300  29.284  26.120  1.00 38.97                 C
ATOM    303  CD   GLU A  53      11          45.33 1.00  25.240  28.838  098.C
ATOM    304  OE1  GLU A  53      10.011  29.546  25.240  1.00 44.51                 O
ATOM    305  OE2  GLU A  53      11.216  27.751  24.546  1.00 42.02                 O
ATOM    306  C    GLU A  53      11.712  32.037  24.703          35.71 1.00         C
ATOM    307  O    GLU A  53      11.770  31.332  23.671  1.00 35.46                 O
ATOM    308  N    ASP A  54      10.720  32.905  24.899  1.00 35.35                 N
ATOM    309  CA   ASP A  54      9.783   33.136  23.808  1.00 35.51                 C
ATOM    310  CB   ASP A  54      8.442   32.431  24.001  1.00 34.20                 C
ATOM    311  CG   ASP A  54      7.738   32.171  22.652  1.00 38.43                 C
```

Fig. 26 (Cont.)

```
ATOM    312  OD1 ASP A  54       8.339  32.416  21.539  1.00 39.84           O
ATOM    313  OD2 ASP A  54       6.555  31.804  22.545  1.00 37.47           O
ATOM    314  C   ASP A  54       9.566  34.624  23.677  1.00 36.04           C
ATOM    315  O   ASP A  54       9.756  35.394  24.633  1.00 34.50           O
ATOM    316  N   LEU A  55          36.48 1.00  22.516  35.029   9.111       N
ATOM    317  CA  LEU A  55       8.847  36.447  22.352  1.00 38.06           C
ATOM    318  CB  LEU A  55      10.121  37.238  22.028  1.00 37.42           C
ATOM    319  CG  LEU A  55      10.993  36.817  20          39.53 1.00   889.C
ATOM    320  CD1 LEU A  55      10.636  37.664  19.628  1.00 38.52           C
ATOM    321  CD2 LEU A  55      12.423  37.147  21.329  1.00 40.87           C
ATOM    322  C   LEU A  55       7.852  36.562  21.227  1.00 38.25           C
ATOM    323  O   LEU A  55       7.719  35.646  20.440  1.00 38.70           O
ATOM    324  N   GLU A  56       7.143  37.679  21.170  1.00 38.51           N
ATOM    325  CA  GLU A  56       6.216  37.921  20.072  1.00 37.64           C
ATOM    326  CB  GLU A  56       4.788  37.391  20.415  1.00 39.63           C
ATOM    327  CG  GLU A  56       3.898  37.485  19.158  1.00 40.53           C
ATOM    328  CD  GLU A  56       2.759  36.533  19.208  1.00 41.85           C
ATOM    329  OE1 GLU A  56          46.69 1.00  18.887  36.927   1.636       O
ATOM    330  OE2 GLU A  56       2.991  35.371  19.544  1.00 43.01           O
ATOM    331  C   GLU A  56       6.182  39.432  19.857  1.00 37.78           C
ATOM    332  O   GLU A  56       6.102  40.226          37.75 1.00   20.810  O
ATOM    333  N   ILE A  57       6.275  39.831  18.596  1.00 37.29           N
ATOM    334  CA  ILE A  57       6.202  41.211  18.239  1.00 36.87           C
ATOM    335  CB  ILE A  57       7.282  41.469  17.163  1.00 36.67           C
ATOM    336  CG1 ILE A  57       8.634  40.949  17.677  1.00 35.29           C
ATOM    337  CD1 ILE A  57       9.887  41.067  16.616  1.00 33.23           C
ATOM    338  CG2 ILE A  57       7.283  42.981  16.834  1.00 35.45           C
ATOM    339  C   ILE A  57       4.804  41.576  17.701  1.00 37.83           C
ATOM    340  O   ILE A  57       4.299  40.870  16.822  1.00 38.53           O
ATOM    341  N   LEU A  58       4.150  42.619  18.230  1.00 36.71           N
ATOM    342  CA  LEU A  58          36.75 1.00  17.640  43.051   2.859       C
ATOM    343  CB  LEU A  58       2.186  44.041  18.563  1.00 35.11           C
ATOM    344  CG  LEU A  58       1.823  43.540  19.993  1.00 37.90           C
ATOM    345  CD1 LEU A  58       1.173  44.586          33.13 1.00   20.784  C
ATOM    346  CD2 LEU A  58       0.928  42.323  19.917  1.00 36.93           C
ATOM    347  C   LEU A  58       3.125  43.778  16.272  1.00 37.80           C
ATOM    348  O   LEU A  58       4.255  44.204  16.045  1.00 37          07.O
ATOM    349  N   PRO A  59       2.127  43.925  15.393  1.00 38.36           N
ATOM    350  CA  PRO A  59       2.228  44.863  14.230  1.00 38.96           C
ATOM    351  CB  PRO A  59       0.754  44.991  13.698  1.00 38.17           C
ATOM    352  CG  PRO A  59       0.096  43.630  14.082  1.00 39.12           C
ATOM    353  CD  PRO A  59       0.825  43.208  15.425  1.00 39.91           C
ATOM    354  C   PRO A  59       2.683  46.287  14.615  1.00 37.80           C
ATOM    355  O   PRO A         38.08 1.00  13.814  46.853   3.334         59 O
ATOM    356  N   ASN A  60       2.359  46.856  15.768  1.00 36.68           N
ATOM    357  CA  ASN A  60       2.843  48.213  16.039  1.00 35.74           C
ATOM    358  CB  ASN A  60       1.953  48.972          35.95 1.00   17.080  C
ATOM    359  CG  ASN A  60       1.945  48.265  18.481  1.00 39.11           C
ATOM    360  OD1 ASN A  60       2.713  47.314  18.702  1.00 32.54           O
ATOM    361  ND2 ASN A  60       1.044  48.688  19.388  1.00         37.73  N
ATOM    362  C   ASN A  60       4.302  48.223  16.481  1.00 35.51           C
ATOM    363  O   ASN A  60       4.805  49.266  16.806  1.00 35.95           O
ATOM    364  N   GLY A  61       4.978  47.065  16.532  1.00 35.97           N
ATOM    365  CA  GLY A  61       6.375  47.046  16.931  1.00 35.62           C
ATOM    366  C   GLY A  61       6.688  46.830  18.420  1.00 34.98           C
ATOM    367  O   GLY A  61       7.863  46.742  18.804  1.00 32.71           O
ATOM    368  N   LEU A  62       5.660  46.745  19.258  1.00 34.79           N
ATOM    369  CA  LEU A  62       5.855  46.329  20.680  1.00 35.23           C
ATOM    370  CB  LEU A  62       4.614  46.660  21.561  1.00 34.59           C
ATOM    371  CG  LEU A  62       4.222          35.76 1.00   21.709  48.143  C
ATOM    372  CD1 LEU A  62       3.048  48.340  22.655  1.00 32.43           C
```

Fig. 26 (Cont.)

```
ATOM    373  CD2  LEU A  62      5.414  48.997  22.156  1.00 34.98           C
ATOM    374  C    LEU A  62      6.198  44.819  20.748  1             34.64 00.C
ATOM    375  O    LEU A  62      5.500  43.977  20.163  1.00 36.80           O
ATOM    376  N    ALA A  63      7.268  44.477  21.440  1.00 34.10           N
ATOM    377  CA   ALA A  63      7.649  43.073  21.611  1.00 34.95           C
ATOM    378  CB   ALA A  63      9.139  42.825  21.132  1.00 33.37           C
ATOM    379  C    ALA A  63      7.504  42.633  23.075  1.00 34.16           C
ATOM    380  O    ALA A  63      7.988  43.312  23.966  1.00 34.79           O
ATOM    381  N    PHE A  64      6.905  41.466  23.283  1.00 34.36           N
ATOM    382  CA   PHE A  64      6.760  40.875  24.618  1.00 36.24           C
ATOM    383  CB   PHE A  64      5.388  40.221  24.754  1.00 36.32           C
ATOM    384  CG   PHE A  64      4            40.80 1.00  24.804  41.207  250.C
ATOM    385  CD1  PHE A  64      3.918  41.849  26.013  1.00 37.80           C
ATOM    386  CE1  PHE A  64      2.870  42.746  26.068  1.00 40.81           C
ATOM    387  CZ   PHE A  64      2.096  43.011  24.953             41.28 1.00 C
ATOM    388  CE2  PHE A  64      2.403  42.401  23.741  1.00 45.84           C
ATOM    389  CD2  PHE A  64      3.490  41.489  23.661  1.00 42.25           C
ATOM    390  C    PHE A  64      7.771  39.765  24.680  1.00 34.84           C
ATOM    391  O    PHE A  64      7.933  39.076  23.675  1.00 34.61           O
ATOM    392  N    ILE A  65      8.418  39.590  25.824  1.00 33.62           N
ATOM    393  CA   ILE A  65      9.404  38.527  25.999  1.00 34.39           C
ATOM    394  CB   ILE A  65     10.801  39.185  26.008  1.00 34.90           C
ATOM    395  CG1  ILE A  65     11.041  40.043  24.742  1.00 34.12           C
ATOM    396  CD1  ILE A  65     12.195  40.924  24.927  1.00 32.55           C
ATOM    397  CG2  ILE A  65            33.43 1.00  26.281  38.185  11.943    C
ATOM    398  C    ILE A  65      9.182  37.813  27.328  1.00 35.34           C
ATOM    399  O    ILE A  65      9.141  38.473  28.358  1.00 36.38           O
ATOM    400  N    SER A  66      9.082  36.487  27            35.61 1.00  360.N
ATOM    401  CA   SER A  66      9.017  35.834  28.656  1.00 35.06           C
ATOM    402  CB   SER A  66      8.269  34.513  28.574  1.00 36.04           C
ATOM    403  OG   SER A  66      8.952  33.709  27.691  1.00 39.18           O
ATOM    404  C    SER A  66     10.454  35.577  29.102  1.00 35.97           C
ATOM    405  O    SER A  66     11.314  35.316  28.285  1.00 36.45           O
ATOM    406  N    SER A  67     10.707  35.628  30.393  1.00 34.80           N
ATOM    407  CA   SER A  67     12.005  35.473  30.879  1.00 36.50           C
ATOM    408  CB   SER A  67     12.720  36.855  30.910  1.00 37.35           C
ATOM    409  OG   SER A  67     12.223  37.624  31.976  1.00 43.15           O
ATOM    410  C    SER A  67            36.01 1.00  32.244  34.858  12.003    C
ATOM    411  O    SER A  67     11.022  34.893  32.963  1.00 34.71           O
ATOM    412  N    GLY A  68     13.171  34.367  32.635  1.00 37.65           N
ATOM    413  CA   GLY A  68     13.355  33.873          39.88 1.00  33.994   C
ATOM    414  C    GLY A  68     12.804  32.476  34.132  1.00 41.21           C
ATOM    415  O    GLY A  68     12.499  32.057  35.242  1.00 42.04           O
ATOM    416  N    LEU A  69     12.675  31.757  33.019  1.00 41.72           N
ATOM    417  CA   LEU A  69     12.261  30.354  33.090  1.00 43.42           C
ATOM    418  CB   LEU A  69     12.095  29.752  31.676  1.00 42.75           C
ATOM    419  CG   LEU A  69     11.608  28.292  31.565  1.00 43.34           C
ATOM    420  CD1  LEU A  69     10.100  28.023  32.027  1.00 39.91           C
ATOM    421  CD2  LEU A  69     11.797  27.853  30.124  1.00 44.52           C
ATOM    422  C    LEU A  69     13.168  29.453  33.983  1.00 44.35           C
ATOM    423  O    LEU A  69            42.92 1.00  33.835  29.458  14.378    O
ATOM    424  N    LYS A  70     12.548  28.699  34.903  1.00 46.34           N
ATOM    425  CA   LYS A  70     13.185  27.551  35.560  1.00 50.33           C
ATOM    426  CB   LYS A  70     13.116  27.648           50.44 1.00  37.065  C
ATOM    427  CG   LYS A  70     13.855  28.824  37.621  1.00 54.87           C
ATOM    428  CD   LYS A  70     12.902  29.721  38.380  1.00 58.02           C
ATOM    429  CE   LYS A  70     13.486  31.127  38.524  1.00 59          44.C
ATOM    430  NZ   LYS A  70     13.821  31.200  40.002  1.00 59.29           N
ATOM    431  C    LYS A  70     12.544  26.186  35.160  1.00 52.65           C
ATOM    432  O    LYS A  70     11.271  25.977  35.139  1.00 50.49           O
ATOM    433  N    TYR A  71     13.474  25.271  34.853  1.00 55.39           N
```

Fig. 26 (Cont.)

```
ATOM    434  CA  TYR A  71      13.231  23.850  34.517  1.00 56.92           C
ATOM    435  CB  TYR A  71      14.572  23.221  33.982  1.00 57.50           C
ATOM    436  CG  TYR A              62.72 1.00  35.019  23.255  15.787    71 C
ATOM    437  CD1 TYR A  71      15.758  22.444  36.212  1.00 63.02           C
ATOM    438  CE1 TYR A  71      16.817  22.438  37.172  1.00 64.48           C
ATOM    439  CZ  TYR A  71      17.941  23            65.14 1.00  36.946 237.C
ATOM    440  OH  TYR A  71      18.939  23.189  37.896  1.00 63.37           O
ATOM    441  CE2 TYR A  71      18.037  24.058  35.763  1.00 66.39           C
ATOM    442  CD2 TYR A  71      16.949  24.071  34.799  1.00          63.42  C
ATOM    443  C   TYR A  71      12.678  23.089  35.770  1.00 56.66           C
ATOM    444  O   TYR A  71      13.145  23.288  36.912  1.00 55.16           O
ATOM    445  N   ASP A  80      18.307  36.478  43.053  1.00 61.40           N
ATOM    446  CA  ASP A  80      16.901  36.225  43.410  1.00 61.37           C
ATOM    447  CB  ASP A  80      16.585  36.896  44.761  1.00 61.28           C
ATOM    448  CG  ASP A  80      16.126  35.905  45.824  1.00 61.41           C
ATOM    449  OD1 ASP A  80      15.259  35.041  45.520  1.00 60.57           O
ATOM    450  OD2 ASP A  80      16.585  35.923  46.997  1.00 61.17           O
ATOM    451  C   ASP A  80      15.922  36.752  42.318  1.00 61.48           C
ATOM    452  O   ASP A  80      15.137          62.12 1.00  42.612  37.685   O
ATOM    453  N   LYS A  81      15.958  36.149  41.104  1.00 60.17           N
ATOM    454  CA  LYS A  81      15.363  36.718  39.862  1.00 58.70           C
ATOM    455  CB  LYS A  81      16.446  36.970  38.762    1           59.06 00.C
ATOM    456  CG  LYS A  81      17.757  36.072  38.847  1.00 59.89           C
ATOM    457  CD  LYS A  81      18.909  36.731  39.652  1.00 60.76           C
ATOM    458  CE  LYS A  81      20.358  36.331  39.176  1.00 62.31           C
ATOM    459  NZ  LYS A  81      20.816  36.999  37.853  1.00 60.80           N
ATOM    460  C   LYS A  81      14.128  35.961  39.290  1.00 57.17           C
ATOM    461  O   LYS A  81      14.238  34.884  38.647  1.00 57.87           O
ATOM    462  N   SER A  82      12.952  36.550  39.515  1.00 53.97           N
ATOM    463  CA  SER A  82      11.666  35.948  39.189  1.00 50.30           C
ATOM    464  CB  SER A  82      10.556  36.847  39.696  1.00 50.65           C
ATOM    465  OG  SER A  82      11.098          50.79 1.00  40.648  37.688   O
ATOM    466  C   SER A  82      11.379  35.704  37.709  1.00 47.88           C
ATOM    467  O   SER A  82      12.064  36.240  36.791  1.00 48.19           O
ATOM    468  N   GLY A  83      10.337  34.911  37.483          43.71 1.00   N
ATOM    469  CA  GLY A  83       9.741  34.859  36.173  1.00 41.45           C
ATOM    470  C   GLY A  83       9.145  36.249  35.929  1.00 39.73           C
ATOM    471  O   GLY A  83       8.571  36.865  36.851  1.00 37.58           O
ATOM    472  N   LYS A  84       9.319  36.766  34.713  1.00 37.76           N
ATOM    473  CA  LYS A  84       8.663  38.032  34.361  1.00 38.30           C
ATOM    474  CB  LYS A  84       9.403  39.263  34.923  1.00 38.98           C
ATOM    475  CG  LYS A  84      10.816  39.346  34.462  1.00 43.83           C
ATOM    476  CD  LYS A  84      11.676  40.343  35.257  1.00 44.31           C
ATOM    477  CE  LYS A  84      12.094  39.737  36.543  1.00 47.82           C
ATOM    478  NZ  LYS A  84      12.868          44.76 1.00  37.350  40.741   N
ATOM    479  C   LYS A  84       8.381  38.151  32.887  1.00 36.25           C
ATOM    480  O   LYS A  84       8.951  37.419  32.046  1.00 36.85           O
ATOM    481  N   ILE A  85       7.470  39.043  32.551          34.76 1.00   N
ATOM    482  CA  ILE A  85       7.275  39.383  31.144  1.00 33.39           C
ATOM    483  CB  ILE A  85       5.776  39.380  30.792  1.00 34.18           C
ATOM    484  CG1 ILE A  85       5.109  38.057  31.198  1.00 33.29           C
ATOM    485  CD1 ILE A  85       5.647  36.842  30.355  1.00 33.85           C
ATOM    486  CG2 ILE A  85       5.551  39.682  29.266  1.00 35.20           C
ATOM    487  C   ILE A  85       7.870  40.762  30.930  1.00 34.48           C
ATOM    488  O   ILE A  85       7.579  41.710  31.704  1.00 31.41           O
ATOM    489  N   LEU A  86       8.659  40.894  29.852  1.00 34.14           N
ATOM    490  CA  LEU A  86       9.365  42.137  29.528  1.00 34.32           C
ATOM    491  CB  LEU A  86              31.55 1.00  29.272  41.893  10.888   C
ATOM    492  CG  LEU A  86      11.654  41.074  30.313  1.00 36.32           C
ATOM    493  CD1 LEU A  86      13.089  40.767  29.832  1.00 36.82           C
ATOM    494  CD2 LEU A  86      11.763  41.825  31.640          32.85 1.00   C
```

Fig. 26 (Cont.)

```
ATOM    495  C   LEU A  86       8.767  42.704  28.263  1.00 34.55           C
ATOM    496  O   LEU A  86       8.267  41.954  27.446  1.00 35.10           O
ATOM    497  N   LEU A  87       8.904  44.018  28.074  1.00 34.40           N
ATOM    498  CA  LEU A  87       8.363  44.725  26.941  1.00 34.92           C
ATOM    499  CB  LEU A  87       7.368  45.771  27.387  1.00 35.47           C
ATOM    500  CG  LEU A  87       6.651  46.493  26.212  1.00 37.95           C
ATOM    501  CD1 LEU A  87       5.700  45.533  25.418  1.00 35.22           C
ATOM    502  CD2 LEU A  87       5.904  47.714  26.703  1.00 35.05           C
ATOM    503  C   LEU A  87       9.497  45.510  26.285  1.00 36.38           C
ATOM    504  O   LEU A  87      34.97 1.00   26.963  46.213  10.236          O
ATOM    505  N   MET A  88       9.590  45.435  24.961  1.00 36.52           N
ATOM    506  CA  MET A  88      10.509  46.309  24.256  1.00 37.56           C
ATOM    507  CB  MET A  88      11.605  45.464          38.06 1.00   23.590  C
ATOM    508  CG  MET A  88      12.809  45.157  24.447  1.00 39.38           C
ATOM    509  SD  MET A  88      13.930  43.972  23.523  1.00 41.13           S
ATOM    510  CE  MET A  88      14.926  45.064  22.630  1.00 36.63           C
ATOM    511  C   MET A  88       9.756  47.012  23.138  1.00 37.44           C
ATOM    512  O   MET A  88       9.019  46.353  22.398  1.00 37.94           O
ATOM    513  N   ASP A  89      10.004  48.296  22.948  1.00 36.32           N
ATOM    514  CA  ASP A  89       9.399  49.026  21.858  1.00 36.83           C
ATOM    515  CB  ASP A  89       9.003  50.446  22.317  1.00 36.38           C
ATOM    516  CG  ASP A  89       8.252  51.233  21.250  1.00 37.11           C
ATOM    517  OD1 ASP A          38.37 1.00   20.061  50.850   8.246       89 O
ATOM    518  OD2 ASP A  89       7.648  52.288  21.498  1.00 42.32           O
ATOM    519  C   ASP A  89      10.426  49.098  20.711  1.00 36.70           C
ATOM    520  O   ASP A  89      11.375  49              38.05 1.00   20.748  893.O
ATOM    521  N   LEU A  90      10.242  48.265  19.699  1.00 36.35           N
ATOM    522  CA  LEU A  90      11.235  48.095  18.656  1.00 35.31           C
ATOM    523  CB  LEU A  90      11.073  46.752  17.990  1.00 35.46           C
ATOM    524  CG  LEU A  90      11.240  45.448  18.800  1.00 34.32           C
ATOM    525  CD1 LEU A  90      11.135  44.146  17.906  1.00 29.82           C
ATOM    526  CD2 LEU A  90      12.541  45.451  19.618  1.00 31.59           C
ATOM    527  C   LEU A  90      11.174  49.231  17.615  1.00 36.97           C
ATOM    528  O   LEU A  90      11.994  49.238  16.699  1.00 36.95           O
ATOM    529  N   ASN A  91      10.258  50.212  17.773  1.00 36.99           N
ATOM    530  CA  ASN A  91      10.333  51.459  17.005  1.00 38.70           C
ATOM    531  CB  ASN A  91       8.987  52.186  16.890  1.00 37.08           C
ATOM    532  CG  ASN A  91       7.916  51.322  16.298  1.00 38.78           C
ATOM    533  OD1 ASN A  91       6.978          39.74 1.00   17.008  50.924  O
ATOM    534  ND2 ASN A  91       8.060  50.954  15.013  1.00 34.37           N
ATOM    535  C   ASN A  91      11.388  52.423  17.569  1.00 40.81           C
ATOM    536  O   ASN A  91      11.781  53.378  16.894  1.00           40.02 O
ATOM    537  N   GLU A  92      11.859  52.199  18.800  1.00 42.98           N
ATOM    538  CA  GLU A  92      12.922  53.088  19.332  1.00 45.52           C
ATOM    539  CB  GLU A  92      13.034  52.914  20.840  1.00 45.36           C
ATOM    540  CG  GLU A  92      12.057  53.735  21.651  1.00 47.03           C
ATOM    541  CD  GLU A  92      11.814  53.097  23.003  1.00 51.90           C
ATOM    542  OE1 GLU A  92      12.789  52.577  23.621  1.00 52.73           O
ATOM    543  OE2 GLU A  92      10.633  53.070  23.447  1.00 55.53           O
ATOM    544  C   GLU A  92      14.277  52.773  18.698  1.00 46.51           C
ATOM    545  O   GLU A  92      14.544  51.615  18.368  1.00 48.06           O
ATOM    546  N   LYS A  93      15.172          48.20 1.00   18.553  53.742  N
ATOM    547  CA  LYS A  93      16.441  53.371  17.912  1.00 49.26           C
ATOM    548  CB  LYS A  93      17.171  54.573  17.269  1.00 49.99           C
ATOM    549  CG  LYS A  93      17.036  54.545  15.688          53.08 1.00   C
ATOM    550  CD  LYS A  93      17.908  55.603  14.957  1.00 55.59           C
ATOM    551  CE  LYS A  93      17.305  56.034  13.593  1.00 55.06           C
ATOM    552  NZ  LYS A  93      17.400  57.532  13.438  1.00 53.03           N
ATOM    553  C   LYS A  93      17.347  52.442  18.770  1.00 49.26           C
ATOM    554  O   LYS A  93      18.015  51.541  18.212  1.00 49.65           O
ATOM    555  N   GLU A  94      17.334  52.635  20.102  1.00 48.09           N
```

Fig. 26 (Cont.)

```
ATOM   556  CA   GLU A  94      18.024  51.739  21.054  1.00 47.70           C
ATOM   557  CB   GLU A  94      18.977  52.515  22.010  1.00 48.56           C
ATOM   558  CG   GLU A  94      19.995  53.500  21.411  1.00 53.12           C
ATOM   559  CD   GLU A  94      21         55.54 1.00  20.772  52.775  180.C
ATOM   560  OE1  GLU A  94      21.039  51.547  20.432  1.00 56.98           O
ATOM   561  OE2  GLU A  94      22.231  53.423  20.615  1.00 53.13           O
ATOM   562  C    GLU A  94      16.944  51.159  21.966         46.61 1.00   C
ATOM   563  O    GLU A  94      16.755  51.675  23.049  1.00 45.78           O
ATOM   564  N    PRO A  95      16.203  50.130  21.569  1.00 46.18           N
ATOM   565  CA   PRO A  95      15.087  49.669  22.429  1.00 45.54           C
ATOM   566  CB   PRO A  95      14.494  48.502  21.655  1.00 44.41           C
ATOM   567  CG   PRO A  95      14.958  48.739  20.271  1.00 46.28           C
ATOM   568  CD   PRO A  95      16.310  49.365  20.320  1.00 45.75           C
ATOM   569  C    PRO A  95      15.596  49.268  23.822  1.00 44.46           C
ATOM   570  O    PRO A  95      16.649  48.659  23.944  1.00 45.48           O
ATOM   571  N    ALA A  96      14.893  49.692  24.849  1.00 43.04           N
ATOM   572  CA   ALA A  96              42.57 1.00  26.225  49.361  15.257   C
ATOM   573  CB   ALA A  96      15.317  50.636  27.049  1.00 41.63           C
ATOM   574  C    ALA A  96      14.164  48.430  26.741  1.00 41.25           C
ATOM   575  O    ALA A  96      13.002  48.591  26              41.30 1.00  371.O
ATOM   576  N    VAL A  97      14.519  47.449  27.556  1.00 40.24           N
ATOM   577  CA   VAL A  97      13.511  46.538  28.067  1.00 39.62           C
ATOM   578  CB   VAL A  97      14.086  45.179  28.435  1.00 39.87           C
ATOM   579  CG1  VAL A  97      14.722  44.539  27.229  1.00 41.61           C
ATOM   580  CG2  VAL A  97      15.089  45.338  29.493  1.00 41.75           C
ATOM   581  C    VAL A  97      12.857  47.091  29.304  1.00 39.47           C
ATOM   582  O    VAL A  97      13.489  47.774  30.120  1.00 38.78           O
ATOM   583  N    SER A  98      11.583  46.823  29.488  1.00 38.59           N
ATOM   584  CA   SER A  98      11.051  47.140  30.819  1.00 37.98           C
ATOM   585  CB   SER A  98              37.84 1.00  30.819  48.475  10.300   C
ATOM   586  OG   SER A  98       9.140  48.356  30.039  1.00 42.34           O
ATOM   587  C    SER A  98      10.242  45.955  31.314  1.00 36.68           C
ATOM   588  O    SER A  98       9.771  45.174          35.99 1.00  30.494   O
ATOM   589  N    GLU A  99      10.179  45.767  32.636  1.00 35.80           N
ATOM   590  CA   GLU A  99       9.385  44.710  33.254  1.00 35.35           C
ATOM   591  CB   GLU A  99       9.800  44.496  34.735  1.00 35.59           C
ATOM   592  CG   GLU A  99       9.269  43.146  35.231  1.00 38.52           C
ATOM   593  CD   GLU A  99       9.454  42.876  36.732  1.00 43.63           C
ATOM   594  OE1  GLU A  99      10.300  43.500  37.367  1.00 46.24           O
ATOM   595  OE2  GLU A  99       8.735  42.042  37.302  1.00 46.36           O
ATOM   596  C    GLU A  99       7.924  45.124  33.255  1.00 34.86           C
ATOM   597  O    GLU A  99       7.578  46.185  33.822  1.00 33.31           O
ATOM   598  N    LEU A 100              33.58 1.00  32.709  44.292   7.045   N
ATOM   599  CA   LEU A 100       5.611  44.619  32.837  1.00 34.16           C
ATOM   600  CB   LEU A 100       4.763  43.911  31.767  1.00 32.59           C
ATOM   601  CG   LEU A 100       5.104  44.269          33.96 1.00  30.309   C
ATOM   602  CD1  LEU A 100       4.385  43.372  29.407  1.00 29.48           C
ATOM   603  CD2  LEU A 100       4.620  45.708  30.079  1.00 33.80           C
ATOM   604  C    LEU A 100       5.105  44.240  34.265  1.00 35        52.C
ATOM   605  O    LEU A 100       5.256  43.093  34.669  1.00 36.14           O
ATOM   606  N    GLU A 101       4.466  45.161  34.984  1.00 34.84           N
ATOM   607  CA   GLU A 101       3.809  44.797  36.243  1.00 36.35           C
ATOM   608  CB   GLU A 101       3.471  46.073  37.052  1.00 35.16           C
ATOM   609  CG   GLU A 101       3.032  45.771  38.478  1.00 41.64           C
ATOM   610  CD   GLU A 101       2.559  47.010  39.230  1.00 47.12           C
ATOM   611  OE1  GLU A         50.39 1.00  38.685  48.131   2.717     101 O
ATOM   612  OE2  GLU A 101       2.041  46.873  40.367  1.00 51.14           O
ATOM   613  C    GLU A 101       2.541  43.930  36.030  1.00 35.47           C
ATOM   614  O    GLU A 101       1.670  44.261          34.90 1.00  35.236   O
ATOM   615  N    ILE A 102       2.443  42.811  36.737  1.00 35.99           N
ATOM   616  CA   ILE A 102       1.204  42.026  36.755  1.00 35.51           C
```

Fig. 26 (Cont.)

```
ATOM   617  CB   ILE A 102    1.494  40.550  36.985  1.00         36.81 C
ATOM   618  CG1  ILE A 102    2.274  39.987  35.794  1.00 35.62         C
ATOM   619  CD1  ILE A 102    2.932  38.588  36.126  1.00 36.89         C
ATOM   620  CG2  ILE A 102    0.198  39.760  37.102  1.00 36.67         C
ATOM   621  C    ILE A 102    0.245  42.540  37.810  1.00 34.21         C
ATOM   622  O    ILE A 102    0.591  42.588  38.962  1.00 33.87         O
ATOM   623  N    ILE A 103   -0.939  42.971  37.395  1.00 33.27         N
ATOM   624  CA   ILE A 103   -1.981  43.283  38.322  1.00 35.10         C
ATOM   625  CB   ILE A 103   -2.473  44.781  38.177  1.00 37.45         C
ATOM   626  CG1  ILE A 103   -3.243  45.008  36.877  1.00 38.74         C
ATOM   627  CD1  ILE A 103   -4.187          41.50  1.00  37.058  46.265 C
ATOM   628  CG2  ILE A 103   -1.258  45.844  38.300  1.00 38.02         C
ATOM   629  C    ILE A 103   -3.118  42.249  38.305  1.00 33.06         C
ATOM   630  O    ILE A 103   -3.347  41.579  37.305  1            33.10 00.O
ATOM   631  N    GLY A 104   -3.773  42.110  39.435  1.00 31.11         N
ATOM   632  CA   GLY A 104   -4.912  41.232  39.614  1.00 29.92         C
ATOM   633  C    GLY A 104   -4.726  40.492  40.918  1.00 29.68         C
ATOM   634  O    GLY A 104   -3.598  40.379  41.383  1.00 31.45         O
ATOM   635  N    ASN A 105   -5.794  39.977  41.518  1.00 27.53         N
ATOM   636  CA   ASN A 105   -5.672  39.158  42.701  1.00 25.31         C
ATOM   637  CB   ASN A 105   -6.582  39.710  43.760  1.00 24.19         C
ATOM   638  CG   ASN A 105   -6.006  40.960  44.403  1.00 26.19         C
ATOM   639  OD1  ASN A 105   -4.840  40.992  44.785  1.00 22.38         O
ATOM   640  ND2  ASN A 105   -6             22.10  1.00  44.557  41.984  839.N
ATOM   641  C    ASN A 105   -5.995  37.679  42.437  1.00 25.35         C
ATOM   642  O    ASN A 105   -6.157  36.899  43.383  1.00 24.92         O
ATOM   643  N    THR A 106   -6.104  37.307  41.170        25.36 1.00    N
ATOM   644  CA   THR A 106   -6.445  35.957  40.796  1.00 27.53         C
ATOM   645  CB   THR A 106   -7.398  36.003  39.573  1.00 27.47         C
ATOM   646  OG1  THR A 106   -6.928  36.994  38.653  1.00 26.93         O
ATOM   647  CG2  THR A 106   -8.830  36.427  39.951  1.00 25.61         C
ATOM   648  C    THR A 106   -5.190  35.072  40.416  1.00 29.67         C
ATOM   649  O    THR A 106   -5.342  33.909  40.000  1.00 31.09         O
ATOM   650  N    LEU A 107   -3.986  35.627  40.493  1.00 29.57         N
ATOM   651  CA   LEU A 107   -2.759  34.939  40.091  1.00 29.85         C
ATOM   652  CB   LEU A 107   -2.123  35.618  38.873  1.00 29.27         C
ATOM   653  CG   LEU A 107          32.79  1.00  38.388  34.954  0.801-  C
ATOM   654  CD1  LEU A 107   -0.996  33.439  38.041  1.00 32.49         C
ATOM   655  CD2  LEU A 107   -0.180  35.617  37.168  1.00 30.28         C
ATOM   656  C    LEU A 107   -1.756  35.016  41            30.88 1.00  258.C
ATOM   657  O    LEU A 107   -1.577  36.085  41.883  1.00 29.93         O
ATOM   658  N    ASP A 108   -1.105  33.903  41.575  1.00 32.69         N
ATOM   659  CA   ASP A 108    0.000  33.964  42.540  1.00 35.00         C
ATOM   660  CB   ASP A 108    0.160  32.578  43.184  1.00 35.45         C
ATOM   661  CG   ASP A 108    1.187  32.564  44.326  1.00 39.16         C
ATOM   662  OD1  ASP A 108    1.993  33.509  44.543  1.00 38.47         O
ATOM   663  OD2  ASP A 108    1.207  31.616  45.125  1.00 51.01         O
ATOM   664  C    ASP A 108    1.271  34.310  41.781  1.00 34.30         C
ATOM   665  O    ASP A 108    1.733  33.450  41.066  1.00 35.43         O
ATOM   666  N    ILE A 109          35.53  1.00  41.855  35.518  1.794   N
ATOM   667  CA   ILE A 109    2.987  35.867  41.049  1.00 40.59         C
ATOM   668  CB   ILE A 109    3.156  37.427  40.806  1.00 42.05         C
ATOM   669  CG1  ILE A 109    3.508  38.123         45.49 1.00  42.125   C
ATOM   670  CD1  ILE A 109    4.475  39.370  42.008  1.00 55.33         C
ATOM   671  CG2  ILE A 109    1.849  38.056  40.334  1.00 45.95         C
ATOM   672  C    ILE A 109    4.287  35.366  41.664  1.00 41.10         C
ATOM   673  O    ILE A 109    5.344  35.468  41.040  1.00 41.85         O
ATOM   674  N    SER A 110    4.253  34.883  42.900  1.00 41.63         N
ATOM   675  CA   SER A 110    5.517  34.477  43.539  1.00 42.28         C
ATOM   676  CB   SER A 110    5.398  34.373  45.081  1.00 42.13         C
ATOM   677  OG   SER A 110    4.611  33.254  45.465  1.00 39.85         O
```

Fig. 26 (Cont.)

```
ATOM    678   C     SER A 110      6.032   33.193   42.889  1.00 42.80           C
ATOM    679   O     SER A 110            44.07 1.00   42.888   32.928   7.204           O
ATOM    680   N     SER A 111      5.165   32.413   42.279  1.00 42.32           N
ATOM    681   CA    SER A 111      5.658   31.211   41.634  1.00 42.01           C
ATOM    682   CB    SER A 111      4.884   30.001            41.91 1.00   42.180  C
ATOM    683   OG    SER A 111      3.550   30.015   41.716  1.00 44.76           O
ATOM    684   C     SER A 111      5.640   31.308   40.067  1.00 40.11           C
ATOM    685   O     SER A 111      5.813   30.303   39.371  1.00 40         26.O
ATOM    686   N     PHE A 112      5.430   32.516   39.548  1.00 37.47           N
ATOM    687   CA    PHE A 112      5.245   32.736   38.132  1.00 34.77           C
ATOM    688   CB    PHE A 112      4.997   34.212   37.915  1.00 35.24           C
ATOM   689    CG    PHE A 112      4.615   34.572   36.513  1.00 34.60           C
ATOM    690   CD1   PHE A 112      3.485   34.038   35.931  1.00 31.92           C
ATOM    691   CE1   PHE A 112      3.098   34.417   34.601  1.00 34.37           C
ATOM    692   CZ    PHE A        32.93 1.00   33.882   35.302   3.891        112 C
ATOM    693   CE2   PHE A 112      5.075   35.822   34.475  1.00 33.02           C
ATOM    694   CD2   PHE A 112      5.420   35.470   35.761  1.00 33.43           C
ATOM    695   C     PHE A 112      6.528   32             34.09 1.00   37.408    313.C
ATOM    696   O     PHE A 112      7.619   32.686   37.792  1.00 30.41           O
ATOM    697   N     ASN A 113      6.373   31.511   36.363  1.00 33.35           N
ATOM    698   CA    ASN A 113      7.516   30.836   35.764  1.00           34.63 C
ATOM    699   CB    ASN A 113      7.730   29.496   36.479  1.00 35.10           C
ATOM    700   CG    ASN A 113      8.949   28.763   35.962  1.00 38.00           C
ATOM    701   OD1   ASN A 113      9.798   29.376   35.370  1.00 38.18           O
ATOM    702   ND2   ASN A 113      9.005   27.442   36.136  1.00 33.49           N
ATOM    703   C     ASN A 113      7.210   30.667   34.276  1.00 34.12           C
ATOM    704   O     ASN A 113      6.783   29.596   33.848  1.00 34.15           O
ATOM    705   N     PRO A 114      7.361   31.746   33.500  1.00 33.35           N
ATOM    706   CA    PRO A 114      6.732   31.838   32.176  1.00 32.35           C
ATOM    707   CB    PRO A 114      6.665   33.373   31.891  1.00 32.32           C
ATOM    708   CG    PRO A 114      7.886            32.10 1.00   32.765   34.012 C
ATOM    709   CD    PRO A 114      8.142   32.947   33.880  1.00 33.30           C
ATOM    710   C     PRO A 114      7.559   31.116   31.100  1.00 34.37           C
ATOM    711   O     PRO A 114      8.777   31.113   31.218  1              32.77 00.O
ATOM    712   N     HIS A 115      6.904   30.579   30.047  1.00 34.79           N
ATOM    713   CA    HIS A 115      7.549   29.748   29.008  1.00 34.40           C
ATOM    714   CB    HIS A 115      7.149   28.295   29.238  1.00 35.35           C
ATOM    715   CG    HIS A 115      7.972   27.265   28.505  1.00 40.54           C
ATOM    716   ND1   HIS A 115      7.815   25.902   28.738  1.00 42.20           N
ATOM    717   CE1   HIS A 115      8.669   25.224   27.965  1.00 44.64           C
ATOM    718   NE2   HIS A 115      9.357   26.091   27.224  1.00 42.76           N
ATOM    719   CD2   HIS A 115      8.936   27.377   27.531  1.00 41.10           C
ATOM    720   C     HIS A 115      7.066   30.282   27.647  1.00 34.52           C
ATOM    721   O     HIS A 115      7.312            34.15 1.00   27.336   31.458 O
ATOM    722   N     GLY A 116      6.360   29.499   26.833  1.00 35.08           N
ATOM    723   CA    GLY A 116      5.865   30.040   25.553  1.00 33.52           C
ATOM    724   C     GLY A 116      4.837   31.139   25.778            35.02 1.00 C
ATOM    725   O     GLY A 116      4.156   31.180   26.832  1.00 37.19           O
ATOM    726   N     ILE A 117      4.615   31.976   24.781  1.00 35.16           N
ATOM    727   CA    ILE A 117      3.609   33.004   24.917  1.00 35.66           C
ATOM    728   CB    ILE A 117      4.214   34.357   25.336  1.00 36.17           C
ATOM    729   CG1   ILE A 117      5.133   34.943   24.221  1.00 33.06           C
ATOM    730   CD1   ILE A 117      5.677   36.352   24.525  1.00 32.42           C
ATOM    731   CG2   ILE A 117      4.831   34.301   26.770  1.00 34.66           C
ATOM    732   C     ILE A 117      2.955   33.164   23.546  1.00 36.61           C
ATOM    733   O     ILE A 117      3.458   32.691   22.566  1.00 35.89           O
ATOM    734   N     SER A 118            37.76 1.00   23.497   33.876   1.844    N
ATOM    735   CA    SER A 118      1.196   34.218   22.213  1.00 37.42           C
ATOM    736   CB    SER A 118      0.311   33.048   21.762  1.00 35.65           C
ATOM    737   OG    SER A 118     -0.184   33.246   20.454            35.15 1.00 O
ATOM    738   C     SER A 118      0.357   35.451   22.506  1.00 37.99           C
```

Fig. 26 (Cont.)

```
ATOM    739  O   SER A 118       0.030  35.684  23.670  1.00 37.65           O
ATOM    740  N   THR A 119      -0.009  36.220  21.479  1.00 37.46           N
ATOM    741  CA  THR A 119      -0.961  37.282  21.668  1.00 36.93           C
ATOM    742  CB  THR A 119      -0.268  38.652  21.313  1.00 37.88           C
ATOM    743  OG1 THR A 119       0.217  38.628  19.965  1.00 39.42           O
ATOM    744  CG2 THR A 119       1.019  38.792  22.087  1.00 37.04           C
ATOM    745  C   THR A 119      -2.157  37.105  20.747  1.00 37.66           C
ATOM    746  O   THR A 119      -2.111  36.375  19.780  1.00 38.23           O
ATOM    747  N   PHE A 120              35.66  1.00    21.021  37.803  3.226- N
ATOM    748  CA  PHE A 120      -4.343  37.806  20.168  1.00 35.40           C
ATOM    749  CB  PHE A 120      -5.426  36.823  20.627  1.00 35.01           C
ATOM    750  CG  PHE A 120      -6.703  36.902  19.792          35.19  1.00  C
ATOM    751  CD1 PHE A 120      -6.761  36.319  18.518  1.00 35.66           C
ATOM    752  CE1 PHE A 120      -7.973  36.436  17.714  1.00 38.85           C
ATOM    753  CZ  PHE A 120      -9.075  37.144  18.173  1.00 34.68           C
ATOM    754  CE2 PHE A 120      -8.996  37.753  19.489  1.00 38.49           C
ATOM    755  CD2 PHE A 120      -7.798  37.610  20.252  1.00 35.32           C
ATOM    756  C   PHE A 120      -4.852  39.234  20.307  1.00 36.18           C
ATOM    757  O   PHE A 120      -5.040  39.768  21.459  1.00 34.94           O
ATOM    758  N   ILE A 121      -5.131  39.837  19.166  1.00 36.24           N
ATOM    759  CA  ILE A 121      -5.720  41.195  19.148  1.00 38.13           C
ATOM    760  CB  ILE A 121              35.98  1.00    18.159  42.075  4.935- C
ATOM    761  CG1 ILE A 121      -3.505  42.202  18.612  1.00 36.83           C
ATOM    762  CD1 ILE A 121      -2.620  42.856  17.541  1.00 42.55           C
ATOM    763  CG2 ILE A 121      -5.533  43.479          36.95  1.00  18.063  C
ATOM    764  C   ILE A 121      -7.182  41.186  18.752  1.00 38.65           C
ATOM    765  O   ILE A 121      -7.467  40.917  17.605  1.00 39.16           O
ATOM    766  N   ASP A 122      -8.114  41.487  19.644  1.00 41.22           N
ATOM    767  CA  ASP A 122      -9.523  41.367  19.255  1.00 44.68           C
ATOM    768  CB  ASP A 122     -10.509  40.961  20.435  1.00 45.77           C
ATOM    769  CG  ASP A 122     -11.006  42.147  21.311  1.00 51.84           C
ATOM    770  OD1 ASP A 122     -10.852  43.344  20.913  1.00 55.94           O
ATOM    771  OD2 ASP A 122     -11.589  41.961  22.454  1.00 55.83           O
ATOM    772  C   ASP A 122     -10.038  42.471  18.284  1.00 46.17           C
ATOM    773  O   ASP A 122              45.30  1.00    17.888  43.379  9.282- O
ATOM    774  N   ASP A 123     -11.316  42.407  17.908  1.00 48.58           N
ATOM    775  CA  ASP A 123     -11.847  43.464  17.050  1.00 51.81           C
ATOM    776  CB  ASP A 123     -13.226  43              53.86  1.00  16.453  116.C
ATOM    777  CG  ASP A 123     -13.195  41.843  15.587  1.00 58.85           C
ATOM    778  OD1 ASP A 123     -12.135  41.489  14.989  1.00 60.93           O
ATOM    779  OD2 ASP A 123     -14.225  41.137  15.458  1.00 65.68           O
ATOM    780  C   ASP A 123     -11.889  44.873  17.659  1.00 51.86           C
ATOM    781  O   ASP A 123     -11.668  45.825  16.901  1.00 52.43           O
ATOM    782  N   ASP A 124     -12.186  45.050  18.966  1.00 50.90           N
ATOM    783  CA  ASP A 124     -12.041  46.420  19.519  1.00 49.91           C
ATOM    784  CB  ASP A 124     -12.926  46.734  20.718  1.00 50.65           C
ATOM    785  CG  ASP A 124     -13.029  45.605  21.722  1.00 54.59           C
ATOM    786  OD1 ASP A 124     -12.024  44.888  22.021  1.00 56.71           O
ATOM    787  OD2 ASP A 124     -14.126  45.409  22.316  1.00 59.29           O
ATOM    788  C   ASP A 124     -10.594  46.853  19.785  1.00 48.18           C
ATOM    789  O   ASP A 124     -10.334          48.13  1.00    20.392  47.887 O
ATOM    790  N   ASN A 125      -9.650  46.056  19.316  1.00 45.93           N
ATOM    791  CA  ASN A 125      -8.253  46.391  19.476  1.00 44.21           C
ATOM    792  CB  ASN A 125      -8.072  47.857  19.155  1.00           44.91 C
ATOM    793  CG  ASN A 125      -7.343  48.050  17.864  1.00 49.51           C
ATOM    794  OD1 ASN A 125      -6.238  47.489  17.648  1.00 55.43           O
ATOM    795  ND2 ASN A 125      -7.932  48.858  16.981  1.00 51.42           N
ATOM    796  C   ASN A 125      -7.568  46.067  20.822  1.00 41.26           C
ATOM    797  O   ASN A 125      -6.391  46.382  20.975  1.00 39.94           O
ATOM    798  N   THR A 126      -8.303  45.504  21.780  1.00 38.03           N
ATOM    799  CA  THR A 126      -7.720  44.857  22.982  1.00 35.93           C
```

Fig. 26 (Cont.)

```
ATOM    800  CB  THR A 126      -8.827  44.152  23.760  1.00 35.95           C
ATOM    801  OG1 THR A 126      -9.850  45.107  24.075  1.00 38.04           O
ATOM    802  CG2 THR A 126      -8.330          36.23 1.00  25.136  43.678   C
ATOM    803  C   THR A 126      -6.675  43.816  22.596  1.00 33.88           C
ATOM    804  O   THR A 126      -6.894  43.035  21.687  1.00 32.94           O
ATOM    805  N   VAL A 127      -5.517  43.870  23.248          32.63 1.00   N
ATOM    806  CA  VAL A 127      -4.445  42.938  23.082  1.00 31.65           C
ATOM    807  CB  VAL A 127      -3.061  43.658  23.057  1.00 33.18           C
ATOM    808  CG1 VAL A 127      -1.939  42.620  23.000  1.00 30.17           C
ATOM    809  CG2 VAL A 127      -2.966  44.668  21.923  1.00 31.19           C
ATOM    810  C   VAL A 127      -4.469  41.969  24.286  1.00 32.76           C
ATOM    811  O   VAL A 127      -4.346  42.396  25.430  1.00 31.99           O
ATOM    812  N   TYR A 128      -4.625  40.675  23.997  1.00 32.89           N
ATOM    813  CA  TYR A 128      -4.461  39.634  24.965  1.00 32.99           C
ATOM    814  CB  TYR A 128      -5.591  38.625  24.840  1.00 32.72           C
ATOM    815  CG  TYR A 128      -6      33.62 1.00  25.057  39.250  954.C
ATOM    816  CD1 TYR A 128      -7.510  39.307  26.328  1.00 31.06           C
ATOM    817  CE1 TYR A 128      -8.770  39.886  26.544  1.00 33.80           C
ATOM    818  CZ  TYR A 128      -9.466  40.444  25.484          34.20 1.00   C
ATOM    819  OH  TYR A 128     -10.691  41.016  25.746  1.00 37.27           O
ATOM    820  CE2 TYR A 128      -8.927  40.431  24.202  1.00 30.23           C
ATOM    821  CD2 TYR A 128      -7.645  39.854  24.009  1.00 34.50           C
ATOM    822  C   TYR A 128      -3.114  38.970  24.853  1.00 34.41           C
ATOM    823  O   TYR A 128      -2.564  38.747  23.733  1.00 34.58           O
ATOM    824  N   LEU A 129      -2.548  38.697  26.034  1.00 34.32           N
ATOM    825  CA  LEU A 129      -1.309  37.936  26.160  1.00 33.21           C
ATOM    826  CB  LEU A 129      -0.286  38.742  26.949  1.00 32.48           C
ATOM    827  CG  LEU A 129       1.049  37.998  27.099  1.00 33.76           C
ATOM    828  CD1 LEU A 129          32.79 1.00  25.765  37.886  1.828       C
ATOM    829  CD2 LEU A 129       1.939  38.741  28.073  1.00 34.22           C
ATOM    830  C   LEU A 129      -1.602  36.616  26.839  1.00 33.42           C
ATOM    831  O   LEU A 129      -2.151  36.592  27              33.82 1.00  922.O
ATOM    832  N   LEU A 130      -1.278  35.500  26.204  1.00 33.27           N
ATOM    833  CA  LEU A 130      -1.387  34.200  26.836  1.00 31.83           C
ATOM    834  CB  LEU A 130      -2.045  33.222  25.854  1.00 32.49           C
ATOM    835  CG  LEU A 130      -3.581  33.398  25.731  1.00 35.57           C
ATOM    836  CD1 LEU A 130      -4.008  34.776  25.183  1.00 36.15           C
ATOM    837  CD2 LEU A 130      -4.182  32.228  24.932  1.00 37.88           C
ATOM    838  C   LEU A 130       0.025  33.711  27.155  1.00 33.29           C
ATOM    839  O   LEU A 130       0.924  33.831  26.307  1.00 31.76           O
ATOM    840  N   VAL A 131       0.225  33.160  28.374  1.00 32.73           N
ATOM    841  CA  VAL A 131          32.23 1.00  28.787  32.774  1.543       C
ATOM    842  CB  VAL A 131       2.037  33.778  29.875  1.00 34.57           C
ATOM    843  CG1 VAL A 131       3.392  33.302  30.472  1.00 32.33           C
ATOM    844  CG2 VAL A 131       2.139  35.210          30.01 1.00  29.333   C
ATOM    845  C   VAL A 131       1.452  31.367  29.436  1.00 33.83           C
ATOM    846  O   VAL A 131       0.650  31.139  30.368  1.00 33.16           O
ATOM    847  N   VAL A 132       2.306  30.466  28.976  1.00 34.09           N
ATOM    848  CA  VAL A 132       2.451  29.153  29.564  1.00 33.65           C
ATOM    849  CB  VAL A 132       3.277  28.221  28.693  1.00 34.80           C
ATOM    850  CG1 VAL A 132       3.424  26.820  29.400  1.00 31.97           C
ATOM    851  CG2 VAL A 132       2.657  28.062  27.287  1.00 33.73           C
ATOM    852  C   VAL A 132       3.195  29.360  30.873  1.00 33.60           C
ATOM    853  O   VAL A 132       4.226  30.026  30.892  1.00 35.01           O
ATOM    854  N   ASN A 133          32.26 1.00  31.961  28.772  2.715       N
ATOM    855  CA  ASN A 133       3.311  29.051  33.254  1.00 33.11           C
ATOM    856  CB  ASN A 133       2.313  29.880  34.069  1.00 32.10           C
ATOM    857  CG  ASN A 133       2.796  30.241          32.62 1.00  35.432   C
ATOM    858  OD1 ASN A 133       4.018  30.344  35.684  1.00 32.92           O
ATOM    859  ND2 ASN A 133       1.833  30.520  36.349  1.00 28.55           N
ATOM    860  C   ASN A 133       3.526  27.668  33.889  1.00 33              78.C
```

Fig. 26 (Cont.)

```
ATOM    861  O    ASN A 133       2.651  26.780  33.719  1.00 32.60           O
ATOM    862  N    HIS A 134       4.649  27.502  34.614  1.00 33.19           N
ATOM    863  CA   HIS A 134       4.977  26.226  35.279  1.00 34.40           C
ATOM    864  CB   HIS A 134       6.241  25.520  34.697  1.00 34.57           C
ATOM    865  CG   HIS A 134       6.141  25.184  33.227  1.00 38.24           C
ATOM    866  ND1  HIS A 134       5.237  24.265  32.729  1.00 37.71           N
ATOM    867  CE1  HIS A          39.92 1.00  31.408  24.222   5.334       134 C
ATOM    868  NE2  HIS A 134       6.313  25.032  31.030  1.00 39.32           N
ATOM    869  CD2  HIS A 134       6.839  25.639  32.150  1.00 39.79           C
ATOM    870  C    HIS A 134       5.187  26.490          36.28 1.00  36.763   C
ATOM    871  O    HIS A 134       6.314  26.467  37.218  1.00 35.71           O
ATOM    872  N    PRO A 135       4.125  26.689  37.536  1.00 37.05           N
ATOM    873  CA   PRO A 135       4.291  26.757  38.980  1.00         39.58   C
ATOM    874  CB   PRO A 135       2.893  27.217  39.481  1.00 39.92           C
ATOM    875  CG   PRO A 135       1.916  27.187  38.286  1.00 37.51           C
ATOM    876  CD   PRO A 135       2.705  26.717  37.108  1.00 37.78           C
ATOM    877  C    PRO A 135       4.584  25.317  39.467  1.00 41.85           C
ATOM    878  O    PRO A 135       3.713  24.424  39.242  1.00 42.09           O
ATOM    879  N    GLY A 136       5.745  25.072  40.101  1.00 43.05           N
ATOM    880  CA   GLY A 136       6.122  23.699  40.506  1.00 43.42           C
ATOM    881  C    GLY A 136       6.257  22.897  39.190  1.00 43.98           C
ATOM    882  O    GLY A 136       6.674  23.479  38.180  1.00 42.58           O
ATOM    883  N    SER A 137       5.846          43.24 1.00   39.138  21.618  N
ATOM    884  CA   SER A 137       5.994  20.923  37.843  1.00 44.40           C
ATOM    885  CB   SER A 137       6.724  19.612  38.029  1.00 43.91           C
ATOM    886  OG   SER A 137       5.884  18.727  38.714  1           46.89 00.0
ATOM    887  C    SER A 137       4.712  20.767  36.951  1.00 44.20           C
ATOM    888  O    SER A 137       4.702  20.050  35.931  1.00 44.90           O
ATOM    889  N    SER A 138       3.651  21.452  37.342  1.00 43.51           N
ATOM    890  CA   SER A 138       2.382  21.488  36.604  1.00 42.28           C
ATOM    891  CB   SER A 138       1.296  21.825  37.651  1.00 42.59           C
ATOM    892  OG   SER A 138       1.370  23.238  37.882  1.00 44.59           O
ATOM    893  C    SER A 138       2.421  22.531  35.450  1.00 40.99           C
ATOM    894  O    SER A 138       3.390  23.313  35.289  1.00 40.71           O
ATOM    895  N    SER A 139       1.436  22.496  34.569  1.00 39.16           N
ATOM    896  CA   SER A 139       1            38.06 1.00  33.569  23.530   342.C
ATOM    897  CB   SER A 139       1.355  22.936  32.134  1.00 38.56           C
ATOM    898  OG   SER A 139       2.632  22.485  31.773  1.00 43.04           O
ATOM    899  C    SER A 139       0.003  24.260  33.705          36.25 1.00   C
ATOM    900  O    SER A 139      -1.029  23.627  33.855  1.00 35.80           O
ATOM    901  N    THR A 140       0.018  25.561  33.453  1.00 34.75           N
ATOM    902  CA   THR A 140      -1.195  26.291  33.196  1.00 34.44           C
ATOM    903  CB   THR A 140      -1.601  27.177  34.370  1.00 34.21           C
ATOM    904  OG1  THR A 140      -0.576  28.184  34.446  1.00 33.39           O
ATOM    905  CG2  THR A 140      -1.559  26.491  35.786  1.00 31.00           C
ATOM    906  C    THR A 140      -0.912  27.246  32.017  1.00 34.94           C
ATOM    907  O    THR A 140       0.265  27.493  31.590  1.00 34.04           O
ATOM    908  N    VAL A 141      -1.992  27.828  31.518  1.00 33.00           N
ATOM    909  CA   VAL A 141            33.35 1.00  30.572  28.953   1.868-    C
ATOM    910  CB   VAL A 141      -2.507  28.579  29.216  1.00 33.38           C
ATOM    911  CG1  VAL A 141      -2.444  29.737  28.267  1.00 33.20           C
ATOM    912  CG2  VAL A 141      -1.775  27.351  28           30.56 1.00  574.C
ATOM    913  C    VAL A 141      -2.568  30.152  31.242  1.00 34.34           C
ATOM    914  O    VAL A 141      -3.770  30.104  31.651  1.00 33.38           O
ATOM    915  N    GLU A 142      -1.828  31.221  31.387  1.00 35.13           N
ATOM    916  CA   GLU A 142      -2.365  32.459  32.027  1.00 33.99           C
ATOM    917  CB   GLU A 142      -1.288  33.083  32.904  1.00 34.14           C
ATOM    918  CG   GLU A 142      -0.613  32.106  33.895  1.00 31.32           C
ATOM    919  CD   GLU A 142      -1.521  31.592  35.007  1.00 35.87           C
ATOM    920  OE1  GLU A 142      -2.711  32.030  35.076  1.00 37.80           O
ATOM    921  OE2  GLU A 142      -1.039  30.730  35.874  1.00 34.52           O
```

Fig. 26 (Cont.)

```
ATOM    922  C   GLU A 142          34.71 1.00  30.975  33.445   2.766-    C
ATOM    923  O   GLU A 142  -2.022  33.686  30.044  1.00 35.61              O
ATOM    924  N   VAL A 143  -3.999  33.941  31.062  1.00 35.10              N
ATOM    925  CA  VAL A 143  -4.490  34.940          34.76 1.00  30.134      C
ATOM    926  CB  VAL A 143  -6.003  34.668  29.722  1.00 35.54              C
ATOM    927  CG1 VAL A 143  -6.440  35.618  28.580  1.00 33.38              C
ATOM    928  CG2 VAL A 143  -6.202  33.223  29.294  1.00 34.33              C
ATOM    929  C   VAL A 143  -4.435  36.320  30.826  1.00 34.29              C
ATOM    930  O   VAL A 143  -4.963  36.479  31.918  1.00 33.69              O
ATOM    931  N   PHE A 144  -3.841  37.294  30.146  1.00 32.78              N
ATOM    932  CA  PHE A 144  -3.709  38.659  30.608  1.00 32.99              C
ATOM    933  CB  PHE A 144  -2.216  39.015  30.724  1.00 33.28              C
ATOM    934  CG  PHE A 144  -1.430  38.182  31.734  1.00 34.27              C
ATOM    935  CD1 PHE A 144          30.92 1.00  33.084  38.527   1.412-    C
ATOM    936  CE1 PHE A 144  -0.646  37.802  33.993  1.00 29.79              C
ATOM    937  CZ  PHE A 144   0.094  36.698  33.574  1.00 29.58              C
ATOM    938  CE2 PHE A 144   0.064  36.294          30.18 1.00  32.214      C
ATOM    939  CD2 PHE A 144  -0.698  37.048  31.310  1.00 32.12              C
ATOM    940  C   PHE A 144  -4.266  39.606  29.531  1.00 33.15              C
ATOM    941  O   PHE A 144  -4.157  39.329  28.332  1.00 34              14.O
ATOM    942  N   LYS A 145  -4.792  40.742  29.937  1.00 31.98              N
ATOM    943  CA  LYS A 145  -5.005  41.844  29.027  1.00 31.75              C
ATOM    944  CB  LYS A 145  -6.342  42.475  29.302  1.00 30.94              C
ATOM    945  CG  LYS A 145  -6.523  43.803  28.585  1.00 35.59              C
ATOM    946  CD  LYS A 145  -7.962  44.286  28.656  1.00 39.32              C
ATOM    947  CE  LYS A 145  -8.083  45.321  29.741  1.00 49.25              C
ATOM    948  NZ  LYS A          51.26 1.00  29.237  46.702   8.385-    145 N
ATOM    949  C   LYS A 145  -3.864  42.886  29.120  1.00 31.38              C
ATOM    950  O   LYS A 145  -3.475  43.320  30.194  1.00 30.89              O
ATOM    951  N   PHE A 146  -3.296  43              31.94 1.00  27.983  254.N
ATOM    952  CA  PHE A 146  -2.266  44.265  27.947  1.00 34.03              C
ATOM    953  CB  PHE A 146  -1.497  44.125  26.649  1.00 34.39              C
ATOM    954  CG  PHE A 146  -0.404  45.140  26.487  1.00         37.03      C
ATOM    955  CD1 PHE A 146   0.515  45.370  27.517  1.00 33.21              C
ATOM    956  CE1 PHE A 146   1.542  46.246  27.371  1.00 34.67              C
ATOM    957  CZ  PHE A 146   1.674  46.978  26.200  1.00 35.72              C
ATOM    958  CE2 PHE A 146   0.740  46.796  25.160  1.00 37.77              C
ATOM    959  CD2 PHE A 146  -0.305  45.887  25.311  1.00 37.01              C
ATOM    960  C   PHE A 146  -2.833  45.701  28.103  1.00 34.66              C
ATOM    961  O   PHE A 146  -3.707  46.107  27.345  1.00 34.08              O
ATOM    962  N   GLN A 147  -2.400  46.425  29.139  1.00 36.08              N
ATOM    963  CA  GLN A 147  -2.782  47.834  29.333  1.00 37.69              C
ATOM    964  CB  GLN A 147  -3.209          37.31 1.00  30.768  48.085      C
ATOM    965  CG  GLN A 147  -4.151  46.988  31.255  1.00 39.30              C
ATOM    966  CD  GLN A 147  -4.781  47.300  32.616  1.00 42.61              C
ATOM    967  OE1 GLN A 147  -4.043  47.467  33.600   1           42.46 00.O
ATOM    968  NE2 GLN A 147  -6.145  47.378  32.682  1.00 40.05              N
ATOM    969  C   GLN A 147  -1.601  48.672  28.899  1.00 39.07              C
ATOM    970  O   GLN A 147  -0.574  48.734  29.584  1.00 38.71              O
ATOM    971  N   GLU A 148  -1.684  49.198  27.672  1.00 42.00              N
ATOM    972  CA  GLU A 148  -0.495  49.761  27.009  1.00 43.96              C
ATOM    973  CB  GLU A 148  -0.713  50.060  25.518  1.00 45.31              C
ATOM    974  CG  GLU A 148   0.539  50.768  24.931  1.00 48.40              C
ATOM    975  CD  GLU A 148   0.576  50.970  23.407  1.00 52.85              C
ATOM    976  OE1 GLU A 148  -0.350  50.549  22.666  1.00 53.14              O
ATOM    977  OE2 GLU A 148   1.592          54.51 1.00  22.945  51.565      O
ATOM    978  C   GLU A 148   0.029  51.021  27.703  1.00 44.53              C
ATOM    979  O   GLU A 148   1.227  51.119  27.985  1.00 44.33              O
ATOM    980  N   GLU A 149  -0.868  51.968  27.954          45.05 1.00      N
ATOM    981  CA  GLU A 149  -0.534  53.195  28.664  1.00 47.14              C
ATOM    982  CB  GLU A 149  -1.814  53.969  28.984  1.00 47.58              C
```

Fig. 26 (Cont.)

```
ATOM    983  CG  GLU A 149      -2.354  54.850  27.880  1.00 51.99           C
ATOM    984  CD  GLU A 149      -2.781  56.222  28.421  1.00 57.90           C
ATOM    985  OE1 GLU A 149      -3.724  56.294  29.276  1.00 57.80           O
ATOM    986  OE2 GLU A 149      -2.159  57.235  28.002  1.00 57.48           O
ATOM    987  C   GLU A 149       0.191  52.953  30.002  1.00 47.07           C
ATOM    988  O   GLU A 149       1.170  53.637  30.324  1.00 46.78           O
ATOM    989  N   GLU A 150      -0.306  51.994  30.785  1.00 46.62           N
ATOM    990  CA  GLU A 150       46.17   1.00  32.122  51.791   0.226        C
ATOM    991  CB  GLU A 150      -0.826  51.238  33.061  1.00 45.87           C
ATOM    992  CG  GLU A 150      -1.982  52.200  33.311  1.00 50.09           C
ATOM    993  CD  GLU A 150      -3.146  51.949  32.347          53.62 1.00   C
ATOM    994  OE1 GLU A 150      -2.953  51.364  31.215  1.00 50.85           O
ATOM    995  OE2 GLU A 150      -4.258  52.363  32.737  1.00 55.00           O
ATOM    996  C   GLU A 150       1.404  50.848  32.097  1.00 45.63           C
ATOM    997  O   GLU A 150       2.088  50.752  33.105  1.00 46.21           O
ATOM    998  N   LYS A 151       1.613  50.136  30.980  1.00 43.75           N
ATOM    999  CA  LYS A 151       2.702  49.165  30.865  1.00 42.87           C
ATOM   1000  CB  LYS A 151       4.043  49.860  31.114  1.00 43.29           C
ATOM   1001  CG  LYS A 151       4.820  50.045  29.832  1.00 47.87           C
ATOM   1002  CD  LYS A 151       4.289  51.253  29.037  1.00 53.13           C
ATOM   1003  CE  LYS A 151       54.31   1.00  29.086  52.470   5.256        C
ATOM   1004  NZ  LYS A 151       6.587  51.997  28.573  1.00 55.30           N
ATOM   1005  C   LYS A 151       2.531  48.035  31.845  1.00 41.01           C
ATOM   1006  O   LYS A 151       3.422  47.739  32.646          41.40 1.00   O
ATOM   1007  N   SER A 152       1.360  47.426  31.810  1.00 38.97           N
ATOM   1008  CA  SER A 152       0.991  46.479  32.833  1.00 36.99           C
ATOM   1009  CB  SER A 152       0.282  47.209  34.008  1.00 37.06           C
ATOM   1010  OG  SER A 152      -1.048  47.537  33.646  1.00 37.77           O
ATOM   1011  C   SER A 152       0.141  45.380  32.191  1.00 36.06           C
ATOM   1012  O   SER A 152      -0.372  45.541  31.065  1.00 37.11           O
ATOM   1013  N   LEU A 153       0.060  44.233  32.846  1.00 33.52           N
ATOM   1014  CA  LEU A 153      -0.694  43.095  32.332  1.00 31.98           C
ATOM   1015  CB  LEU A 153       0.225  41.900  32.235  1.00 30.46           C
ATOM   1016  CG  LEU A 153       33.27   1.00  31.047  41.926   1.201        C
ATOM   1017  CD1 LEU A 153       2.244  40.792  31.250  1.00 31.59           C
ATOM   1018  CD2 LEU A 153       0.458  41.743  29.702  1.00 28.83           C
ATOM   1019  C   LEU A 153      -1.756  42.851          32.54 1.00  33.408   C
ATOM   1020  O   LEU A 153      -1.411  42.709  34.607  1.00 31.76           O
ATOM   1021  N   LEU A 154      -3.028  42.922  33.031  1.00 31.40           N
ATOM   1022  CA  LEU A 154      -4.116  42.628  33.983  1.00 30.33           C
ATOM   1023  CB  LEU A 154      -5.358  43.441  33.604  1.00 28.85           C
ATOM   1024  CG  LEU A 154      -6.675  42.995  34.258  1.00 32.21           C
ATOM   1025  CD1 LEU A 154      -6.648  43.056  35.851  1.00 30.17           C
ATOM   1026  CD2 LEU A 154      -7.936  43.769  33.724  1.00 33.37           C
ATOM   1027  C   LEU A 154      -4.405  41.113  33.843  1.00 29.14           C
ATOM   1028  O   LEU A 154      -4.704  40.650  32.733  1.00 28.63           O
ATOM   1029  N   HIS A 155       28.69   1.00  34.919  40.347   4.274-       N
ATOM   1030  CA  HIS A 155      -4.538  38.914  34.853  1.00 29.23           C
ATOM   1031  CB  HIS A 155      -4.021  38.186  36.069  1.00 30.89           C
ATOM   1032  CG  HIS A 155      -4.169  36            31.74 1.00  35.973  697.C
ATOM   1033  ND1 HIS A 155      -5.043  36.000  36.767  1.00 31.01           N
ATOM   1034  CE1 HIS A 155      -5.001  34.717  36.436  1.00 30.82           C
ATOM   1035  NE2 HIS A 155      -4.078  34.555  35.509  1.00 31.99           N
ATOM   1036  CD2 HIS A 155      -3.544  35.779  35.195  1.00 30.24           C
ATOM   1037  C   HIS A 155      -6.034  38.679  34.709  1.00 29.61           C
ATOM   1038  O   HIS A 155      -6.810  39.307  35.337  1.00 25.45           O
ATOM   1039  N   LEU A 156      -6.413  37.833  33.762  1.00 31.18           N
ATOM   1040  CA  LEU A 156      -7.835  37.550  33.565  1.00 31.32           C
ATOM   1041  CB  LEU A 156      -8.242  37.704  32.099  1.00 30.04           C
ATOM   1042  CG  LEU A 156      -8.073  39.184  31.676  1.00 33.80           C
ATOM   1043  CD1 LEU A 156      -8.395  39.265  30.176  1.00 35.69           C
```

Fig. 26 (Cont.)

| | | | | | | | | | |
|---|---|---|---|---|---|---|---|---|---|
| ATOM | 1044 | CD2 | LEU A 156 | -9.054 | 40.099 | 32.482 | 1.00 | 30.36 | C |
| ATOM | 1045 | C | LEU A 156 | -8.118 | | 32.01 | 1.00 | 34.040 | 36.161 C |
| ATOM | 1046 | O | LEU A 156 | -9.106 | 35.937 | 34.723 | 1.00 | 32.91 | O |
| ATOM | 1047 | N | LYS A 157 | -7.274 | 35.223 | 33.688 | 1.00 | 32.02 | N |
| ATOM | 1048 | CA | LYS A 157 | -7.569 | 33.874 | 34.069 | 1.00 | | 34.57 C |
| ATOM | 1049 | CB | LYS A 157 | -8.897 | 33.450 | 33.449 | 1.00 | 36.17 | C |
| ATOM | 1050 | CG | LYS A 157 | -8.944 | 32.420 | 32.398 | 1.00 | 37.38 | C |
| ATOM | 1051 | CD | LYS A 157 | -10.480 | 32.110 | 32.248 | 1.00 | 45.13 | C |
| ATOM | 1052 | CE | LYS A 157 | -10.838 | 30.631 | 32.199 | 1.00 | 43.29 | C |
| ATOM | 1053 | NZ | LYS A 157 | -11.977 | 30.413 | 33.111 | 1.00 | 40.66 | N |
| ATOM | 1054 | C | LYS A 157 | -6.467 | 32.846 | 33.913 | 1.00 | 33.46 | C |
| ATOM | 1055 | O | LYS A 157 | -5.509 | 33.049 | 33.178 | 1.00 | 34.54 | O |
| ATOM | 1056 | N | THR A 158 | -6.599 | 31.794 | 34.703 | 1.00 | 33.86 | N |
| ATOM | 1057 | CA | THR A 158 | -5.668 | 30.661 | 34.760 | 1.00 | 34.12 | C |
| ATOM | 1058 | CB | THR A 158 | -5.338 | | 33.79 | 1.00 | 36.292 | 30.376 C |
| ATOM | 1059 | OG1 | THR A 158 | -4.538 | 31.441 | 36.778 | 1.00 | 33.45 | O |
| ATOM | 1060 | CG2 | THR A 158 | -4.422 | 29.120 | 36.491 | 1.00 | 32.76 | C |
| ATOM | 1061 | C | THR A 158 | -6.407 | 29.457 | 34.179 | | 33.68 | 1.00 C |
| ATOM | 1062 | O | THR A 158 | -7.454 | 29.044 | 34.658 | 1.00 | 33.67 | O |
| ATOM | 1063 | N | ILE A 159 | -5.854 | 28.893 | 33.148 | 1.00 | 34.56 | N |
| ATOM | 1064 | CA | ILE A 159 | -6.403 | 27.700 | 32.505 | 1.00 | 34.28 | C |
| ATOM | 1065 | CB | ILE A 159 | -6.451 | 27.967 | 31.002 | 1.00 | 34.20 | C |
| ATOM | 1066 | CG1 | ILE A 159 | -7.533 | 29.040 | 30.739 | 1.00 | 35.19 | C |
| ATOM | 1067 | CD1 | ILE A 159 | -7.485 | 29.599 | 29.286 | 1.00 | 32.73 | C |
| ATOM | 1068 | CG2 | ILE A 159 | -6.713 | 26.664 | 30.204 | 1.00 | 28.67 | C |
| ATOM | 1069 | C | ILE A 159 | -5.545 | 26.475 | 32.779 | 1.00 | 34.90 | C |
| ATOM | 1070 | O | ILE A 159 | -4.341 | 26.518 | 32.578 | 1.00 | 34.74 | O |
| ATOM | 1071 | N | ARG A 160 | -6 | | 36.12 | 1.00 | 33.235 | 25.383 141.N |
| ATOM | 1072 | CA | ARG A 160 | -5.442 | 24.082 | 33.207 | 1.00 | 37.28 | C |
| ATOM | 1073 | CB | ARG A 160 | -4.956 | 23.587 | 34.574 | 1.00 | 39.03 | C |
| ATOM | 1074 | CG | ARG A 160 | -5.100 | 24.511 | 35.640 | | 44.21 | 1.00 C |
| ATOM | 1075 | CD | ARG A 160 | -5.469 | 23.891 | 36.978 | 1.00 | 47.10 | C |
| ATOM | 1076 | NE | ARG A 160 | -5.605 | 25.077 | 37.804 | 1.00 | 49.73 | N |
| ATOM | 1077 | CZ | ARG A 160 | -4.578 | 25.643 | 38.409 | 1.00 | 52.72 | C |
| ATOM | 1078 | NH1 | ARG A 160 | -3.392 | 25.043 | 38.354 | 1.00 | 47.56 | N |
| ATOM | 1079 | NH2 | ARG A 160 | -4.744 | 26.766 | 39.121 | 1.00 | 55.30 | N |
| ATOM | 1080 | C | ARG A 160 | -6.401 | 22.997 | 32.772 | 1.00 | 36.47 | C |
| ATOM | 1081 | O | ARG A 160 | -7.616 | 23.150 | 32.859 | 1.00 | 34.99 | O |
| ATOM | 1082 | N | HIS A 161 | -5.841 | 21.847 | 32.438 | 1.00 | 33.40 | N |
| ATOM | 1083 | CA | HIS A 161 | -6.661 | 20.847 | 31.836 | 1.00 | 33.03 | C |
| ATOM | 1084 | CB | HIS A 161 | | 31.64 | 1.00 | 30.388 | 21.242 | 7.106- C |
| ATOM | 1085 | CG | HIS A 161 | -8.336 | 20.504 | 29.933 | 1.00 | 33.60 | C |
| ATOM | 1086 | ND1 | HIS A 161 | -8.278 | 19.255 | 29.322 | 1.00 | 33.78 | N |
| ATOM | 1087 | CE1 | HIS A 161 | -9.506 | 18.819 | 29 | | 32.25 | 1.00 086.C |
| ATOM | 1088 | NE2 | HIS A 161 | -10.362 | 19.691 | 29.594 | 1.00 | 33.24 | N |
| ATOM | 1089 | CD2 | HIS A 161 | -9.660 | 20.770 | 30.113 | 1.00 | 30.87 | C |
| ATOM | 1090 | C | HIS A 161 | -5.839 | 19.588 | 31.848 | 1.00 | 32.89 | C |
| ATOM | 1091 | O | HIS A 161 | -4.603 | 19.602 | 31.720 | 1.00 | 33.71 | O |
| ATOM | 1092 | N | LYS A 162 | -6.527 | 18.495 | 31.960 | 1.00 | 33.49 | N |
| ATOM | 1093 | CA | LYS A 162 | -5.891 | 17.205 | 31.839 | 1.00 | 35.30 | C |
| ATOM | 1094 | CB | LYS A 162 | -6.935 | 16.142 | 32.197 | 1.00 | 36.18 | C |
| ATOM | 1095 | CG | LYS A 162 | -6.853 | 14.904 | 31.364 | 1.00 | 40.99 | C |
| ATOM | 1096 | CD | LYS A 162 | -8.092 | 14.020 | 31.518 | 1.00 | 48.68 | C |
| ATOM | 1097 | CE | LYS A 162 | | 53.51 | 1.00 | 31.059 | 12.570 | 7.733- C |
| ATOM | 1098 | NZ | LYS A 162 | -7.905 | 11.628 | 32.242 | 1.00 | 53.91 | N |
| ATOM | 1099 | C | LYS A 162 | -5.203 | 16.971 | 30.472 | 1.00 | 34.56 | C |
| ATOM | 1100 | O | LYS A 162 | -4.204 | 16.279 | | 35.10 | 1.00 | 30.424 O |
| ATOM | 1101 | N | LEU A 163 | -5.697 | 17.587 | 29.396 | 1.00 | 34.41 | N |
| ATOM | 1102 | CA | LEU A 163 | -5.071 | 17.508 | 28.045 | 1.00 | 34.07 | C |
| ATOM | 1103 | CB | LEU A 163 | -6.149 | 17.582 | 26.942 | 1.00 | 32.01 | C |
| ATOM | 1104 | CG | LEU A 163 | -7.179 | 16.467 | 26.981 | 1.00 | 33.91 | C |

Fig. 26 (Cont.)

```
ATOM   1105  CD1  LEU A 163      -8.233  16.644  25.881  1.00  32.64           C
ATOM   1106  CD2  LEU A 163      -6.532  15.085  26.893  1.00  30.09           C
ATOM   1107  C    LEU A 163      -3.974  18.615  27.850  1.00  34.30           C
ATOM   1108  O    LEU A 163      -3.476  18.859  26.752  1.00  33.73           O
ATOM   1109  N    LEU A 164      -3.658  19.320  28.934  1.00  34.53           N
ATOM   1110  CA   LEU A 164        35.03 1.00  28.928  20.303   2.569-         C
ATOM   1111  CB   LEU A 164      -3.142  21.688  29.241  1.00  34.30           C
ATOM   1112  CG   LEU A 164      -4.057  22.311  28.170  1.00  35.07           C
ATOM   1113  CD1  LEU A 164      -4.621  23.701          31.74 1.00   28.663   C
ATOM   1114  CD2  LEU A 164      -3.278  22.421  26.851  1.00  31.41           C
ATOM   1115  C    LEU A 164      -1.566  19.905  30.029  1.00  35.23           C
ATOM   1116  O    LEU A 164      -1.302  20.707  30.943  1.00  35           12.O
ATOM   1117  N    PRO A 165      -1.056  18.670  29.968  1.00  34.95           N
ATOM   1118  CA   PRO A 165      -0.183  18.130  31.026  1.00  34.71           C
ATOM   1119  CB   PRO A 165      -0.060  16.632  30.651  1.00  34.55           C
ATOM   1120  CG   PRO A 165      -0.267  16.553  29.143  1.00  34.10           C
ATOM   1121  CD   PRO A 165      -1.258  17.681  28.876  1.00  35.74           C
ATOM   1122  C    PRO A 165       1.213  18.771  31.090  1.00  34.23           C
ATOM   1123  O    PRO A          33.56 1.00   32.194  18.994   1.704      165  O
ATOM   1124  N    SER A 166       1.785  19.126  29.950  1.00  33.21           N
ATOM   1125  CA   SER A 166       3.207  19.529  29.871  1.00  34.68           C
ATOM   1126  CB   SER A 166       4.103  18.289          34.52 1.00   29.695   C
ATOM   1127  OG   SER A 166       5.463  18.633  29.855  1.00  38.52           O
ATOM   1128  C    SER A 166       3.416  20.513  28.723  1.00  34.30           C
ATOM   1129  O    SER A 166       4.006  20.169  27.668  1.00          37.14   O
ATOM   1130  N    VAL A 167       2.932  21.741  28.917  1.00  33.58           N
ATOM   1131  CA   VAL A 167       2.704  22.646  27.808  1.00  33.08           C
ATOM   1132  CB   VAL A 167       1.579  23.674  28.135  1.00  33.48           C
ATOM   1133  CG1  VAL A 167       1.445  24.696  26.996  1.00  32.56           C
ATOM   1134  CG2  VAL A 167       0.209  22.999  28.502  1.00  29.00           C
ATOM   1135  C    VAL A 167       4.023  23.387  27.551  1.00  33.26           C
ATOM   1136  O    VAL A 167       4.744  23.754  28.481  1.00  32.66           O
ATOM   1137  N    ASN A 168       4.333  23.584  26.294  1.00  33.98           N
ATOM   1138  CA   ASN A 168       5.598  24.197  25.895  1.00  32.75           C
ATOM   1139  CB   ASN A 168       6.279           34.28 1.00  24.838   23.299  C
ATOM   1140  CG   ASN A 168       7.712  23.810  24.487  1.00  34.93           C
ATOM   1141  OD1  ASN A 168       7.846  24.894  23.900  1.00  36.68           O
ATOM   1142  ND2  ASN A 168       8.758  23.113  24.994  1           31.94 00.N
ATOM   1143  C    ASN A 168       5.298  25.550  25.247  1.00  34.00           C
ATOM   1144  O    ASN A 168       5.800  26.603  25.682  1.00  34.55           O
ATOM   1145  N    ASP A 169       4.438  25.547  24.226  1.00  32.85           N
ATOM   1146  CA   ASP A 169       4.055  26.804  23.600  1.00  33.69           C
ATOM   1147  CB   ASP A 169       4.903  27.082  22.367  1.00  31.39           C
ATOM   1148  CG   ASP A 169       4.921  28.607  22.004  1.00  37.35           C
ATOM   1149  OD1  ASP A 169       4.352  29.484  22.694  1.00  33.53           O
ATOM   1150  OD2  ASP A 169       5.448  29.052  21.008  1.00  35.57           O
ATOM   1151  C    ASP A 169       2.548  26.804  23.185  1.00  34.34           C
ATOM   1152  O    ASP A 169       1         33.47 1.00  23.137   25.732  955.O
ATOM   1153  N    ILE A 170       1.974  27.994  22.869  1.00  33.68           N
ATOM   1154  CA   ILE A 170       0.578  28.080  22.408  1.00  32.64           C
ATOM   1155  CB   ILE A 170      -0.511  28.410  23.542          34.15 1.00    C
ATOM   1156  CG1  ILE A 170      -0.590  29.902  23.876  1.00  32.84           C
ATOM   1157  CD1  ILE A 170       0.686  30.476  24.593  1.00  30.90           C
ATOM   1158  CG2  ILE A 170      -0.311  27.527  24.801  1.00  29.34           C
ATOM   1159  C    ILE A 170       0.502  29.067  21.259  1.00  34.06           C
ATOM   1160  O    ILE A 170       1.348  29.969  21.148  1.00  33.34           O
ATOM   1161  N    VAL A 171      -0.509  28.918  20.396  1.00  33.57           N
ATOM   1162  CA   VAL A 171      -0.803  30.016  19.512  1.00  33.79           C
ATOM   1163  CB   VAL A 171      -0.468  29.659  18.004  1.00  34.75           C
ATOM   1164  CG1  VAL A 171      -1.142  28.324  17.527  1.00  33.41           C
ATOM   1165  CG2  VAL A 171        33.55 1.00  17.143  30.760   0.935-         C
```

Fig. 26 (Cont.)

| | | | | | | | | |
|---|---|---|---|---|---|---|---|---|
| ATOM | 1166 | C | VAL A 171 | -2.291 | 30.411 | 19.748 | 1.00 34.61 | C |
| ATOM | 1167 | O | VAL A 171 | -3.176 | 29.598 | 19.635 | 1.00 33.42 | O |
| ATOM | 1168 | N | ALA A 172 | -2.532 | 31.661 | 20 | 34.65 1.00 093.N | |
| ATOM | 1169 | CA | ALA A 172 | -3.866 | 32.130 | 20.409 | 1.00 34.53 | C |
| ATOM | 1170 | CB | ALA A 172 | -3.772 | 33.473 | 21.116 | 1.00 33.21 | C |
| ATOM | 1171 | C | ALA A 172 | -4.685 | 32.313 | 19.130 | 1.00 35.97 | C |
| ATOM | 1172 | O | ALA A 172 | -4.192 | 32.895 | 18.148 | 1.00 35.88 | O |
| ATOM | 1173 | N | VAL A 173 | -5.933 | 31.837 | 19.137 | 1.00 35.55 | N |
| ATOM | 1174 | CA | VAL A 173 | -6.845 | 32.131 | 18.037 | 1.00 36.82 | C |
| ATOM | 1175 | CB | VAL A 173 | -7.241 | 30.855 | 17.237 | 1.00 37.26 | C |
| ATOM | 1176 | CG1 | VAL A 173 | -5.978 | 30.267 | 16.545 | 1.00 36.68 | C |
| ATOM | 1177 | CG2 | VAL A 173 | -7.919 | 29.769 | 18.156 | 1.00 35.00 | C |
| ATOM | 1178 | C | VAL A 173 | | 37.12 1.00 | 18.579 | 32.842 8.082- | C |
| ATOM | 1179 | O | VAL A 173 | -9.059 | 32.988 | 17.879 | 1.00 37.60 | O |
| ATOM | 1180 | N | GLY A 174 | -8.011 | 33.330 | 19.824 | 1.00 36.94 | N |
| ATOM | 1181 | CA | GLY A 174 | -9.101 | 34.078 | | 35.34 1.00 20.460 | C |
| ATOM | 1182 | C | GLY A 174 | -8.535 | 34.458 | 21.843 | 1.00 37.36 | C |
| ATOM | 1183 | O | GLY A 174 | -7.460 | 33.985 | 22.215 | 1.00 36.10 | O |
| ATOM | 1184 | N | PRO A 175 | -9.250 | 35.284 | 22.614 | 1.00 37.77 | N |
| ATOM | 1185 | CA | PRO A 175 | -8.833 | 35.663 | 23.976 | 1.00 37.78 | C |
| ATOM | 1186 | CB | PRO A 175 | -10.006 | 36.489 | 24.503 | 1.00 37.36 | C |
| ATOM | 1187 | CG | PRO A 175 | -10.836 | 36.807 | 23.368 | 1.00 38.55 | C |
| ATOM | 1188 | CD | PRO A 175 | -10.533 | 35.887 | 22.209 | 1.00 36.90 | C |
| ATOM | 1189 | C | PRO A 175 | -8.622 | 34.450 | 24.925 | 1.00 38.97 | C |
| ATOM | 1190 | O | PRO A 175 | -7.754 | 34.550 | 25.826 | 1.00 41.79 | O |
| ATOM | 1191 | N | GLU A 176 | | 37.43 1.00 | 24.721 | 33.323 9.307- | N |
| ATOM | 1192 | CA | GLU A 176 | -9.125 | 32.115 | 25.559 | 1.00 38.03 | C |
| ATOM | 1193 | CB | GLU A 176 | -10.288 | 31.983 | 26.608 | 1.00 38.87 | C |
| ATOM | 1194 | CG | GLU A 176 | -10.123 | 32.976 | | 41.42 1.00 27.675 | C |
| ATOM | 1195 | CD | GLU A 176 | -11.255 | 33.044 | 28.679 | 1.00 51.60 | C |
| ATOM | 1196 | OE1 | GLU A 176 | -12.175 | 32.138 | 28.695 | 1.00 43.41 | O |
| ATOM | 1197 | OE2 | GLU A 176 | -11.134 | 34.054 | 29.489 | 1.00 53 | 44.O |
| ATOM | 1198 | C | GLU A 176 | -9.283 | 30.897 | 24.716 | 1.00 38.03 | C |
| ATOM | 1199 | O | GLU A 176 | -9.929 | 29.963 | 25.163 | 1.00 38.43 | O |
| ATOM | 1200 | N | HIS A 177 | -8.821 | 30.941 | 23.474 | 1.00 38.07 | N |
| ATOM | 1201 | CA | HIS A 177 | -8.859 | 29.820 | 22.595 | 1.00 38.35 | C |
| ATOM | 1202 | CB | HIS A 177 | -9.847 | 30.127 | 21.471 | 1.00 39.71 | C |
| ATOM | 1203 | CG | HIS A 177 | -11.147 | 30.726 | 21.933 | 1.00 44.72 | C |
| ATOM | 1204 | ND1 | HIS A | 48.89 1.00 | 22.674 | 31.906 | 11.219- | 177 N |
| ATOM | 1205 | CE1 | HIS A 177 | -12.493 | 32.210 | 22.899 | 1.00 43.34 | C |
| ATOM | 1206 | NE2 | HIS A 177 | -13.249 | 31.262 | 22.343 | 1.00 42.62 | N |
| ATOM | 1207 | CD2 | HIS A 177 | -12.437 | 30 | | 42.17 1.00 21.742 | 321.C |
| ATOM | 1208 | C | HIS A 177 | -7.453 | 29.689 | 22.004 | 1.00 38.33 | C |
| ATOM | 1209 | O | HIS A 177 | -6.878 | 30.708 | 21.588 | 1.00 36.52 | O |
| ATOM | 1210 | N | PHE A 178 | -6.897 | 28.467 | 21.938 | 1.00 | 36.18 N |
| ATOM | 1211 | CA | PHE A 178 | -5.505 | 28.356 | 21.493 | 1.00 36.06 | C |
| ATOM | 1212 | CB | PHE A 178 | -4.492 | 28.869 | 22.566 | 1.00 34.24 | C |
| ATOM | 1213 | CG | PHE A 178 | -4.651 | 28.218 | 23.924 | 1.00 34.87 | C |
| ATOM | 1214 | CD1 | PHE A 178 | -3.998 | 27.015 | 24.215 | 1.00 31.96 | C |
| ATOM | 1215 | CE1 | PHE A 178 | -4.086 | 26.440 | 25.483 | 1.00 30.70 | C |
| ATOM | 1216 | CZ | PHE A 178 | -4.951 | 27.029 | 26.471 | 1.00 36.03 | C |
| ATOM | 1217 | CE2 | PHE A 178 | -5.617 | 28.246 | 26.174 | 1.00 33.08 | C |
| ATOM | 1218 | CD2 | PHE A 178 | -5.451 | 28.819 | 24.905 | 1.00 33.43 | C |
| ATOM | 1219 | C | PHE A 178 | -5.222 | 26.941 | 21.134 | 1.00 35.50 | C |
| ATOM | 1220 | O | PHE A 178 | -5.904 | | 37.17 1.00 | 21.631 26.053 | O |
| ATOM | 1221 | N | TYR A 179 | -4.233 | 26.729 | 20.286 | 1.00 33.98 | N |
| ATOM | 1222 | CA | TYR A 179 | -3.612 | 25.413 | 20.164 | 1.00 34.03 | C |
| ATOM | 1223 | CB | TYR A 179 | -3.179 | 25.153 | 18.717 | 1 | 34.72 00.C |
| ATOM | 1224 | CG | TYR A 179 | -4.338 | 25.030 | 17.752 | 1.00 35.16 | C |
| ATOM | 1225 | CD1 | TYR A 179 | -4.981 | 23.823 | 17.588 | 1.00 33.38 | C |
| ATOM | 1226 | CE1 | TYR A 179 | -6.033 | 23.667 | 16.635 | 1.00 35.83 | C |

Fig. 26 (Cont.)

```
ATOM   1227  CZ   TYR A 179      -6.469  24.759  15.881  1.00 38.08           C
ATOM   1228  OH   TYR A 179      -7.519  24.591  14.994  1.00 42.96           O
ATOM   1229  CE2  TYR A 179      -5.837  26.013  16.025  1.00 38.52           C
ATOM   1230  CD2  TYR A 179      -4.769  26.138  16.971  1.00 35.03           C
ATOM   1231  C    TYR A 179      -2.378  25.369  21.060  1.00 33.89           C
ATOM   1232  O    TYR A 179      -1.610  26.305  21.111  1.00 33.88           O
ATOM   1233  N    ALA A 180      -2.180          34.70 1.00  21.763  24.262   N
ATOM   1234  CA   ALA A 180      -1.052  24.128  22.674  1.00 34.91           C
ATOM   1235  CB   ALA A 180      -1.580  23.969  24.124  1.00 33.30           C
ATOM   1236  C    ALA A 180      -0.210  22.907  22.307          35.04 1.00   C
ATOM   1237  O    ALA A 180      -0.760  21.802  22.098  1.00 34.78           O
ATOM   1238  N    THR A 181       1.117  23.051  22.310  1.00 34.55           N
ATOM   1239  CA   THR A 181       1.896  21.838  22.283  1.00 33.59           C
ATOM   1240  CB   THR A 181       3.246  22.057  21.586  1.00 35.33           C
ATOM   1241  OG1  THR A 181       3.977  23.097  22.235  1.00 33.90           O
ATOM   1242  CG2  THR A 181       3.084  22.496  20.094  1.00 34.42           C
ATOM   1243  C    THR A 181       2.156  21.337  23.685  1.00 34.01           C
ATOM   1244  O    THR A 181       2.375  22.103  24.609  1.00 34.67           O
ATOM   1245  N    ASN A 182       2.169  20.034  23.843  1.00 33.85           N
ATOM   1246  CA   ASN A 182          34.84 1.00  25.055  19.440  2.681        C
ATOM   1247  CB   ASN A 182       1.696  18.391  25.614  1.00 32.92           C
ATOM   1248  CG   ASN A 182       0.426  19.013  26.185  1.00 36.43           C
ATOM   1249  OD1  ASN A 182       0.459  19.600  27.294          36.21 1.00   O
ATOM   1250  ND2  ASN A 182      -0.710  18.890  25.444  1.00 32.77           N
ATOM   1251  C    ASN A 182       3.992  18.727  24.668  1.00 35.26           C
ATOM   1252  O    ASN A 182       3.992  17.821  23.803  1.00 36.02           O
ATOM   1253  N    ASP A 183       5.090  19.096  25.317  1.00 35.56           N
ATOM   1254  CA   ASP A 183       6.378  18.491  24.964  1.00 35.27           C
ATOM   1255  CB   ASP A 183       7.546  19.402  25.295  1.00 35.00           C
ATOM   1256  CG   ASP A 183       7.544  19.902  26.709  1.00 38.10           C
ATOM   1257  OD1  ASP A 183       7.077  19.194  27.659  1.00 37.92           O
ATOM   1258  OD2  ASP A 183       7.969  21.066  26.936  1.00 38.64           O
ATOM   1259  C    ASP A 183          35.15 1.00  25.549  17.064  6.557        C
ATOM   1260  O    ASP A 183       7.470  16.365  25.201  1.00 35.27           O
ATOM   1261  N    HIS A 184       5.682  16.642  26.449  1.00 33.77           N
ATOM   1262  CA   HIS A 184       5.805  15.297  27.011          33.82 1.00   C
ATOM   1263  CB   HIS A 184       6.533  15.258  28.366  1.00 33.63           C
ATOM   1264  CG   HIS A 184       7.995  15.568  28.307  1.00 35.59           C
ATOM   1265  ND1  HIS A 184       8.486  16.857  28.216  1.00 36.05           N
ATOM   1266  CE1  HIS A 184       9.813  16.824  28.226  1.00 37.00           C
ATOM   1267  NE2  HIS A 184      10.195  15.568  28.368  1.00 40.08           N
ATOM   1268  CD2  HIS A 184       9.079  14.765  28.437  1.00 38.43           C
ATOM   1269  C    HIS A 184       4.408  14.847  27.286  1.00 33.44           C
ATOM   1270  O    HIS A 184       3.513  15.658  27.405  1.00 32.58           O
ATOM   1271  N    TYR A 185       4.222  13.550  27.458  1.00 34.15           N
ATOM   1272  CA   TYR A 185          35.00 1.00  27.799  13.045  2.940        C
ATOM   1273  CB   TYR A 185       2.812  11.662  27.163  1.00 37.80           C
ATOM   1274  CG   TYR A 185       1.622  10.872  27.649  1.00 39.78           C
ATOM   1275  CD1  TYR A 185       0.456  10.765          42.61 1.00  26.865   C
ATOM   1276  CE1  TYR A 185      -0.657  10.069  27.344  1.00 46.90           C
ATOM   1277  CZ   TYR A 185      -0.567   9.474  28.626  1.00 48.51           C
ATOM   1278  OH   TYR A 185      -1.599   8.743  29.161  1.00 52.21           O
ATOM   1279  CE2  TYR A 185       0.586   9.590  29.404  1.00 46.28           C
ATOM   1280  CD2  TYR A 185       1.645  10.286  28.920  1.00 42.69           C
ATOM   1281  C    TYR A 185       2.851  13.022  29.333  1.00 35.70           C
ATOM   1282  O    TYR A 185       1.791  13.273  29.911  1.00 35.70           O
ATOM   1283  N    PHE A 186       3.957  12.735  30.011  1.00 36.34           N
ATOM   1284  CA   PHE A 186       3.946  12.628  31.489  1.00 37.07           C
ATOM   1285  CB   PHE A 186          36.46 1.00  31.945  11.588  4.958        C
ATOM   1286  CG   PHE A 186       4.531  10.176  31.676  1.00 38.39           C
ATOM   1287  CD1  PHE A 186       3.408   9.616  32.348  1.00 38.29           C
```

Fig. 26 (Cont.)

```
ATOM   1288  CE1 PHE A 186       3.011    8          40.85 1.00  32.085   279.C
ATOM   1289  CZ  PHE A 186       3.736    7.507  31.163  1.00 38.09          C
ATOM   1290  CE2 PHE A 186       4.858    8.076  30.498  1.00 38.85          C
ATOM   1291  CD2 PHE A 186       5.251    9.383  30.772  1.00 36.55          C
ATOM   1292  C   PHE A 186       4.197   13.959  32.221  1.00 37.87          C
ATOM   1293  O   PHE A 186       4.800   14.866  31.697  1.00 39.13          O
ATOM   1294  N   ILE A 187       3.723   14.089  33.442  1.00 40.18          N
ATOM   1295  CA  ILE A 187       3.977   15.315  34.198  1.00 41.06          C
ATOM   1296  CB  ILE A 187       2.730   15.717  34.965  1.00 41.74          C
ATOM   1297  CG1 ILE A 187       1.609   16.064  33.986  1.00 39.46          C
ATOM   1298  CD1 ILE A 187       0.227   15.890  34.625  1.00 37.47          C
ATOM   1299  CG2 ILE A 187       3.075   16.835  36.006  1.00 41.74          C
ATOM   1300  C   ILE A 187       5.153   15.132  35.170  1.00 41.68          C
ATOM   1301  O   ILE A 187       5.990          42.19 1.00  35.314   16.025  O
ATOM   1302  N   ASP A 188       5.224   13.973  35.816  1.00 42.34          N
ATOM   1303  CA  ASP A 188       6.272   13.734  36.803  1.00 43.99          C
ATOM   1304  CB  ASP A 188       6.107   12.367  37.445  1.00         43.99  C
ATOM   1305  CG  ASP A 188       7.166   12.103  38.498  1.00 46.71          C
ATOM   1306  OD1 ASP A 188       6.771   12.113  39.674  1.00 54.14          O
ATOM   1307  OD2 ASP A 188       8.395   11.890  38.288  1.00 46.00          O
ATOM   1308  C   ASP A 188       7.669   13.854  36.152  1.00 44.28          C
ATOM   1309  O   ASP A 188       7.903   13.274  35.100  1.00 44.24          O
ATOM   1310  N   PRO A 189       8.579   14.619  36.756  1.00 44.93          N
ATOM   1311  CA  PRO A 189       9.864   14.915  36.102  1.00 45.08          C
ATOM   1312  CB  PRO A 189      10.533   15.903  37.071  1.00 45.61          C
ATOM   1313  CG  PRO A 189       9.354   16.486  37.816  1.00 46.54          C
ATOM   1314  CD  PRO A 189       8.478          44.80 1.00  38.077   15.276  C
ATOM   1315  C   PRO A 189      10.725   13.657  35.875  1.00 43.88          C
ATOM   1316  O   PRO A 189      11.359   13.568  34.824  1.00 44.54          O
ATOM   1317  N   TYR A 190      10.719   12.705  36.788         42.19 1.00   N
ATOM   1318  CA  TYR A 190      11.443   11.450  36.578  1.00 42.19          C
ATOM   1319  CB  TYR A 190      11.381   10.565  37.831  1.00 42.69          C
ATOM   1320  CG  TYR A 190      12.615   10.500  38.724  1.00 46.62          C
ATOM   1321  CD1 TYR A 190      13.892   10.953  38.315  1.00 51.01          C
ATOM   1322  CE1 TYR A 190      15.054   10.845  39.215  1.00 53.20          C
ATOM   1323  CZ  TYR A 190      14.877   10.293  40.514  1.00 55.24          C
ATOM   1324  OH  TYR A 190      15.910   10.121  41.462  1.00 56.77          O
ATOM   1325  CE2 TYR A 190      13.599    9.858  40.906  1.00 54.03          C
ATOM   1326  CD2 TYR A 190      12.497    9.954  40.016  1.00 52.80          C
ATOM   1327  C   TYR A 190      10          40.57 1.00  35.367   10.707  860.C
ATOM   1328  O   TYR A 190      11.596   10.319  34.452  1.00 40.37          O
ATOM   1329  N   LEU A 191       9.540   10.544  35.350  1.00 38.75          N
ATOM   1330  CA  LEU A 191       8.862    9.844  34.263         38.05 1.00   C
ATOM   1331  CB  LEU A 191       7.372    9.674  34.534  1.00 38.10          C
ATOM   1332  CG  LEU A 191       6.944    8.245  34.960  1.00 38.94          C
ATOM   1333  CD1 LEU A 191       7.911    7.627  35.957  1.00 37.28          C
ATOM   1334  CD2 LEU A 191       5.529    8.208  35.514  1.00 36.41          C
ATOM   1335  C   LEU A 191       9.134   10.506  32.922  1.00 38.09          C
ATOM   1336  O   LEU A 191       9.462    9.841  31.947  1.00 37.65          O
ATOM   1337  N   LYS A 192       8.987   11.827  32.879  1.00 37.85          N
ATOM   1338  CA  LYS A 192       9.101   12.518  31.633  1.00 39.20          C
ATOM   1339  CB  LYS A 192       8.502   13.953  31.684  1.00 38.95          C
ATOM   1340  CG  LYS A 192              40.20 1.00  32.334   14.970    9.364  C
ATOM   1341  CD  LYS A 192       8.579   16.265  32.703  1.00 41.75          C
ATOM   1342  CE  LYS A 192       7.792   16.872  31.595  1.00 37.21          C
ATOM   1343  NZ  LYS A 192       7.452   18.283  31          41.51 1.00  960.N
ATOM   1344  C   LYS A 192      10.539   12.441  31.109  1.00 39.66          C
ATOM   1345  O   LYS A 192      10.753   12.355  29.908  1.00 39.59          O
ATOM   1346  N   SER A 193      11.528   12.470  31.991  1.00 39.94          N
ATOM   1347  CA  SER A 193      12.896   12.416  31.492  1.00 40.75          C
ATOM   1348  CB  SER A 193      13.902   12.837  32.565  1.00 40.72          C
```

Fig. 26 (Cont.)

```
ATOM   1349  OG   SER A 193      14.899   11.855   32.701  1.00 43.71           O
ATOM   1350  C    SER A 193      13.179   11.009   30.907  1.00 40.75           C
ATOM   1351  O    SER A 193      13.764   10.890   29.823  1.00 41.25           O
ATOM   1352  N    TRP A 194      12.710    9.959   31.571  1.00 39.07           N
ATOM   1353  CA   TRP A 194                39.61 1.00   30.935    8.647   12.746   C
ATOM   1354  CB   TRP A 194      12.166    7.606   31.838  1.00 39.71           C
ATOM   1355  CG   TRP A 194      13.020    7.048   32.886  1.00 44.92           C
ATOM   1356  CD1  TRP A 194      12.974    7.351           47.60 1.00    34.222   C
ATOM   1357  NE1  TRP A 194      13.821    6.532   34.929  1.00 51.38           N
ATOM   1358  CE2  TRP A 194      14.433    5.659   34.061  1.00 51.80           C
ATOM   1359  CD2  TRP A 194      13.943    5.946   32.757  1.00 51.01           C
ATOM   1360  CE3  TRP A 194      14.415    5.169   31.667  1.00 50.56           C
ATOM   1361  CZ3  TRP A 194      15.348    4.175   31.906  1.00 49.13           C
ATOM   1362  CH2  TRP A 194      15.825    3.923   33.217  1.00 51.31           C
ATOM   1363  CZ2  TRP A 194      15.382    4.650   34.304  1.00 51.07           C
ATOM   1364  C    TRP A 194      11.953    8.572   29.629  1.00 38.30           C
ATOM   1365  O    TRP A 194      12.432    7.992   28.640  1.00 37.45           O
ATOM   1366  N    GLU A 195                37.39 1.00   29.642    9.108   10.728   N
ATOM   1367  CA   GLU A 195       9.895    9.158   28.435  1.00 37.90           C
ATOM   1368  CB   GLU A 195       8.594    9.978   28.672  1.00 37.28           C
ATOM   1369  CG   GLU A 195       7.931   10.528           35.53 1.00    27.420   C
ATOM   1370  CD   GLU A 195       6.738   11.470   27.677  1.00 34.81           C
ATOM   1371  OE1  GLU A 195       6.363   11.775   28.851  1.00 33.01           O
ATOM   1372  OE2  GLU A 195       6.159   11.943   26.674  1.00 31           80.O
ATOM   1373  C    GLU A 195      10.707    9.739   27.262  1.00 38.60           C
ATOM   1374  O    GLU A 195      10.698    9.202   26.146  1.00 38.88           O
ATOM   1375  N    MET A 196      11.427   10.824   27.515  1.00 39.25           N
ATOM   1376  CA   MET A 196      12.205   11.430   26.464  1.00 41.10           C
ATOM   1377  CB   MET A 196      12.699   12.810   26.881  1.00 42.06           C
ATOM   1378  CG   MET A 196      13.511   13.452   25.769  1.00 42.76           C
ATOM   1379  SD   MET A          51.57 1.00   26.381   14.916   14.339      196 S
ATOM   1380  CE   MET A 196      15.633   14.177   27.586  1.00 43.59           C
ATOM   1381  C    MET A 196      13.381   10.557   25.969  1.00 42.12           C
ATOM   1382  O    MET A 196      13.563   10.396           42.18 1.00    24.730   O
ATOM   1383  N    HIS A 197      14.150    9.996   26.925  1.00 42.21           N
ATOM   1384  CA   HIS A 197      15.345    9.205   26.636  1.00 43.42           C
ATOM   1385  CB   HIS A 197      16.099    8.812   27.939  1.00           44.39 C
ATOM   1386  CG   HIS A 197      16.927    9.925   28.518  1.00 47.16           C
ATOM   1387  ND1  HIS A 197      18.297    9.842   28.655  1.00 49.28           N
ATOM   1388  CE1  HIS A 197      18.752   10.966   29.181  1.00 49.10           C
ATOM   1389  NE2  HIS A 197      17.729   11.777   29.385  1.00 49.11           N
ATOM   1390  CD2  HIS A 197      16.577   11.152   28.976  1.00 48.23           C
ATOM   1391  C    HIS A 197      14.991    7.944   25.872  1.00 42.96           C
ATOM   1392  O    HIS A 197      15.797    7.442   25.122  1.00 42.13           O
ATOM   1393  N    LEU A 198      13.774    7.441   26.069  1.00 42.35           N
ATOM   1394  CA   LEU A 198      13.378    6.217   25.391  1.00 41.91           C
ATOM   1395  CB   LEU A 198      12.346            41.46 1.00   26.218    5.439   C
ATOM   1396  CG   LEU A 198      12.899    4.761   27.484  1.00 42.82           C
ATOM   1397  CD1  LEU A 198      11.775    4.214   28.373  1.00 42.85           C
ATOM   1398  CD2  LEU A 198      13.890    3.656   27.156    1           40.77 00.C
ATOM   1399  C    LEU A 198      12.864    6.481   23.969  1.00 41.23           C
ATOM   1400  O    LEU A 198      12.662    5.541   23.212  1.00 41.86           O
ATOM   1401  N    GLY A 199      12.640    7.745   23.615  1.00 40.03           N
ATOM   1402  CA   GLY A 199      12.053    8.094   22.322  1.00 38.77           C
ATOM   1403  C    GLY A 199      10.646    7.542   22.051  1.00 37.47           C
ATOM   1404  O    GLY A 199      10.292    7.253   20.903  1.00 36.49           O
ATOM   1405  N    LEU A 200       9.854    7.416   23.113  1.00 36.79           N
ATOM   1406  CA   LEU A 200       8.436    7.034   23.052  1.00 36.92           C
ATOM   1407  CB   LEU A 200       7.791    7.101   24.457  1.00 36.26           C
ATOM   1408  CG   LEU A 200       8              37.87 1.00   25.509    6.065      193.C
ATOM   1409  CD1  LEU A 200       7.385    6.228   26.845  1.00 38.91           C
```

Fig. 26 (Cont.)

```
ATOM   1410  CD2  LEU A 200       8.061    4.609   24.964  1.00 37.18           C
ATOM   1411  C    LEU A 200       7.602    7.898   22.086       36.88 1.00      C
ATOM   1412  O    LEU A 200       6.682    7.374   21.459  1.00 38.03           O
ATOM   1413  N    ALA A 201       7.895    9.206   21.988  1.00 36.42           N
ATOM   1414  CA   ALA A 201       7.156   10.128   21.114  1.00 35.63           C
ATOM   1415  CB   ALA A 201       7.490    9.874   19.599  1.00 35.48           C
ATOM   1416  C    ALA A 201       5.642   10.081   21.353  1.00 35.21           C
ATOM   1417  O    ALA A 201       4.881    9.818   20.441  1.00 34.83           O
ATOM   1418  N    TRP A 202       5.218   10.330   22.600  1.00 36.17           N
ATOM   1419  CA   TRP A 202       3.805   10.329   23.007  1.00 35.90           C
ATOM   1420  CB   TRP A 202       3.647    9.587   24.313  1.00 35.09           C
ATOM   1421  CG   TRP A 202          36.25 1.00   24.224    8.116    3.761      C
ATOM   1422  CD1  TRP A 202       3.933    7.360   23.091  1.00 35.22           C
ATOM   1423  NE1  TRP A 202       3.976    6.027   23.421  1.00 30.37           N
ATOM   1424  CE2  TRP A 202       3.874    5.890   24       34.24 1.00    777.C
ATOM   1425  CD2  TRP A 202       3.725    7.187   25.323  1.00 33.98           C
ATOM   1426  CE3  TRP A 202       3.573    7.323   26.718  1.00 35.51           C
ATOM   1427  CZ3  TRP A 202       3.566    6.170   27.514  1.00 36.58           C
ATOM   1428  CH2  TRP A 202       3.715    4.884   26.937  1.00 36.85           C
ATOM   1429  CZ2  TRP A 202       3.863    4.719   25.575  1.00 36.13           C
ATOM   1430  C    TRP A 202       3.330   11.755   23.256  1.00 36.55           C
ATOM   1431  O    TRP A 202       2.251   11.973   23.807  1.00 37.44           O
ATOM   1432  N    SER A 203       4.152   12.714   22.911  1.00 35.70           N
ATOM   1433  CA   SER A 203       3.769   14.092   23.098  1.00 37.59           C
ATOM   1434  CB   SER A 203          37.00 1.00   23.098   14.968    5.039      C
ATOM   1435  OG   SER A 203       5.070   15.767   21.982  1.00 38.93           O
ATOM   1436  C    SER A 203       2.699   14.511   22.053  1.00 36.66           C
ATOM   1437  O    SER A 203       2.579   13.907            36.47 1.00    20.994 O
ATOM   1438  N    PHE A 204       1.921   15.531   22.366  1.00 35.35           N
ATOM   1439  CA   PHE A 204       0.746   15.814   21.550  1.00 36.01           C
ATOM   1440  CB   PHE A 204      -0.420   14.835   21.933  1.00 34.15           C
ATOM   1441  CG   PHE A 204      -0.892   14.996   23.336  1.00 35.45           C
ATOM   1442  CD1  PHE A 204      -1.998   15.778   23.621  1.00 32.40           C
ATOM   1443  CE1  PHE A 204      -2.444   15.959   24.957  1.00 31.73           C
ATOM   1444  CZ   PHE A 204      -1.792   15.314   26.033  1.00 34.00           C
ATOM   1445  CE2  PHE A 204      -0.693   14.497   25.755  1.00 36.88           C
ATOM   1446  CD2  PHE A 204      -0.217   14.371   24.412  1.00 37.67           C
ATOM   1447  C    PHE A 204          34.75 1.00   21.643   17.267    0.280      C
ATOM   1448  O    PHE A 204       0.725   18.032   22.538  1.00 36.33           O
ATOM   1449  N    VAL A 205      -0.635   17.614   20.749  1.00 34.02           N
ATOM   1450  CA   VAL A 205      -1.121   18.985            33.36 1.00    20.524 C
ATOM   1451  CB   VAL A 205      -0.925   19.335   19.104  1.00 32.87           C
ATOM   1452  CG1  VAL A 205      -1.524   20.723   18.846  1.00 33.78           C
ATOM   1453  CG2  VAL A 205       0.581   19.360   18.805  1.00 35        25.C
ATOM   1454  C    VAL A 205      -2.640   19.062   20.807  1.00 33.87           C
ATOM   1455  O    VAL A 205      -3.372   18.168   20.415  1.00 32.64           O
ATOM   1456  N    THR A 206      -3.073   20.106   21.549  1.00 34.41           N
ATOM   1457  CA   THR A 206      -4.426   20.200   22.122  1.00 34.15           C
ATOM   1458  CB   THR A 206      -4.322   20.220   23.649  1.00 33.81           C
ATOM   1459  OG1  THR A 206      -3.923   18.928   24.072  1.00 35.89           O
ATOM   1460  CG2  THR A           31.04 1.00   24.332   20.341    5.678-   206 C
ATOM   1461  C    THR A 206      -4.974   21.529   21.636  1.00 33.88           C
ATOM   1462  O    THR A 206      -4.257   22.515   21.651  1.00 33.11           O
ATOM   1463  N    TYR A 207      -6.229   21              33.18 1.00    21.207  522.N
ATOM   1464  CA   TYR A 207      -6.984   22.722   20.902  1.00 32.30           C
ATOM   1465  CB   TYR A 207      -7.959   22.432   19.748  1.00 31.79           C
ATOM   1466  CG   TYR A 207      -8.966   23.565   19.620  1.00          34.07 C
ATOM   1467  CD1  TYR A 207      -8.544   24.893   19.251  1.00 35.44           C
ATOM   1468  CE1  TYR A 207      -9.472   25.964   19.197  1.00 35.03           C
ATOM   1469  CZ   TYR A 207     -10.806   25.686   19.416  1.00 39.56           C
ATOM   1470  OH   TYR A 207     -11.731   26.690   19.331  1.00 42.12           O
```

Fig. 26 (Cont.)

```
ATOM   1471  CE2 TYR A 207     -11.231  24.406  19.808  1.00 36.43           C
ATOM   1472  CD2 TYR A 207     -10.286  23.361  19.912  1.00 33.51           C
ATOM   1473  C   TYR A 207      -7.785  22.989  22.160  1.00 30.71           C
ATOM   1474  O   TYR A 207      -8.486  22.101  22.617  1.00 31.92           O
ATOM   1475  N   TYR A 208      -7.703  24.189  22.726  1.00 32.09           N
ATOM   1476  CA  TYR A 208      -8.431          32.10 1.00  23.968  24.523   C
ATOM   1477  CB  TYR A 208      -7.493  25.086  25.064  1.00 32.59           C
ATOM   1478  CG  TYR A 208      -8.293  25.529  26.307  1.00 32.32           C
ATOM   1479  CD1 TYR A 208      -8.567  24.641  27.360  1            31.65 00.C
ATOM   1480  CE1 TYR A 208      -9.395  25.014  28.470  1.00 31.66           C
ATOM   1481  CZ  TYR A 208      -9.915  26.291  28.462  1.00 35.28           C
ATOM   1482  OH  TYR A 208     -10.707  26.778  29.480  1.00 42.53           O
ATOM   1483  CE2 TYR A 208      -9.670  27.169  27.417  1.00 34.37           C
ATOM   1484  CD2 TYR A 208      -8.843  26.796  26.355  1.00 32.42           C
ATOM   1485  C   TYR A 208      -9.409  25.623  23.653  1.00 33.74           C
ATOM   1486  O   TYR A 208      -9.027  26.611  23.050  1.00 35.53           O
ATOM   1487  N   SER A 209     -10.666  25.493  24.052  1.00 34.12           N
ATOM   1488  CA  SER A 209     -11.575  26.635  24.041  1.00 34.18           C
ATOM   1489  CB  SER A 209     -12.385          32.98 1.00  22.728  26.638   C
ATOM   1490  OG  SER A 209     -13.343  25.606  22.742  1.00 32.66           O
ATOM   1491  C   SER A 209     -12.500  26.513  25.269  1.00 36.12           C
ATOM   1492  O   SER A 209     -12.624  25.425  25.834         35.32 1.00    O
ATOM   1493  N   PRO A 210     -13.196  27.588  25.681  1.00 38.21           N
ATOM   1494  CA  PRO A 210     -14.197  27.438  26.740  1.00 39.98           C
ATOM   1495  CB  PRO A 210     -14.984  28.788  26.719  1.00 40.45           C
ATOM   1496  CG  PRO A 210     -13.966  29.841  26.093  1.00 40.19           C
ATOM   1497  CD  PRO A 210     -13.115  28.980  25.170  1.00 39.38           C
ATOM   1498  C   PRO A 210     -15.172  26.258  26.397  1.00 40.69           C
ATOM   1499  O   PRO A 210     -15.499  25.437  27.262  1.00 41.13           O
ATOM   1500  N   ASN A 211     -15.627  26.165  25.155  1.00 39.29           N
ATOM   1501  CA  ASN A 211     -16.716  25.212  24.891  1.00 41.22           C
ATOM   1502  CB  ASN A 211     -17.585          40.75 1.00  23.679  25.681   C
ATOM   1503  CG  ASN A 211     -16.717  25.951  22.406  1.00 46.82           C
ATOM   1504  OD1 ASN A 211     -15.930  26.931  22.329  1.00 49.42           O
ATOM   1505  ND2 ASN A 211     -16.813  25.029  21.436         49.92 1.00    N
ATOM   1506  C   ASN A 211     -16.198  23.735  24.793  1.00 39.70           C
ATOM   1507  O   ASN A 211     -16.920  22.789  25.119  1.00 41.33           O
ATOM   1508  N   ASP A 212     -14.924  23.561  24.447  1.00 38.23           N
ATOM   1509  CA  ASP A 212     -14.448  22.269  23.898  1.00 37.70           C
ATOM   1510  CB  ASP A 212     -14.871  22.121  22.417  1.00 37.36           C
ATOM   1511  CG  ASP A 212     -14.723  20.683  21.894  1.00 41.06           C
ATOM   1512  OD1 ASP A 212     -14.967  19.711  22.640  1.00 42.10           O
ATOM   1513  OD2 ASP A 212     -14.400  20.422  20.725  1.00 47.53           O
ATOM   1514  C   ASP A 212     -12.933  22.120  23.941  1.00 35.09           C
ATOM   1515  O   ASP A 212           34.27 1.00  23.453  23.005  12.224-     O
ATOM   1516  N   VAL A 213     -12.462  20.995  24.469  1.00 33.06           N
ATOM   1517  CA  VAL A 213     -11.023  20.776  24.590  1.00 32.70           C
ATOM   1518  CB  VAL A 213     -10.462  20.941  26.046         32.33 1.00    C
ATOM   1519  CG1 VAL A 213      -8.934  20.868  26.036  1.00 29.18           C
ATOM   1520  CG2 VAL A 213     -10.883  22.316  26.682  1.00 30.93           C
ATOM   1521  C   VAL A 213     -10.692  19.426  24.014  1.00 33.38           C
ATOM   1522  O   VAL A 213     -11.220  18.446  24.434  1.00 35.21           O
ATOM   1523  N   ARG A 214      -9.832  19.364  23.023  1.00 34.57           N
ATOM   1524  CA  ARG A 214      -9.581  18.053  22.449  1.00 36.05           C
ATOM   1525  CB  ARG A 214     -10.708  17.638  21.464  1.00 37.44           C
ATOM   1526  CG  ARG A 214     -10.618  18.255  20.056  1.00 41.30           C
ATOM   1527  CD  ARG A 214     -11.954  18.063  19.253  1.00 48.50           C
ATOM   1528  NE  ARG A 214           47.81 1.00  19.142  19.333  12.666-     N
ATOM   1529  CZ  ARG A 214     -12.620  20.175  18.089  1.00 47.92           C
ATOM   1530  NH1 ARG A 214     -11.944  19.902  16.975  1.00 44.27           N
ATOM   1531  NH2 ARG A 214     -13.297  21.313          50.14 1.00  18.166   N
```

Fig. 26 (Cont.)

```
ATOM   1532  C    ARG A 214      -8.178  17.952  21.839  1.00 35.49           C
ATOM   1533  O    ARG A 214      -7.568  18.975  21.442  1.00 35.13           O
ATOM   1534  N    VAL A 215      -7.671  16.719  21.792  1.00 35.46           N
ATOM   1535  CA   VAL A 215      -6.390  16.438  21.159  1.00 36.10           C
ATOM   1536  CB   VAL A 215      -5.892  15.001  21.504  1.00 37.17           C
ATOM   1537  CG1  VAL A 215      -4.480  14.680  20.726  1.00 36.30           C
ATOM   1538  CG2  VAL A 215      -5.765  14.871  22.990  1.00 35.21           C
ATOM   1539  C    VAL A 215      -6.549  16.565  19.633  1.00 36.21           C
ATOM   1540  O    VAL A 215      -7.468  16.011  19.071  1.00 35.76           O
ATOM   1541  N    VAL A 216              36.46 1.00   18.969  17.287   5.653- N
ATOM   1542  CA   VAL A 216      -5.797  17.486  17.524  1.00 35.77           C
ATOM   1543  CB   VAL A 216      -5.926  19.002  17.131  1.00 34.87           C
ATOM   1544  CG1  VAL A 216      -7.317  19              36.99 1.00   17.442   527.C
ATOM   1545  CG2  VAL A 216      -4.877  19.802  17.768  1.00 31.92           C
ATOM   1546  C    VAL A 216      -4.668  16.870  16.713  1.00 35.54           C
ATOM   1547  O    VAL A 216      -4.770  16.832  15.524  1.00 35.08           O
ATOM   1548  N    ALA A 217      -3.604  16.415  17.361  1.00 35.18           N
ATOM   1549  CA   ALA A 217      -2.524  15.685  16.701  1.00 35.16           C
ATOM   1550  CB   ALA A 217      -1.642  16.630  15.876  1.00 34.45           C
ATOM   1551  C    ALA A 217      -1.674  15.035  17.795  1.00 36.43           C
ATOM   1552  O    ALA A 217      -1.573  15.563  18.970  1.00 35.76           O
ATOM   1553  N    GLU A 218      -1.058  13.903  17.438  1.00 36.01           N
ATOM   1554  CA   GLU A 218      -0.283  13.170  18.428  1.00 36.92           C
ATOM   1555  CB   GLU A 218      -1.217  12.189  19.140  1.00 36.85           C
ATOM   1556  CG   GLU A 218      -2.007  11.319  18.211  1.00 41.31           C
ATOM   1557  CD   GLU A 218      -3.192           48.35 1.00   18.937  10.712 C
ATOM   1558  OE1  GLU A 218      -3.812   9.825  18.372  1.00 49.59           O
ATOM   1559  OE2  GLU A 218      -3.484  11.103  20.086  1.00 51.24           O
ATOM   1560  C    GLU A 218       0.961  12.459  17.882  1.00         35.60 C
ATOM   1561  O    GLU A 218       1.309  12.638  16.721  1.00 36.76           O
ATOM   1562  N    GLY A 219       1.615  11.650  18.715  1.00 33.76           N
ATOM   1563  CA   GLY A 219       2.759  10.852  18.269  1.00 32.34           C
ATOM   1564  C    GLY A 219       4.047  11.661  18.089  1.00 33.60           C
ATOM   1565  O    GLY A 219       4.916  11.228  17.385  1.00 33.73           O
ATOM   1566  N    PHE A 220       4.167  12.836  18.715  1.00 33.06           N
ATOM   1567  CA   PHE A 220       5.340  13.697  18.561  1.00 34.63           C
ATOM   1568  CB   PHE A 220       4.972  15.145  18.840  1.00 34.25           C
ATOM   1569  CG   PHE A 220       4.084  15.733  17.817  1.00 37.73           C
ATOM   1570  CD1  PHE A 220       4.610           41.73 1.00   16.709  16.380 C
ATOM   1571  CE1  PHE A 220       3.756  16.934  15.723  1.00 43.00           C
ATOM   1572  CZ   PHE A 220       2.384  16.846  15.858  1.00 39.52           C
ATOM   1573  CE2  PHE A 220       1.859  16.257  17.013          45.41 1.00   C
ATOM   1574  CD2  PHE A 220       2.710  15.694  17.978  1.00 42.24           C
ATOM   1575  C    PHE A 220       6.508  13.366  19.480  1.00 34.67           C
ATOM   1576  O    PHE A 220       6.325  13.095  20.695  1.00 35.59           O
ATOM   1577  N    ASP A 221       7.706  13.435  18.904  1.00 33.89           N
ATOM   1578  CA   ASP A 221       8.948  13.416  19.663  1.00 33.44           C
ATOM   1579  CB   ASP A 221      10.020  12.854  18.721  1.00 33.92           C
ATOM   1580  CG   ASP A 221      11.304  12.473  19.436  1.00 35.43           C
ATOM   1581  OD1  ASP A 221      11.437  12.839  20.617  1.00 35.11           O
ATOM   1582  OD2  ASP A 221      12.234  11.801  18.899  1.00 41.97           O
ATOM   1583  C    ASP A 221       9              34.54 1.00   20.086  14.891   282.C
ATOM   1584  O    ASP A 221      10.005  15.619  19.361  1.00 33.14           O
ATOM   1585  N    PHE A 222       8.747  15.330  21.231  1.00 33.94           N
ATOM   1586  CA   PHE A 222       9.047  16.674  21.761          33.30 1.00   C
ATOM   1587  CB   PHE A 222      10.566  16.854  22.053  1.00 32.65           C
ATOM   1588  CG   PHE A 222      10.891  17.773  23.255  1.00 33.66           C
ATOM   1589  CD1  PHE A 222      11.593  17.277  24.372  1.00 36.34           C
ATOM   1590  CE1  PHE A 222      11.880  18.160  25.505  1.00 38.03           C
ATOM   1591  CZ   PHE A 222      11.494  19.546  25.450  1.00 36.47           C
ATOM   1592  CE2  PHE A 222      10.813  20.032  24.345  1.00 34.11           C
```

Fig. 26 (Cont.)

```
ATOM   1593  CD2 PHE A 222      10.496  19.131  23.269  1.00 35.96           C
ATOM   1594  C   PHE A 222       8.420  17.855  20.958  1.00 34.04           C
ATOM   1595  O   PHE A 222       9.126  18.730  20.423  1.00 32.37           O
ATOM   1596  N   ALA A 223          34.22 1.00  20.913  17.908   7.074       N
ATOM   1597  CA  ALA A 223       6.406  19.013  20.213  1.00 34.27           C
ATOM   1598  CB  ALA A 223       4.863  18.822  20.190  1.00 34.06           C
ATOM   1599  C   ALA A 223       6.760  20.296  20          35.31 1.00   960.C
ATOM   1600  O   ALA A 223       6.821  20.301  22.191  1.00 37.19           O
ATOM   1601  N   ASN A 224       6.980  21.390  20.253  1.00 34.59           N
ATOM   1602  CA  ASN A 224       7.650  22.488  20.880  1.00 35.73           C
ATOM   1603  CB  ASN A 224       9.202  22.365  20.626  1.00 36.23           C
ATOM   1604  CG  ASN A 224      10.002  23.318  21.552  1.00 40.60           C
ATOM   1605  OD1 ASN A 224       9.567  24.480  21.767  1.00 42.19           O
ATOM   1606  ND2 ASN A 224      11.090  22.851  22.138  1.00 36.47           N
ATOM   1607  C   ASN A 224       7.000  23.782  20.315  1.00 36.15           C
ATOM   1608  O   ASN A 224       5.852  24.113  20.682  1.00 36.50           O
ATOM   1609  N   GLY A 225          35.82 1.00  19.364  24.471   7.628       N
ATOM   1610  CA  GLY A 225       6.993  25.684  18.820  1.00 34.57           C
ATOM   1611  C   GLY A 225       5.700  25.371  18.073  1.00 35.14           C
ATOM   1612  O   GLY A 225       5.492  24.256          35.30 1.00   17.572  O
ATOM   1613  N   ILE A 226       4.834  26.372  17.997  1.00 34.19           N
ATOM   1614  CA  ILE A 226       3.637  26.320  17.256  1.00 34.22           C
ATOM   1615  CB  ILE A 226       2.522  25.670  18.071  1.00 35.34           C
ATOM   1616  CG1 ILE A 226       1.258  25.449  17.205  1.00 32.85           C
ATOM   1617  CD1 ILE A 226       0.353  24.265  17.910  1.00 33.04           C
ATOM   1618  CG2 ILE A 226       2.238  26.412  19.407  1.00 32.98           C
ATOM   1619  C   ILE A 226       3.229  27.743  16.836  1.00 35.59           C
ATOM   1620  O   ILE A 226       3.402  28.751  17.578  1.00 35.03           O
ATOM   1621  N   ASN A 227       2.680  27.825  15.641  1.00 33.34           N
ATOM   1622  CA  ASN A 227          35.08 1.00  15.208  29.118   2.221       C
ATOM   1623  CB  ASN A 227       3.443  30.028  14.830  1.00 33.87           C
ATOM   1624  CG  ASN A 227       3.156  31.492  15.149  1.00 39.07           C
ATOM   1625  OD1 ASN A 227       2.038  32.013          38.03 1.00   14.811  O
ATOM   1626  ND2 ASN A 227       4.091  32.142  15.857  1.00 33.37           N
ATOM   1627  C   ASN A 227       1.219  28.898  14.047  1.00 33.72           C
ATOM   1628  O   ASN A 227       0.829  27.759  13.755  1.00 32          82.0
ATOM   1629  N   ILE A 228       0.810  29.989  13.426  1.00 33.95           N
ATOM   1630  CA  ILE A 228      -0.287  29.998  12.491  1.00 34.03           C
ATOM   1631  CB  ILE A 228      -1.607  30.305  13.267  1.00 34.51           C
ATOM   1632  CG1 ILE A 228      -2.817  29.997  12.400  1.00 34.96           C
ATOM   1633  CD1 ILE A 228      -4.091  29.933  13.306  1.00 35.98           C
ATOM   1634  CG2 ILE A 228      -1.676  31.847  13.851  1.00 34.14           C
ATOM   1635  C   ILE A           35.04 1.00  11.358  31.026   0.012-    228  C
ATOM   1636  O   ILE A 228       0.711  31.993  11.575  1.00 35.49           O
ATOM   1637  N   SER A 229      -0.545  30.805  10.160  1.00 35.67           N
ATOM   1638  CA  SER A 229      -0.343  31.728          35.66 1.00    9.058  C
ATOM   1639  CB  SER A 229      -0.757  31.066   7.765  1.00 34.71           C
ATOM   1640  OG  SER A 229      -2.137  30.758   7.799  1.00 38.04           O
ATOM   1641  C   SER A 229      -1.237  32.962   9.309  1.00         36.98  C
ATOM   1642  O   SER A 229      -2.203  32.858  10.016  1.00 36.31           O
ATOM   1643  N   PRO A 230      -0.901  34.131   8.747  1.00 38.20           N
ATOM   1644  CA  PRO A 230      -1.669  35.371   8.996  1.00 37.65           C
ATOM   1645  CB  PRO A 230      -1.003  36.404   8.092  1.00 36.93           C
ATOM   1646  CG  PRO A 230       0.448  35.846   7.906  1.00 39.20           C
ATOM   1647  CD  PRO A 230       0.250  34.343   7.851  1.00 37.52           C
ATOM   1648  C   PRO A 230      -3.131  35.243   8.566  1.00 38.23           C
ATOM   1649  O   PRO A 230      -3.966  35.905   9.150  1.00 37.26           O
ATOM   1650  N   ASP A 231      -3.450  34.417   7.579  1.00 38.05           N
ATOM   1651  CA  ASP A 231      -4.865          38.03 1.00    7.213  34.269  C
ATOM   1652  CB  ASP A 231      -5.010  33.982   5.712  1.00 38.26           C
ATOM   1653  CG  ASP A 231      -4.456  32.603   5.293  1.00 39.32           C
```

Fig. 26 (Cont.)

```
ATOM   1654  OD1 ASP A 231      -4.033  31.814   6.154  1            38.99 00.O
ATOM   1655  OD2 ASP A 231      -4.404  32.212   4.081  1.00 44.52         O
ATOM   1656  C   ASP A 231      -5.574  33.180   8.043  1.00 37.92         C
ATOM   1657  O   ASP A 231      -6.713  32.863   7.769  1.00 37.83         O
ATOM   1658  N   GLY A 232      -4.869  32.544   8.974  1.00 36.65         N
ATOM   1659  CA  GLY A 232      -5.503  31.580   9.847  1.00 37.03         C
ATOM   1660  C   GLY A 232      -5.762  30.189   9.274  1.00 37.14         C
ATOM   1661  O   GLY A 232      -6.376  29.336   9.953  1.00 36.74         O
ATOM   1662  N   LYS A 233      -5.318  29.949   8.043  1.00 37.01         N
ATOM   1663  CA  LYS A 233      -5.631  28.710   7.327  1.00 36.22         C
ATOM   1664  CB  LYS A 233      -5            36.25 1.00  5.838   28.948  577.C
ATOM   1665  CG  LYS A 233      -6.931  29.462   5.201  1.00 41.63         C
ATOM   1666  CD  LYS A 233      -6.707  29.815   3.703  1.00 46.11         C
ATOM   1667  CE  LYS A 233      -7.778  30.744   3.113        51.09 1.00   C
ATOM   1668  NZ  LYS A 233      -8.057  30.295   1.697  1.00 50.52         N
ATOM   1669  C   LYS A 233      -4.669  27.561   7.658  1.00 35.76         C
ATOM   1670  O   LYS A 233      -5.015  26.408   7.464  1.00 35.59         O
ATOM   1671  N   TYR A 234      -3.462  27.869   8.145  1.00 35.12         N
ATOM   1672  CA  TYR A 234      -2.410  26.871   8.263  1.00 34.22         C
ATOM   1673  CB  TYR A 234      -1.330  27.053   7.145  1.00 34.06         C
ATOM   1674  CG  TYR A 234      -1.896  26.919   5.732  1.00 32.79         C
ATOM   1675  CD1 TYR A 234      -2.148  25.670   5.174  1.00 32.97         C
ATOM   1676  CE1 TYR A 234      -2.745  25.543   3.856  1.00 33.54         C
ATOM   1677  CZ  TYR A 234             33.71 1.00   3.140   26.720   3.064- C
ATOM   1678  OH  TYR A 234      -3.580  26.644   1.890  1.00 36.22         O
ATOM   1679  CE2 TYR A 234      -2.815  27.975   3.694  1.00 33.01         C
ATOM   1680  CD2 TYR A 234      -2.221  28.061   4            33.12 1.00   974.C
ATOM   1681  C   TYR A 234      -1.819  26.963   9.637  1.00 34.94         C
ATOM   1682  O   TYR A 234      -1.568  28.074  10.114  1.00 34.72         O
ATOM   1683  N   VAL A 235      -1.623  25.809  10.293  1.00 35.14         N
ATOM   1684  CA  VAL A 235      -0.927  25.757  11.582  1.00 33.30         C
ATOM   1685  CB  VAL A 235      -1.784  25.013  12.660  1.00 34.41         C
ATOM   1686  CG1 VAL A 235      -0.989  24.687  13.999  1.00 32.89         C
ATOM   1687  CG2 VAL A 235      -3.024  25.863  13.023  1.00 30.91         C
ATOM   1688  C   VAL A 235       0.404  25.042  11.360  1.00 34.91         C
ATOM   1689  O   VAL A 235       0.468  24.051  10.587  1.00 35.77         O
ATOM   1690  N   TYR A 236             35.36 1.00  12.040   25.521   1.455 N
ATOM   1691  CA  TYR A 236       2.834  24.989  11.942  1.00 34.33         C
ATOM   1692  CB  TYR A 236       3.740  26.156  11.579  1.00 33.89         C
ATOM   1693  CG  TYR A 236       3.267  26.934         33.74 1.00  10.372  C
ATOM   1694  CD1 TYR A 236       3.099  26.288   9.127  1.00 34.90         C
ATOM   1695  CE1 TYR A 236       2.669  27.002   8.003  1.00 34.10         C
ATOM   1696  CZ  TYR A 236       2.457  28.374   8.130  1.00 32.56         C
ATOM   1697  OH  TYR A 236       2.046  29.045   7.039  1.00 30.56         O
ATOM   1698  CE2 TYR A 236       2.570  29.034   9.349  1.00 31.47         C
ATOM   1699  CD2 TYR A 236       3.009  28.334  10.450  1.00 31.61         C
ATOM   1700  C   TYR A 236       3.310  24.506  13.324  1.00 34.81         C
ATOM   1701  O   TYR A 236       3.156  25.201  14.358  1.00 33.79         O
ATOM   1702  N   ILE A 237       3.895  23.321  13.373  1.00 34.17         N
ATOM   1703  CA  ILE A 237             33.45 1.00  14.684   22.734   4.228 C
ATOM   1704  CB  ILE A 237       3.213  21.589  15.038  1.00 33.13         C
ATOM   1705  CG1 ILE A 237       1.748  22.142  15.043  1.00 32.08         C
ATOM   1706  CD1 ILE A 237       0.668  21.123         33.48 1.00  15.510  C
ATOM   1707  CG2 ILE A 237       3.519  21.003  16.437  1.00 31.16         C
ATOM   1708  C   ILE A 237       5.650  22.201  14.644  1.00 34.69         C
ATOM   1709  O   ILE A 237       5.961  21.381  13.808  1.00 34            41.O
ATOM   1710  N   ALA A 238       6.505  22.641  15.561  1.00 34.85         N
ATOM   1711  CA  ALA A 238       7.872  22.144  15.541  1.00 36.25         C
ATOM   1712  CB  ALA A 238       8.873  23.180  16.073  1.00 34.69         C
ATOM   1713  C   ALA A 238       7.958  20.846  16.328  1.00 36.17         C
ATOM   1714  O   ALA A 238       7.392  20.736  17.403  1.00 37.20         O
```

Fig. 26 (Cont.)

```
ATOM   1715  N   GLU A 239       8.703  19.888  15.799  1.00 34.77           N
ATOM   1716  CA  GLU A          35.09  1.00  16.527  18.654   8.956         239 C
ATOM   1717  CB  GLU A 239       8.442  17.456  15.732  1.00 31.86           C
ATOM   1718  CG  GLU A 239       8.367  16.212  16.541  1.00 31.78           C
ATOM   1719  CD  GLU A 239       8.051  14              34.25  1.00  15.664  954.C
ATOM   1720  OE1 GLU A 239       7.968  15.046  14.428  1.00 32.40           O
ATOM   1721  OE2 GLU A 239       7.888  13.868  16.217  1.00 31.65           O
ATOM   1722  C   GLU A 239      10.503  18.571  16.849  1.00            35.45 C
ATOM   1723  O   GLU A 239      11.326  18.085  16.017  1.00 34.63           O
ATOM   1724  N   LEU A 240      10.865  18.992  18.072  1.00 35.01           N
ATOM   1725  CA  LEU A 240      12.246  19.327  18.366  1.00 35.44           C
ATOM   1726  CB  LEU A 240      12.392  19.738  19.828  1.00 35.07           C
ATOM   1727  CG  LEU A 240      13.820  20.118  20.250  1.00 36.87           C
ATOM   1728  CD1 LEU A 240      14.025  21.662  20.091  1.00 34.53           C
ATOM   1729  CD2 LEU A 240      13.853  19.729  21.724  1.00 35.75           C
ATOM   1730  C   LEU A 240      13.204  18.198  18.043  1.00 34.48           C
ATOM   1731  O   LEU A 240      14.136  18.385  17.290  1.00 35.08           O
ATOM   1732  N   LEU A 241      12.961              33.89  1.00  18.643  17.026  N
ATOM   1733  CA  LEU A 241      13.903  15.948  18.584  1.00 33.80           C
ATOM   1734  CB  LEU A 241      13.876  15.078  19.843  1.00 33.54           C
ATOM   1735  CG  LEU A 241      14.353  15.748  21.142   1               34.64  00.C
ATOM   1736  CD1 LEU A 241      14.050  14.802  22.404  1.00 34.17           C
ATOM   1737  CD2 LEU A 241      15.889  16.154  21.148  1.00 34.36           C
ATOM   1738  C   LEU A 241      13.734  15.125  17.312  1.00 33.66           C
ATOM   1739  O   LEU A 241      14.592  14.349  16.982  1.00 35.43           O
ATOM   1740  N   ALA A 242      12.680  15.330  16.562  1.00 32.37           N
ATOM   1741  CA  ALA A 242      12.623  14.706  15.244  1.00 32.65           C
ATOM   1742  CB  ALA A 242      11.163  14.415  14.859  1.00 31.55           C
ATOM   1743  C   ALA A 242      13.256  15.662  14.238  1.00 32.61           C
ATOM   1744  O   ALA A 242      13.515  15.246  13.123  1.00 30.32           O
ATOM   1745  N   HIS A 243      13.469              32.82  1.00  14.620  16.945  N
ATOM   1746  CA  HIS A 243      14.081  17.947  13.709  1.00 34.94           C
ATOM   1747  CB  HIS A 243      15.457  17.478  13.059  1.00 34.98           C
ATOM   1748  CG  HIS A 243      16.451  16.816  13.983             35.62 1.00  C
ATOM   1749  ND1 HIS A 243      16.402  16.898  15.368  1.00 37.40           N
ATOM   1750  CE1 HIS A 243      17.429  16.237  15.879  1.00 35.13           C
ATOM   1751  NE2 HIS A 243      18.158  15.755  14.878  1.00 34.26           N
ATOM   1752  CD2 HIS A 243      17.579  16.120  13.691  1.00 33.81           C
ATOM   1753  C   HIS A 243      13.153  18.231  12.500  1.00 35.27           C
ATOM   1754  O   HIS A 243      13.632  18.266  11.377  1.00 35.17           O
ATOM   1755  N   LYS A 244      11.857  18.450  12.752  1.00 36.19           N
ATOM   1756  CA  LYS A 244      10.822  18.552  11.707  1.00 37.11           C
ATOM   1757  CB  LYS A 244      10.004  17.272  11.640  1.00 35.54           C
ATOM   1758  CG  LYS A 244      10.703              38.78  1.00  11.009  16.044  C
ATOM   1759  CD  LYS A 244       9.741  14.818  11.142  1.00 38.63           C
ATOM   1760  CE  LYS A 244      10.174  13.473  10.451  1.00 44.51           C
ATOM   1761  NZ  LYS A 244      11.534  13.637   9.940            45.51 1.00  N
ATOM   1762  C   LYS A 244       9.828  19.697  11.984  1.00 36.10           C
ATOM   1763  O   LYS A 244       9.600  20.046  13.126  1.00 37.18           O
ATOM   1764  N   ILE A 245       9.255  20.275  10.942  1.00 34.68           N
ATOM   1765  CA  ILE A 245       8.171  21.181  11.125  1.00 34.01           C
ATOM   1766  CB  ILE A 245       8.518  22.635  10.739  1.00 35.09           C
ATOM   1767  CG1 ILE A 245       9.496  23.233  11.786  1.00 36.46           C
ATOM   1768  CD1 ILE A 245       9.980  24.701  11.527  1.00 35.88           C
ATOM   1769  CG2 ILE A 245       7.225  23.456  10.774  1.00 34.11           C
ATOM   1770  C   ILE A 245       7.023  20.630  10.342  1.00 34.14           C
ATOM   1771  O   ILE A 245              32.50 1.00   9.176  20.321   7.169   O
ATOM   1772  N   HIS A 246       5.908  20.419  11.028  1.00 33.94           N
ATOM   1773  CA  HIS A 246       4.698  19.875  10.435  1.00 36.13           C
ATOM   1774  CB  HIS A 246       3.983  18.964  11.459            37.40 1.00  C
ATOM   1775  CG  HIS A 246       4.800  17.786  11.876  1.00 40.85           C
```

Fig. 26 (Cont.)

```
ATOM   1776  ND1  HIS A 246      4.511   16.493   11.475  1.00 40.37           N
ATOM   1777  CE1  HIS A 246      5.426   15.671   11.960  1.00 41.19           C
ATOM   1778  NE2  HIS A 246      6.288   16.384   12.673  1.00 42.78           N
ATOM   1779  CD2  HIS A 246      5.934   17.713   12.612  1.00 41.46           C
ATOM   1780  C    HIS A 246      3.755   21.028   10.057  1.00 35.27           C
ATOM   1781  O    HIS A 246      3.528   21.946   10.834  1.00 34.92           O
ATOM   1782  N    VAL A 247      3.196   20.949    8.867  1.00 34.55           N
ATOM   1783  CA   VAL A 247      2.257   21.965    8.411  1.00 33.69           C
ATOM   1784  CB   VAL A 247              33.00 1.00    7.016   22.477   2.633  C
ATOM   1785  CG1  VAL A 247      1.596   23.524    6.525  1.00 32.18           C
ATOM   1786  CG2  VAL A 247      4.117   22.931    6.967  1.00 30.96           C
ATOM   1787  C    VAL A 247      0.859   21.329            33.03 1.00   8.325  C
ATOM   1788  O    VAL A 247      0.706   20.276    7.730  1.00 33.28           O
ATOM   1789  N    TYR A 248     -0.163   21.996    8.844  1.00 33.01           N
ATOM   1790  CA   TYR A 248     -1.514   21.417    8.818  1.00 33.18           C
ATOM   1791  CB   TYR A 248     -1.993   21.150   10.255  1.00 32.34           C
ATOM   1792  CG   TYR A 248     -1.165   20.148   11.021  1.00 33.30           C
ATOM   1793  CD1  TYR A 248     -1.553   18.769   11.097  1.00 36.14           C
ATOM   1794  CE1  TYR A 248     -0.794   17.840   11.787  1.00 32.15           C
ATOM   1795  CZ   TYR A 248      0.380   18.290   12.425  1.00 37.72           C
ATOM   1796  OH   TYR A 248      1.167   17.426   13.152  1.00 37.96           O
ATOM   1797  CE2  TYR A 248              36.39 1.00   12.404   19.630   0.759  C
ATOM   1798  CD2  TYR A 248      0.006   20.546   11.677  1.00 35.95           C
ATOM   1799  C    TYR A 248     -2.456   22.426    8.211  1.00 34.62           C
ATOM   1800  O    TYR A 248     -2.283   23                36.34 1.00   8.426     634.O
ATOM   1801  N    GLU A 249     -3.464   21.964    7.493  1.00 34.62           N
ATOM   1802  CA   GLU A 249     -4.632   22.778    7.217  1.00 36.83           C
ATOM   1803  CB   GLU A 249     -5.435   22.161    6.106  1.00 37.13           C
ATOM   1804  CG   GLU A 249     -5.532   23.024    4.872  1.00 41.49           C
ATOM   1805  CD   GLU A 249     -5.984   22.180    3.685  1.00 48.05           C
ATOM   1806  OE1  GLU A 249     -5.206   22.074    2.711  1.00 52.01           O
ATOM   1807  OE2  GLU A 249     -7.081   21.574    3.757  1.00 49.57           O
ATOM   1808  C    GLU A 249     -5.532   22.824    8.442  1.00 37.27           C
ATOM   1809  O    GLU A 249     -5.920   21.759    8.983  1.00 37.16           O
ATOM   1810  N    LYS A 250     -5.860   24.041    8.877  1.00 38.48           N
ATOM   1811  CA   LYS A 250     -6.791   24.273    9.983  1.00 39.55           C
ATOM   1812  CB   LYS A 250     -6.439   25.558   10.658  1.00 39.73           C
ATOM   1813  CG   LYS A 250     -7.575            42.77 1.00   11.482   26.197  C
ATOM   1814  CD   LYS A 250     -6.838   26.983   12.568  1.00 45.98           C
ATOM   1815  CE   LYS A 250     -7.589   28.251   13.103  1.00 48.52           C
ATOM   1816  NZ   LYS A 250     -8.159   29.168   12.046  1.00                44.19 N
ATOM   1817  C    LYS A 250     -8.203   24.489    9.442  1.00 41.62           C
ATOM   1818  O    LYS A 250     -8.425   25.516    8.813  1.00 41.69           O
ATOM   1819  N    HIS A 251     -9.129   23.557    9.709  1.00 42.98           N
ATOM   1820  CA   HIS A 251    -10.588   23.703    9.378  1.00 44.92           C
ATOM   1821  CB   HIS A 251    -11.248   22.305    9.247  1.00 43.65           C
ATOM   1822  CG   HIS A 251    -10.583   21.476    8.181  1.00 45.89           C
ATOM   1823  ND1  HIS A 251     -9.401   20.793    8.399  1.00 47.41           N
ATOM   1824  CE1  HIS A 251     -9.011   20.218    7.269  1.00 45.50           C
ATOM   1825  NE2  HIS A 251     -9.864   20.551    6.318  1.00 43.93           N
ATOM   1826  CD2  HIS A 251    -10.842            43.66 1.00    6.853   21.354  C
ATOM   1827  C    HIS A 251    -11.417   24.703   10.253  1.00 45.28           C
ATOM   1828  O    HIS A 251    -11.040   25.031   11.368  1.00 45.73           O
ATOM   1829  N    ALA A 252    -12.516   25.215    9.694            45.70 1.00  N
ATOM   1830  CA   ALA A 252    -13.409   26.175   10.350  1.00 44.79           C
ATOM   1831  CB   ALA A 252    -14.680   26.478    9.452  1.00 45.82           C
ATOM   1832  C    ALA A 252    -13.835   25.722   11.751  1.00 44.37           C
ATOM   1833  O    ALA A 252    -13.919   26.594   12.654  1.00 44.24           O
ATOM   1834  N    ASN A 253    -14.098   24.400   11.909  1.00 42.76           N
ATOM   1835  CA   ASN A 253    -14.238   23.686   13.207  1.00 40.47           C
ATOM   1836  CB   ASN A 253    -15.012   22.415   12.963  1.00 41.89           C
```

Fig. 26 (Cont.)

```
ATOM   1837  CG  ASN A 253     -14.189  21.349  12.301  1.00 40.91           C
ATOM   1838  OD1 ASN A 253     -13.009  21.510  12.099  1.00 38.94           O
ATOM   1839  ND2 ASN A 253     -14      44.42 1.00  11.942  20.239   832.N
ATOM   1840  C   ASN A 253     -12.976  23.299  14.060  1.00 40.89           C
ATOM   1841  O   ASN A 253     -13.076  22.445  15.009  1.00 40.45           O
ATOM   1842  N   TRP A 254     -11.794  23.878  13.717       37.62 1.00      N
ATOM   1843  CA  TRP A 254     -10.558  23.719  14.465  1.00 36.82           C
ATOM   1844  CB  TRP A 254     -10.704  24.179  15.932  1.00 37.12           C
ATOM   1845  CG  TRP A 254     -11.568  25.369  16.005  1.00 37.87           C
ATOM   1846  CD1 TRP A 254     -12.935  25.413  16.252  1.00 38.34           C
ATOM   1847  NE1 TRP A 254     -13.375  26.720  16.188  1.00 40.57           N
ATOM   1848  CE2 TRP A 254     -12.300  27.530  15.883  1.00 41.09           C
ATOM   1849  CD2 TRP A 254     -11.155  26.703  15.769  1.00 36.76           C
ATOM   1850  CE3 TRP A 254      -9.922  27.294  15.454  1.00 39.99           C
ATOM   1851  CZ3 TRP A 254      -9.861  28.691  15.277  1.00 41.21           C
ATOM   1852  CH2 TRP A 254       41.39 1.00  15.427  29.480  11.002-         C
ATOM   1853  CZ2 TRP A 254     -12.236  28.928  15.717  1.00 42.68           C
ATOM   1854  C   TRP A 254      -9.834  22.393  14.387  1.00 36.97           C
ATOM   1855  O   TRP A 254      -8.801  22.231  14        38.32 1.00   977.O
ATOM   1856  N   THR A 255     -10.343  21.454  13.632  1.00 36.63           N
ATOM   1857  CA  THR A 255      -9.619  20.255  13.242  1.00 36.57           C
ATOM   1858  CB  THR A 255     -10.656  19.501  12.336  1.00 36.57           C
ATOM   1859  OG1 THR A 255     -11.817  19.214  13.159  1.00 38.45           O
ATOM   1860  CG2 THR A 255     -10.198  18.171  11.849  1.00 33.27           C
ATOM   1861  C   THR A 255      -8.309  20.583  12.465  1.00 37.10           C
ATOM   1862  O   THR A 255      -8.290  21.584  11.733  1.00 38.03           O
ATOM   1863  N   LEU A 256      -7.262  19.744  12.572  1.00 36.14           N
ATOM   1864  CA  LEU A 256      -6.017  19.923  11.808  1.00 37.54           C
ATOM   1865  CB  LEU A 256       36.50 1.00  12.772  20.061   4.819-         C
ATOM   1866  CG  LEU A 256      -4.843  21.299  13.693  1.00 34.37           C
ATOM   1867  CD1 LEU A 256      -3.547  21.451  14.513  1.00 34.14           C
ATOM   1868  CD2 LEU A 256      -5.083  22.531          30.29 1.00  12.881   C
ATOM   1869  C   LEU A 256      -5.764  18.753  10.844  1.00 38.98           C
ATOM   1870  O   LEU A 256      -5.777  17.611  11.286  1.00 41.04           O
ATOM   1871  N   THR A 257      -5.549  18.979   9.548  1.00 38.73           N
ATOM   1872  CA  THR A 257      -5.203  17.829   8.724  1.00 39.22           C
ATOM   1873  CB  THR A 257      -6.232  17.572   7.571  1.00 40.16           C
ATOM   1874  OG1 THR A 257      -6.423  18.767   6.811  1.00 42.00           O
ATOM   1875  CG2 THR A 257      -7.650  17.261   8.146  1.00 38.88           C
ATOM   1876  C   THR A 257      -3.784  17.969   8.190  1.00 39.91           C
ATOM   1877  O   THR A 257      -3.442  19.014   7.635  1.00 40.06           O
ATOM   1878  N   PRO A 258       40.23 1.00   8.316  16.923   2.949-         N
ATOM   1879  CA  PRO A 258      -1.541  17.056   7.913  1.00 39.16           C
ATOM   1880  CB  PRO A 258      -0.956  15.667   8.155  1.00 38.49           C
ATOM   1881  CG  PRO A 258      -2.156  14.732          40.70 1.00   8.220   C
ATOM   1882  CD  PRO A 258      -3.286  15.554   8.791  1.00 40.04           C
ATOM   1883  C   PRO A 258      -1.478  17.438   6.433  1.00 38.89           C
ATOM   1884  O   PRO A 258      -2.216  16.926   5.563  1.00 38         18.O
ATOM   1885  N   LEU A 259      -0.614  18.385   6.136  1.00 39.12           N
ATOM   1886  CA  LEU A 259      -0.420  18.756   4.737  1.00 39.83           C
ATOM   1887  CB  LEU A 259      -0.902  20.191   4.549  1.00 40.10           C
ATOM   1888  CG  LEU A 259      -0.963  20.721   3.137  1.00 44.26           C
ATOM   1889  CD1 LEU A 259      -2.276  20.374   2.407  1.00 46.73           C
ATOM   1890  CD2 LEU A 259      -0.773  22.211   3.283  1.00 47.50           C
ATOM   1891  C   LEU A           39.16 1.00   4.217  18.484   1.015     259 C
ATOM   1892  O   LEU A 259       1.203  17.954   3.106  1.00 39.34           O
ATOM   1893  N   ARG A 260       2.025  18.848   4.994  1.00 38.61           N
ATOM   1894  CA  ARG A 260       3.404  18.445          38.48 1.00   4.700
ATOM   1895  CB  ARG A 260       4.201  19.383   3.776  1.00 39.66           C
ATOM   1896  CG  ARG A 260       3.742  20.726   3.426  1.00 40.88           C
ATOM   1897  CD  ARG A 260       3.847  20.826   1.876  1.00        51.43   C
```

Fig. 26 (Cont.)

```
ATOM   1898  NE   ARG A 260      2.587  20.284   1.335  1.00 53.92           N
ATOM   1899  CZ   ARG A 260      2.221  20.249   0.082  1.00 52.78           C
ATOM   1900  NH1  ARG A 260      3.063  20.646  -0.866  1.00 56.34           N
ATOM   1901  NH2  ARG A 260      1.023  19.730  -0.216  1.00 55.10           N
ATOM   1902  C    ARG A 260      4.262  18.423   5.935  1.00 37.66           C
ATOM   1903  O    ARG A 260      3.931  19.017   6.945  1.00 37.77           O
ATOM   1904  N    VAL A 261      5.458  17.888   5.764  1.00 37.57           N
ATOM   1905  CA   VAL A 261      6.448  17.816   6.819  1.00 38.02           C
ATOM   1906  CB   VAL A 261      6.521  16.357   7.401  1.00 38.76           C
ATOM   1907  CG1  VAL A 261      7.766                 39.41 1.00   8.295    16.189  C
ATOM   1908  CG2  VAL A 261      5.223  16.048   8.198  1.00 38.00           C
ATOM   1909  C    VAL A 261      7.795  18.277   6.269  1.00 37.12           C
ATOM   1910  O    VAL A 261      8.288  17.729   5.297  1             38.13 00.0
ATOM   1911  N    LEU A 262      8.366  19.303   6.865  1.00 37.51           N
ATOM   1912  CA   LEU A 262      9.737  19.713   6.531  1.00 38.67           C
ATOM   1913  CB   LEU A 262      9.883  21.269   6.572  1.00 38.26           C
ATOM   1914  CG   LEU A 262      9.412  21.981   5.286  1.00 41.28           C
ATOM   1915  CD1  LEU A 262      7.869  21.808   5.122  1.00 43.41           C
ATOM   1916  CD2  LEU A 262      9.776  23.472   5.339  1.00 39.71           C
ATOM   1917  C    LEU A 262     10.725  19.062   7.488  1.00 37.27           C
ATOM   1918  O    LEU A 262     10.500  19.067   8.700  1.00 36.24           O
ATOM   1919  N    SER A 263     11.832  18.583   6.941  1.00 36.36           N
ATOM   1920  CA   SER A 263     12             38.04 1.00   7.731    18.047    943.C
ATOM   1921  CB   SER A 263     13.368  16.666   7.148  1.00 36.52           C
ATOM   1922  OG   SER A 263     12.346  15.772   7.523  1.00 40.72           O
ATOM   1923  C    SER A 263     14.168  18.972   7.718         37.83 1.00    C
ATOM   1924  O    SER A 263     14.446  19.538   6.686  1.00 38.42           O
ATOM   1925  N    PHE A 264     14.919  19.043   8.827  1.00 36.61           N
ATOM   1926  CA   PHE A 264     16.083  19.936   8.980  1.00 36.30           C
ATOM   1927  CB   PHE A 264     15.726  21.115   9.935  1.00 36.87           C
ATOM   1928  CG   PHE A 264     14.507  21.889   9.475  1.00 37.45           C
ATOM   1929  CD1  PHE A 264     14.649  22.910   8.511  1.00 37.79           C
ATOM   1930  CE1  PHE A 264     13.553  23.568   8.018  1.00 39.33           C
ATOM   1931  CZ   PHE A 264     12.287  23.215   8.456  1.00 39.36           C
ATOM   1932  CE2  PHE A 264     12.122  22.176   9.378  1.00 38.00           C
ATOM   1933  CD2  PHE A 264            34.60 1.00   9.870    21.504    13.241 C
ATOM   1934  C    PHE A 264     17.206  19.136   9.592  1.00 36.50           C
ATOM   1935  O    PHE A 264     16.970  18.070  10.158  1.00 36.85           O
ATOM   1936  N    ASP A 265     18.421  19.660   9            36.87 1.00     563.N
ATOM   1937  CA   ASP A 265     19.516  18.968  10.283  1.00 37.94           C
ATOM   1938  CB   ASP A 265     20.831  18.952   9.457  1.00 38.26           C
ATOM   1939  CG   ASP A 265     21.274  20.364   9.035  1.00 43.72           C
ATOM   1940  OD1  ASP A 265     20.777  21.396   9.578  1.00 45.33           O
ATOM   1941  OD2  ASP A 265     22.149  20.550   8.151  1.00 54.99           O
ATOM   1942  C    ASP A 265     19.765  19.579  11.669  1.00 37.07           C
ATOM   1943  O    ASP A 265     20.901  19.509  12.156  1.00 37.89           O
ATOM   1944  N    THR A 266     18.737  20.195  12.282  1.00 35.90           N
ATOM   1945  CA   THR A 266     18.895  20.966  13.500  1.00 35.44           C
ATOM   1946  CB   THR A 266            36.08 1.00  13.157    22.460    19.248 C
ATOM   1947  OG1  THR A 266     19.646  23.162  14.358  1.00 36.78           O
ATOM   1948  CG2  THR A 266     18.081  23.261  12.662  1.00 34.22           C
ATOM   1949  C    THR A 266     17.632  20.812         36.81 1.00    14.372  C
ATOM   1950  O    THR A 266     16.584  20.461  13.841  1.00 37.12           O
ATOM   1951  N    LEU A 267     17.743  21.018  15.696  1.00 37.50           N
ATOM   1952  CA   LEU A 267     16.608  20.894  16.630  1.00 37.98           C
ATOM   1953  CB   LEU A 267     17.103  20.588  18.067  1.00 35.64           C
ATOM   1954  CG   LEU A 267     17.568  19.192  18.430  1.00 35.22           C
ATOM   1955  CD1  LEU A 267     18.899  18.818  17.688  1.00 30.53           C
ATOM   1956  CD2  LEU A 267     17.760  19.016  19.885  1.00 31.11           C
ATOM   1957  C    LEU A 267     15.808  22.190  16.606  1.00 39.17           C
ATOM   1958  O    LEU A 267     16.283  23.202  17.095  1.00 42.51           O
```

Fig. 26 (Cont.)

```
ATOM   1959  N    VAL A 268           39.30  1.00  16.078  22.176  14.599          N
ATOM   1960  CA   VAL A 268   13.806  23.403  15.880   1.00  37.75                 C
ATOM   1961  CB   VAL A 268   12.877  23.234  14.640   1.00  38.35                 C
ATOM   1962  CG1  VAL A 268   13.732  23.136          38.24  1.00   13.328         C
ATOM   1963  CG2  VAL A 268   12.104  21.903  14.690   1.00  35.74                 C
ATOM   1964  C    VAL A 268   12.984  23.638  17.179   1.00  38.43                 C
ATOM   1965  O    VAL A 268   12.308  22.717  17.683   1.00  37            53.O
ATOM   1966  N    ASP A 269   13.037  24.853  17.699   1.00  37.17                 N
ATOM   1967  CA   ASP A 269   12.410  25.205  18.945   1.00  37.21                 C
ATOM   1968  CB   ASP A 269   13.412  25.883  19.851   1.00  35.99                 C
ATOM   1969  CG   ASP A 269   13.025  25.735  21.335   1.00  42.48                 C
ATOM   1970  OD1  ASP A 269   13.811  25.162  22.161   1.00  42.40                 O
ATOM   1971  OD2  ASP A 269   11.908  26.084  21.787   1.00  41.03                 O
ATOM   1972  C    ASP A       36.62   1.00    18.672  26.058  11.140       269 C
ATOM   1973  O    ASP A 269   10.140  25.514  18.234   1.00  35.87                 O
ATOM   1974  N    ASN A 270   11.167  27.376  18.880   1.00  35.81                 N
ATOM   1975  CA   ASN A 270    9.976  28              34.09  1.00  18.661  198.C
ATOM   1976  CB   ASN A 270    9.900  29.328  19.686   1.00  33.24                 C
ATOM   1977  CG   ASN A 270    9.777  28.797  21.125   1.00  37.60                 C
ATOM   1978  OD1  ASN A 270    9.474  27.592  21.334   1.00              37.71 O
ATOM   1979  ND2  ASN A 270   10.002  29.650  22.109   1.00  40.19                 N
ATOM   1980  C    ASN A 270    9.906  28.754  17.220   1.00  35.29                 C
ATOM   1981  O    ASN A 270   10.942  29.118  16.630   1.00  33.80                 O
ATOM   1982  N    ILE A 271    8.669  28.838  16.701   1.00  34.26                 N
ATOM   1983  CA   ILE A 271    8.309  29.431  15.432   1.00  34.37                 C
ATOM   1984  CB   ILE A 271    7.282  28.512  14.723   1.00  34.35                 C
ATOM   1985  CG1  ILE A 271    7.860  27.083  14.520   1.00  34.42                 C
ATOM   1986  CD1  ILE A 271    6.757  25.991  13.994   1.00  31.41                 C
ATOM   1987  CG2  ILE A 271    6.835  29.095  13.364   1.00  33.52                 C
ATOM   1988  C    ILE A 271    7.660          36.19   1.00  15.644  30.812         C
ATOM   1989  O    ILE A 271    6.680  30.907  16.442   1.00  35.72                 O
ATOM   1990  N    SER A 272    8.168  31.845  14.917   1.00  34.15                 N
ATOM   1991  CA   SER A 272    7.482  33.144  14.663   1          35.58  00.C
ATOM   1992  CB   SER A 272    8.475  34.344  14.746   1.00  34.34                 C
ATOM   1993  OG   SER A 272    8.930  34.237  16.116   1.00  45.11                 O
ATOM   1994  C    SER A 272    7.065  33.167  13.217   1.00  34.65                 C
ATOM   1995  O    SER A 272    7.662  32.503  12.369   1.00  35.86                 O
ATOM   1996  N    VAL A 273    6.072  33.983  12.942   1.00  34.06                 N
ATOM   1997  CA   VAL A 273    5.552  34.186  11.611   1.00  33.23                 C
ATOM   1998  CB   VAL A 273    4.048  33.706  11.516   1.00  32.49                 C
ATOM   1999  CG1  VAL A 273    3.485  34.051  10.187   1.00  30.14                 C
ATOM   2000  CG2  VAL A 273    4.023  32.178  11.700   1.00  34.15                 C
ATOM   2001  C    VAL A 273    5.671          33.51   1.00  11.290  35.692         C
ATOM   2002  O    VAL A 273    5.210  36.545  12.066   1.00  33.38                 O
ATOM   2003  N    ASP A 274    6.297  36.008  10.151   1.00  33.40                 N
ATOM   2004  CA   ASP A 274    6.292  37.355   9.675          33.25  1.00          C
ATOM   2005  CB   ASP A 274    7.408  37.537   8.672   1.00  33.45                 C
ATOM   2006  CG   ASP A 274    7.375  38.935   8.011   1.00  37.92                 C
ATOM   2007  OD1  ASP A 274    6.923  39.900   8.673   1.00  40.51                 O
ATOM   2008  OD2  ASP A 274    7.758  39.199   6.831   1.00  42.64                 O
ATOM   2009  C    ASP A 274    4.888  37.647   9.072   1.00  34.23                 C
ATOM   2010  O    ASP A 274    4.488  37.020   8.088   1.00  33.77                 O
ATOM   2011  N    PRO A 275    4.140  38.586   9.653   1.00  35.07                 N
ATOM   2012  CA   PRO A 275    2.729  38.798   9.218   1.00  36.57                 C
ATOM   2013  CB   PRO A 275    2.165  39.873  10.199   1.00  35.47                 C
ATOM   2014  CG   PRO A 275           38.43   1.00   10.741  40.623   3.583        C
ATOM   2015  CD   PRO A 275    4.541  39.431  10.820   1.00  34.55                 C
ATOM   2016  C    PRO A 275    2.686  39.285   7.791   1.00  37.81                 C
ATOM   2017  O    PRO A 275    1.696  38.995   7.080          38.36  1.00          O
ATOM   2018  N    VAL A 276    3.744  39.984   7.329   1.00  38.59                 N
ATOM   2019  CA   VAL A 276    3.675  40.547   5.973   1.00  36.29                 C
```

Fig. 26 (Cont.)

```
ATOM   2020  CB   VAL A 276     4.694  41.683   5.742  1.00 37.07           C
ATOM   2021  CG1  VAL A 276     4.540  42.240   4.371  1.00 36.17           C
ATOM   2022  CG2  VAL A 276     4.506  42.816   6.733  1.00 37.33           C
ATOM   2023  C    VAL A 276     3.879  39.460   4.934  1.00 36.27           C
ATOM   2024  O    VAL A 276     3.203  39.417   3.957  1.00 37.78           O
ATOM   2025  N    THR A 277     4.792  38.544   5.108  1.00 35.62           N
ATOM   2026  CA   THR A 277     5.058  37.601   3.995  1.00 34.69           C
ATOM   2027  CB   THR A 277           35.19 1.00   3.845   37.326   6.630   C
ATOM   2028  OG1  THR A 277     7.177  36.964   5.135  1.00 30.50           O
ATOM   2029  CG2  THR A 277     7.394  38.542   3.375  1.00 35.59           C
ATOM   2030  C    THR A 277     4.474  36.221          34.81 1.00    4.344  C
ATOM   2031  O    THR A 277     4.446  35.356   3.473  1.00 32.82           O
ATOM   2032  N    GLY A 278     4.208  35.978   5.643  1.00 33.60           N
ATOM   2033  CA   GLY A 278     3.989  34.616   6.100  1.00 34.17           C
ATOM   2034  C    GLY A 278     5.206  33.698   6.375  1.00 35.09           C
ATOM   2035  O    GLY A 278     5.017  32.527   6.812  1.00 35.28           O
ATOM   2036  N    ASP A 279     6.433  34.167   6.115  1.00 34.69           N
ATOM   2037  CA   ASP A 279     7.656  33.401   6.391  1.00 34.40           C
ATOM   2038  CB   ASP A 279     8.945  34.272   6.187  1.00 35.43           C
ATOM   2039  CG   ASP A 279     9.145  34.732   4.776  1.00 34.63           C
ATOM   2040  OD1  ASP A 279           39.15 1.00   3.816   34.305   8.400   O
ATOM   2041  OD2  ASP A 279    10.086  35.524   4.515  1.00 37.56           O
ATOM   2042  C    ASP A 279     7.721  32.961   7.835  1.00 35.01           C
ATOM   2043  O    ASP A 279     7.336  33.729          35.36 1.00    8.728  O
ATOM   2044  N    LEU A 280     8.206  31.733   8.066  1.00 33.92           N
ATOM   2045  CA   LEU A 280     8.508  31.285   9.406  1.00 34.98           C
ATOM   2046  CB   LEU A 280     8.380  29.757   9.477  1.00 35.21           C
ATOM   2047  CG   LEU A 280     6.944  29.217   9.510  1.00 34.96           C
ATOM   2048  CD1  LEU A 280     6.240  29.563   8.189  1.00 37.82           C
ATOM   2049  CD2  LEU A 280     7.065  27.655   9.748  1.00 33.44           C
ATOM   2050  C    LEU A 280     9.945  31.695   9.758  1.00 35.04           C
ATOM   2051  O    LEU A 280    10.832  31.675   8.879  1.00 34.34           O
ATOM   2052  N    TRP A 281    10.153  32.127  11.007  1.00 33.43           N
ATOM   2053  CA   TRP A 281           34.97 1.00  11.500   32.436  11.486   C
ATOM   2054  CB   TRP A 281    11.596  33.923  11.934  1.00 33.74           C
ATOM   2055  CG   TRP A 281    11.665  34.802  10.738  1.00 35.21           C
ATOM   2056  CD1  TRP A 281    10.611  35              33.44 1.00   9.929   196.C
ATOM   2057  NE1  TRP A 281    11.096  35.979   8.919  1.00 35.39           N
ATOM   2058  CE2  TRP A 281    12.467  36.030   9.003  1.00 33.61           C
ATOM   2059  CD2  TRP A 281    12.847  35.299  10.131  1.00 33.93           C
ATOM   2060  CE3  TRP A 281    14.224  35.231  10.454  1.00 36.39           C
ATOM   2061  CZ3  TRP A 281    15.150  35.865   9.626  1.00 35.04           C
ATOM   2062  CH2  TRP A 281    14.720  36.608   8.529  1.00 38.12           C
ATOM   2063  CZ2  TRP A 281    13.390  36.690   8.203  1.00 36.72           C
ATOM   2064  C    TRP A 281    11.635  31.534  12.706  1.00 35.53           C
ATOM   2065  O    TRP A 281    10.721  31.512  13.579  1.00 35.08           O
ATOM   2066  N    VAL A 282    12.734  30.785  12.747  1.00 35.23           N
ATOM   2067  CA   VAL A 282    12.804  29.647  13.654  1.00 35.76           C
ATOM   2068  CB   VAL A 282    12.674  28.314  12.870  1.00 35.91           C
ATOM   2069  CG1  VAL A 282    12.641           34.14 1.00  13.838  27.059  C
ATOM   2070  CG2  VAL A 282    11.363  28.325  12.102  1.00 34.49           C
ATOM   2071  C    VAL A 282    14.032  29.700  14.534  1.00 36.31           C
ATOM   2072  O    VAL A 282    15.164  29.866  14.046  1.00            37.64 O
ATOM   2073  N    GLY A 283    13.846  29.552  15.829  1.00 35.84           N
ATOM   2074  CA   GLY A 283    14.993  29.482  16.734  1.00 36.35           C
ATOM   2075  C    GLY A 283    15.415  28.014  16.892  1.00 37.25           C
ATOM   2076  O    GLY A 283    14.544  27.172  17.155  1.00 38.11           O
ATOM   2077  N    CYS A 284    16.701  27.706  16.751  1.00 35.43           N
ATOM   2078  CA   CYS A 284    17.173  26.285  16.745  1.00 36.36           C
ATOM   2079  CB   CYS A 284    17.664  25.903  15.329  1.00 38.08           C
ATOM   2080  SG   CYS A 284    16.369  26.160  14.079  1.00 38.55           S
```

Fig. 26 (Cont.)

```
ATOM   2081  C   CYS A 284      18.402  26.044  17.626  1.00 35.59           C
ATOM   2082  O   CYS A 284      19.202          34.97 1.00  17.896  26.959   O
ATOM   2083  N   HIS A 285      18.547  24.798  18.042  1.00 35.57           N
ATOM   2084  CA  HIS A 285      19.703  24.277  18.733  1.00 34.90           C
ATOM   2085  CB  HIS A 285      19.242  23.522  19.989          35.13 1.00   C
ATOM   2086  CG  HIS A 285      18.358  24.331  20.870  1.00 35.99           C
ATOM   2087  ND1 HIS A 285      18.771  25.516  21.435  1.00 38.14           N
ATOM   2088  CE1 HIS A 285      17.795  25.998  22.199  1.00 39.90           C
ATOM   2089  NE2 HIS A 285      16.764  25.172  22.135  1.00 39.47           N
ATOM   2090  CD2 HIS A 285      17.089  24.118  21.315  1.00 40.71           C
ATOM   2091  C   HIS A 285      20.411  23.286  17.842  1.00 34.03           C
ATOM   2092  O   HIS A 285      19.916  22.151  17.681  1.00 33.69           O
ATOM   2093  N   PRO A 286      21.590  23.665  17.315  1.00 33.15           N
ATOM   2094  CA  PRO A 286      22.401  22.766  16.465  1.00 32.00           C
ATOM   2095  CB  PRO A 286      23              31.30 1.00  16.236  23.571  720.C
ATOM   2096  CG  PRO A 286      23.257  25.016  16.382  1.00 34.51           C
ATOM   2097  CD  PRO A 286      22.238  24.965  17.555  1.00 32.15           C
ATOM   2098  C   PRO A 286      22.734  21.430  17.151          32.05 1.00   C
ATOM   2099  O   PRO A 286      22.743  20.386  16.486  1.00 32.50           O
ATOM   2100  N   ASN A 287      23.012  21.459  18.458  1.00 32.77           N
ATOM   2101  CA  ASN A 287      23.553  20.284  19.184  1.00 34.73           C
ATOM   2102  CB  ASN A 287      25.055  20.480  19.528  1.00 33.92           C
ATOM   2103  CG  ASN A 287      25.691  19.232  20.173  1.00 35.28           C
ATOM   2104  OD1 ASN A 287      25.215  18.754  21.189  1.00 36.25           O
ATOM   2105  ND2 ASN A 287      26.798  18.736  19.605  1.00 32.23           N
ATOM   2106  C   ASN A 287      22.694  20.037  20.409  1.00 35.00           C
ATOM   2107  O   ASN A 287      22.555  20.898  21.275  1.00 34.09           O
ATOM   2108  N   GLY A 288              37.42 1.00  20.454  18.854  22.082   N
ATOM   2109  CA  GLY A 288      21.085  18.518  21.479  1.00 37.60           C
ATOM   2110  C   GLY A 288      21.784  18.243  22.802  1.00 37.64           C
ATOM   2111  O   GLY A 288      21.250  18.536  23              38.35 1.00  875.O
ATOM   2112  N   MET A 289      23.016  17.768  22.732  1.00 37.85           N
ATOM   2113  CA  MET A 289      23.762  17.457  23.971  1.00 38.03           C
ATOM   2114  CB  MET A 289      25.070  16.761  23.666  1.00 37.67           C
ATOM   2115  CG  MET A 289      24.888  15.399  23.042  1.00 41.85           C
ATOM   2116  SD  MET A 289      23.939  14.291  24.171  1.00 50.34           S
ATOM   2117  CE  MET A 289      25.464  13.782  25.263  1.00 37.58           C
ATOM   2118  C   MET A 289      24.028  18.717  24.787  1.00 37.36           C
ATOM   2119  O   MET A 289      23.968  18.679  26.029  1.00 37.56           O
ATOM   2120  N   ARG A 290      24.314  19.819  24.091  1.00 35.15           N
ATOM   2121  CA  ARG A 290              35.57 1.00  24.740  20.993  24.878   C
ATOM   2122  CB  ARG A 290      25.619  21.921  23.767  1.00 34.46           C
ATOM   2123  CG  ARG A 290      27.026  21.515  23.429  1.00 37.28           C
ATOM   2124  CD  ARG A 290      27.582  22.348          40.66 1.00  22.248   C
ATOM   2125  NE  ARG A 290      28.784  21.717  21.803  1.00 41.34           N
ATOM   2126  CZ  ARG A 290      29.132  21.502  20.545  1.00 39.79           C
ATOM   2127  NH1 ARG A 290      28.382  21.917  19.510  1.00 33.83           N
ATOM   2128  NH2 ARG A 290      30.265  20.850  20.355  1.00 33.16           N
ATOM   2129  C   ARG A 290      23.748  21.750  25.353  1.00 36.26           C
ATOM   2130  O   ARG A 290      23.952  22.453  26.346  1.00 35.82           O
ATOM   2131  N   ILE A 291      22.564  21.629  24.743  1.00 36.88           N
ATOM   2132  CA  ILE A 291      21.380  22.223  25.317  1.00 38.88           C
ATOM   2133  CB  ILE A 291      20.380  22.730  24.223  1.00 38.73           C
ATOM   2134  CG1 ILE A 291              42.08 1.00  24.819  23.809  19.468   C
ATOM   2135  CD1 ILE A 291      20.177  25.146  24.995  1.00 40.92           C
ATOM   2136  CG2 ILE A 291      19.560  21.612  23.706  1.00 38.94           C
ATOM   2137  C   ILE A 291      20.700  21.410          40.12 1.00  26.422   C
ATOM   2138  O   ILE A 291      20.185  22.026  27.368  1.00 41.63           O
ATOM   2139  N   PHE A 292      20.675  20.071  26.329  1.00 40.96           N
ATOM   2140  CA  PHE A 292      20.029  19.214  27.354  1.00 41            48.C
ATOM   2141  CB  PHE A 292      19.474  17.893  26.746  1.00 40.75           C
```

Fig. 26 (Cont.)

```
ATOM   2142  CG   PHE A 292      18.157  18.077  26.009  1.00 43.64           C
ATOM   2143  CD1  PHE A 292      16.929  18.027  26.712  1.00 44.72           C
ATOM   2144  CE1  PHE A 292      15.714  18.265  26.061  1.00 44.23           C
ATOM   2145  CZ   PHE A 292      15.715  18.515  24.701  1.00 44.35           C
ATOM   2146  CE2  PHE A 292      16.916  18.543  23.989  1.00 41.07           C
ATOM   2147  CD2  PHE A            37.68 1.00  24.636  18.331  18.134   292   C
ATOM   2148  C    PHE A 292      20.935  18.898  28.558  1.00 42.81           C
ATOM   2149  O    PHE A 292      20.468  18.866  29.693  1.00 44.34           O
ATOM   2150  N    PHE A 293      22.213  18.645          42.69 1.00  28.311   N
ATOM   2151  CA   PHE A 293      23.173  18.293  29.349  1.00 43.21           C
ATOM   2152  CB   PHE A 293      23.788  16.910  29.038  1.00 43.75           C
ATOM   2153  CG   PHE A 293      22.740  15.901  28.717  1.00          48.75  C
ATOM   2154  CD1  PHE A 293      22.126  15.175  29.736  1.00 55.30           C
ATOM   2155  CE1  PHE A 293      21.065  14.302  29.434  1.00 58.20           C
ATOM   2156  CZ   PHE A 293      20.598  14.191  28.096  1.00 57.23           C
ATOM   2157  CE2  PHE A 293      21.203  14.915  27.100  1.00 54.30           C
ATOM   2158  CD2  PHE A 293      22.247  15.780  27.414  1.00 52.21           C
ATOM   2159  C    PHE A 293      24.180  19.417  29.507  1.00 42.79           C
ATOM   2160  O    PHE A 293      25.315  19.326  29.100  1.00 41.80           O
ATOM   2161  N    TYR A 294      23.702  20.479  30.135  1.00 43.57           N
ATOM   2162  CA   TYR A 294      24.401  21.746  30.284  1.00 45.02           C
ATOM   2163  CB   TYR A 294      23.526           46.01 1.00  31.037  22.799  C
ATOM   2164  CG   TYR A 294      24.152  24.205  30.977  1.00 47.51           C
ATOM   2165  CD1  TYR A 294      24.006  24.985  29.812  1.00 44.90           C
ATOM   2166  CE1  TYR A 294      24.593  26.224  29.694  1             44.75 00.C
ATOM   2167  CZ   TYR A 294      25.352  26.741  30.744  1.00 47.58           C
ATOM   2168  OH   TYR A 294      25.905  28.003  30.542  1.00 46.57           O
ATOM   2169  CE2  TYR A 294      25.551  25.993  31.946  1.00 48.38           C
ATOM   2170  CD2  TYR A 294      24.959  24.713  32.045  1.00 47.99           C
ATOM   2171  C    TYR A 294      25.714  21.656  30.995  1.00 45.14           C
ATOM   2172  O    TYR A 294      25.856  20.952  31.994  1.00 44.98           O
ATOM   2173  N    ASP A 295      26.696  22.369  30.458  1.00 45.72           N
ATOM   2174  CA   ASP A 295      27.841  22.770  31.289  1.00 44.85           C
ATOM   2175  CB   ASP A 295      28.846  21.656  31.525  1.00 45.38           C
ATOM   2176  CG   ASP A 295      29              45.74 1.00  30.410  21.533  826.C
ATOM   2177  OD1  ASP A 295      29.314  21.714  29.268  1.00 51.35           O
ATOM   2178  OD2  ASP A 295      31.049  21.298  30.557  1.00 29.57           O
ATOM   2179  C    ASP A 295      28.482  24.038  30.778          44.90 1.00   C
ATOM   2180  O    ASP A 295      28.721  24.215  29.559  1.00 43.68           O
ATOM   2181  N    ALA A 296      28.691  24.946  31.730  1.00 45.37           N
ATOM   2182  CA   ALA A 296      29.368  26.229  31.514  1.00 45.73           C
ATOM   2183  CB   ALA A 296      29.614  26.940  32.916  1.00 45.62           C
ATOM   2184  C    ALA A 296      30.688  26.163  30.637  1.00 45.45           C
ATOM   2185  O    ALA A 296      30.946  27.107  29.875  1.00 46.29           O
ATOM   2186  N    GLU A 297      31.471  25.070  30.697  1.00 43.77           N
ATOM   2187  CA   GLU A 297      32.705  24.932  29.849  1.00 44.04           C
ATOM   2188  CB   GLU A 297      33.700  23.883  30.400  1.00 43.14           C
ATOM   2189  CG   GLU A 297              49.50 1.00  30.341  24.294  35.192   C
ATOM   2190  CD   GLU A 297      35.787  24.492  28.910  1.00 53.17           C
ATOM   2191  OE1  GLU A 297      35.807  25.653  28.377  1.00 52.55           O
ATOM   2192  OE2  GLU A 297      36.267  23.486  28              53.99 1.00  314.O
ATOM   2193  C    GLU A 297      32.483  24.644  28.344  1.00 42.21           C
ATOM   2194  O    GLU A 297      33.424  24.716  27.554  1.00 42.70           O
ATOM   2195  N    ASN A 298      31.267  24.289  27.961  1.00 40.33           N
ATOM   2196  CA   ASN A 298      30.946  23.865  26.612  1.00 39.13           C
ATOM   2197  CB   ASN A 298      31.202  22.346  26.506  1.00 40.35           C
ATOM   2198  CG   ASN A 298      30.966  21.794  25.094  1.00 41.67           C
ATOM   2199  OD1  ASN A 298      31.206  22.476  24.090  1.00 41.46           O
ATOM   2200  ND2  ASN A 298      30.453  20.561  25.020  1.00 43.79           N
ATOM   2201  C    ASN A 298      29.488  24.274  26.247  1.00 38.55           C
ATOM   2202  O    ASN A 298              37.77 1.00  25.985  23.441  28.605   O
```

Fig. 26 (Cont.)

```
ATOM   2203  N    PRO A 299      29.221  25.579  26.255  1.00 36.84           N
ATOM   2204  CA   PRO A 299      27.834  26.019  26.174  1.00 35.68           C
ATOM   2205  CB   PRO A 299      27.901  27.514          35.75 1.00  26.553   C
ATOM   2206  CG   PRO A 299      29.323  27.943  26.181  1.00 36.52           C
ATOM   2207  CD   PRO A 299      30.191  26.702  26.355  1.00 37.08           C
ATOM   2208  C    PRO A 299      27.255  25.788  24.769  1.00 34.77           C
ATOM   2209  O    PRO A 299      28.038  25.687  23.782  1.00 33.59           O
ATOM   2210  N    PRO A 300      25.923  25.696  24.690  1.00 32.17           N
ATOM   2211  CA   PRO A 300      25.229  25.526  23.391  1.00 32.30           C
ATOM   2212  CB   PRO A 300      23.735  25.351  23.792  1.00 31.15           C
ATOM   2213  CG   PRO A 300      23.648  26.069  25.204  1.00 30.01           C
ATOM   2214  CD   PRO A 300      24.993  25.853  25.836  1.00 32.39           C
ATOM   2215  C    PRO A 300             32.34 1.00  22.554  26.797  25.362    C
ATOM   2216  O    PRO A 300      25.383  27.905  23.147  1.00 33.39           O
ATOM   2217  N    GLY A 301      25.413  26.655  21.229  1.00 31.94           N
ATOM   2218  CA   GLY A 301      25.392  27.792          32.75 1.00  20.343   C
ATOM   2219  C    GLY A 301      23.982  28.245  19.999  1.00 34.70           C
ATOM   2220  O    GLY A 301      22.986  27.985  20.726  1.00 35.06           O
ATOM   2221  N    SER A 302      23.870  28.924  18.868  1.00 34           81.N
ATOM   2222  CA   SER A 302      22.566  29.439  18.418  1.00 34.70           C
ATOM   2223  CB   SER A 302      22.423  30.929  18.756  1.00 34.64           C
ATOM   2224  OG   SER A 302      22.385  31.153  20.152  1.00 37.96           O
ATOM   2225  C    SER A 302      22.462  29.348  16.892  1.00 34.82           C
ATOM   2226  O    SER A 302      23.496  29.357  16.180  1.00 33.53           O
ATOM   2227  N    GLU A 303      21.216  29.255  16.405  1.00 33.94           N
ATOM   2228  CA   GLU A         34.57 1.00  14.992  29.180  20.959       303  C
ATOM   2229  CB   GLU A 303      21.179  27.770  14.478  1.00 33.10           C
ATOM   2230  CG   GLU A 303      20.760  27.578  13.023  1.00 37.29           C
ATOM   2231  CD   GLU A 303      20.942  26           44.41 1.00  12.506  143.C
ATOM   2232  OE1  GLU A 303      20.864  25.112  13.265  1.00 47.93           O
ATOM   2233  OE2  GLU A 303      21.185  26.019  11.295  1.00 49.48           O
ATOM   2234  C    GLU A 303      19.511  29.660  14.705  1.00           35.72 C
ATOM   2235  O    GLU A 303      18.551  29.309  15.456  1.00 36.17           O
ATOM   2236  N    VAL A 304      19.383  30.463  13.638  1.00 35.06           N
ATOM   2237  CA   VAL A 304      18.100  31.054  13.256  1.00 34.47           C
ATOM   2238  CB   VAL A 304      18.056  32.637  13.431  1.00 34.01           C
ATOM   2239  CG1  VAL A 304      16.692  33.197  12.839  1.00 32.39           C
ATOM   2240  CG2  VAL A 304      18.317  33.093  14.934  1.00 32.02           C
ATOM   2241  C    VAL A 304      17.872  30.700  11.762  1.00 34.27           C
ATOM   2242  O    VAL A 304      18.733  30.964  10.925  1.00 32.33           O
ATOM   2243  N    LEU A 305      16.702  30.143  11.475  1.00 32.99           N
ATOM   2244  CA   LEU A 305      16.351          35.13 1.00  10.127  29.737   C
ATOM   2245  CB   LEU A 305      15.795  28.295  10.107  1.00 32.88           C
ATOM   2246  CG   LEU A 305      16.737  27.149  10.494  1.00 37.33           C
ATOM   2247  CD1  LEU A 305      15.985  25.811  10.257  1            37.45 00.C
ATOM   2248  CD2  LEU A 305      17.966  27.235   9.615  1.00 34.93           C
ATOM   2249  C    LEU A 305      15.190  30.609   9.616  1.00 35.01           C
ATOM   2250  O    LEU A 305      14.251  30.923  10.372  1.00 34.81           O
ATOM   2251  N    ARG A 306      15.236  30.939   8.333  1.00 32.90           N
ATOM   2252  CA   ARG A 306      14.104  31.591   7.759  1.00 32.92           C
ATOM   2253  CB   ARG A 306      14.555  32.865   7.026  1.00 30.94           C
ATOM   2254  CG   ARG A 306      13.433  33.508   6.277  1.00 32.03           C
ATOM   2255  CD   ARG A 306      13.965  34.592   5.244  1.00 30.57           C
ATOM   2256  NE   ARG A 306      12.838  35.385   4.716  1.00 30.42           N
ATOM   2257  CZ   ARG A 306      13.043          32.05 1.00   3.868   36.420  C
ATOM   2258  NH1  ARG A 306      14.261  36.672   3.472  1.00 24.57           N
ATOM   2259  NH2  ARG A 306      12.044  37.104   3.316  1.00 28.69           N
ATOM   2260  C    ARG A 306      13.532  30.531   6.780          32.38 1.00   C
ATOM   2261  O    ARG A 306      14.344  29.904   6.071  1.00 31.43           O
ATOM   2262  N    ILE A 307      12.187  30.379   6.748  1.00 31.20           N
ATOM   2263  CA   ILE A 307      11.503  29.503   5.798  1.00 32.30           C
```

Fig. 26 (Cont.)

```
ATOM   2264  CB   ILE A 307      10.849  28.279   6.485  1.00 33.51           C
ATOM   2265  CG1  ILE A 307      11.927  27.577   7.338  1.00 34.04           C
ATOM   2266  CD1  ILE A 307      11.284  26.848   8.510  1.00 36.39           C
ATOM   2267  CG2  ILE A 307      10.210  27.308   5.411  1.00 29.05           C
ATOM   2268  C    ILE A 307      10.465  30.218   5.018  1.00 32.29           C
ATOM   2269  O    ILE A 307       9.518  30.733   5.572  1.00 32.83           O
ATOM   2270  N    GLN A 308      10.671          31.49 1.00   3.723    30.243 N
ATOM   2271  CA   GLN A 308       9.808  30.948   2.760  1.00 33.45           C
ATOM   2272  CB   GLN A 308      10.662  31.827   1.780  1.00 32.08           C
ATOM   2273  CG   GLN A 308      11.357  32.995   2.545         31.42 1.00    C
ATOM   2274  CD   GLN A 308      12.353  33.681   1.630  1.00 35.03           C
ATOM   2275  OE1  GLN A 308      13.580  33.383   1.654  1.00 35.64           O
ATOM   2276  NE2  GLN A 308      11.844  34.551   0.780  1.00 26.57           N
ATOM   2277  C    GLN A 308       9.046  29.937   1.909  1.00 33.56           C
ATOM   2278  O    GLN A 308       9.621  28.911   1.481  1.00 33.92           O
ATOM   2279  N    ASP A 309       7.790  30.269   1.591  1.00 35.41           N
ATOM   2280  CA   ASP A 309       6.969  29.462   0.653  1.00 36.64           C
ATOM   2281  CB   ASP A 309       7.667  29.401  -0.729  1.00 36.59           C
ATOM   2282  CG   ASP A 309       7.896  30.761  -1.278  1.00 42.67           C
ATOM   2283  OD1  ASP A 309             48.64 1.00  1.251-  31.517   6.908    O
ATOM   2284  OD2  ASP A 309       9.017  31.206  -1.723  1.00 52.49           O
ATOM   2285  C    ASP A 309       6.830  28.039   1.152  1.00 35.97           C
ATOM   2286  O    ASP A 309       7.160  27.104          35.17 1.00    0.427  O
ATOM   2287  N    ILE A 310       6.373  27.885   2.388  1.00 37.23           N
ATOM   2288  CA   ILE A 310       6.356  26.582   3.013  1.00 38.56           C
ATOM   2289  CB   ILE A 310       6.101  26.753   4.536  1.00 39.56           C
ATOM   2290  CG1  ILE A 310       6.617  25.510   5.299  1.00 38.66           C
ATOM   2291  CD1  ILE A 310       6.648  25.707   6.865  1.00 40.54           C
ATOM   2292  CG2  ILE A 310       4.625  27.186   4.794  1.00 36.29           C
ATOM   2293  C    ILE A 310       5.419  25.545   2.328  1.00 40.77           C
ATOM   2294  O    ILE A 310       5.595  24.336   2.522  1.00 41.99           O
ATOM   2295  N    LEU A 311       4.502  25.998   1.461  1.00 42.27           N
ATOM   2296  CA   LEU A 311             44.50 1.00  0.771  25.115   3.574     C
ATOM   2297  CB   LEU A 311       2.209  25.797   0.532  1.00 44.55           C
ATOM   2298  CG   LEU A 311       1.544  26.192   1.822  1.00 45.84           C
ATOM   2299  CD1  LEU A 311       0.079  26.701          47.10 1.00   1.592   C
ATOM   2300  CD2  LEU A 311       1.580  24.905   2.675  1.00 49.09           C
ATOM   2301  C    LEU A 311       4.073  24.653  -0.572  1.00 45.43           C
ATOM   2302  O    LEU A 311       3.456  23.746  -1.159  1.00 45.84           O
ATOM   2303  N    SER A 312       5.121  25.305  -1.098  1.00 45.20           N
ATOM   2304  CA   SER A 312       5.545  25.028  -2.459  1.00 45.64           C
ATOM   2305  CB   SER A 312       6.444  26.145  -3.016  1.00 44.81           C
ATOM   2306  OG   SER A 312       7.633  26.269  -2.237  1.00 46.77           O
ATOM   2307  C    SER A 312       6.252  23.675  -2.438  1.00 45.99           C
ATOM   2308  O    SER A 312       6.459  23.085  -1.335  1.00 45.29           O
ATOM   2309  N    GLU A 313             45.62 1.00  3.632-  23.191   6.606    N
ATOM   2310  CA   GLU A 313       7.414  21.973  -3.787  1.00 47.22           C
ATOM   2311  CB   GLU A 313       7.584  21.619  -5.267  1.00 47.95           C
ATOM   2312  CG   GLU A 313       6.853  22          51.59 1.00   6.202-  586.C
ATOM   2313  CD   GLU A 313       6.113  21.871  -7.346  1.00 56.25           C
ATOM   2314  OE1  GLU A 313       6.712  21.737  -8.458  1.00 53.22           O
ATOM   2315  OE2  GLU A 313       4.932  21.461  -7.131  1.00 57.42           O
ATOM   2316  C    GLU A 313       8.800  22.047  -3.093  1.00 46.93           C
ATOM   2317  O    GLU A 313       9.113  21.145  -2.300  1.00 46.13           O
ATOM   2318  N    GLU A 314       9.639  23.060  -3.414  1.00 46.96           N
ATOM   2319  CA   GLU A 314      10.798  23.407  -2.511  1.00 46.16           C
ATOM   2320  CB   GLU A 314      12.208  23.167  -3.070  1.00 45.38           C
ATOM   2321  CG   GLU A 314      12.366  23.309  -4.543  1.00 51.80           C
ATOM   2322  CD   GLU A 314      12.522  21.947  -5.205  1.00 55.04           C
ATOM   2323  OE1  GLU A 314      13.021  21.902  -6.346  1.00 52.19           O
ATOM   2324  OE2  GLU A 314      12.138  20.926  -4.560  1.00 58.46           O
```

Fig. 26 (Cont.)

| | | | | | | | | | |
|---|---|---|---|---|---|---|---|---|---|
| ATOM | 2325 | C | GLU | A | 314 | 10.765 | | 43.66 1.00 | 1.745- 24.735 C |
| ATOM | 2326 | O | GLU | A | 314 | 11.088 | 25.825 | -2.240 1.00 | 42.48 O |
| ATOM | 2327 | N | PRO | A | 315 | 10.412 | 24.599 | -0.496 1.00 | 42.48 N |
| ATOM | 2328 | CA | PRO | A | 315 | 10.575 | 25.689 | 0.454 1.00 | 41.36 C |
| ATOM | 2329 | CB | PRO | A | 315 | 10.272 | 25.024 | 1.774 1.00 | 40.46 C |
| ATOM | 2330 | CG | PRO | A | 315 | 9.264 | 24.029 | 1.374 1.00 | 42.34 C |
| ATOM | 2331 | CD | PRO | A | 315 | 9.857 | 23.382 | 0.132 1.00 | 42.09 C |
| ATOM | 2332 | C | PRO | A | 315 | 12.014 | 26.136 | 0.443 1.00 | 41.18 C |
| ATOM | 2333 | O | PRO | A | 315 | 12.987 | 25.366 | 0.379 1.00 | 40.20 O |
| ATOM | 2334 | N | LYS | A | 316 | 12.144 | 27.443 | 0.517 1.00 | 40.96 N |
| ATOM | 2335 | CA | LYS | A | 316 | 13.442 | 28.055 | 0.542 1.00 | 40.82 C |
| ATOM | 2336 | CB | LYS | A | 316 | 13.327 | 29.368 | -0.226 1.00 | 40.10 C |
| ATOM | 2337 | CG | LYS | A | 316 | 14.535 | 30.205 | -0.153 1.00 | 46.23 C |
| ATOM | 2338 | CD | LYS | A | 316 | 14.628 | | 53.48 1.00 | 1.344- 31.196 C |
| ATOM | 2339 | CE | LYS | A | 316 | 15.848 | 32.141 | -1.107 1.00 | 55.35 C |
| ATOM | 2340 | NZ | LYS | A | 316 | 17.066 | 31.298 | -1.135 1.00 | 53.94 N |
| ATOM | 2341 | C | LYS | A | 316 | 13.818 | 28.210 | 2.052 | 39.44 1.00 C |
| ATOM | 2342 | O | LYS | A | 316 | 13.137 | 28.891 | 2.763 1.00 | 39.57 O |
| ATOM | 2343 | N | VAL | A | 317 | 14.873 | 27.529 | 2.507 1.00 | 38.15 N |
| ATOM | 2344 | CA | VAL | A | 317 | 15.280 | 27.513 | 3.910 1.00 | 36.46 C |
| ATOM | 2345 | CB | VAL | A | 317 | 15.331 | 26.047 | 4.446 1.00 | 37.28 C |
| ATOM | 2346 | CG1 | VAL | A | 317 | 15.665 | 26.005 | 5.958 1.00 | 37.33 C |
| ATOM | 2347 | CG2 | VAL | A | 317 | 13.990 | 25.272 | 4.141 1.00 | 34.34 C |
| ATOM | 2348 | C | VAL | A | 317 | 16.673 | 28.172 | 3.973 1.00 | 36.41 C |
| ATOM | 2349 | O | VAL | A | 317 | 17.567 | 27.818 | 3.193 1.00 | 34.02 O |
| ATOM | 2350 | N | THR | A | 318 | 16.849 | 29.142 | 4.876 1.00 | 35.15 N |
| ATOM | 2351 | CA | THR | A | 318 | 18 | | 36.18 1.00 | 4.924 29.936 071.C |
| ATOM | 2352 | CB | THR | A | 318 | 17.856 | 31.403 | 4.403 1.00 | 36.44 C |
| ATOM | 2353 | OG1 | THR | A | 318 | 17.248 | 31.353 | 3.114 1.00 | 38.74 O |
| ATOM | 2354 | CG2 | THR | A | 318 | 19.266 | 32.099 | 4.094 | 38.78 1.00 C |
| ATOM | 2355 | C | THR | A | 318 | 18.530 | 30.041 | 6.373 1.00 | 36.12 C |
| ATOM | 2356 | O | THR | A | 318 | 17.742 | 30.358 | 7.230 1.00 | 34.95 O |
| ATOM | 2357 | N | VAL | A | 319 | 19.826 | 29.782 | 6.621 1.00 | 36.69 N |
| ATOM | 2358 | CA | VAL | A | 319 | 20.351 | 30.045 | 7.929 1.00 | 35.01 C |
| ATOM | 2359 | CB | VAL | A | 319 | 21.699 | 29.259 | 8.175 1.00 | 36.15 C |
| ATOM | 2360 | CG1 | VAL | A | 319 | 22.132 | 29.588 | 9.594 1.00 | 34.57 C |
| ATOM | 2361 | CG2 | VAL | A | 319 | 21.488 | 27.700 | 8.025 1.00 | 31.36 C |
| ATOM | 2362 | C | VAL | A | 319 | 20.627 | 31.560 | 7.999 1.00 | 34.45 C |
| ATOM | 2363 | O | VAL | A | 319 | 21.507 | 32.024 | 7.330 1.00 | 31.52 O |
| ATOM | 2364 | N | VAL | A | 320 | | 32.67 1.00 | 8.823 | 32.328 19.932 N |
| ATOM | 2365 | CA | VAL | A | 320 | 20.196 | 33.784 | 8.790 1.00 | 33.50 C |
| ATOM | 2366 | CB | VAL | A | 320 | 18.854 | 34.537 | 9.030 1.00 | 35.95 C |
| ATOM | 2367 | CG1 | VAL | A | 320 | 19.040 | 36.042 | 9 | 34.52 1.00 078.C |
| ATOM | 2368 | CG2 | VAL | A | 320 | 17.834 | 34.128 | 7.883 1.00 | 33.77 C |
| ATOM | 2369 | C | VAL | A | 320 | 21.267 | 34.211 | 9.806 1.00 | 33.50 C |
| ATOM | 2370 | O | VAL | A | 320 | 21.968 | 35.220 | 9.631 1.00 | 33.28 O |
| ATOM | 2371 | N | TYR | A | 321 | 21.422 | 33.389 | 10.847 1.00 | 33.06 N |
| ATOM | 2372 | CA | TYR | A | 321 | 22.326 | 33.668 | 11.963 1.00 | 32.96 C |
| ATOM | 2373 | CB | TYR | A | 321 | 21.704 | 34.599 | 13.021 1.00 | 31.81 C |
| ATOM | 2374 | CG | TYR | A | 321 | 22.689 | 34.969 | 14.119 1.00 | 33.38 C |
| ATOM | 2375 | CD1 | TYR | A | 321 | 23.706 | 35.909 | 13.900 1.00 | 32.58 C |
| ATOM | 2376 | CE1 | TYR | A | 321 | 24.679 | 36.214 | 14.905 1.00 | 30.44 C |
| ATOM | 2377 | CZ | TYR | A | 321 | | 35.55 1.00 | 16.151 | 35.566 24.523 C |
| ATOM | 2378 | OH | TYR | A | 321 | 25.321 | 35.809 | 17.184 1.00 | 36.87 O |
| ATOM | 2379 | CE2 | TYR | A | 321 | 23.544 | 34.647 | 16.382 1.00 | 31.93 C |
| ATOM | 2380 | CD2 | TYR | A | 321 | 22.624 | 34.335 | | 34.48 1.00 15.364 C |
| ATOM | 2381 | C | TYR | A | 321 | 22.681 | 32.322 | 12.590 1.00 | 32.12 C |
| ATOM | 2382 | O | TYR | A | 321 | 21.785 | 31.502 | 12.803 1.00 | 33.37 O |
| ATOM | 2383 | N | ALA | A | 322 | 23.982 | 32.115 | 12.887 1.00 | 31.45 N |
| ATOM | 2384 | CA | ALA | A | 322 | 24.462 | 30.916 | 13.583 1.00 | 30.50 C |
| ATOM | 2385 | CB | ALA | A | 322 | 24.621 | 29.797 | 12.619 1.00 | 29.06 C |

Fig. 26 (Cont.)

```
ATOM   2386  C    ALA A 322      25.816  31.246  14.266  1.00 31.39           C
ATOM   2387  O    ALA A 322      26.622  31.953  13.686  1.00 30.97           O
ATOM   2388  N    GLU A 323      26.073  30.747  15.469  1.00 30.36           N
ATOM   2389  CA   GLU A 323      27.353  31.050  16.114  1.00 32.61           C
ATOM   2390  CB   GLU A 323              32.00  1.00   16.762  32.461  27.340 C
ATOM   2391  CG   GLU A 323      26.298  32.463  17.875  1.00 35.44           C
ATOM   2392  CD   GLU A 323      26.727  33.300  19.056  1.00 39.61           C
ATOM   2393  OE1  GLU A 323      25.967  34.276          38.78 1.00   19.309  O
ATOM   2394  OE2  GLU A 323      27.798  33.022  19.695  1.00 37.11           O
ATOM   2395  C    GLU A 323      27.539  29.953  17.192  1.00 32.54           C
ATOM   2396  O    GLU A 323      26.565  29.263  17.554  1.00 30         85.0
ATOM   2397  N    ASN A 324      28.786  29.768  17.621  1.00 31.60           N
ATOM   2398  CA   ASN A 324      29.095  28.722  18.577  1.00 32.76           C
ATOM   2399  CB   ASN A 324      30.544  28.251  18.448  1.00 31.19           C
ATOM   2400  CG   ASN A 324      31.523  29.293  18.880  1.00 32.35           C
ATOM   2401  OD1  ASN A 324      31.145  30.300  19.459  1.00 28.40           O
ATOM   2402  ND2  ASN A 324      32.811  29.050  18.631  1.00 35.19           N
ATOM   2403  C    ASN A          33.96  1.00   20.055  29.006  28.704   324 C
ATOM   2404  O    ASN A 324      28.958  28.180  20.926  1.00 34.06           O
ATOM   2405  N    GLY A 325      28.009  30.107  20.325  1.00 34.86           N
ATOM   2406  CA   GLY A 325      27.626  30.381          36.73 1.00   21.688  C
ATOM   2407  C    GLY A 325      28.651  31.196  22.453  1.00 38.13           C
ATOM   2408  O    GLY A 325      28.507  31.347  23.650  1.00 40.83           O
ATOM   2409  N    THR A 326      29.703  31.716  21.838  1.00           37.15 N
ATOM   2410  CA   THR A 326      30.534  32.580  22.637  1.00 36.52           C
ATOM   2411  CB   THR A 326      32.042  32.569  22.228  1.00 37.65           C
ATOM   2412  OG1  THR A 326      32.306  33.560  21.232  1.00 40.25           O
ATOM   2413  CG2  THR A 326      32.425  31.271  21.578  1.00 36.84           C
ATOM   2414  C    THR A 326      29.927  33.984  22.798  1.00 36.02           C
ATOM   2415  O    THR A 326      30.375  34.737  23.642  1.00 35.49           O
ATOM   2416  N    VAL A 327      28.904  34.334  22.006  1.00 34.74           N
ATOM   2417  CA   VAL A 327      28.210  35.573  22.213  1.00 33.79           C
ATOM   2418  CB   VAL A 327      28.111  36.444  20.917  1.00 34.65           C
ATOM   2419  CG1  VAL A 327      27.041          34.73  1.00   21.090  37.598 C
ATOM   2420  CG2  VAL A 327      29.480  37.047  20.526  1.00 33.11           C
ATOM   2421  C    VAL A 327      26.817  35.192  22.751  1.00 34.33           C
ATOM   2422  O    VAL A 327      26.471  35.577  23.846  1          35.26 00.0
ATOM   2423  N    LEU A 328      26.037  34.406  22.015  1.00 32.87           N
ATOM   2424  CA   LEU A 328      24.671  34.063  22.409  1.00 32.60           C
ATOM   2425  CB   LEU A 328      23.636  34.653  21.410  1.00 30.22           C
ATOM   2426  CG   LEU A 328      22.163  34.591  21.883  1.00 33.68           C
ATOM   2427  CD1  LEU A 328      21.843  35.670  22.998  1.00 31.39           C
ATOM   2428  CD2  LEU A 328      21.165  34.666  20.712  1.00 32.41           C
ATOM   2429  C    LEU A 328      24.496  32.537  22.573  1.00 33.15           C
ATOM   2430  O    LEU A 328      24.635  31.784  21.620  1.00 34.69           O
ATOM   2431  N    GLN A 329      24.152  32.092  23.779  1.00 33.03           N
ATOM   2432  CA   GLN A 329      24             32.71  1.00   24.103  30.673  009.C
ATOM   2433  CB   GLN A 329      24.520  30.421  25.505  1.00 32.14           C
ATOM   2434  CG   GLN A 329      25.987  30.568  25.658  1.00 35.91           C
ATOM   2435  CD   GLN A 329      26.415  30.467  27.176          39.08 1.00   C
ATOM   2436  OE1  GLN A 329      25.625  30.109  28.058  1.00 41.20           O
ATOM   2437  NE2  GLN A 329      27.614  30.807  27.429  1.00 37.75           N
ATOM   2438  C    GLN A 329      22.552  30.286  24.113  1.00 32.52           C
ATOM   2439  O    GLN A 329      21.766  30.951  24.784  1.00 33.15           O
ATOM   2440  N    GLY A 330      22.200  29.232  23.364  1.00 32.96           N
ATOM   2441  CA   GLY A 330      20.928  28.523  23.460  1.00 33.47           C
ATOM   2442  C    GLY A 330      19.722  29.201  22.837  1.00 36.19           C
ATOM   2443  O    GLY A 330      18.685  29.210  23.467  1.00 37.52           O
ATOM   2444  N    SER A 331      19.833  29.771  21.623  1.00 36.46           N
ATOM   2445  CA   SER A 331              36.80  1.00   20.977  30.408  18.689 C
ATOM   2446  CB   SER A 331      19.016  30.858  19.517  1.00 36.23           C
```

Fig. 26 (Cont.)

```
ATOM   2447  OG   SER A 331      19.530  29.750  18.760  1.00 34.76           O
ATOM   2448  C    SER A 331      17.507  29.500  20           36.85 1.00    902.C
ATOM   2449  O    SER A 331      17.651  28.311  20.518  1.00 37.28           O
ATOM   2450  N    THR A 332      16.332  30.068  21.202  1.00 35.77           N
ATOM   2451  CA   THR A 332      15.070  29.368  21.029  1.00 34.22           C
ATOM   2452  CB   THR A 332      14.361  29.198  22.374  1.00 36.00           C
ATOM   2453  OG1  THR A 332      14.299  30.461  23.097  1.00 32.94           O
ATOM   2454  CG2  THR A 332      15.130  28.232  23.293  1.00 32.12           C
ATOM   2455  C    THR A 332      14.089  30.071  20.106  1.00 35.91           C
ATOM   2456  O    THR A 332      13.113  29.446  19.702  1.00 37.18           O
ATOM   2457  N    VAL A 333      14.248  31.378  19.838  1.00 34.78           N
ATOM   2458  CA   VAL A 333            32.96 1.00  19.157  32.060  13.190     C
ATOM   2459  CB   VAL A 333      12.151  32.527  20.197  1.00 32.77           C
ATOM   2460  CG1  VAL A 333      12.785  33.526  21.167  1.00 32.29           C
ATOM   2461  CG2  VAL A 333      10.948  33.191          30.74 1.00  19.472   C
ATOM   2462  C    VAL A 333      13.808  33.246  18.428  1.00 33.51           C
ATOM   2463  O    VAL A 333      14.841  33.783  18.852  1.00 35.47           O
ATOM   2464  N    ALA A 334      13.217  33.645  17.333  1.00 33.44           N
ATOM   2465  CA   ALA A 334      13.703  34.831  16.584  1.00 35.26           C
ATOM   2466  CB   ALA A 334      14.847  34.444  15.577  1.00 34.38           C
ATOM   2467  C    ALA A 334      12.553  35.397  15.810  1.00 34.75           C
ATOM   2468  O    ALA A 334      11.709  34.626  15.354  1.00 35.65           O
ATOM   2469  N    ALA A 335      12.517  36.724  15.678  1.00 33.81           N
ATOM   2470  CA   ALA A 335      11.469  37.408  14.944  1.00 33.51           C
ATOM   2471  CB   ALA A 335            34.69 1.00  15.895  37.745  10.282     C
ATOM   2472  C    ALA A 335      12.040  38.697  14.421  1.00 33.33           C
ATOM   2473  O    ALA A 335      13.008  39.228  14.977  1.00 32.05           O
ATOM   2474  N    VAL A 336      11.396  39.222          33.22 1.00  13.371   N
ATOM   2475  CA   VAL A 336      11.948  40.294  12.586  1.00 33.00           C
ATOM   2476  CB   VAL A 336      12.294  39.889  11.095  1.00 34.01           C
ATOM   2477  CG1  VAL A 336      13.532  38.912  11.054  1.00 35           22.C
ATOM   2478  CG2  VAL A 336      11.082  39.248  10.332  1.00 30.46           C
ATOM   2479  C    VAL A 336      10.991  41.451  12.638  1.00 34.58           C
ATOM   2480  O    VAL A 336       9.760  41.264  12.574  1.00 34.26           O
ATOM   2481  N    TYR A 337      11.563  42.654  12.677  1.00 33.45           N
ATOM   2482  CA   TYR A 337      10.760  43.825  12.636  1.00 32.42           C
ATOM   2483  CB   TYR A 337      10.314  44.238  14.059  1.00 33.08           C
ATOM   2484  CG   TYR A          31.65 1.00  14.029  45.436   9.389       337 C
ATOM   2485  CD1  TYR A 337       8.042  45.297  13.612  1.00 30.15           C
ATOM   2486  CE1  TYR A 337       7.186  46.349  13.597  1.00 29.45           C
ATOM   2487  CZ   TYR A 337       7.670  47           33.39 1.00  13.948   619.C
ATOM   2488  OH   TYR A 337       6.822  48.691  13.925  1.00 35.91           O
ATOM   2489  CE2  TYR A 337       9.002  47.815  14.326  1.00 32.75           C
ATOM   2490  CD2  TYR A 337       9.852  46.693  14.364  1.00          31.83  C
ATOM   2491  C    TYR A 337      11.558  44.912  12.005  1.00 32.19           C
ATOM   2492  O    TYR A 337      12.650  45.295  12.498  1.00 33.04           O
ATOM   2493  N    LYS A 338      11.044  45.388  10.877  1.00 31.70           N
ATOM   2494  CA   LYS A 338      11.638  46.529  10.184  1.00 31.53           C
ATOM   2495  CB   LYS A 338      11.189  47.858  10.793  1.00 30.25           C
ATOM   2496  CG   LYS A 338       9.678  48.002  10.597  1.00 34.31           C
ATOM   2497  CD   LYS A 338       9.159  49.413  10.881  1.00 37.55           C
ATOM   2498  CE   LYS A 338       7.585  49.436  10.862  1.00 39.59           C
ATOM   2499  NZ   LYS A 338       7.082  49.079   9.501  1.00 40.16           N
ATOM   2500  C    LYS A 338      13.150          31.22 1.00  10.024  46.474   C
ATOM   2501  O    LYS A 338      13.845  47.456  10.343  1.00 29.04           O
ATOM   2502  N    GLY A 339      13.631  45.349   9.466  1.00 31.17           N
ATOM   2503  CA   GLY A 339      15.053  45.226   9.078  1           31.84 00.C
ATOM   2504  C    GLY A 339      15.948  44.749  10.227  1.00 32.40           C
ATOM   2505  O    GLY A 339      17.178  44.771  10.121  1.00 33.32           O
ATOM   2506  N    LYS A 340      15.316  44.375  11.339  1.00 32.48           N
ATOM   2507  CA   LYS A 340      16.000  43.943  12.540  1.00 33.84           C
```

Fig. 26 (Cont.)

```
ATOM   2508  CB   LYS A 340      15.680  44.909  13.666  1.00 35.56           C
ATOM   2509  CG   LYS A 340      16.856  45.690  13.979  1.00 38.06           C
ATOM   2510  CD   LYS A 340      16.791  47.031  13.596  1.00 40.83           C
ATOM   2511  CE   LYS A 340      18.041  47.619  14.256  1.00 48.53           C
ATOM   2512  NZ   LYS A 340      18.012  49.139  14.319  1.00 51.84           N
ATOM   2513  C    LYS A 340      15.541          33.15   1.00 13.008  42.595  C
ATOM   2514  O    LYS A 340      14.378  42.198  12.799  1.00 32.21           O
ATOM   2515  N    LEU A 341      16.462  41.904  13.657  1.00 32.75           N
ATOM   2516  CA   LEU A 341      16.249  40.537  14.086          32.13 1.00   C
ATOM   2517  CB   LEU A 341      17.286  39.627  13.421  1.00 31.36           C
ATOM   2518  CG   LEU A 341      17.184  38.115  13.775  1.00 31.96           C
ATOM   2519  CD1  LEU A 341      15.775  37.521  13.403  1.00 33.12           C
ATOM   2520  CD2  LEU A 341      18.201  37.258  13.124  1.00 32.42           C
ATOM   2521  C    LEU A 341      16.409  40.472  15.599  1.00 32.38           C
ATOM   2522  O    LEU A 341      17.451  40.847  16.151  1.00 33.16           O
ATOM   2523  N    LEU A 342      15.393  39.992  16.289  1.00 32.83           N
ATOM   2524  CA   LEU A 342      15.495  39.842  17.721  1.00 33.35           C
ATOM   2525  CB   LEU A 342      14.313  40.520  18.439  1.00 31.97           C
ATOM   2526  CG   LEU A 342      14.297          34.68   1.00 19.977  40.437  C
ATOM   2527  CD1  LEU A 342      15.513  41.130  20.653  1.00 29.46           C
ATOM   2528  CD2  LEU A 342      12.955  41.030  20.513  1.00 31.54           C
ATOM   2529  C    LEU A 342      15.539  38.371  18.069          33.83 1.00   C
ATOM   2530  O    LEU A 342      14.604  37.649  17.722  1.00 34.86           O
ATOM   2531  N    ILE A 343      16.582  37.941  18.787  1.00 33.16           N
ATOM   2532  CA   ILE A 343      16.776  36.529  19.083  1.00 32.18           C
ATOM   2533  CB   ILE A 343      18.169  35.989  18.502  1.00 32.76           C
ATOM   2534  CG1  ILE A 343      18.451  36.450  17.020  1.00 31.94           C
ATOM   2535  CD1  ILE A 343      19.960  36.080  16.509  1.00 31.84           C
ATOM   2536  CG2  ILE A 343      18.240  34.460  18.589  1.00 28.32           C
ATOM   2537  C    ILE A 343      16.789  36.305  20.591  1.00 34.11           C
ATOM   2538  O    ILE A 343      17.551  36.977  21.304  1.00 34.14           O
ATOM   2539  N    GLY A 344              33.18   1.00 21.079  35.322  16.037  N
ATOM   2540  CA   GLY A 344      16.062  35.053  22.493  1.00 34.05           C
ATOM   2541  C    GLY A 344      16.535  33.633  22.780  1.00 35.49           C
ATOM   2542  O    GLY A 344      16.694  32.844  21.823          36.09 1.00   O
ATOM   2543  N    THR A 345      16.771  33.295  24.063  1.00 34.56           N
ATOM   2544  CA   THR A 345      17.365  31.999  24.451  1.00 34.01           C
ATOM   2545  CB   THR A 345      18.893  32.177  24.799  1.00 34.75           C
ATOM   2546  OG1  THR A 345      19.034  32.920  26.021  1.00 31.95           O
ATOM   2547  CG2  THR A 345      19.610  33.085  23.747  1.00 33.41           C
ATOM   2548  C    THR A 345      16.659  31.410  25.676  1.00 35.17           C
ATOM   2549  O    THR A 345      15.935  32.109  26.394  1.00 34.61           O
ATOM   2550  N    VAL A 346      16.925  30.145  25.987  1.00 36.14           N
ATOM   2551  CA   VAL A 346      16.134  29.487  27.026  1.00 35.62           C
ATOM   2552  CB   VAL A 346              35.92   1.00 26.973  27.932  16.250  C
ATOM   2553  CG1  VAL A 346      17.712  27.485  27.145  1.00 38.59           C
ATOM   2554  CG2  VAL A 346      15.396  27.286  28.079  1.00 36.02           C
ATOM   2555  C    VAL A 346      16.510  30.126          36.16   1.00 28.373  C
ATOM   2556  O    VAL A 346      15.602  30.492  29.140  1.00 35.64           O
ATOM   2557  N    PHE A 347      17.802  30.389  28.605  1.00 35.43           N
ATOM   2558  CA   PHE A 347      18.265  30.715  29.961  1.00 38.68           C
ATOM   2559  CB   PHE A 347      19.042  29.511  30.600  1.00 39.33           C
ATOM   2560  CG   PHE A 347      18.135  28.340  30.969  1.00 45.18           C
ATOM   2561  CD1  PHE A 347      16.801  28.582  31.464  1.00 48.30           C
ATOM   2562  CE1  PHE A 347      15.893  27.476  31.831  1.00 50.09           C
ATOM   2563  CZ   PHE A 347      16.369  26.104  31.681  1.00 51.06           C
ATOM   2564  CE2  PHE A 347      17.737  25.855  31.175  1.00 48.00           C
ATOM   2565  CD2  PHE A 347              48.28   1.00 30.821  26.987  18.592  C
ATOM   2566  C    PHE A 347      19.166  31.908  30.074  1.00 39.98           C
ATOM   2567  O    PHE A 347      19.564  32.283  31.186  1.00 40.10           O
ATOM   2568  N    HIS A 348      19.563  32              40.83 1.00  28.950  499.N
```

Fig. 26 (Cont.)

```
ATOM   2569  CA   HIS A 348      20.558  33.528  29.101  1.00 41.72           C
ATOM   2570  CB   HIS A 348      21.948  32.970  28.832  1.00 43.21           C
ATOM   2571  CG   HIS A 348      22.409  32.036  29.935  1.00 49.93           C
ATOM   2572  ND1  HIS A 348      22.721  32.486  31.219  1.00 52.33           N
ATOM   2573  CE1  HIS A 348      23.070  31.455  31.974  1.00 51.53           C
ATOM   2574  NE2  HIS A 348      22.978  30.352  31.243  1.00 54.82           N
ATOM   2575  CD2  HIS A 348      22.545  30.679  29.967  1.00 50.39           C
ATOM   2576  C    HIS A 348      20.259  34.903  28.529  1.00 40.57           C
ATOM   2577  O    HIS A 348      19.492  35.643  29.132  1.00 40.88           O
ATOM   2578  N    LYS A 349      20.860  35.267  27.399  1.00 38.67           N
ATOM   2579  CA   LYS A 349      20.765  36.630  26.942  1.00 35.44           C
ATOM   2580  CB   LYS A 349      22.170  37.123  26.571  1.00 34.83           C
ATOM   2581  CG   LYS A 349      23.067          31.45  1.00 27.804  37.129   C
ATOM   2582  CD   LYS A 349      24.444  37.769  27.573  1.00 30.24           C
ATOM   2583  CE   LYS A 349      25.461  37.279  28.605  1.00 29.62           C
ATOM   2584  NZ   LYS A 349      26.808  37.959  28.269  1.00         32.99   N
ATOM   2585  C    LYS A 349      19.779  36.743  25.803  1.00 34.65           C
ATOM   2586  O    LYS A 349      19.028  35.812  25.511  1.00 34.18           O
ATOM   2587  N    ALA A 350      19.796  37.896  25.162  1.00 33.77           N
ATOM   2588  CA   ALA A 350      19.099  38.088  23.887  1.00 33.49           C
ATOM   2589  CB   ALA A 350      17.681  38.681  24.111  1.00 32.05           C
ATOM   2590  C    ALA A 350      19.933  39.036  23.012  1.00 32.27           C
ATOM   2591  O    ALA A 350      20.647  39.882  23.524  1.00 31.81           O
ATOM   2592  N    LEU A 351      19.734  38.941  21.704  1.00 32.03           N
ATOM   2593  CA   LEU A 351      20.548  39.614  20.730  1.00 32.98           C
ATOM   2594  CB   LEU A 351      21.404          32.08  1.00 20.013  38.577   C
ATOM   2595  CG   LEU A 351      22.578  39.087  19.200  1.00 34.41           C
ATOM   2596  CD1  LEU A 351      23.686  39.792  20.060  1.00 36.80           C
ATOM   2597  CD2  LEU A 351      23.175  37.919  18.364         33.03  1.00   C
ATOM   2598  C    LEU A 351      19.666  40.378  19.746  1.00 33.10           C
ATOM   2599  O    LEU A 351      18.644  39.883  19.309  1.00 34.98           O
ATOM   2600  N    TYR A 352      20.028  41.622  19.485  1.00 34.23           N
ATOM   2601  CA   TYR A 352      19.295  42.497  18.583  1.00 35.12           C
ATOM   2602  CB   TYR A 352      18.793  43.715  19.321  1.00 34.78           C
ATOM   2603  CG   TYR A 352      17.662  44.464  18.621  1.00 34.31           C
ATOM   2604  CD1  TYR A 352      16.644  43.781  18.011  1.00 30.74           C
ATOM   2605  CE1  TYR A 352      15.594  44.464  17.377  1.00 33.11           C
ATOM   2606  CZ   TYR A 352      15.581  45.852  17.328  1.00 34.26           C
ATOM   2607  OH   TYR A 352      14              37.46  1.00 16.697  46.465 546.0
ATOM   2608  CE2  TYR A 352      16.601  46.599  17.892  1.00 34.76           C
ATOM   2609  CD2  TYR A 352      17.668  45.888  18.536  1.00 34.22           C
ATOM   2610  C    TYR A 352      20.225  42.913  17.479         34.64  1.00   C
ATOM   2611  O    TYR A 352      21.229  43.545  17.773  1.00 36.10           O
ATOM   2612  N    CYS A 353      19.941  42.480  16.239  1.00 35.79           N
ATOM   2613  CA   CYS A 353      20.886  42.635  15.055  1.00 37.35           C
ATOM   2614  CB   CYS A 353      21.311  41.272  14.463  1.00 37.59           C
ATOM   2615  SG   CYS A 353      21.597  39.936  15.687  1.00 44.94           S
ATOM   2616  C    CYS A 353      20.238  43.322  13.858  1.00 37.04           C
ATOM   2617  O    CYS A 353      19.023  43.197  13.679  1.00 36.03           O
ATOM   2618  N    ASP A 354      21.040  43.962  13.006  1.00 36.33           N
ATOM   2619  CA   ASP A 354      20.573  44.285  11.660  1.00 37.32           C
ATOM   2620  CB   ASP A 354              37.30  1.00 10.994  45.320  21.475   C
ATOM   2621  CG   ASP A 354      21.496  46.683  11.742  1.00 39.53           C
ATOM   2622  OD1  ASP A 354      20.610  47.011  12.520  1.00 35.09           O
ATOM   2623  OD2  ASP A 354      22.406  47.509  11              47.05  1.00 625.0
ATOM   2624  C    ASP A 354      20.516  43.000  10.783  1.00 39.24           C
ATOM   2625  O    ASP A 354      21.443  42.201  10.844  1.00 39.21           O
ATOM   2626  N    LEU A 355      19.460  42.828   9.958  1.00 39.69           N
ATOM   2627  CA   LEU A 355      19.429  41.815   8.875  1.00 40.83           C
ATOM   2628  CB   LEU A 355      18.058  41.723   8.209  1.00 39.93           C
ATOM   2629  CG   LEU A 355      16.980  41.104   9.077  1.00 39.47           C
```

Fig. 26 (Cont.)

```
ATOM   2630  CD1 LEU A 355      15.610  41.160   8.360  1.00 38.70           C
ATOM   2631  CD2 LEU A 355      17.363  39.650   9.400  1.00 36.95           C
ATOM   2632  C   LEU A 355      20.492  42.064   7.798  1.00 42.04           C
ATOM   2633  O   LEU A 355              42.68 1.00   7.649   43.214  20.963  O
ATOM   2634  OT  LEU A 355      20.869  41.067   7.149  1.00 42.29           O
ATOM   2635  CA  CA  B 400       4.902  31.422  21.076  1.00 37.87          CA
ATOM   2636  CA  CA  B 401       9.862  26.279          37.77 1.00  23.131  CA
ATOM   2637  P   PO4 B 402      12.263  24.882  25.290  1.00 47.29           P
ATOM   2638  O1  PO4 B 402      10.821  25.112  24.781  1.00 41.35           O
ATOM   2639  O2  PO4 B 402      12.995  23.970  24.323  1.00 44.02           O
ATOM   2640  O3  PO4 B 402      12.237  24.170  26.585  1.00 43.60           O
ATOM   2641  O4  PO4 B 402      13.018  26.210  25.500  1.00 49.26           O
ATOM   2642  O   HOH C   1      25.416  24.056  19.747  1.00 18.97           O
ATOM   2643  O   HOH C   2      14.777  31.585   3.318  1.00 31.43           O
ATOM   2644  O   HOH C   3      -2.838  22.102  32.773  1.00 34.21           O
ATOM   2645  O   HOH C   4       2.443  31.629   7.007  1.00 30.71           O
ATOM   2646  O   HOH C           38.23 1.00  20.249  33.617   4.934      5   O
ATOM   2647  O   HOH C   6      13.472  32.347  29.984  1.00 35.48           O
ATOM   2648  O   HOH C   7       4.732  35.100  15.815  1.00 36.10           O
ATOM   2649  O   HOH C   8       6.795  31.628          36.29 1.00  19.665   O
ATOM   2650  O   HOH C   9      21.431  25.874  21.319  1.00 36.22           O
ATOM   2651  O   HOH C  10      10.779  32.224  29.452  1.00 36.57           O
ATOM   2652  O   HOH C  11       6.449  29.013  18.581  1.00 34             88.O
ATOM   2653  O   HOH C  12      22.786  23.625  20.765  1.00 28.77           O
ATOM   2654  O   HOH C  13      -1.362  24.630  38.658  1.00 42.56           O
ATOM   2655  O   HOH C  14       8.208  27.701  24.353  1.00 37.72           O
ATOM   2656  O   HOH C  15       6.452  37.826  16.477  1.00 41.78           O
ATOM   2657  O   HOH C  16      -8.766  31.917  36.839  1.00 38.98           O
ATOM   2658  O   HOH C  17       3.247  30.704  19.507  1.00 36.33           O
ATOM   2659  O   HOH C           46.90 1.00   1.141   21.870   6.424     18  O
ATOM   2660  O   HOH C  19      30.634  31.425  16.498  1.00 27.70           O
ATOM   2661  O   HOH C  20       1.750  33.065  18.713  1.00 38.81           O
ATOM   2662  O   HOH C  21       2.111  31.472          40.55 1.00  39.170   O
ATOM   2663  O   HOH C  22      20.248  29.991  27.165  1.00 37.04           O
ATOM   2664  O   HOH C  23      25.057  34.217  26.293  1.00 46.33           O
ATOM   2665  O   HOH C  24       9.035  37.144  12.537  1.00         35.56   O
ATOM   2666  O   HOH C  25       8.566  41.109   5.556  1.00 34.21           O
ATOM   2667  O   HOH C  26       6.861  22.115  29.280  1.00 38.56           O
ATOM   2668  O   HOH C  27      22.244  36.251   7.273  1.00 38.34           O
ATOM   2669  O   HOH C  28       0.557  11.252  21.591  1.00 43.77           O
ATOM   2670  O   HOH C  29      -2.123  31.614  40.953  1.00 34.78           O
ATOM   2671  O   HOH C  30      21.112  40.250  26.898  1.00 35.06           O
ATOM   2672  O   HOH C  31      -9.076  25.997  33.766  1.00 36.50           O
ATOM   2673  O   HOH C  32      -3.513  49.009  26.259  1.00 37.66           O
ATOM   2674  O   HOH C  33       8.125  14.064  23.832  1.00 33.99           O
ATOM   2675  O   HOH C  34       2.622          30.17 1.00  35.173  11.524   O
ATOM   2676  O   HOH C  35       6.216  21.134  31.899  1.00 38.41           O
ATOM   2677  O   HOH C  36       9.787  10.559  23.826  1.00 36.64           O
ATOM   2678  O   HOH C  37      -8.082  25.521  41.012  1           47.14 00.O
ATOM   2679  O   HOH C  38      16.237  25.619   0.821  1.00 39.12           O
ATOM   2680  O   HOH C  39     -11.257  28.900  18.934  1.00 51.23           O
ATOM   2681  O   HOH C  40      -9.574  18.677  32.756  1.00 37.09           O
ATOM   2682  O   HOH C  41      17.141  35.834   4.392  1.00 39.65           O
ATOM   2683  O   HOH C  42      34.118  26.392  32.175  1.00 35.06           O
ATOM   2684  O   HOH C  43       7.193  11.711  24.368  1.00 26.04           O
ATOM   2685  O   HOH C  44       0.406  12.036  33.279  1.00 51.34           O
ATOM   2686  O   HOH C  45       0.263  34.604  12.212  1.00 40.95           O
ATOM   2687  O   HOH C  46       6.843  34.374  18.048  1.00 47.69           O
ATOM   2688  O   HOH C  47      21             46.41 1.00   5.289  34.395  888.O
ATOM   2689  O   HOH C  48      -5.426  46.033  25.055  1.00 40.26           O
ATOM   2690  O   HOH C  49       6.523  32.834   2.939  1.00 37.13           O
```

Fig. 26 (Cont.)

```
ATOM   2691  O   HOH C   50      18.508  24.117   6.259         52.30 1.00    O
ATOM   2692  O   HOH C   51      18.335  22.263   7.981   1.00 45.60          O
ATOM   2693  O   HOH C   52      -2.154  35.559  13.235   1.00 48.07          O
ATOM   2694  O   HOH C   54       2.611  13.006  14.424   1.00 41.91          O
ATOM   2695  O   HOH C   55      26.270  22.668  27.332   1.00 30.96          O
ATOM   2696  O   HOH C   56      -0.309  40.005  16.952   1.00 57.62          O
ATOM   2697  O   HOH C   57      10.206  37.442   6.580   1.00 37.46          O
ATOM   2698  O   HOH C   58      -1.683  33.893   5.328   1.00 42.44          O
ATOM   2699  O   HOH C   59       3.798  28.537   0.632   1.00 45.82          O
ATOM   2700  O   HOH C   60       3.980  20.668  33.282   1.00 36.07          O
ATOM   2701  O   HOH C   61           47.51 1.00  13.548  31.638   7.651-     O
ATOM   2702  O   HOH C   62      -1.415  29.958  38.148   1.00 40.19          O
ATOM   2703  O   HOH C   63      -4.150  31.418  39.301   1.00 35.73          O
ATOM   2704  O   HOH C   64       2.632  38.223  16           54.94 1.00  361.O
ATOM   2705  O   HOH C   65       1.160  32.335   4.746   1.00 39.33          O
ATOM   2706  O   HOH C   66      -0.191  46.319  17.177   1.00 43.43          O
ATOM   2707  O   HOH C   67      -4.515  38.523  16.699   1.00 44.18          O
ATOM   2708  O   HOH C   68       0.004   5.610  21.831   1.00 42.81          O
ATOM   2709  O   HOH C   69       6.755  38.052  13.941   1.00 45.39          O
ATOM   2710  O   HOH C   70       1.484  36.838  11.727   1.00 48.01          O
ATOM   2711  O   HOH C   71      11.347  38.766   1.463   1.00 40.35          O
ATOM   2712  O   HOH C   72      10.803   2.521  21.920   1.00 39.86          O
ATOM   2713  O   HOH C   73       6.257  46.235   9.482   1.00 32.20          O
ATOM   2714  O   HOH C   74           36.72 1.00   4.068  18.604  12.273      O
ATOM   2715  O   HOH C   75      26.852  43.345  22.771   1.00 36.45          O
ATOM   2716  O   HOH C   76       4.545  42.095  38.551   1.00 37.17          O
ATOM   2717  O   HOH C   77       6.173  40.625          29.69 1.00   34.445  O
ATOM   2718  O   HOH C   78      17.757  39.446  33.552   1.00 33.40          O
ATOM   2719  O   HOH C   79      -1.810  47.142  19.553   1.00 43.25          O
ATOM   2720  O   HOH C   80      -0.261   5.530  24.453   1.00 41.11          O
ATOM   2721  O   HOH C   81      27.755  41.917  14.870   1.00 40.21          O
ATOM   2722  O   HOH C   82      -2.810  43.733  41.772   1.00 30.48          O
ATOM   2723  O   HOH C   83      23.268  46.982   8.565   1.00 47.12          O
ATOM   2724  O   HOH C   84       9.064  35.101   1.155   1.00 36.99          O
ATOM   2725  O   HOH C   85      -9.299  14.474  22.813   1.00 40.07          O
ATOM   2726  O   HOH C   86      -7.301  17.445  14.157   1.00 37.86          O
ATOM   2727  O   HOH C   87           33.93 1.00  18.618   6.795  13.806      O
ATOM   2728  O   HOH C   88      13.004   8.186  42.001   1.00 38.57          O
ATOM   2729  O   HOH C   89     -14.146  19.502  26.726   1.00 51.48          O
ATOM   2730  O   HOH C   90      24.308   8.974          49.15 1.00   26.646  O
ATOM   2731  O   HOH C   91      34.768  31.860  18.488   1.00 35.21          O
ATOM   2732  O   HOH C   92      21.505  28.792   4.395   1.00 43.28          O
ATOM   2733  O   HOH C   93       0.147  20.019  34.435   1.00 37         26.O
ATOM   2734  O   HOH C   94      -4.020  47.145  19.051   1.00 42.42          O
ATOM   2735  O   HOH C   95      24.891  27.086   9.597   1.00 44.39          O
ATOM   2736  O   HOH C   97      18.602  46.192   8.814   1.00 40.24          O
ATOM   2737  O   HOH C   98       2.232  15.638  10.158   1.00 42.49          O
ATOM   2738  O   HOH C   99       7.589  33.943  -0.709   1.00 43.47          O
ATOM   2739  O   HOH C  100       5.528  15.536   3.834   1.00 44.16          O
ATOM   2740  O   HOH C          39.62 1.00  12.801  14.851   0.629        101 O
ATOM   2741  O   HOH C  102       6.812   4.456  20.770   1.00 48.37          O
ATOM   2742  O   HOH C  103      -1.949  14.371  12.595   1.00 39.66          O
ATOM   2743  O   HOH C  104       0.844  34           53.95 1.00  16.486  429.O
ATOM   2744  O   HOH C  105       7.768   1.761  21.718   1.00 38.28          O
ATOM   2745  O   HOH C  106     -13.022  19.911  29.013   1.00 37.60          O
ATOM   2746  O   HOH C  107      12.029   0.880  23.767   1.00           33.66 O
ATOM   2747  O   HOH C  108      20.457  38.723   6.443   1.00 38.04          O
ATOM   2748  O   HOH C  110     -10.534  30.508  36.167   1.00 43.56          O
ATOM   2749  O   HOH C  111      -2.490  19.454  33.945   1.00 45.84          O
ATOM   2750  O   HOH C  112      -2.624  11.620  23.689   1.00 54.05          O
ATOM   2751  O   HOH C  113      -8.535  28.736  37.398   1.00 47.83          O
```

Fig. 26 (Cont.)

```
ATOM   2752  O    HOH C 114       4.993  12.357  14.030  1.00 48.45           O
ATOM   2753  O    HOH C 115      21.043   6.659  26.003  1.00 43.96           O
ATOM   2754  O    HOH C 116      11.046  31.860  16.286  1.00 31.59           O
ATOM   2755  O    HOH C 117       4.213  51.982  15.574  1.00 45.89           O
ATOM   2756  O    HOH C 118      13.73           45.89 1.00   29.31    24.01  O
```

Fig. 26 (Cont.)

PON POLYPEPTIDES, POLYNUCLEOTIDES ENCODING SAME AND COMPOSITIONS AND METHODS UTILIZING SAME

RELATED PATENT APPLICATIONS

This application is a division of U.S. patent application Ser. No. 12/723,725 filed on Mar. 15, 2010, which is a continuation of U.S. patent application Ser. No. 10/547,771 filed on Feb. 28, 2006, now U.S. Pat. No. 7,786,071 which is a National Phase of PCT Patent Application No. PCT/IL2004/000216 having International Filing Date of Mar. 4, 2004, which claims the benefit of priority of U.S. Provisional Patent Application Nos. 60/512,925 filed on Oct. 22, 2003, and 60/451,267 filed on Mar. 4, 2003. The contents of the above applications are all incorporated herein by reference.

STATEMENT REGARDING FEDERALLY SPONSORED RESEARCH

This invention was made with government support under No. DAMD17-02-1-0675 awarded by the Army/MRMC. The government has certain rights in the invention.

SEQUENCE LISTING STATEMENT

The ASCII file, entitled 57631SequenceListing.txt, created on Oct. 20, 2013, comprising 334,336 bytes, submitted concurrently with the filing of this application is incorporated herein by reference.

FIELD AND BACKGROUND OF THE INVENTION

The present invention relates to novel PON polypeptides and polynucleotides encoding same and to compositions and methods utilizing same. More particularly, the present invention relates to compositions including mutated PON polynucleotides or polypeptides and to methods of utilizing same for detoxification and decontamination, and for treating PON-associated diseases such as atherosclerosis.

Serum paraoxonases (PON1s) are calcium dependent phosphotriesterases which are essential to the detoxification process of organophosphates (OPs) such as the insecticide paraoxon and the nerve agents sarin and soman (Davies et al., 1996). Approximately 16% of the population is deficient in this enzyme and at high risk for damage from exposure to these and other OP agents, which are effected by the enzyme. PON1s also catalyze the hydrolysis of a broad range of carboxy-esters including lactones and thiolactones (Billecke et al., 2000; Jakubowski, 2000). PON1 resides within the cholesterol-carrying particles HDL ("good cholesterol") and exhibits a multitude of activities related to the metabolism of drugs, lipids and other molecules associated with atheroscleorotic vascular and cardiac diseases (Ahmed et al., 2001; Billecke et al., 2000; Rodrigo et al., 2001). The levels of PON1 in the blood and its catalytic proficiency appear to have a major impact on susceptibility to athreosclerosis, cardiac and vascular diseases, cholesterol reducing drugs and various toxins and pollutants including insecticides (Smolen et al., 1991). It was also shown that mice lacking the PON1 gene are susceptible to atherosclerosis and organophosphate toxicity much more than PON1-carrying mice (Shih et al., 1998).

Despite its physiological and therapeutic importance, the structure and mechanism of action of PON1 have yet to be elucidated. PON1 appears to exhibit a curiously broad range of hydrolytic activities—catalyzing both phosphotriesters and carboxy-esters, as well as thiolactones (Billeclke et al., 2000). In addition, PON1 has been implicated in the reduction of lipid peroxides suggesting that it may also function as a peroxireductase (Aviram et al., 1998). Whether the latter is related to PON1's hydrolytic activities or not, is yet to be determined.

Almost all the research on PON1 has been performed on protein samples purified from sera. However, the yields of sera-purified PON1 are low, and the intimate association of PON1 with HDL can result in contamination by other HDL-associated enzymes including PON3 (Ahmed et al., 2001). The newly-reported activities of PON1 are orders of magnitude lower than with its well-characterized substrates—For example, hydrolysis of homocysteine thiolactone by such purified enzymes is 2,800-25000 times lower than with phenylacetate depending on the enzyme preparation (Billeclke et al., 2000; Jakubowski, 2000). Such low activities may result from miniscule amounts of a contaminating enzyme, such as PON3 [i.e., a variant of PON1 which is also found in HDL; (Ahmed et al., 2001)], or other serum enzymes. The difficulties in characterizing PON1 are highlighted by the recent discussion regarding its hydrolytic activity with PAF [i.e., platelet activating factor; (Rodrigo et al., 2001)]. Whilst one set of experiments suggests that PAF hydrolysis is mediated by PON1 and is not due to contamination of the purified PON1 with PAFAH (PAF acetyl hydrolase), a more recent publication argues that this activity is due to very low PAFAH contaminations (Marathe et al., 2002).

Amongst the issues yet to be clarified is the role of PON1 glycosylation in the enzyme's activity. Josse et al mutated two putative N-linked glycosylation sites (N252 and N323) of hPON1 expressed in human embryonic kidney cell line with no effect on its esterolytic activity (Josse et al., 1999). In contrast, enzymatic deglycosilation of hPON1 expressed in baculovirus abolished the enzyme's arylesterase activity, suggesting that glycosylation is essential to the enzyme's activity, and that sites other than N252 and N323 may be involved (Brushia et al., 2001). It was also shown that PON1 could not be functionally expressed in *E. coli*, presumably due to the absence of glycosylation in prokaryotes and the aggregation of the over-expressed protein into inclusion bodies (Brushia et al., 2001; Josse et al., 2002). PON1s also posses a disulphide bond, the formation of which may be hindered by the reducing environment present in *E. coli*'s cytoplasm. Indeed, attempts to express hPON1 in *E. coli* under a broad range of conditions failed to yield soluble and active protein.

The availability of bacterially over-expressed PON1 that is soluble and catalytically active is of prime clinical value. Furthermore, the expression and purification of PON1 from *E. coli* can shed light on the different activities attributed to the enzyme, making it possible to explore its less pronounced activities while unambiguously ruling out contamination by other mammalian enzymes. The mechanism of PON1 activity could be investigated using biophysical methods which require high amounts of purified protein. Finally, functional expression in *E. coli* is the key for future attempts to engineer or directly evolve PON1 to have improved catalytic efficiencies towards therapeutic targets such as highly toxic nerve agents, or cardiac and vascular diseases related substrates such as lipid peroxides and homocysteine thiolactone.

Low solubility of proteins expressed in host systems is a major obstacle in the structural and functional characterization of numerous proteins (Waldo, 2003). Several methods have been developed to screen for mutant proteins with increased solubility. One approach using GFP fusion protein as a folding reporter is based on the correlation between folding of the target protein and the fluorescence of the E. coli cells expressing the GFP fusion (Waldo et al., 1999; Yang et al., 2003). Another approach is based on fusion of chloramphenicol acyltransferase (CAT) to the target protein allowing soluble mutants to be selected by growths at high levels on chloramphenicol (Maxwell et al., 1999). The main drawback of these approaches is, that selection pressure for solubility can only generate soluble mutant proteins with significant structural alterations and no function. In contrast, a direct screening for function ensures that soluble protein variants retain function [for the evolution of a soluble galactose oxidase in E. coli by a functional screen see Sun et al. (2001)].

While reducing the present invention to practice, the present inventors employed a directed evolution approach in order to engineer highly expressed recombinant variants of PON exhibiting activity spectra comparable to that of respective wild-type PONs purified from sera. Using the same approach, the present inventors also generated PON variants with specialized catalytic activities.

As is further described in the Examples section which follows, the availability of recombinant PON variants exhibiting kinetic parameters similar to those reported for PONs purified from sera enabled elucidation of the three dimensional (3D) structure of PON1, shedding light on its unique active site and catalytic mechanism. These findings allow, for the first time, to generate and use PON enzymes with improved catalytic efficiencies towards therapeutic targets such as highly toxic nerve agents, or cardiac and vascular diseases related substrates such as lipid peroxides and homocysteine thiolactone.

SUMMARY OF THE INVENTION

According to one aspect of the present invention there is provided an isolated polynucleotide comprising a nucleic acid sequence encoding a mutated PON1 enzyme, the mutated PON1 enzyme being characterized by: (i) a substrate specificity which is substantially identical to that of a respective wild-type PON; and (ii) no substantial formation of aggregates when expressed in bacteria.

According to another aspect of the present invention there is provided an isolated polypeptide comprising an amino acid sequence of a mutated PON1 enzyme, the mutated PON1 enzyme being characterized by: (i) a substrate specificity which is substantially identical to that of a respective wild-type PON; and (ii) no substantial formation of aggregates when expressed in bacteria.

According to yet another aspect of the present invention there is provided an isolated polynucleotide comprising a nucleic acid sequence encoding a mutated PON1 enzyme, wherein an amino acid sequence of a hydrophobic region of the mutated PON1 enzyme includes at least one amino acid substitution with respect to an amino acid sequence of a respective hydrophobic region of a human PON1, the mutated PON1 enzyme being characterized by: (i) a substrate specificity which is substantially identical to that of a respective wild-type PON; and (ii) no substantial formation of aggregates when expressed in bacteria.

According to still another aspect of the present invention there is provided an isolated polypeptide comprising an amino acid sequence of a mutated PON1 enzyme, wherein an amino acid sequence of a hydrophobic region of the mutated PON1 enzyme includes at least one amino acid substitution with respect to an amino acid sequence of a respective hydrophobic region of a human PON1, the mutated PON1 enzyme being characterized by: (i) a substrate specificity which is substantially identical to that of a respective wild-type PON; and (ii) no substantial formation of aggregates when expressed in bacteria.

According to still further features in the described preferred embodiments the bacteria is E. coli.

According to still further features in the described preferred embodiments the E. coli is selected from the group of strains consisting of BL21, BL21 (DE3), Origami B (DE3) and RIL (DE3).

According to still further features in the described preferred embodiments the isolated polypeptide further comprising a tag, the tag being fused in-frame to the mutated PON1 enzyme.

According to still further features in the described preferred embodiments the tag is selected from the group consisting of thioredoxin, NUS, GST and MBP.

According to still further features in the described preferred embodiments the isolated polypeptide is as set forth in SEQ ID NO: 57, 58, 59, 60, 61 or 56.

According to still further features in the described preferred embodiments the amino acid sequence of the mutated PON1 enzyme is of an origin selected from the group consisting of a mouse, a human, a rat, a rabbit and a combination thereof.

According to still further features in the described preferred embodiments the mutated PON1 enzyme further includes a lysine at a position equivalent to amino acid coordinate 192 of rabbit PON1.

According to still further features in the described preferred embodiments the hydrophobic region of the human PON1 is set forth by amino acid coordinates 126-142 of SEQ ID NO: 36 and/or amino acid coordinates 301-343 of SEQ ID NO: 36.

According to still further features in the described preferred embodiments the at least one amino acid substitution is of amino acid I126, M130, K137, L142, A301, A320 M341 or V343 of the human PON1.

According to still further features in the described preferred embodiments the mutated PON1 enzyme is as set forth in SEQ ID NO: 57, 58, 59, 60, 61 or 56.

According to an additional aspect of the present invention there is provided an isolated polypeptide as set forth in SEQ ID NO: 49, 50, 51, 52, 53, 54, 56, 57, 58, 59, 60, 61, 63, 65, 67, 69, 71, 73, 75 or 77.

According to yet an additional aspect of the present invention there is provided an isolated polynucleotide as set forth in SEQ ID NO: 25, 26, 27, 28, 29, 43, 44, 45, 46, 47, 48, 55, 62, 64, 66, 68, 70, 72, 74 or 76.

According to still an additional aspect of the present invention there is provided an isolated polypeptide comprising an amino acid sequence as set forth in SEQ ID NO: 49, 50, 51, 52, 53, 54, 56, 57, 58, 59, 60, 61, 63, 65, 67, 69, 71, 73, 75 or 77.

According to a further aspect of the present invention there is provided an isolated polynucleotide comprising a nucleic acid sequence as set forth in SEQ ID NO: 25, 26, 27, 28, 29, 43, 44, 45, 46, 47, 48, 55, 62, 64, 66, 68, 70, 72, 74 or 76.

According to yet a further aspect of the present invention there is provided an isolated polynucleotide comprising a nucleic acid sequence encoding a mutated PON enzyme exhibiting an increased substrate specificity to at least one known PON substrate as compared to a respective wild-type PON.

According to still further features in the described preferred embodiments the at least one known PON substrate is selected from the group consisting of an ester, a phosphotriesters, such as paraoxon, sarin and soman; a lactone, such as, dihydrocuomarin and γ-butyrolactone; thiolactones, such as, γ-butyrothiolactone and homocysteine thiolactone.

According to still further features in the described preferred embodiments the ester is selected from the group consisting of naphtyl, benzyl acetate and lipids.

According to still further features in the described preferred embodiments the phosphotriester is selected from the group consisting of paraoxon, sarin and soman, According to still further features in the described preferred embodiments the lactone is selected from the group consisting of dihydrocuomarin and γ-butyrolactone.

According to still further features in the described preferred embodiments the thiolactone is selected from the group consisting of γ-butyrothiolactone and homocysteine thiolactone.

According to still a further aspect of the present invention there is provided an isolated polypeptide comprising an amino acid sequence of a mutated PON enzyme exhibiting an increased substrate specificity to at least one known PON substrate as compared to a respective wild-type PON.

According to still further features in the described preferred embodiments the at least one known PON substrate is selected from the group consisting of esters, phosphotriesters, lactones and thiolactones.

According to still further features in the described preferred embodiments the mutated PON enzyme includes at least one amino acid substitution which is equivalent to an amino acid coordinate located in an active site of human PON1.

According to still further features in the described preferred embodiments the active site of human PON1 is distant by no more than 15 Å from a Calcium ion of the active site.

According to still further features in the described preferred embodiments the Calcium ion is Ca401.

According to still further features in the described preferred embodiments the increased substrate specificity is at least 3 fold higher $K_{cat}/K_M$ ratio for phosphotriester hysrolysis.

According to still further features in the described preferred embodiments the increased substrate specificity is at least 3 fold higher $K_{cat}/K_M$ ratio for ester hydrolysis.

According to still further features in the described preferred embodiments the increased substrate specificity is at least 3 fold higher $K_{cat}/K_M$ ratio for lactone hydrolysis.

According to still further features in the described preferred embodiments the increased substrate specificity is at least 3 fold higher $K_{cat}/K_M$ ratio for thiolactone hydrolysis.

According to still further features in the described preferred embodiments the increased substrate specificity is at least 3 fold higher $K_{cat}/K_M$ ratio for lipid hydrolysis.

According to still further features in the described preferred embodiments the increased substrate specificity is at least 3 fold higher $K_{cat}/K_M$ ratio for lipid peroxide hydrolysis.

According to still a further aspect of the present invention there is provided an isolated polynucleotide comprising a nucleic acid sequence encoding a mutated PON enzyme exhibiting a modified substrate range as compared to a corresponding wild-type PON.

According to still further features in the described preferred embodiments the PON enzyme is selected from the group consisting of PON1, PON2 and PON3.

According to still further features in the described preferred embodiments the narrower substrate range is manifested in an increased phosphotriesterase activity and a decreased esterase activity.

According to still further features in the described preferred embodiments the narrower substrate range is manifested in an increased thiolactonase activity and a decreased phosphotriesterase activity.

According to still further features in the described preferred embodiments the PON1 enzyme includes amino acid substitutions equivalent to amino acid coordinates selected from the group consisting of 69, 74, 75, 76, 78, 190, 192, 193, 196, 222, 240, 291, 292, 293, 332, and 346 of human PON1.

According to still further features in the described preferred embodiments the PON1 enzyme includes amino acid substitutions equivalent to amino acid coordinates S193, N287, G19 and V346 of human PON1.

According to still further features in the described preferred embodiments the PON1 enzyme includes amino acid substitutions equivalent to amino acid coordinates L69 and E218 of human PON1.

According to still a further aspect of the present invention there is provided a nucleic acid construct comprising an isolated polynucleotide of the present invention.

According to still further features in the described preferred embodiments a host cell comprising the nucleic acid construct of the present invention.

According to still a further aspect of the present invention there is provided a method of identifying proteins amenable to an in-vitro evolution process, the method comprising identifying proteins which exhibit at least two distinct catalytic activities and/or structural plasticity, the proteins being amenable to the in-vitro evolution process.

According to still further features in the described preferred embodiments the method further comprising subjecting the proteins to the in-vitro evolution process, to thereby test amenability of the proteins to the in-vitro evolution process.

According to still a further aspect of the present invention there is provided a method of generating proteins with desired traits, the method comprising: (a) identifying proteins exhibiting at least two distinct catalytic activities and/or structural plasticity, the proteins being amenable to the in-vitro evolution process; and (b) subjecting the proteins to the in-vitro evolution process, thereby generating proteins with desired traits.

According to still further features in the described preferred embodiments the proteins are selected from the group consisting of *E. coli* thioesterase/protease I and human carboxylesterase 1.

According to still further features in the described preferred embodiments identifying the proteins having the at least two distinct catalytic activities is effected by: (a) database annotations; (b) screening for the catalytic activities; and (c) screening for substrate binding.

According to still further features in the described preferred embodiments the identifying the proteins having the structural plasticity is effected by: (a) a biophysical method; and (b) database annotations.

According to still further features in the described preferred embodiments the biophysical method is selected from the group consisting of NMR, X-ray crystallography and circular-dischroism.

According to still a further aspect of the present invention there is provided a composition-of-matter comprising a crystalline form of PON1 at a resolution higher than or equal to 2.2 Å.

According to still a further aspect of the present invention there is provided a method of identifying a putative small molecule inhibitor of PON1, the method comprising: (a) constructing a model using a set of atomic structural coordinates defining a three-dimensional atomic structure of a crystallized PON1; and (b) computationally screening a plurality of compounds for a compound capable of specifically binding an active site of the model, thereby identifying the small molecule inhibitor of PON1.

According to still a further aspect of the present invention there is provided a computing platform for generating a three-dimensional model of PON1, the computing platform comprising: (a) a data-storage device storing the set of atomic structural coordinates listed in FIG. 26; and (b) a processing unit being for generating the three-dimensional model from the data stored in the data-storage device.

According to still a further aspect of the present invention there is provided a method of treating or preventing a PON1-related disease or condition in a subject, the method is effected by administering to the subject a therapeutically effective amount of a mutated PON1 enzyme which: (i) has substrate specificity which is substantially identical to that of human PON1; and (ii) does not substantially form aggregates when expressed in bacteria.

According to still further features in the described preferred embodiments the PON1-related disease or condition is selected from the group consisting of hyperlipidemia, atherosclerosis, neurological disease, cancer and organophosphate poisoning.

According to still further features in the described preferred embodiments the neurological disease is selected from the group consisting of Alzheimer's disease, neurofibromatosis, Huntington's disease, depression, amyotrophic lateral sclerosis, multiple sclerosis, stroke, Parkinson's disease, or multi-infarct dementia.

According to still a further aspect of the present invention there is provided a method of treating or preventing a PON-related disease or condition in a subject, the method is effected by administering to the subject a therapeutically effective amount of a mutated PON enzyme exhibiting an increased substrate specificity to at least one known PON substrate as compared to a respective wild-type PON.

According to still a further aspect of the present invention there is provided a method of treating or preventing a PON-related disease or condition in a subject, the method is effected by administering to the subject a therapeutically effective amount of a mutated PON enzyme exhibiting a modified substrate range as compared to a corresponding wild-type PON.

According to still a further aspect of the present invention there is provided a pharmaceutical composition comprising a therapeutically effective amount of the isolated polypeptide of the present invention.

According to still a further aspect of the present invention there is provided a pharmaceutical composition comprising a therapeutically effective amount of the isolated polynucleotide of the present invention.

According to still a further aspect of the present invention there is provided the compound 7-O-Diethylphosphoryl-(3-cyano-7-hydroxycuomarin).

The present invention successfully addresses the shortcomings of the presently known configurations by providing novel PON polypeptides and polynucleotides encoding same and compositions and methods utilizing same.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The patent or application file contains at least one drawing executed in color. Copies of this patent or patent application publication with color drawings will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figure 1:
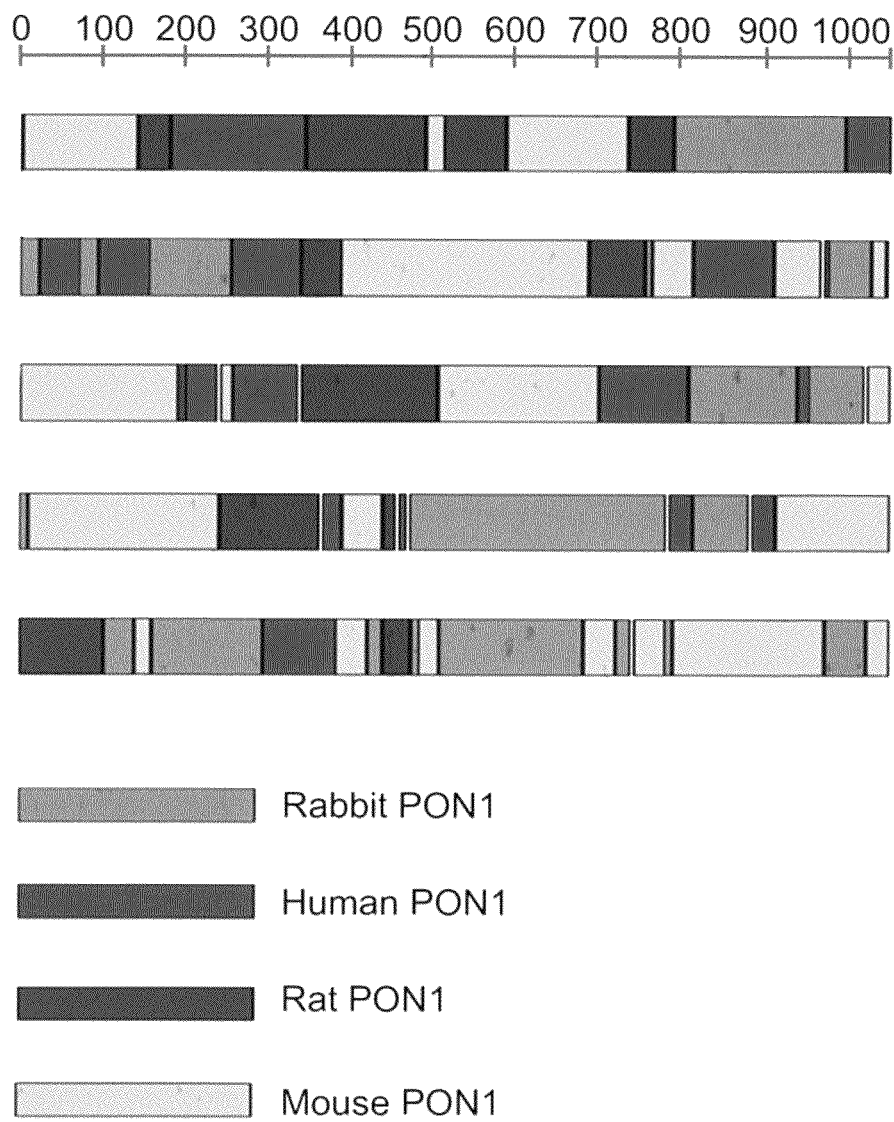

FIG. 1 is a schematic representation of the DNA sequence of five unselected clones from the family shuffling of the PON1 wild-type genes (i.e., G1 library). Different colors are assigned to each parental gene as follows: red, hPON1; yellow, mPON1; blue, RatPON1; green, RabPON1. Complete identity regions between the library clones and each of the four parental genes were followed to the point where a nucleotide, or a stretch of nucleotides, from another parental gene could be identified, allowing the identification of crossover points between parental genes.

Figure 2A:
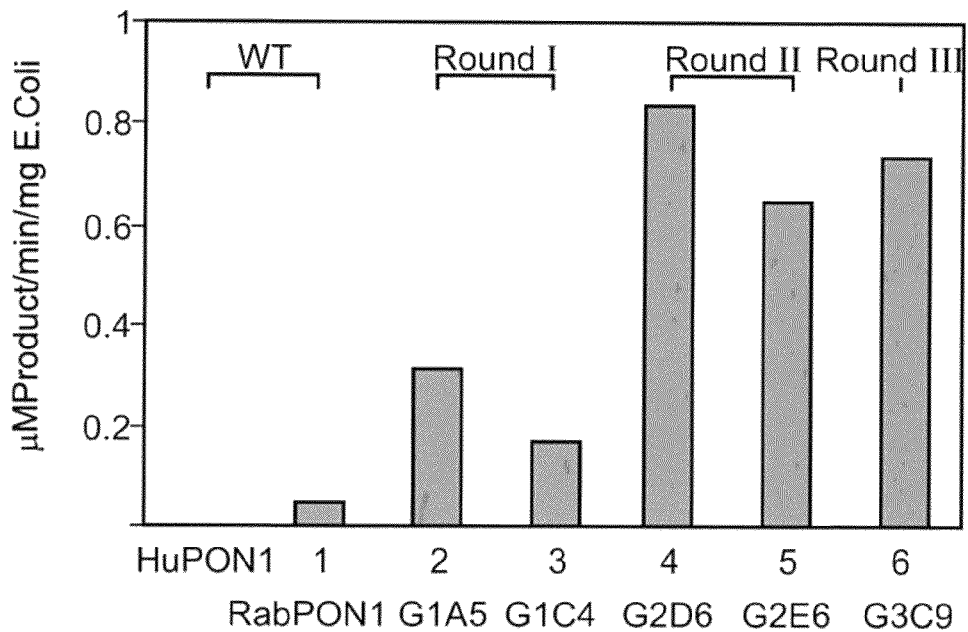

FIG. 2a is a histogram depicting paraoxonase activity of PON1 variants in crude E. coli lysates calculated per mg of E. coli cells. Activity is shown for the wild-type hPON1 and RabPON1, G1A5 and G1C4 variants from first round of evolution, G2D6 and G2E6 of the second round and G3C9 from the third round of evolution (i.e., without protein tags)

Figure 2B:
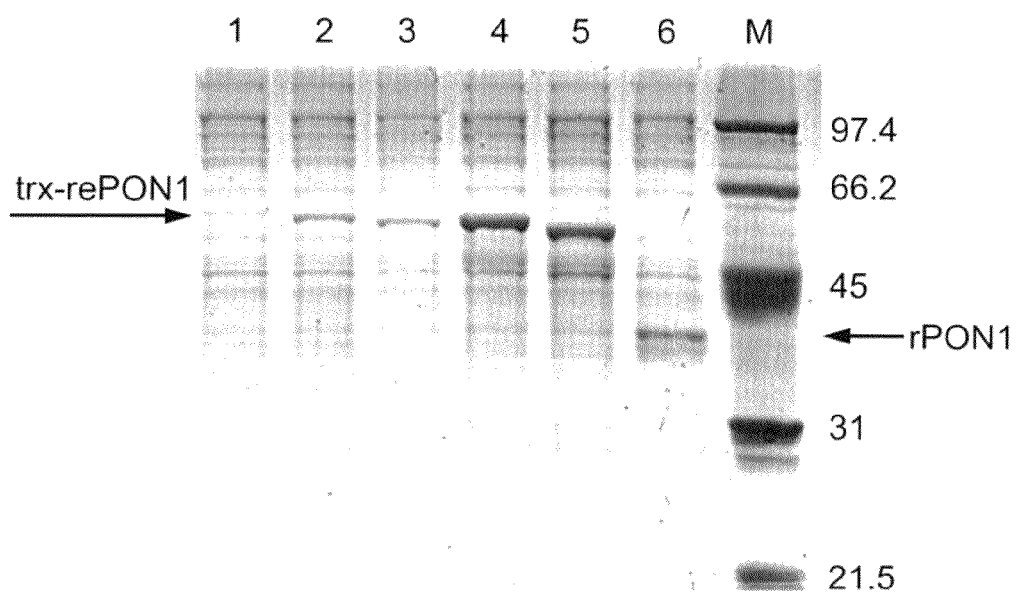

FIG. 2b is a photograph depicting SDS-PAGE (12%) analysis of the crude cell lysates of FIG. 2a. Lane 1 shows a crude lysate expression of the RabPON1 in pET32b, Lanes 2-5 show crude lysate expression of variants G1A5 G1C4 from first round of evolution and G2D6, G2E6 from second round of evolution (all in pET32b), respectively. Lane 6 shows crude lysate expression of G3C9 in modified pET32 with no protein tags.

Figure 3:
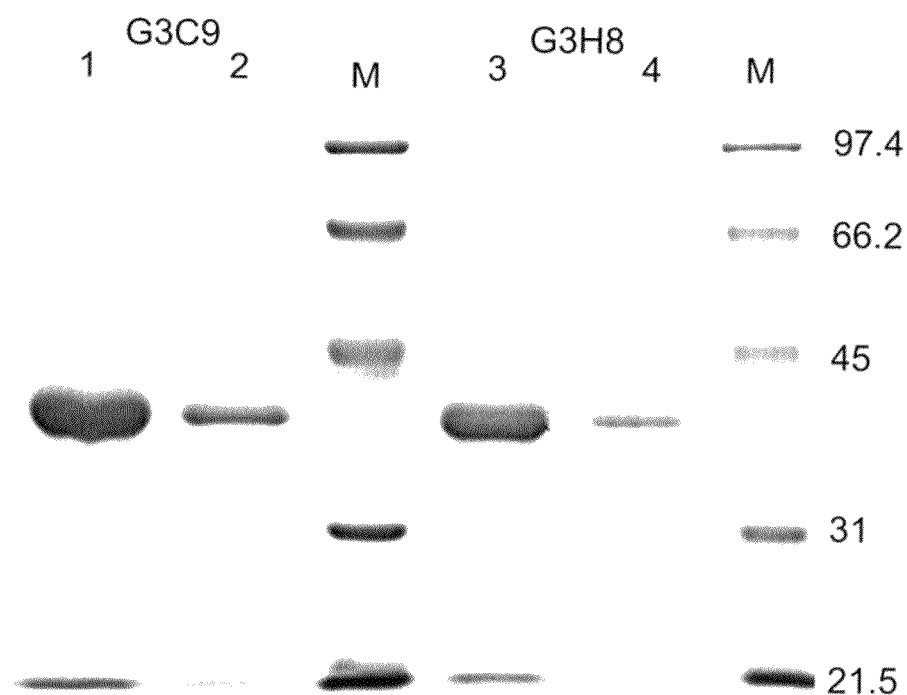

FIG. 3 is a photograph depicting SDS-PAGE (12%) analysis of purified rPON1 variants G3C9 and G3H8 from the third round of evolution. The protein is expressed with no tags in a modified pET32b vector. Lanes 1 and 2 are purified G3C9 and lanes 3 and 4 are purified G3H8.

Figure 4A:
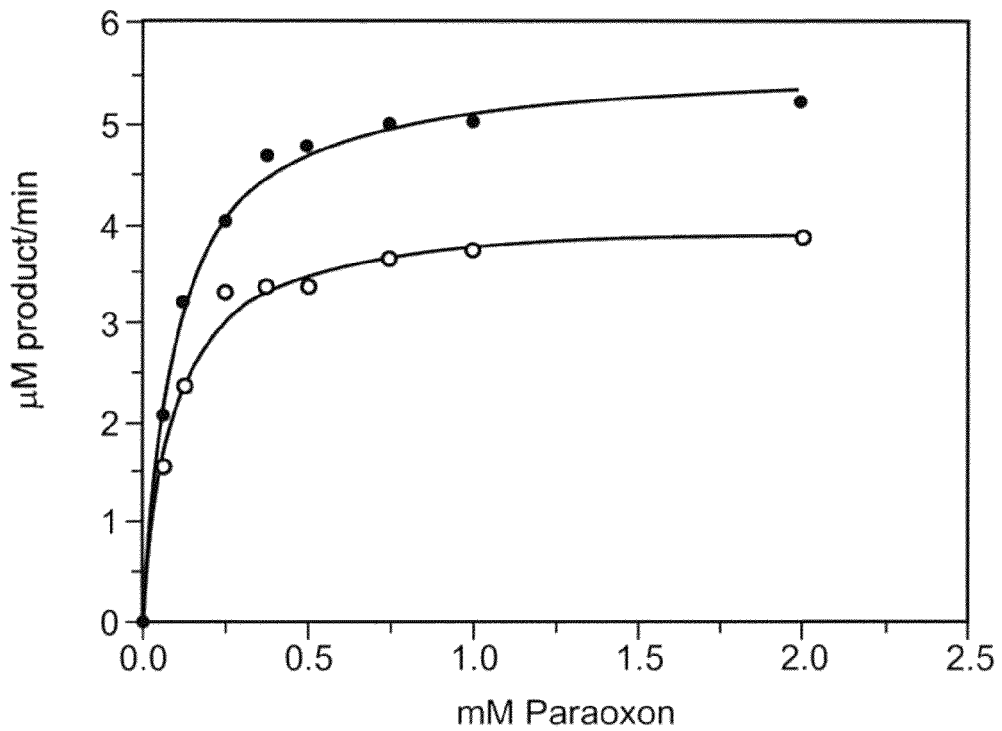
Figure 4B:
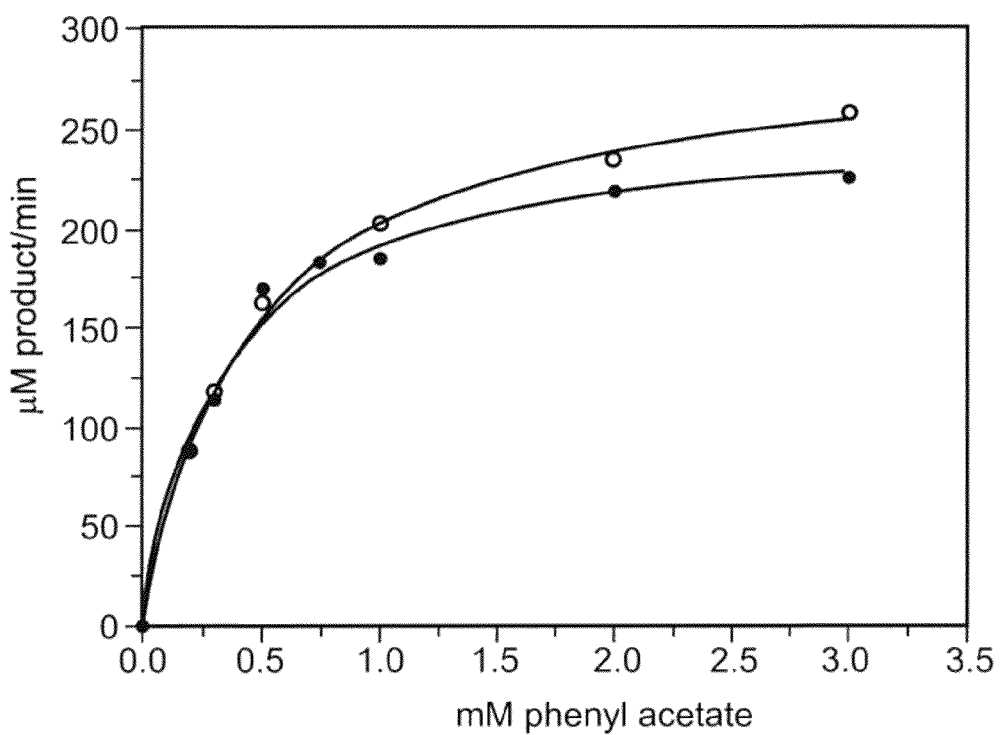

FIGS. 4a-b are graphs depicting Michaelis-Menten analysis for the paraoxon (FIG. 4a) and phenyl acetate hydrolysis (FIG. 4b) by variants G2E6 (open symbols) and G3C9 (closed symbols) from the second and third round of evolution, respectively. The rPON1 concentrations for the two variants are the same and are 0.078 µM in (FIG. 4a) and 0.0052 µM in (FIG. 4b). The kinetic parameters derived from the fit of the data to Michaelis-Menten model are listed in Table 2 below.

Figure 5C:
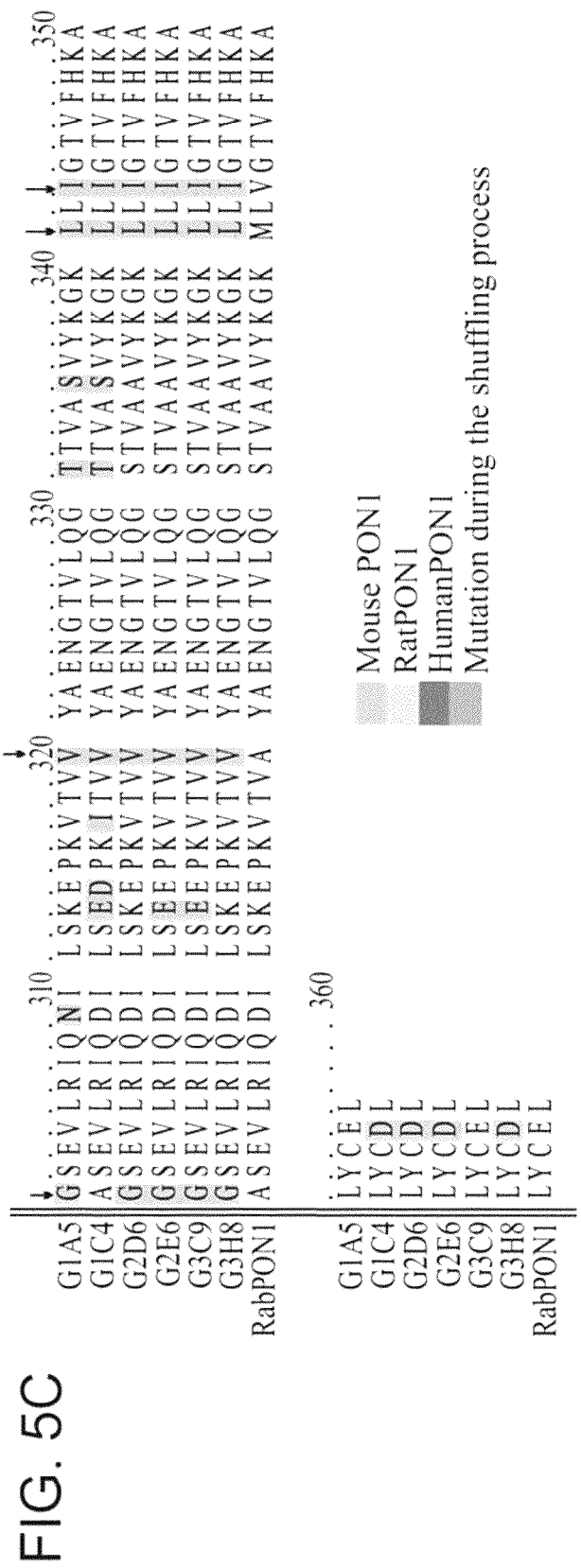

FIG. 5 is a sequence alignment of PON1 variants (G3C9, G1A5, G1C4, G2D6, G2E6, and G3H8 (SEQ ID NOs: 56-61 respectively) from different rounds of evolution aligned against the sequence of RabPON1 (SEQ ID NO: 39). Mutations in the sequence relative to the RabPON1 are colored according to their parental origin: red, hPON1; yellow, mPON1; blue, RatPON1; pink, for mutations that occurred during the shuffling and amplification processes. Conserved mutations in the directly-evolved variants are marked with an arrow.

Figure 6:
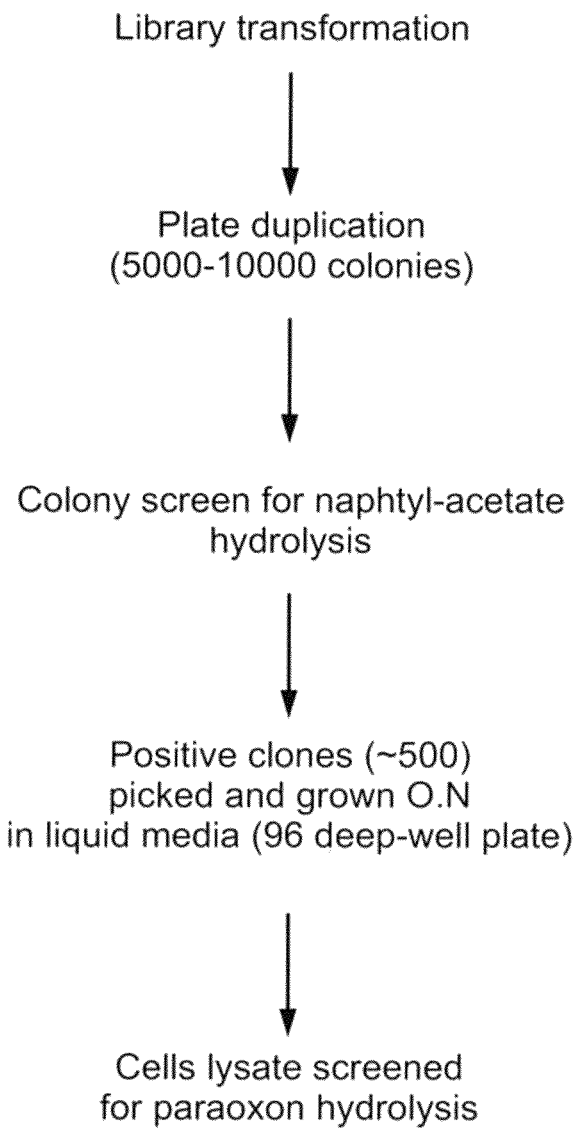

FIG. 6 is a flow chart depicting the steps of directed evolution and screening for soluble PON variants with desired spectrum of activities.

Figures 7A, 7B, 7C:
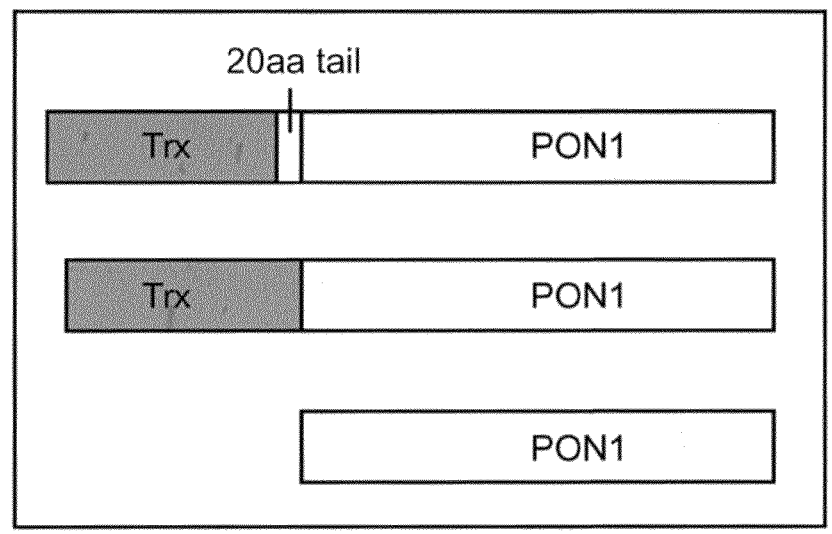

FIGS. 7a-c are schematic illustrations depicting the structure of thioredoxin fused rPON1 (trx-rPON1, FIG. 7a), thioredoxin fused to N-terminally deleted rPON1 (trx-rPON1-20, FIG. 7b) and rPON1 (FIG. 7c).

Figure 8A:
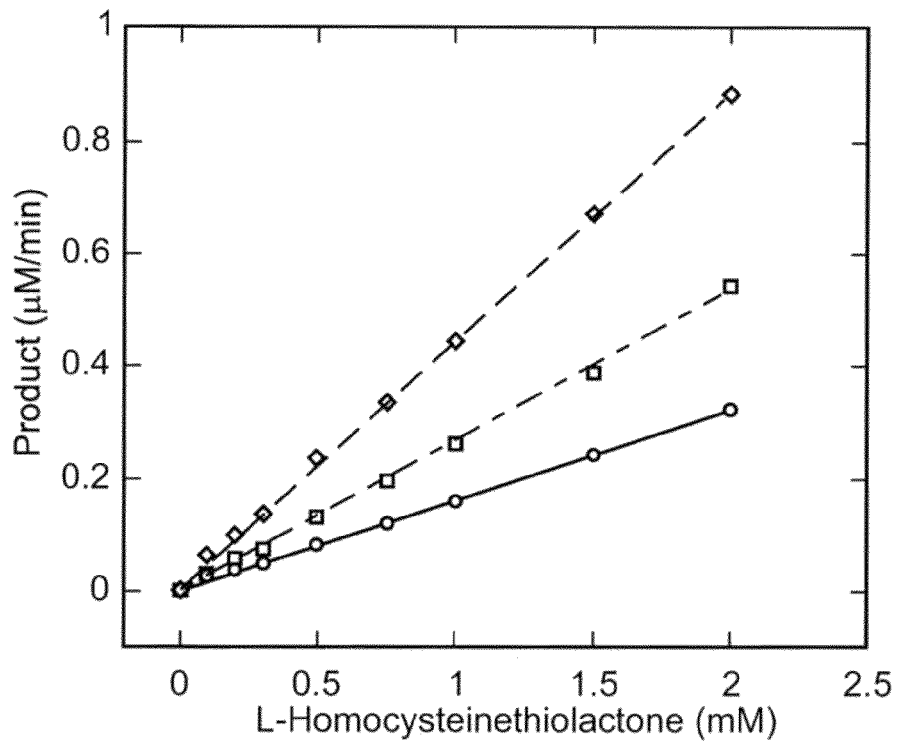
Figure 8B:
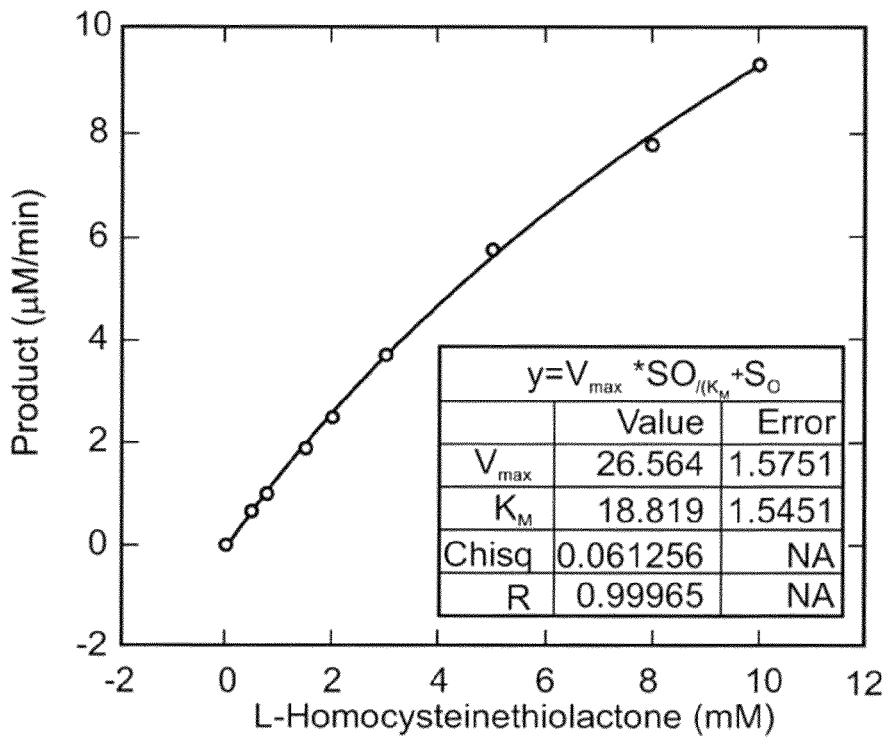

FIGS. 8a-b are steady-state plots for L-homocysteine thiolactone (L-Hcy) hydrolysis by trx-RabPON1 (FIG. 8a) and rePON1 (G3H8, expressed without fusion proteins, FIG. 8b). Diamonds denote a 1.42 µM concentration of trx-RabPON1; Squares denote an 0.6 µM concentration of trx-RabPON1; Circles denote the absence of enzyme. The concentration of rePON1 (G3H8) in FIG. 8b is 1.2 Data in FIG. 8b was fitted to Michaelis Menten equation and the $K_M$ is estimated to be ~19 mM.

Figure 9A:
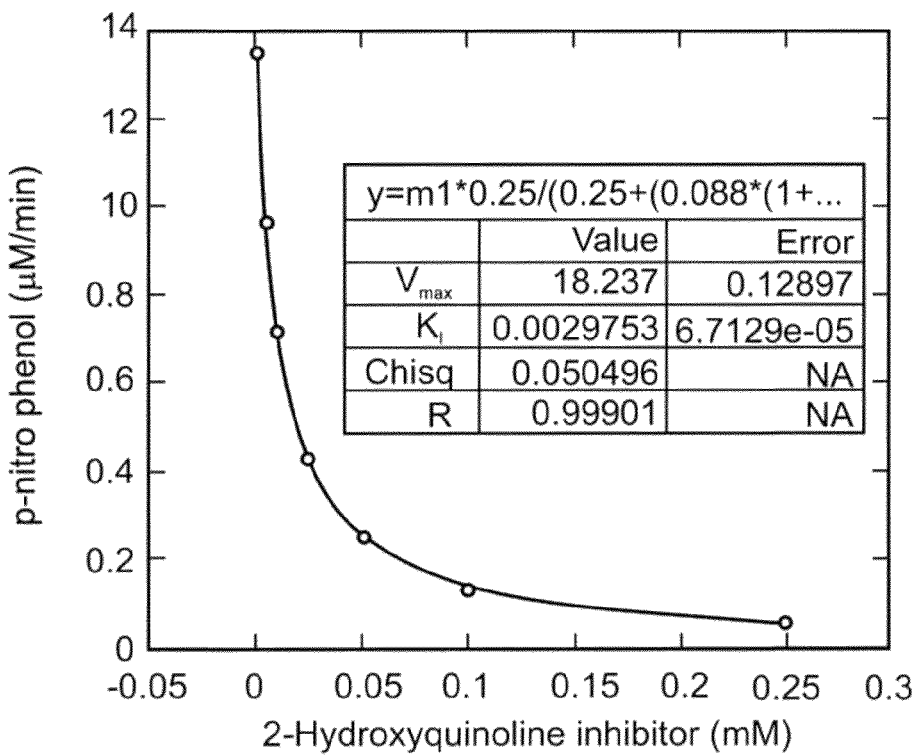
Figure 9B:
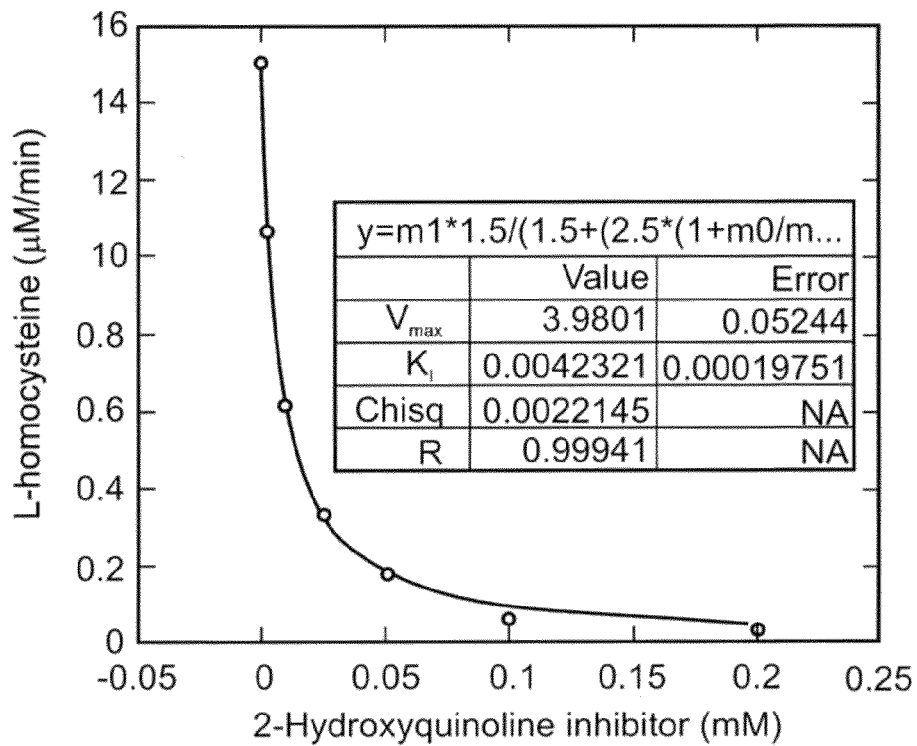

FIGS. 9a-b are plots depicting competitive inhibition of the hydrolysis of paraoxon (FIG. 9a) by 2-hydroxyquinoline and of the hydrolysis of L-Hcy (FIG. 9b) by rePON1 (G3H8, expressed without fusion proteins). Substrate concentrations were 0.25 mM for paraoxon and 1.5 mM for L-Hcy. Data was fitted to the competitive inhibition model $V_o = V_{max}[S]_0/([S]_0 + K_M(1+[I]/K_i))$. Enzyme concentrations for paraoxon and L-Hcy hydrolysis were 0.625 µM and 1.9 µM respectively.

Figure 10:
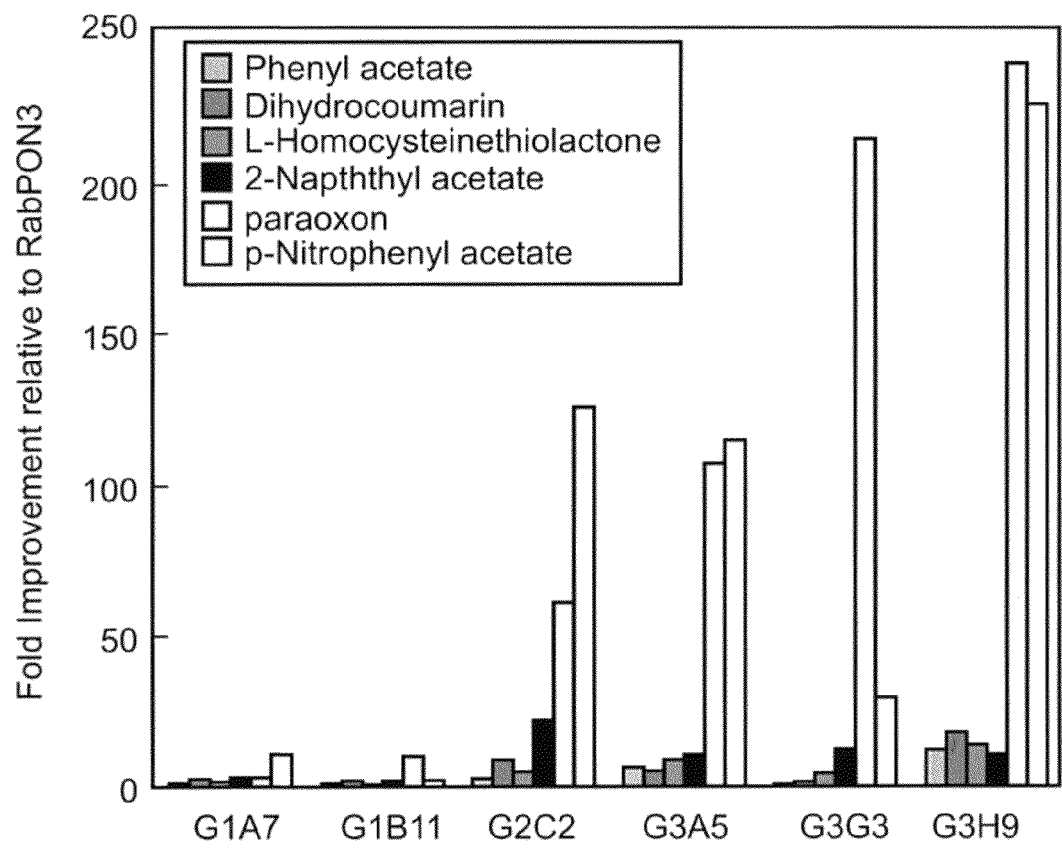

FIG. 10 is a histogram depicting improvement in catalytic specificity ($K_{cat}/K_M$) toward various substrates of variants of trx-rPON3 from different rounds of evolution as compared to wild-type trx-RabPON3. G1A7 and G1B11 are first generation variants; G2C2 is a second-generation variant; and G3A5, G3G3 and G3H9 are third generation variants. The kinetic parameters are presented in Table 7-8, below.

Figure 11A:
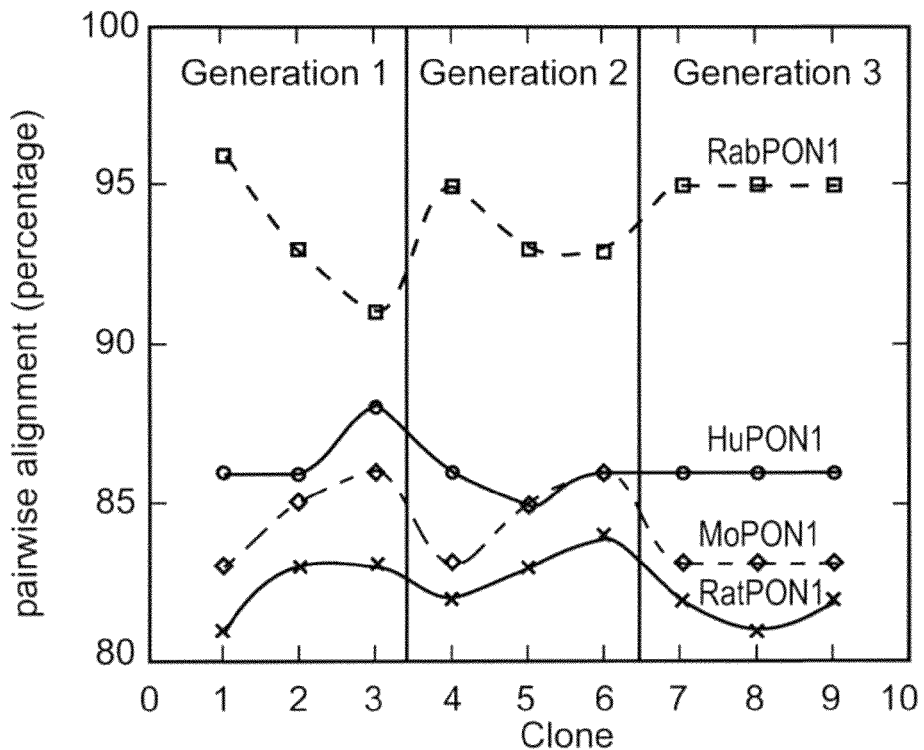
Figure 11B:
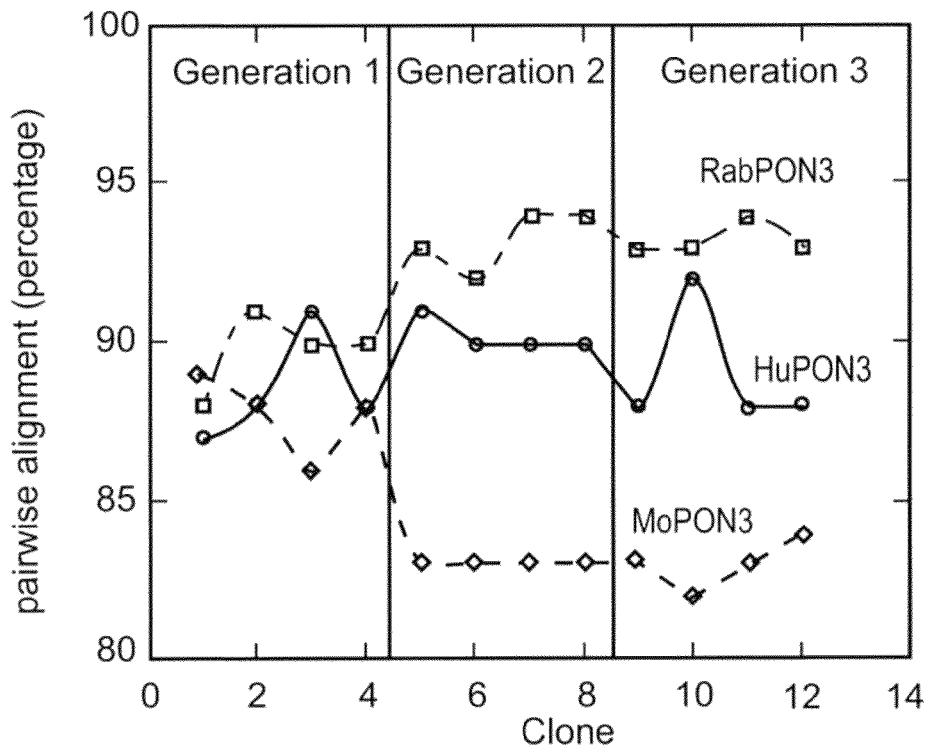

FIG. 11a-b are graphs depicting nucleic acid sequence alignments of selected clones from three rounds of evolution with their parental genes. FIG. 11a shows selected clones from directed evolution of PON1 pairwise aligned to the HuPON1, RabPON1, MoPON1 and Rat PON1 genes [First generation clones 1-3 are G1C4, G1A5 and G1A9 (SEQ ID NOs: 26, 25 and 78 respectively) respectively; second-generation clones 3-5 are G2D6, G2E6 and G2D4 (SEQ ID NOs: 27, 28 and 79 respectively); third-generation clones 7-9 are G3C9, G3H8 and G3H10 (SEQ ID NOs: 55, 61 and 80 respectively). FIG. 11b shows selected clones from directed evolution of PON3 pairwise aligned to the HuPON3, RabPON3 and MoPON1 genes [First generation clones 1-4 are G1A7, G1B11, G1E10 and G1G7 (SEQ ID NOs: 43, 44, 81 and 82 respectively); second-generation clones 5-8 are G2E11, G2A7, G2C2 and G2F8 (SEQ ID NOs: 83, 84, 45 and 85 respectively). third-generation clones 9-12 are G3C6, G3G5, G3H9 and G3A5, (SEQ ID NOs: 86, 87, 48 and 46 respectively).

Figure 12A:
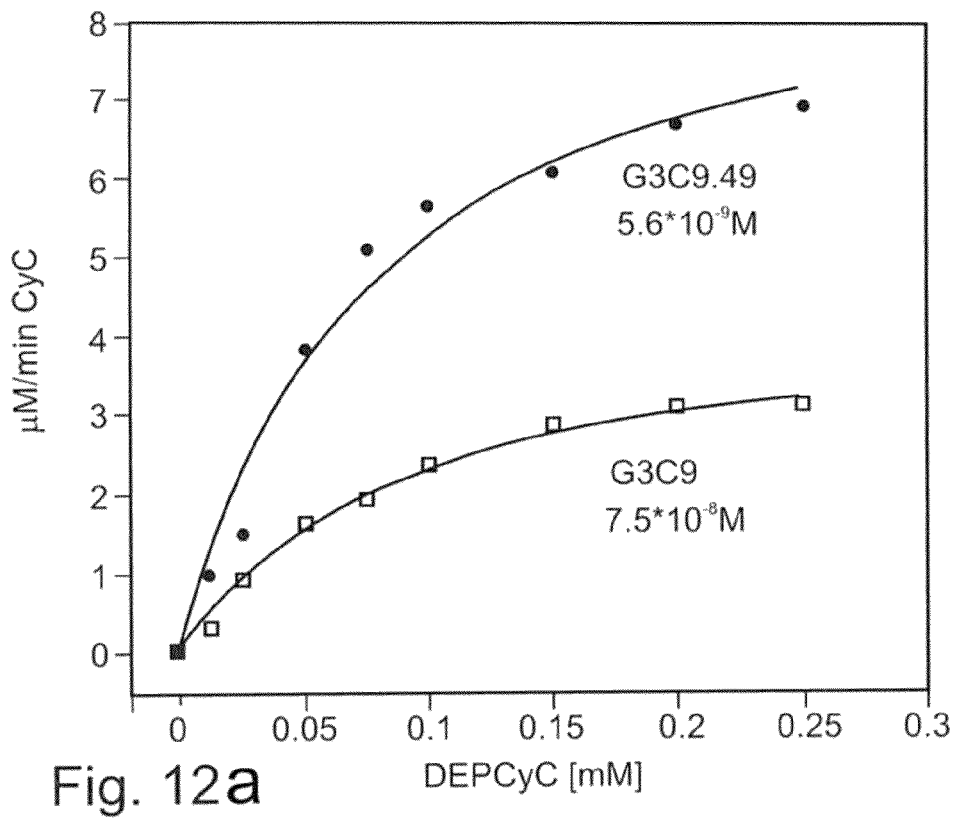
Figure 12B:
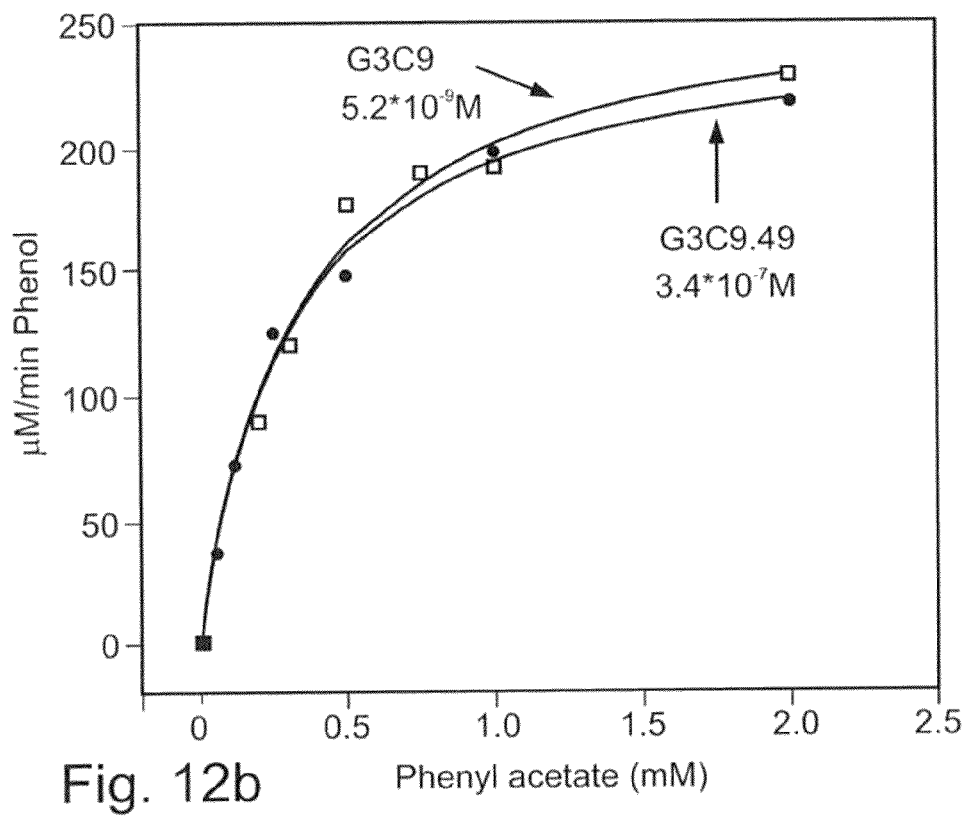

FIGS. 12a-b are Michealis-Menten plots depicting hydrolysis of DEPCyC (FIG. 12a) and phenylacetate (FIG. 12b) by rPON1 variant G3C9 and its variant G3C9.49 that displays greatly enhanced OP-hydrolyzing activity. Enzyme concentrations are $7.5 \cdot 10^{-8}$ M and $5.6 \cdot 10^{-9}$ M in FIG. 12a and $3.4 \cdot 10^{-7}$ M in FIG. 12b for G3C9 and G3C9.49, respectively. The kinetic parameters derived from the fits are listed in Table 9, below.

Figure 13:
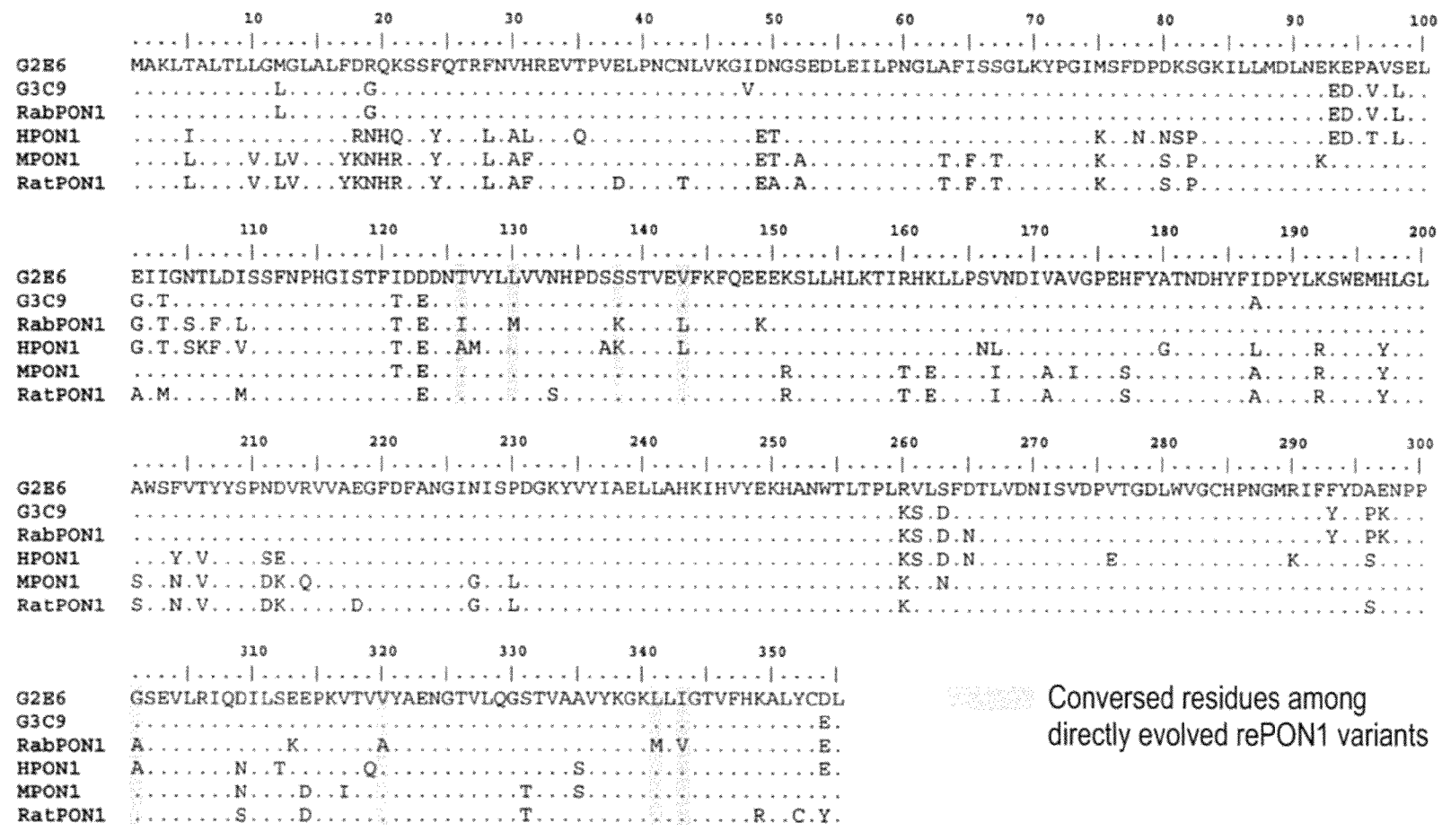

FIG. 13 is a multiple sequence alignment of human (H) (SEQ ID NO: 36), rat (SEQ ID NO: 39), mouse (M) (SEQ ID NO: 38) and rabbit (Rab) PON1 (SEQ ID NO: 39), and rPON1 variants G2E6 and G3C9 (SEQ ID NOs: 60 and 56 respectively).

Figure 14A:
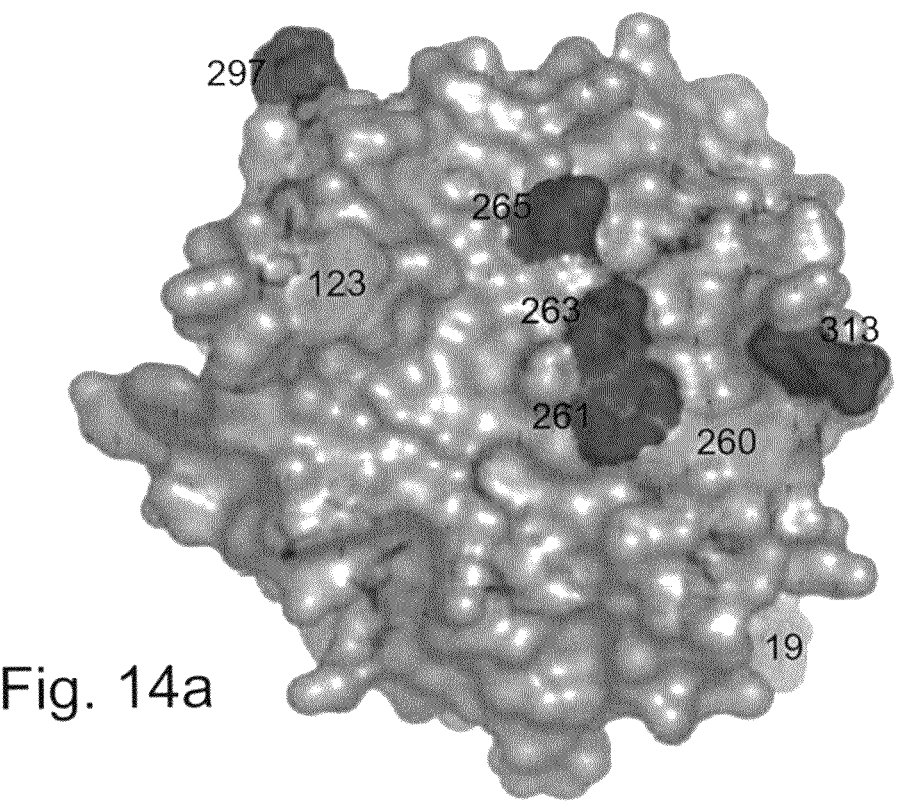
Figure 14B:
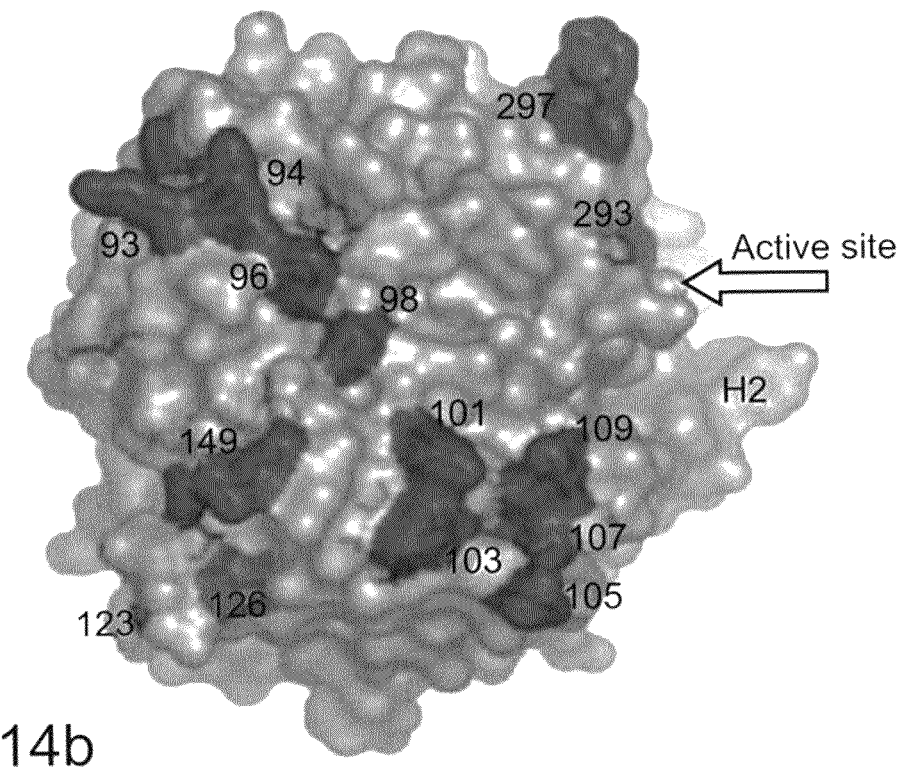

FIGS. 14a-b are schematic illustrations depicting two surface representations of the side of the β-propeller—one rotated 180° relative to the other. The amino acid variations between rPON1 variant G2E6 and wt RabPON1 are marked: In red are amino acids that originate from Human, Mouse and Rat PON1 and are conserved among all the E. coli expressed rPON1 variants (Table 14, below, group I). In blue—amino acids that originate from Human, Mouse and Rat PON1 and are not conserved among soluble rPON1 variants (Table 14, below, group II). In green—amino acids that were mutated during the DNA shuffling process (Table 14, below, group III).

FIGS. 15a-b are schematic representations depicting the overall structure of PON1. FIG. 15a is a view of the 6-bladed β-propeller from the top. The top of the propeller is, by convention, the face carrying the loops connecting the outer β-strand of each blade (strand D) with the inner strand (A) of the next blade [E. I. Scharff, J. Koepke, G. Fritzsch, C. Lucke, H. Ruterjans, Structure 9, 493 (2001)]. Shown are the N- and C-termini, and the two calcium atoms in the central tunnel of the propeller. FIG. 15b is a side view of the propeller. Shown are the three helices at the top of the propeller (H1-H3) and the calcium atoms (Ca-1, in green, Ca-2 in red). Figures were generated using PyMol (pymol.sourceforge.net/).

Figure 16:
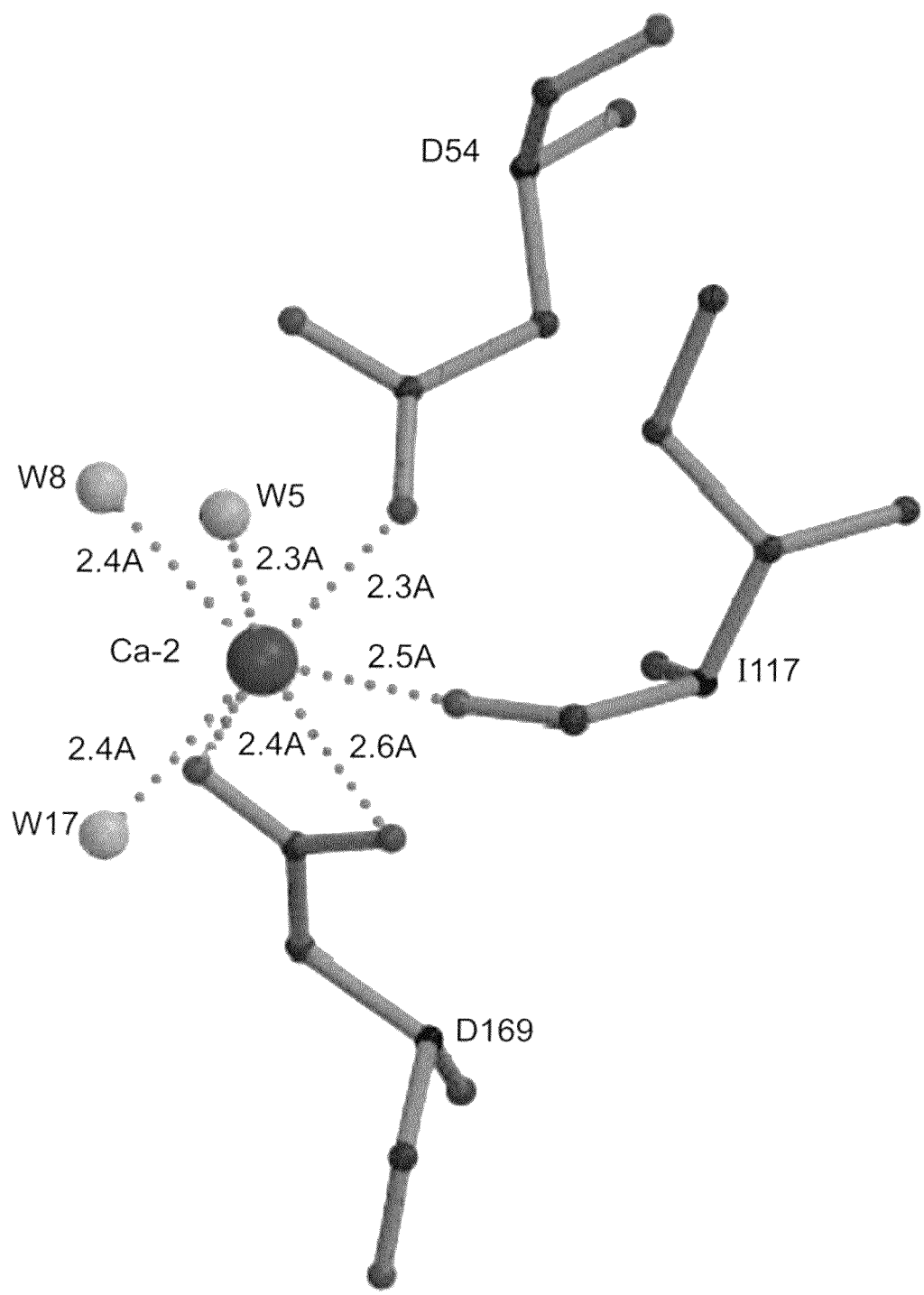

FIG. 16 is a view of the binding site for the inner calcium (Ca-2) in crystallized PON 1.

Figure 17:
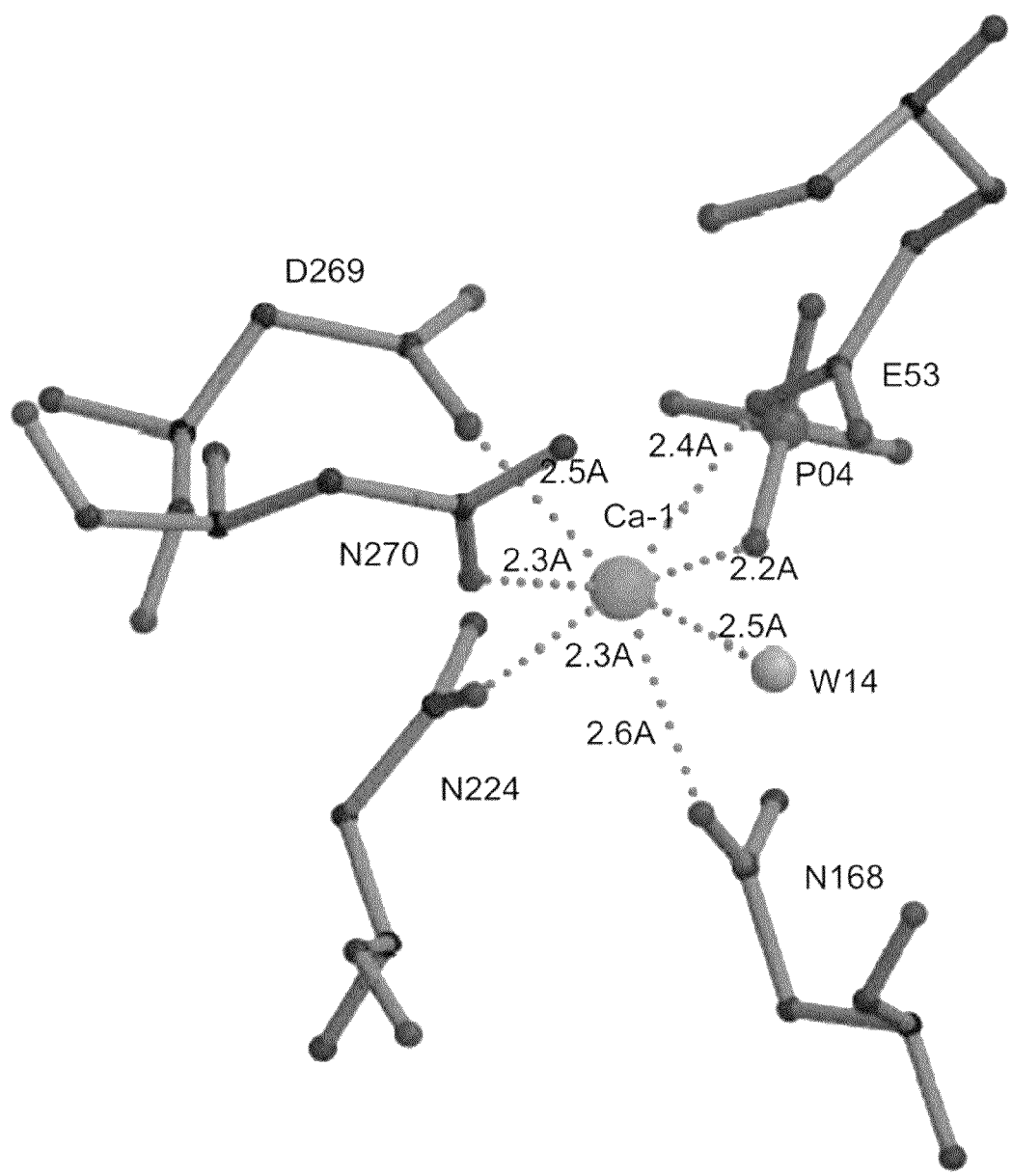

FIG. 17 is a view of the binding site for the upper calcium (Ca-1) in crystallized PON 1.

Figure 18B:
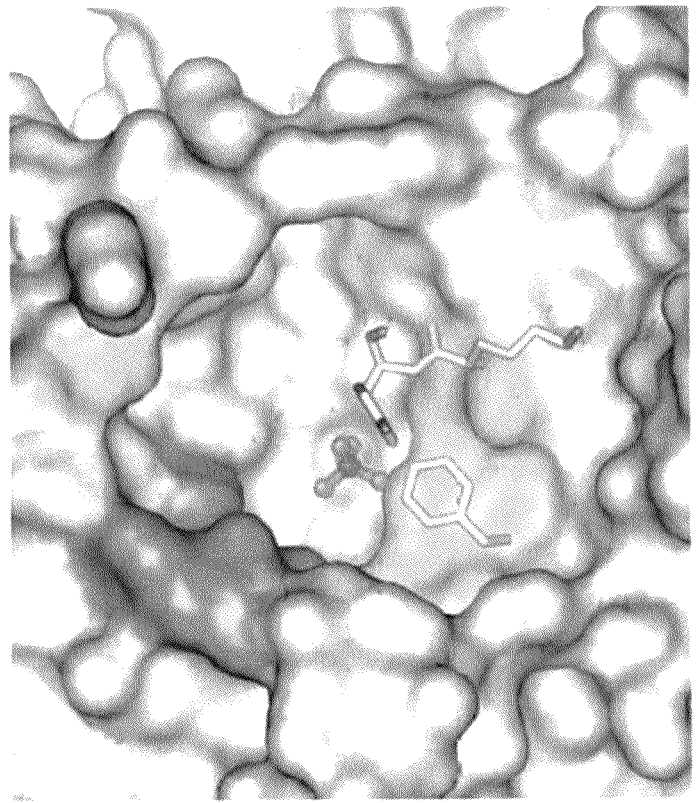
Figure 18A:
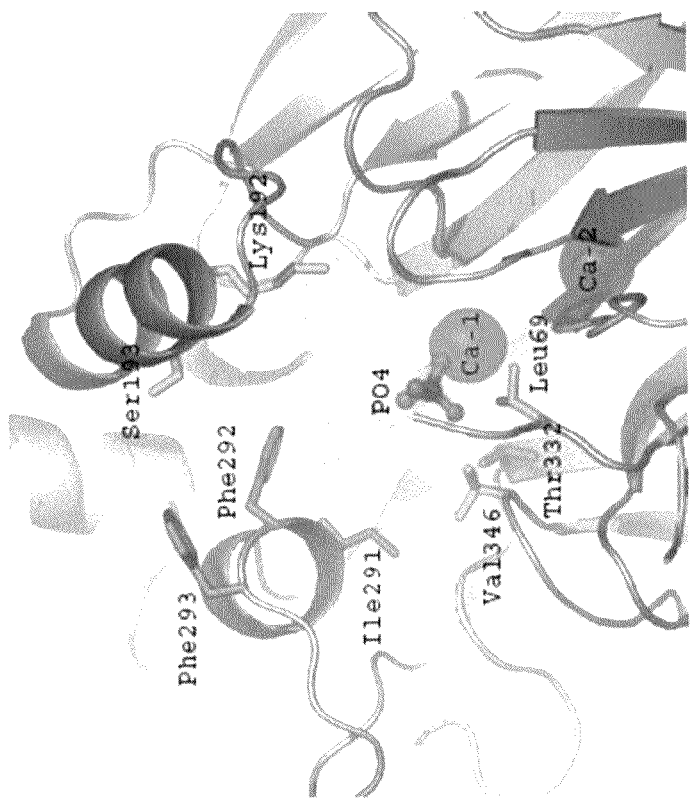

FIGS. 18a-b are schematic illustrations showing PON1's active site viewed from the top of the propeller. FIG. 18a shows the central tunnel of the propeller with the two calcium atoms, and the side-chains of the residues found to be mutated in the newly-evolved PON1 variants for esterase and lactonase (in orange) or for phosphotriesterase activity (in yellow), including position 192 of the Q/R human polymorphism. FIG. 18b is a surface view of the active site. Lys70, Tyr71 and Phe347 are shown as sticks to permit a better view of the active site. At the deepest point of the cavity lies the upper calcium atom (Ca-1, in green) to which a phosphate ion (PO4) is bound.

Figure 19:
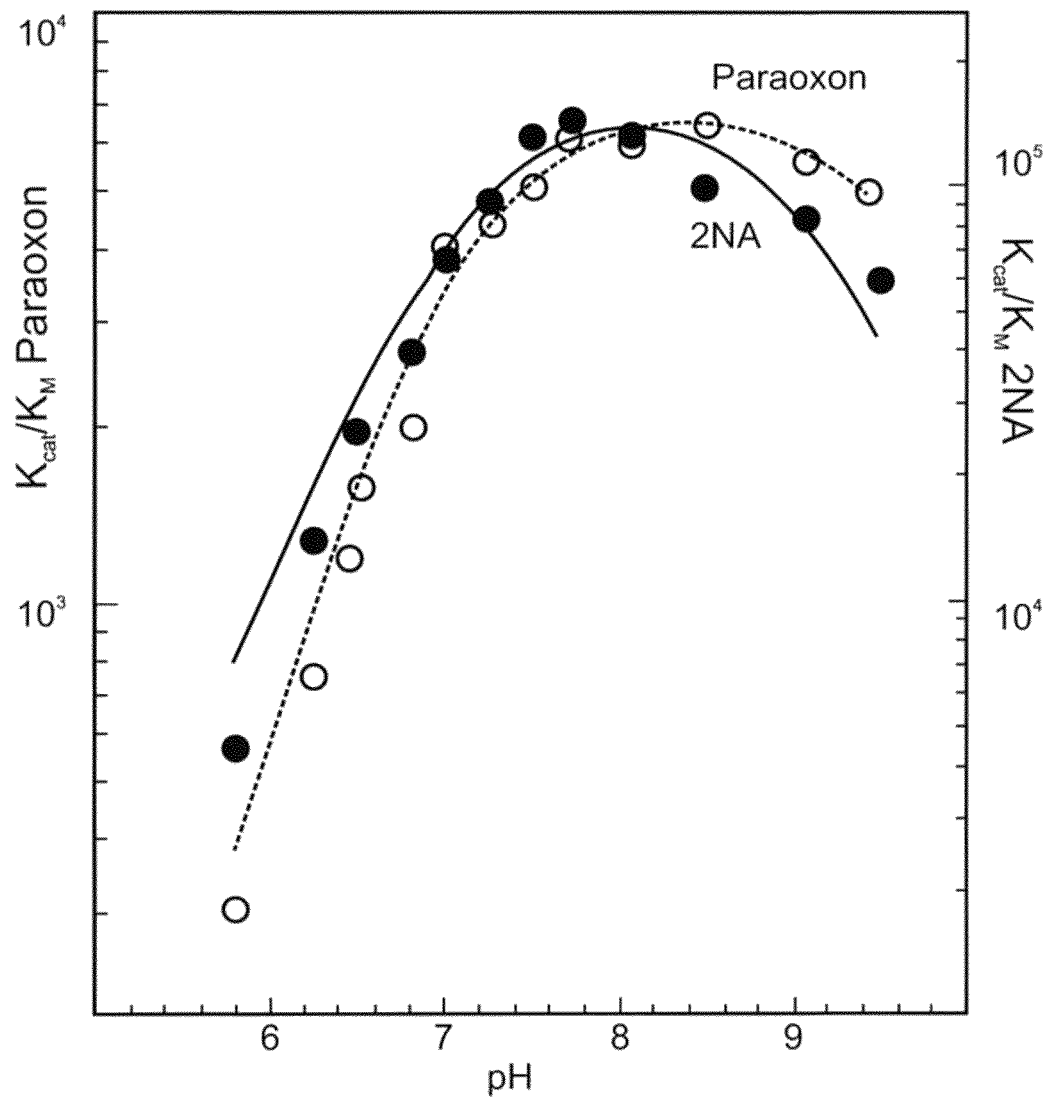

FIG. 19 is a graph depicting pH-rate profiles of PON1. $k_{cat}$ and $K_M$ values were determined for rPON1-G2E6 with 2-naphthyl acetate (2NA) and paraoxon [A. Aharoni et al., Proc. Natl. Acad. Sci. USA 101, 482 (2004)] at pH 5.6-9.5. $k_{cat}/K_M$ values for each pH value (($k_{cat}/K_M)^H$) were fitted to a 'bell-shaped' model using the equation: $(k_{cat}/K_M)^H = (k_{cat}/K_M)^{max}/[(10^{-pH}/10^{-pKa1}) + (10^{-pKa2}/10^{-pH}) + 1]$ where $(k_{cat}/K_M)^{max}$ is the pH-independent (or plateau value) of $k_{cat}/K_M$, and $pK_a^1$ and $pK_a^2$, are the $pK_a$ values for the acidic and basic groups, respectively. The fit gave the following values for paraoxon: $(k_{cat}/K_M)^{max} = 7016$ $M^{-1}s^{-1}$, $pK_a^1 = 7.06$ and $pK_a^2 = 9.78$; for 2NA: $(k_{cat}/K_M)^{max} = 1.67 \times 10^5$ $M^{-1}s^{-1}$, $pK_a^1 = 7.15$ and $pK_a^2 = 9.03$. Kinetic parameters were obtained from 3-5 independent measurements averaged with standard deviations of 2-23%. Buffers used: MES (pH 5.6-6.5) and bis-tris propane (pH 6.5-9.4) at 0.1M, plus 1 mM $CaCl_2$; the ionic strength was adjusted to 0.2M with NaCl.

Figures 20A, 20B:
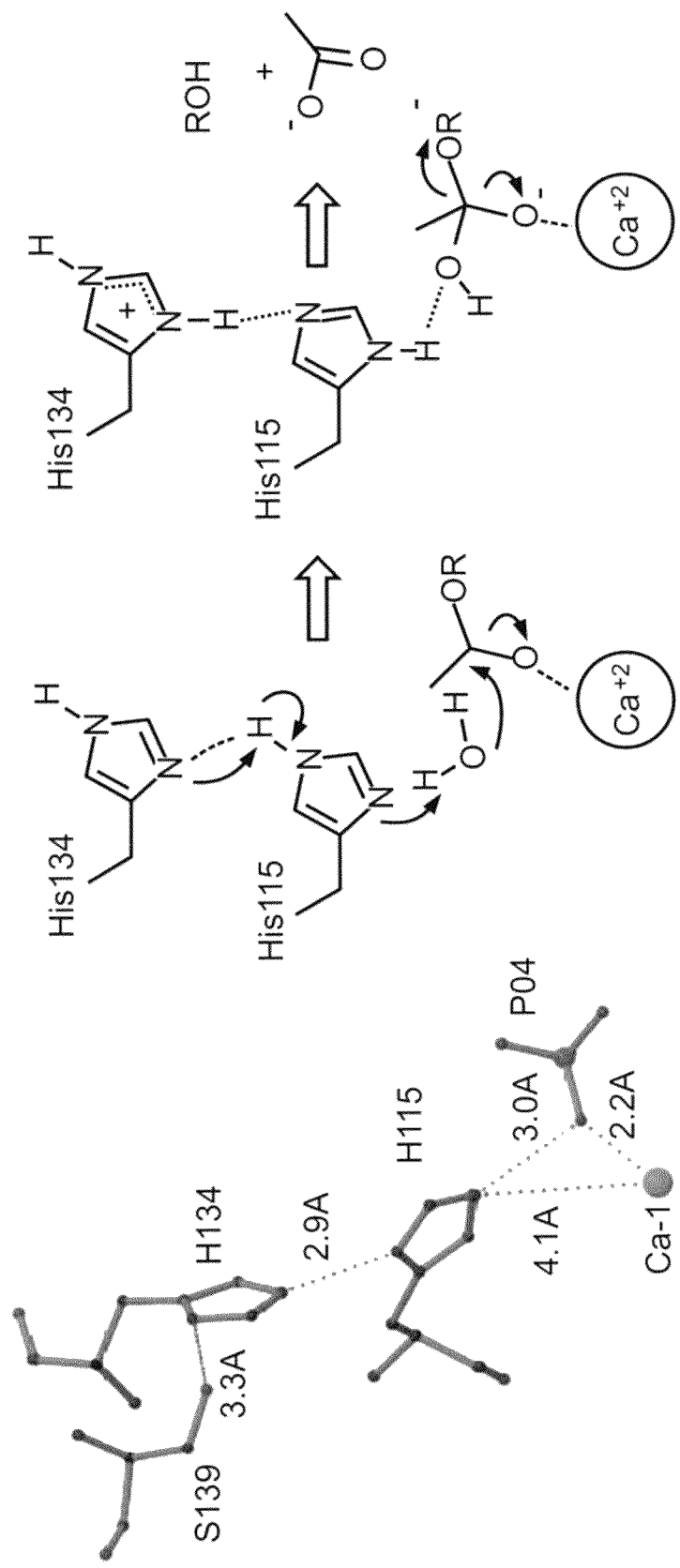

FIGS. 20a-b are proposed catalytic site and mechanism of action of PON1 enzyme. FIG. 20a is a schematic illustration of PON1's catalytic site: the upper calcium atom (Ca-1), the phosphate ion found at the bottom of the active site, and the postulated His-dyad. FIG. 20b is a schematic representation of the proposed mechanism of action of PON1 on ester substrates such as phenyl and 2-naphthylacetate. The first step involves deprotonation of a water molecule by the His-dyad to generate an hydroxide anion which attacks the ester carbonyl, producing an oxyanionic, tetrahedral intermediate. This intermediate breaks down (second step) to an acetate ion and either phenol or 2-naphthol.

Figure 21:
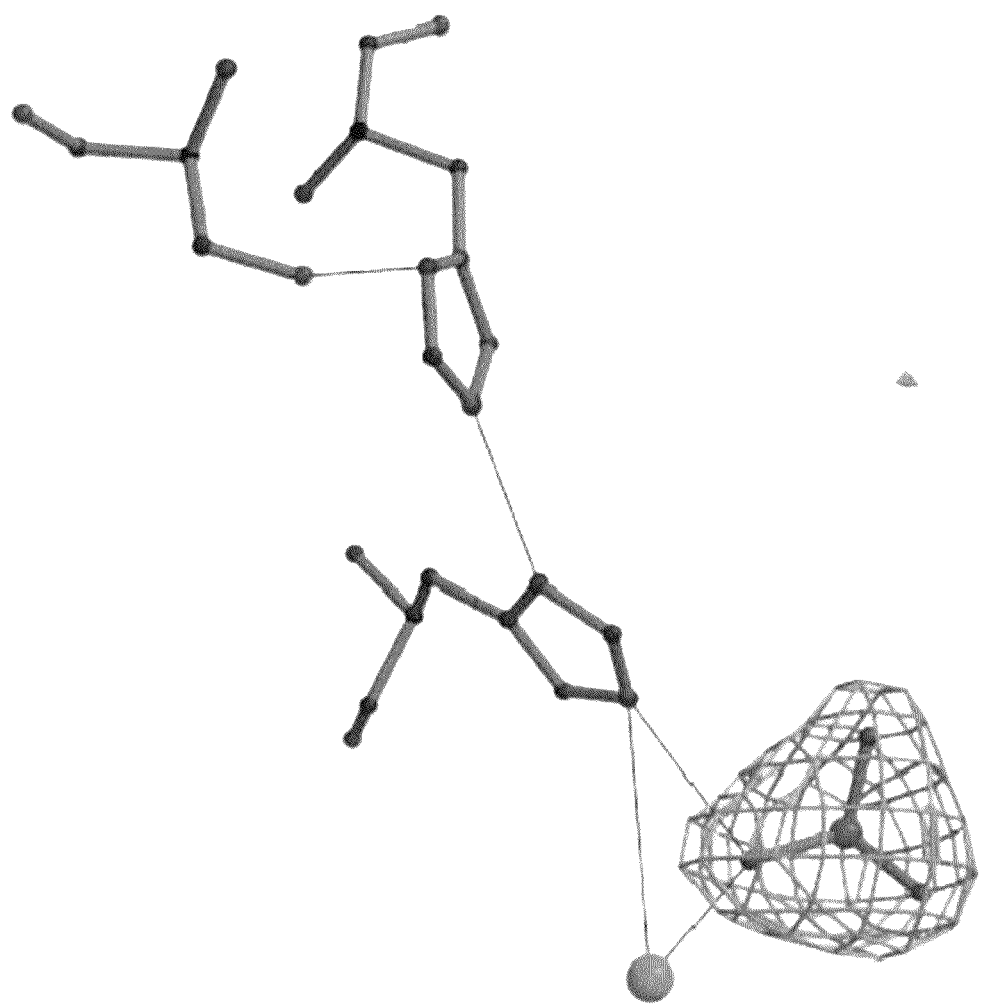

FIG. 21 is an Fo-Fc OMIT map of the phosphate ion at 46. Crystallization mother liquor of the native rPON1 contained 0.2M $NaH_2PO_4$. The electron density map of the SeMet protein, which was crystallized with no phosphate, showed no peak at this location. The presence of the phosphate was verified by atomic absorption measurements after dialysis against 20 mM Tris pH 8 buffer that did not contain phosphate ions, using the ICP instrument, Spectroflame Modula E (Specto, Kleve, Germany). The Instrument was first calibrated against various pre-mix metal ions standards (Merck) at concentration of 1 ppm and the allowed maximal variation was ±5%. The amount of phosphate found was 0.72 mole per 1 mole of rPON1-G2E6.

Figure 22:
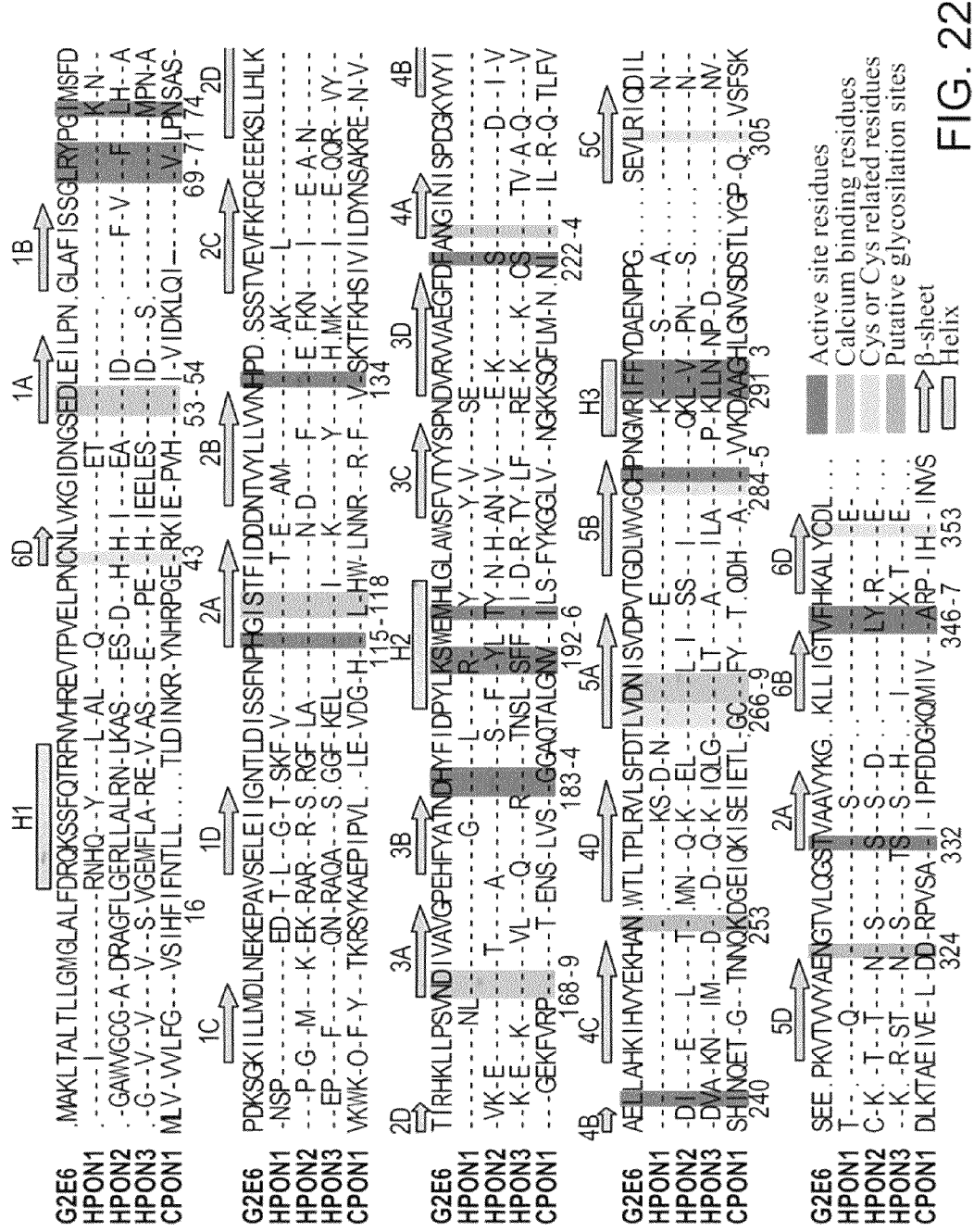

FIG. 22 is a sequence alignment of representative members of the PON family. Shown are human PON1, PON2 and PON3 (with an 'H' prefix) (SEQ ID NOs: 36, 40 and 88 respectively), C. elegans PON1 (CPON1) (SEQ ID NO: 89), and rPON1 variant G2E6 (SEQ ID NO: 60), the structure of which was solved.

Figure 23B:
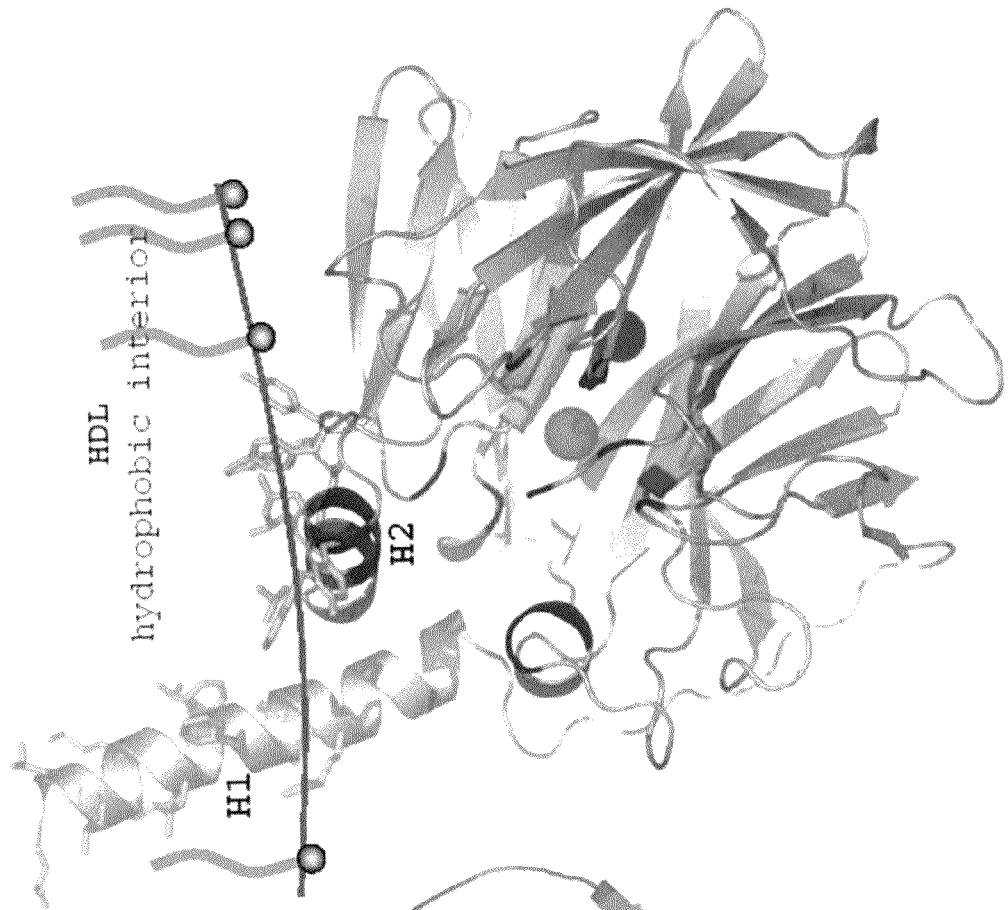
Figure 23A:
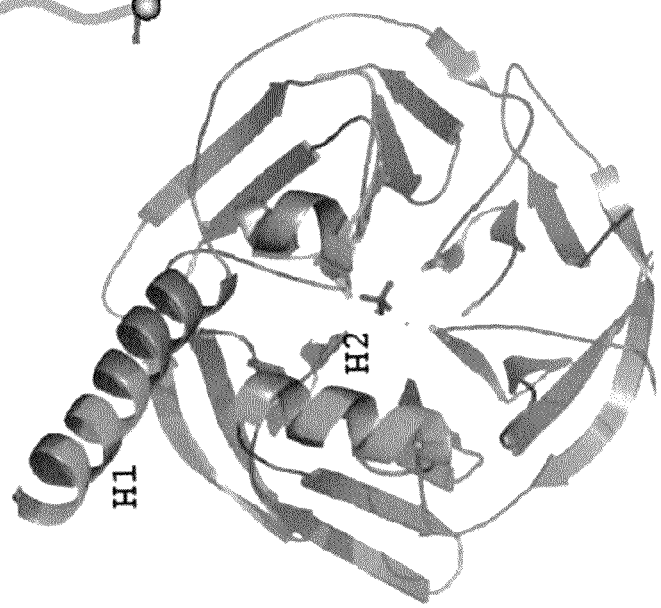

FIGS. 23a-b show a model of anchoring of PON1 to the surface of HDL. FIG. 23a is a tertiary structure cartoon of rPON1 showing its exposed hydrophobic surfaces. N-terminal residues 7-18 missing in the crystal structure and predicted to be helical were modeled as part of H1. Indicated in green are all the hydrophobic residues (L, F, P, I, Y, W, V) appearing with accessible surface area greater than 20 Å$^2$ as calculated by the program AREAIMOL in the CCP4 package [B. Lee, F. M. Richards, J Mol Biol 55, 379 (1971)]. FIG. 23b shows the hydrophobic residues proposed to be involved in HDL-anchoring with their side-chains in yellow. The line— defined by the side chains of Tyr185, Phe 186, Tyr190, Trp194, Trp202 (helix H2 and the adjacent loops) and Lys21 (helix H1)—models the putative interface between HDL's hydrophobic interior and the exterior aqueous phase. The hydrophobic side chains of Leu and Phe residues of H1 are found primarily within the apolar region [J. A. Killian, G. von Heijne, Trends Biochem Sci 25, 429 (2000)]. The active site and the selectivity-determining residues (Table 13, below) are marked in blue, and the proposed glycosylation sites (Asn253 and Asn324) in red.

Figure 24:
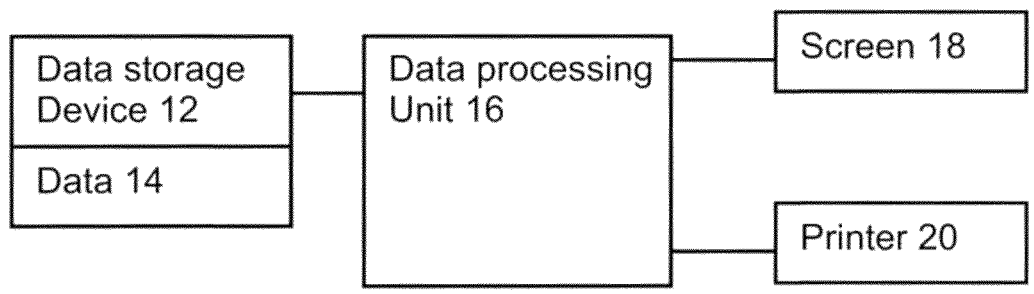

FIG. 24 is a box diagram showing a computing platform 10 which can be used for practicing the present invention and which comprises computer readable medium, e.g., a data storage device 12, storing therein data 14 which is retrievable and processable by data processing unit 16 and the data or processed data can be displayed via a display such as a display screen 18 and/or a printer 20.

Figure 25:
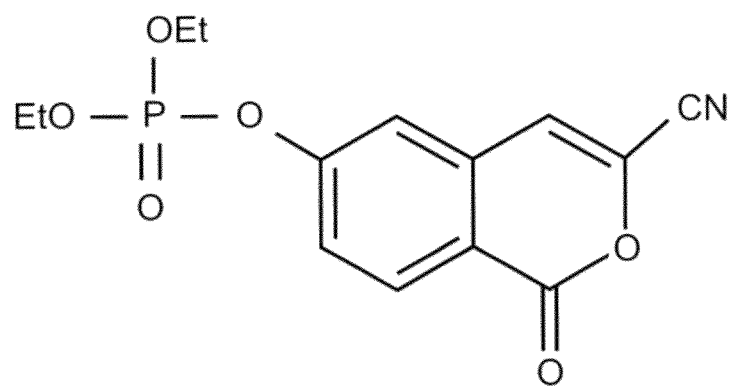

FIG. 25 is a schematic illustration depicting the structure of DEPCyC; and

FIG. 26 present the coordinates of the three-dimensional model of PON1 variant G2E6 (SEQ ID NO: 60).

DESCRIPTION OF THE PREFERRED EMBODIMENTS

The present invention is of PON polypeptides, polynucleotides encoding same and compositions and methods utilizing same. Specifically, the present invention can be used for decontamination and detoxification of toxic agents and for treatment of PON-associated diseases and conditions, such as atherosclerosis.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Directed evolution is a powerful tool that enables generation of new protein variants.

Rather than rely upon natural variation, directed evolution generates new variation in one of two ways. The first is by inducing mutations in the gene of interest, either by using mutator strains, or by error-prone PCR (in which the fidelity of Taq polymerase is decreased rather than optimised). The second involves shuffling different regions of members of the same gene family to produce genes in which the inherent variation of the family is recombined to give novel gene products.

Once a population has been produced, screening and selection can isolate those members which most closely match the desired attributes. The whole process can then be repeated using these members as the starting point for the generation of new variation. [Tao (2002) Curr. Opin. Chem. Biol. 6(6):858-64].

Unlike natural evolution, directed evolution has a specific goal, to produce variants which exhibit enhanced functions, lack of unwanted functions or new functions altogether.

One severe drawback of directed evolution is the inability at present to select targets which are more "responsive" to directed evolution.

To date, there is no approach which enables to predict the evolutionary response of a starting point protein and thus in many cases, it is difficult if not impossible to predict the outcome of a directed evolution study.

While reducing the present invention to practice the present inventors designed an approach for the identification of genes that are highly amenable to directed evolution processes. As is further illustrated hereinbelow, the present inventors showed that structural promiscuity and structural plasticity can be used as probes for the evolvability of proteins. Using this approach, the present inventors uncovered one such starting point, the enzyme family of serum paraoxonases, which meets these criteria and serves as starting point for the directed evolution of a variety of hydrolases with pre-determined specificities.

Thus, according to one aspect of the present invention there is provided a method of identifying proteins amenable to an in-vitro evolution process.

As used herein the phrase "in vitro evolution process" (also referred to as "a directed evolution process") refers to the manipulation of genes and selection or screening of a desired activity. A number of methods, which can be utilized to effect in vitro evolution, are known in the art. One approach of executing the in-vitro evolution process is provided in Example 2 of the Examples section.

A protein which is amenable to an in vitro evolution process is a protein, which would exhibit the desired trait selected for (e.g., catalytic activity, thermostability), at early generations of the directed evolution process; preferably, following one cycle of evolution (one generation).

The method, according to this aspect of the present invention is effected by identifying proteins which exhibit at least two distinct catalytic activities and/or structural plasticity. As is described in detail hereinbelow, the present inventors have uncovered that proteins exhibiting such traits are highly amenable to the in-vitro evolution process.

As used herein the phrase "at least two distinct catalytic activities" refers to the ability of a protein to catalyze the turn over of at least two substrates, which differ in the chemical group reacting with the active site of the enzyme, or in groups adjacent thereto (e.g., steric effect). For example, the ability of an enzyme to hydrolyze carboxy esters and phosphotriesters, or, the ability of an enzyme to hydrolyze esters of different carboxylic acids, or esters having different alkoxy or phenoxy leaving groups.

A number of biochemical methods are known in the art which can be efficiently used to screen for enzyme catalysis. These methods employ fluorogenic and chromogenic substrates for detecting hydrolytic activity such as, for example, esterase, lipase, amidase, epoxi hydrolase and phosphatase activities. More recently product sensitive sensors have been used for screening catalysis. Examples of such sensors include monoclonal anti product antibodies and metal chelators [see Lorenz (2002) Curr. Opin. Biotechnol. 13:572-7; Wahler (2001) Curr. Opin. Biotechnol. 12:535-44].

Alternatively, high throughput screening methods can be used to identify substrate binding and thus be used to identify enzymes which exhibit at least two distinct catalytic activities.

Information regarding the catalytic activity of a protein (i.e., annotative information) can also be retrieved from publicly available or proprietary databases. Examples of such databases include, but are not limited to, the Gene Ontology Consortium (geneontologydotorg/GOdotannotationdothtml), the GeneCards database of the Weizmann institute of Science (rzpddotde/cards/indexdothtml), GenBank (ncbidotnlmdotnihdotgov/GenBank/), Swiss-Prot (expasydotch/sprot/sprot-topdothtml), GDB (gdbdotorg/), PIR (wwwdot-mipsdotbiochemdotmpgdotde/proj/prostseqdb/), YDB (mipsdotbiochemdotmpg.de/proj/yeast/), MIPS (mipsdotbiochemdotmpgdotde/proj/human), HGI (tigrdotorg/tdb/hgi/), Celera Assembled Human Genome (celeradotcom/products/human_ann.cfm and LifeSeq Gold (lifeseqgolddotincytedotcom) and specialized annotated databases of metabolic pathways (genomedotaddotjp/kegg/metabolismdothtml).

As used herein the phrase "structural plasticity" refers to proteins which have at least two distinct structural isomers (e.g., independent of ligand binding). Examples of proteins which exhibit structural plasticity include, but are not limited to, the prion protein PrPc which interconverts between an all α-helix or all β-sheet conformation [Derreumaux (2001) Biophys J. 81:1657-65].

A number of biophysical methods for determining the structural plasticity of proteins are well known in the art [Bhattacharjya, Xu (2001) Protein Science 10(5): 934-942; Eliezer, Kutluay (2001) Journal of Molecular Biology 307 (4): 1061-1073; Hitchens, Mannervik (2001) Biochemistry 40(39): 11660-11669; and Spoerner, Hermann (2001) Proc Natl Acad Sci USA 98(9): 4944-9]. Examples of such methods include, but are not limited to, NMR, X-ray crystallography and circular-dischroism. For example, NMR analysis has shown that a considerable number of distinct conformers can prevail in a single protein (≤60) and the structures of some of these conformers can vary dramatically [Choy and Forman-Kay (2001) Journal of Molecular Biology 308(5): 1011-1032]. Single molecule techniques offer unique opportunities to monitor the activity and conformation of protein molecules. Such measurements have already shown that protein molecules exist in various states or conformations that exhibit different levels of activity [Xue and Yeung (1995) Nature 373(6516): 681-3; Dyck and Craig (2002) Luminescence 17: 15-18].

Other tools which provide dynamic structural information include spectroscopic techniques such as fluorescence studies [e.g., FRET, ChaKraborty, Ittah (2001) Biochemistry 40:7228-7238] and scattering techniques such as quasi-elastic and dynamic light scattering, and X-ray and neutron small-angle scattering (for further information see Protein crystallography, DOE Genomes to Life, US doegenomestolife.org/technology/crystallography.html).

Structural data can also be retrieved from protein structure databases. Examples of such databases include, but are not limited to, the Protein Data Bank (PDB at the Brookhaven National Laboratory) and the Database of Molecular Movement, (molmovdb.mbb.yale.edu/molmovdb/). It will be appreciated that in such a case (i.e., retrieval from PDB), further computer modeling should be employed to uncover the distinct conformations of the protein (see further hereinbelow).

Alternatively, protein structural information can be bioinformatically obtained, by using, for example, structural homology algorithms. The combinatorial extension method (CE) finds structural alignments by selecting from sequences from the PDB. The software calculates structural alignments for two chains either from the PDB or uploaded by the user. Structural neighbors are then identified (cl.sdsc.edu/ce.html).

In any case, once such catalytic data and/or structural data are obtained for a given protein, the applicability of this protein to directed evolution can be qualified.

The following describes in detail parameters, which can be used by the present invention to qualify proteins for directed evolution.

Position of Structural Variance within the Protein—

Proteins having flexible active sites are considered evolvable, since such proteins would in all likelihood facilitate binding and/or catalysis of multiple ligands or substrates [Huang, Y. T., Liaw, Y. C., Gorbatyuk, V. Y. & Huang, T. H. Backbone dynamics of *Escherichia coli* thioesterase/protease I: Evidence of a flexible active-site environment for a serine protease. Journal of Molecular Biology 307, 1075-1090 (2001); and Bencharit, S., Morton, C. L., Xue, Y., Potter, P. M. & Redinbo, M. R. Structural basis of heroin and cocaine metabolism by a promiscuous human drug-processing enzyme. Nature Structural Biology 10, 349-356 (2003)].

Functional Diversity and Structural Plasticity—

Proteins which exhibit both functional diversity (i.e., more than two distinct binding or catalytic activities) and structural plasticity are considered the most amenable to directed evolution, since these properties may be interlinked [James L C, Roversi P, Tawfik D S (2003) Antibody multispecificity mediated by conformational diversity. Science 299: 1362-1367].

Functional Promiscuity or Diversity—

Proteins which exhibit functional promiscuity, or diversity or a broad substrate range, which terms are by enlarge synonymous [James L C, Tawfik D S (2003) Conformational diversity and protein evolution—a 60-year-old hypothesis revisited. Trends Biochem Sci 28: 361-368]. Namely, proteins that exhibit more than two distinct binding or catalytic activities, are considered the most amenable to directed evolution.

Selection of evolvable proteins can be effected on the basis of a single parameter or several parameters considered individually or in combination.

Proteins, which are considered amenable to an in-vitro evolution process are tested in the laboratory (see Example 2 of the Examples section).

Using the above-described methodology the present inventors were able to identify proteins, which are amenable to an in-vitro evolution. Examples include, but are not limited to the *Escherichia coli* thioesterase/protease I [Tyukhtenko, S. I. et al. Sequential structural changes of *Escherichia coli* thioesterase/protease I in the serial formation of Michaelis and tetrahedral complexes with diethyl p-nitrophenyl phosphate. Biochemistry 42, 8289-8297 (2003); Huang, Y. T., Liaw, Y. C., Gorbatyuk, V. Y. & Huang, T. H. Backbone dynamics of *Escherichia coli* thioesterase/protease I: Evidence of a flexible active-site environment for a serine protease. Journal of Molecular Biology 307, 1075-1090 (2001)], and the human carboxylesterase 1 [hCE1, Bencharit, S., Morton, C. L., Xue, Y., Potter, P. M. & Redinbo, M. R. Structural basis of heroin and cocaine metabolism by a promiscuous human drug-processing enzyme. Nature Structural Biology 10, 349-356 (2003)].

Additionally, using the above-described methodology and existing literature, the present inventors identified the PON family (PONs) of enzymes as being highly evolvable. The PONs are catalytically diverse, as they catalyze the hydrolysis of a very broad range of substrates including, but not limited to, carboxy esters, lactones, phosphotriesters [or organophosphates (OPs)], platelet activating factor (PAF), homocysteine thiolactone (L-Hyc; a known factor for atherosclerotic vascular diseases), as well as the reduction and hydrolysis of lipid peroxides (for further details see the preceding Background section). In addition, structural analysis of PON1 identified structural plasticity in the PON family (see Example 6 of the Examples section). Thus, PONs were deemed highly suitable for directed evolution and were used herein as starting points for the evolution of bacteria expressible hydrolases.

As is illustrated in Examples 2-5 of the Examples section which follows, directed evolution studies employing PONs as a starting point yielded PONs with modified substrate range (see Tables 7-9 and 11, below), thus conclusively proving that this family of enzymes is highly amenable to directed evolution.

Thus, according to another aspect of the present invention there is provided an isolated polynucleotide including a nucleic acid sequence, which encodes a mutated PON1 enzyme.

As used herein the phrase "an isolated polynucleotide" refers to a single or a double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

As used herein the phrase "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

As used herein the phrase "genomic polynucleotide sequence" refers to a sequence derived (isolated) from a chromosome and thus it represents a contiguous portion of a chromosome.

As used herein the phrase "composite polynucleotide sequence" refers to a sequence, which is at least partially complementary and at least partially genomic. A composite sequence can include some exonal sequences required to encode the polypeptide of the present invention, as well as some intronic sequences interposing therebetween. The intronic sequences can be of any source, including of other genes, and typically will include conserved splicing signal sequences. Such intronic sequences may further include cis acting expression regulatory elements.

The "mutated PON1 enzyme" of this aspect of the present invention refers to a protein which differs from a respective wild-type PON (i.e., the starting point PON) by at least one mutation (e.g., insertion, deletion, substitution).

The mutated PON1 enzyme of this aspect of the present invention is characterized by:

(i) a substrate specificity which is substantially identical to that of a respective wild-type PON (see preceding Background section, Examples 2-4 of the examples section which follows and U.S. Pat. No. 6,573,370); and (ii) no substantial formation of aggregates (i.e., non-recoverable aggregates) when expressed in bacteria such as *E. coli* [e.g., BL21, BL21 (DE3), Origami B (DE3), available from Novagen (wwwdotcalbiochemdotcom) and RIL (DE3) available from Stratagene, (wwwdotstratagenedotcom). Essentially, at least 2%, at least 5%, at least 10%, at least 20%, at least 30%, at least 40%, at least 50%, at least 60%, at least 70%, at least 80%, at least 90%, at least 95% or more, say 100%, of bacterially expressed protein remains soluble (i.e., does not precipitate into inclusion bodies).

According to a preferred embodiment of this aspect of the present invention the nucleic acid sequence which encodes the mutated PON1 enzyme is of a mammalian origin, such as a mouse origin, a human origin, a rat origin, a rabbit origin or a combination thereof (e.g., a result of gene shuffling).

The mutated PON1 enzyme of this aspect of the present invention is characterized by at least one amino acid substitution with respect to an amino acid sequence of a respective hydrophobic region of the wild type PON1. For example, in the case of human PON1, such a substitution would be in a region encompassed by amino acid coordinates 126-142 and/or 301-343 of SEQ ID NO: 36). These amino acid substitutions may be of amino acids I126, M130, K137, L142, A301, A320 M341 or V343 of human PON1.

Additionally or alternatively, the mutated PON1 enzyme of this aspect of the present invention preferably includes a lysine at a position equivalent to amino acid coordinate 192 of rabbit PON1 (GenBank Accession No. AF220943, SEQ ID NO: 37).

As used herein, an equivalent amino acid refers to an amino acid which is homologous (i.e., corresponding in position in either primary or tertiary structure) and/or analogous to a specific residue or portion thereof in a given PON sequence.

In addition to the mutations described above, the isolated polynucleotide encoding the mutated PON1 of this aspect of the present invention may also include an additional nucleic acid sequence, which encodes a tag fused in-frame to the nucleic acid sequence which encodes the mutated PON1 enzyme of this aspect of the present invention. Such a tag may promote receptor solubility (as exemplified in Examples one of the Examples section) and/or may simplify the purification process of the recombinant proteins, as is further described hereinbelow.

According to preferred embodiments of this aspect of the present invention the isolated polynucleotide encoding the mutated PON1 of this aspect of the present invention is as set forth in SEQ ID NO: 25, 26, 27, 28, 29 or 55.

According to other preferred embodiments of this aspect of the present invention the amino acid sequence of the mutated PON1 enzyme is set forth in SEQ ID NO: 57, 58, 59, 60, 61 or 56.

As is illustrated in Example 2 of the Examples section, the above-described soluble PON1 polynucleotide was used as a starting point for the evolution of substrate specialized PON hydrolases.

Thus, according to yet another aspect of the present invention, there is provided an isolated polynucleotide including a nucleic acid sequence encoding a mutated PON enzyme which exhibits a modified substrate range as compared to a respective wild-type PON.

As used herein the phrase "PON enzyme" refers to a nucleic acid or amino acid sequence of a known PON family member (e.g., PON1, PON2 or PON3) and variants thereof. Examples of PON family members include, but are not limited to, Human PON1 (GenBank Accession Nos. NM_00046, S64696, S64615, M63012, U55877, I42585), Rabbit PON1 (GenBank Accession Nos. AF220943, S64616), Mouse PON1 (GenBank Accession Nos. NM_011134, U32684, L40488), Rat PON1 (GenBank Accession Nos. XM_342639, U94856), *C. elegans* PON1 (GenBank Accession No. AF003141), Dog PON2 (GenBank Accession No. L48515), Human PON2 (GenBank Accession Nos. L48513, AF001602, AR022313, NM_00035), Mouse PON2 (GenBank Accession Nos. L48514, NM_008896), Chicken PON2 (GenBank Accession Nos. L47573), Turkey PON2 (GenBank Accession No. L47572) rabbit PON3 (GenBank Accession No. AF220944), Human PON3 (GenBank Accession No. NM_000940, AC005021), Mouse PON3 (GenBank Accession No. L76193), As used herein the phrase "modified substrate range" refers to an increase or a decrease in the catalytic activity of the respective wild-type PON to at least one known natural or synthetic substrate thereof. In certain cases, a decrease in activity towards one substrate, can be accompanied by an increase in activity towards another substrate.

For example, the modified substrate range of the mutated PON enzyme can be manifested by an increased phosphotriesterase activity and a decreased esterate activity. Such a mutated PON enzyme is expected to find valuable utility in the decontamination of chemical warfare and industrial OP-based insecticides. Other examples include increased thiolactonase activity (e.g., towards Homocysteince thiolactone) or lipase-like activity (e.g., towards oxidized lipids and lipid peroxides).

Table 13 below lists a set of 16 residues which define the perimeter of the active site of the PON family of genes, and thus govern substrates selectivity. Each of these residues can be modified to obtain substrate specialized PON hydrolazes as described in this Table.

For example, the mutated PON enzyme of thus aspect of the present invention may include amino acid substitutions which are equivalent to amino acid coordinates S193, N287, G19 and V346 of human PON1, which results in highly expressible, highly active phosphotriesterase.

Alternatively, the mutated PON enzyme of thus aspect of the present invention may include amino acid substitutions which are equivalent to amino acid coordinates I291 and T332 of human PON1, which result in highly expressible, highly active lactonase which may be used for the hydrolysis of Homocysteine thiolactone (HcyT).

Yet alternatively, the mutated PON enzyme of this aspect of the present invention may include amino acid substitutions which are equivalent to amino acid coordinates I74, I291, F292, F293 of human PON1, which result in highly expressible, highly active esterase including hydrolysis of hydrophobic esters (see Table 11, below).

Using this structural data, the present inventors also generated a mutated PON enzyme which exhibits increased substrate specificity to at least one known PON substrate as compared to a respective (i.e., of the same origin) wild-type PON (e.g., see Example 5 of the Examples section which follows).

As used herein the phrase "increased substrate specificity" refers to an increase in the $K_{cat}/K_M$ ratio of the mutated PON enzyme for a specific substrate as compared to the respective wild-type PON. PON mutants with increased or diminished $K_{cat}/K_M$ ratios are described in the Examples section which follows.

Examples of known synthetic and naturally occurring PON substrates include, but are not limited to, esters, such as phenyl, naphtyl and benzyl acetate, and lipids; phosphotriesters, such as DEPCyc, paraoxon, sarin and soman; lactones, such as, α-angelicolactone, dihydrocuomarin and γ-butyrolactone; thiolactones, such as, γ-butyrothiolactone and homocysteine thiolactone [Draganov, D. I. & La Du, B. N. Pharmacogenetics of paraoxonases: a brief review. *Nau Schm Arch Pharmacol* (2003); and references therein].

Mutated PON enzymes of this aspect of the present invention preferably include at least one amino acid substitution in an amino acid equivalent to amino acid coordinate that is located in the active site of human PON1, which is preferably defined by a distant not exceeding 15 Å from a Calcium ion, preferably Ca401). Examples of such substitutions are illustrated in Table 13 hereinbelow.

According to one preferred embodiment of this aspect of the present invention the mutated PON enzyme exhibits at least 3 folds higher $K_{cat}/K_M$ ratio for phosphotriester hydrolysis, ester hydrolysis, carboxy-ester, lactone hydrolysis, thiolactone hydrolysis, lipid hydrolysis and/or lipid peroxide hydrolysis as compared to the respective wild-type PON.

According to other preferred embodiments of this aspect of the present invention, the isolated polynucleotide encoding the mutated PON enzyme is as set forth in SEQ ID NO: 62, 64, 66, 68, 70, 72, 74 or 76.

According to yet other preferred embodiments of this aspect of the present invention the amino acid sequence of this mutated PON enzyme is as set forth in SEQ ID NO: 63, 65, 67, 69, 71, 73, 75 or 77.

Thus, the present invention encompasses nucleic acid sequences described hereinabove; fragments thereof, sequences hybridizable therewith, sequences homologous thereto, sequences encoding similar polypeptides with different codon usage, altered sequences characterized by mutations, such as deletion, insertion or substitution of one or more nucleotides, either naturally occurring or man induced, either randomly or in a targeted fashion.

Since the polynucleotide sequences of the present invention encode previously unidentified polypeptides, the present invention also encompasses novel PON polypeptides or portions thereof, which are encoded by the isolated polynucleotide and respective nucleic acid fragments thereof described hereinabove.

Thus, the present invention also encompasses polypeptides encoded by the novel PON nucleotide sequences of the present invention. The amino acid sequences of these novel polypeptides are set forth in SEQ ID NO: 49, 50, 51, 52, 53, 54, 56, 57, 58, 59, 60, 61, 63, 65, 67, 69, 71, 73, 75 or 77. The present invention also encompasses functional homologues of these polypeptides, such homologues can be at least 50%, at least 55%, at least 60%, at least 65%, at least 70%, at least 75%, at least 80%, at least 85%, at least 95% or more say 100% homologous to SEQ ID NO: 49, 50, 51, 52, 53, 54, 56, 57, 58, 59, 60, 61, 63, 65, 67, 69, 71, 73, 75 or 77. Finally, the present invention also encompasses fragments of the above described polypeptides and polypeptides having mutations, such as deletions, insertions or substitutions of one or more amino acids, either naturally occurring or man induced, either randomly or in a targeted fashion.

Recombinant techniques are preferably used to generate the polypeptides of the present invention. Such recombinant techniques are described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463.

To produce a polypeptide of the present invention using recombinant technology, a polynucleotide encoding a polypeptide of the present invention (e.g., SEQ ID NO: 62, 64, 66, 68, 70, 72, 74 or 76) is ligated into a nucleic acid expression construct, which includes the polynucleotide sequence under the transcriptional control of a promoter sequence suitable for directing constitutive or inducible transcription in the host cells, as further described hereinbelow.

Other than containing the necessary elements for the transcription and translation of the inserted coding sequence, the expression construct of the present invention can also include sequences (i.e., tags) engineered to enhance stability, production, purification, yield or toxicity of the expressed polypeptide. Such a fusion protein can be designed so that the fusion protein can be readily isolated by affinity chromatography; e.g., by immobilization on a column specific for the heterologous protein. Where a cleavage site is engineered between the peptide moiety and the heterologous protein, the peptide can be released from the chromatographic column by treatment with an appropriate enzyme or agent that disrupts the cleavage site [e.g., see Booth et al. (1988) Immunol. Lett. 19:65-70; and Gardella et al., (1990) J. Biol. Chem. 265:15854-15859].

A variety of prokaryotic or eukaryotic cells can be used as host-expression systems to express the peptide coding sequence. These include, but are not limited to, microorganisms, such as bacteria transformed with a recombinant bacteriophage DNA, plasmid DNA or cosmid DNA expression vector containing the peptide coding sequence; yeast transformed with recombinant yeast expression vectors containing the polypeptide coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the polypeptide coding sequence. Mammalian expression systems can also be used to express the peptides of the present invention. Bacterial systems are preferably used to produce recombinant polypeptides, according to the present invention, thereby enabling a high production volume at low cost.

Other expression systems such as insects and mammalian host cell systems, which are well known in the art can also be used by the present invention.

In any case, transformed cells are cultured under effective conditions, which allow for the expression of high amounts of recombinant polypeptides. Effective culture conditions include, but are not limited to, effective media, bioreactor, temperature, pH and oxygen conditions that permit protein production. An effective medium refers to any medium in which a cell is cultured to produce the recombinant peptides of the present invention. Such a medium typically includes an aqueous solution having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art (see Example 1 of the Examples section).

Depending on the vector and host system used for production, resultant proteins of the present invention may either remain within the recombinant cell; be secreted into the fermentation medium; be secreted into a space between two cellular membranes, such as the periplasmic space in E. coli; or be retained on the outer surface of a cell or viral membrane.

Following a certain time in culture, recovery of the recombinant protein is effected. The phrase "recovering the recombinant protein" refers to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

The availability of large amounts of recombinant PON1 allowed the present inventors to elucidate the three dimensional (3D) structure of the protein, using x-ray crystallography. As is exemplified in Example 6 of the Examples section which follows, the 3D structure of PON1 provides key insights as to how the substrate and reaction selectivity of different PONs is determined. As mentioned hereinabove, a set of 16 residues which constitute the walls and perimeter of the PON active site and governs substrate selectivity was defined (see Table 13 below).

Using this structural information it is possible to computationally identify inhibitor molecules (e.g., small molecules) of PONs, such as PON1. These inhibitors may be complete inhibitors, or partial inhibitors which can modify substrate specificity, as described above. For example, such small molecule inhibitors may shift the substrate specificity of PON1 towards the thiolactonase active configuration of the protein, thereby serving as valuable therapeutics in the treatment of atherosclerosis.

Thus, the present invention also provides a method of identifying a putative inhibitor of PON1.

As used herein the phrase "an inhibitor of PON1" refers to an inhibitor or a partial inhibitor of PON1 (e.g., modifies the substrate range of PON1), preferably human PON1. It will be appreciated that due to structural conservation shared between PON1 and other members of this protein family (i.e., PON2 and PON3), compounds of the present invention may serve as inhibitors of these proteins as well.

The method of this aspect of the present invention is effected by constructing a model using a set of atomic structural coordinates defining a three-dimensional atomic structure of a crystallized PON1 and computationally screening a plurality of compounds for a compound capable of specifically binding the active site of the model, to thereby identify the PON1 inhibitor.

Typically, obtaining the set of atomic coordinates which define the three dimensional structure of an enzyme (e.g., PON1) can be effected using various approaches which are well known in the art. Preferably used, is X-ray crystallography which can be effected as described in Examples 6 of the Examples section, which follows.

Structural data obtained is preferably recorded on a computer readable medium so as to enable data manipulation and construction of computational models. As used herein, "computer readable medium" refers to any medium which can be read and accessed directly by a computer. Such media include, but are not limited to, magnetic storage media, such as floppy discs, hard disc storage medium, and magnetic tape; optical storage media such as optical discs or CD-ROM; electrical storage media such as RAM and ROM; and hybrids of these categories such as magnetic/optical storage media. Selection and use of appropriate storage media is well within the capabilities of one of ordinary skill in the art.

As used herein, "recorded" refers to a process of storing information on computer readable medium.

It will be appreciated that a number of data storage devices can be used for creating a computer readable medium having recorded thereon the structural data of the present invention. The choice of the data storage structure is typically based on the means chosen to access the stored information. In addition, a variety of data processor programs and formats can be used to store the data information of the present invention on computer readable medium. The sequence information can be represented in a word processing text file, formatted in commercially-available software such as WordPerfect and MICROSOFT Word, or represented in the form of an ASCII file, stored in a database application, such as DB2, Sybase, Oracle, or the like.

According to preferred embodiments of this aspect of the present invention, the coordinate data used to define the structure of PON1 or a portion thereof is derived from the set of coordinates set forth in the FIG. 26.

It will be appreciated that structure models of the present invention are preferably generated by a computing platform, which generates a graphic output of the models via a display generating device such as screen or printer. The computing platform generates graphic representations of atomic structure models via a processing unit which processes structure coordinate data stored in a retrievable format in the data storage device (such as described above, see FIG. 24).

Suitable software applications, well known to those of skill in the art, which may be used by the processing unit to process structure coordinate data so as to provide a graphic output of three-dimensional structure models generated therewith via display include RIBBONS (Carson, M., 1997. Methods in Enzymology 277, 25), O (Jones, T A. et al., 1991. Acta Crystallogr A47, 110), DINO (DINO: Visualizing Structural Biology (2001) dino3d.org); and QUANTA, CHARMM, INSIGHT, SYBYL, MACROMODE, ICM, MOLMOL, RASMOL and GRASP (reviewed in Kraulis, J., 1991. Appl Crystallogr. 24, 946).

As mentioned hereinabove, once a structural model of PON1 is obtained compounds which specifically bind the active site of the model are identifiable. This is preferably effected using Rational Drug Design (RDD).

RDD is a potent means of identifying enzyme inhibitors which, for example, has notably been used to identify HIV protease (Lam et al., 1994. Science 263, 380; Wlodawer et al., 1993. Ann Rev Biochem. 62, 543; Appelt, 1993. Perspectives in Drug Discovery and Design 1, 23; Erickson, 1993. Perspectives in Drug Discovery and Design 1, 109), and bcr-abl tyrosine kinase inhibitors (Mauro M J. et al., 2002. J Clin Oncol. 20, 325-34) used to provide the first effective pharmacological cures for human acquired immunodeficiency syndrome (AIDS) caused by human immunodeficiency virus (HIV)), and a human cancer (chronic myeloid leukemia), respectively.

One approach to identify a putative inhibitor via rational drug design is by screening a chemical structure database ("3D database"), using software employing "scanner" type algorithms. Such software applications utilize atomic coordinates defining the three-dimensional structure of a binding pocket of a molecule and of a chemical structure stored in the database to computationally model the "docking" of the screened chemical structure with the binding pocket so as to qualify the binding of the binding pocket with the chemical structure. Iterating this process with each of a plurality of chemical structures stored in the database therefore enables computational screening of such a plurality to identify a chemical structure potentially having a desired binding interaction with the binding pocket, and hence the putative inhibitor.

Examples of suitable chemical structure databases for identifying the inhibitor molecules of the present invention include ISIS (MDL Information Systems, San Leandro, molinfo.com), MACCS-3D (Martin, Y. C., 1992. J. Med. Chem. 35, 2145-2154), The Cambridge Structural Database (CSD; cam.ac.uk/prods/csd/csd.html), Fine Chemical Database (reviewed in Rusinko A., 1993. Chem Des Auto. News 8, 44-47), and the NCBI's Molecular Modeling DataBase: MMDB; ncbi.nlm.nih.gov/Structure/MMDB/mmdb.shtml.

Other libraries of chemicals are commercially available from, for example, Merck, GlaxoWelcome, Bristol Meyers Squib, Monsanto/Searle, Eli Lilly, Novartis and Pharmacia UpJohn.

Alternatively, identifying the inhibitor molecule can be effected using de novo rational drug design, or via modification of a known chemical structure. In such case, software comprising "builder" type algorithms utilizes a set of atomic coordinates defining a three-dimensional structure of the binding pocket and the three-dimensional structures of basic chemical building blocks to computationally assemble a putative inhibitor. Such an approach may be employed to structurally refine a putative inhibitor identified, for example, via chemical database screening as described above.

Ample guidance for performing rational drug design by utilizing software employing such "scanner" and "builder" type algorithms is available in the literature (see, for example, Halperin I. et al., 2002. Proteins 47, 409-43; Gohlke H. and Klebe G., 2001. Curr Opin Struct Biol. 11, 231-5; Zeng J., 2000. Comb Chem High Throughput Screen. 3, 355-62; and RACHEL: Theory of drug design, newdrugdesign.com/Rachel_Theory.htm#Software). Additional guidance is provided hereinbelow and in the Examples section which follows.

Criteria employed by software programs used in rational drug design to qualify the binding of screened chemical structures with binding pockets include gap space, hydrogen bonding, electrostatic interactions, van der Waals forces, hydrophilicity/hydrophobicity, etc. Generally, the greater the contact area between the screened molecule and the binding region of the PON1, the lower the steric hindrance, the lower the "gap space", the greater the number of hydrogen bonds, and the greater the sum total of the van der Waals forces between the screened molecule and the substrate docking site of the PON1 protein, the greater will be the capacity of the screened molecule to bind with the active site of PON1.

The "gap space" refers to unoccupied space between the van der Waals surface of a screened molecule positioned within a binding pocket and the surface of the binding pocket defined by amino acid residues in the binding pocket. Gap space may be identified, for example, using an algorithm based on a series of cubic grids surrounding the docked molecule.

Contact area between compounds may be directly calculated from the coordinates of the compounds in docked conformation using the MS program (Connolly M L., 1983. Science 221, 709-713).

Suitable software employing "scanner" type algorithms include, for example, docking software such as GRAM, DOCK, or AUTODOCK (reviewed in Dunbrack et al., 1997. Folding and Design 2, 27), AFFINITY software of the INSIGHTII package (Molecular Simulations Inc., 1996, San Diego, Calif.), GRID (Goodford P J., 1985. "A Computational Procedure for Determining Energetically Favorable Binding Sites on Biologically Important Macromolecules", J. Med. Chem. 28, 849-857; GRID is available from Oxford University, Oxford, UK), and MCSS (Miranker A. and Karplus M., 1991. "Functionality Maps of Binding Sites: A Multiple Copy Simultaneous Search Method", Proteins: Structure Function and Genetics 11, 29-34; MCSS is available from Molecular Simulations, Burlington, Mass.).

The AUTODOCK program (Goodsell D S. and Olson A J., 1990. Proteins: Struct Funct Genet. 8, 195-202; available from Scripps Research Institute, La Jolla, Calif.) helps in docking screened molecules to binding pockets in a flexible manner using a Monte Carlo simulated annealing approach. The procedure enables a search without bias introduced by the researcher which can influence orientation and conformation of a screened molecule in the targeted binding pocket.

The DOCK program (Kuntz I D. et al., 1982. J Mol. Biol. 161, 269-288; available from University of California, San Francisco), is based on a description of the negative image of a space-filling representation of the binding pocket, and includes a force field for energy evaluation, limited conformational flexibility and consideration of hydrophobicity in the energy evaluation.

Modeling or docking may be followed by energy minimization with standard molecular mechanics force fields or dynamics with programs such as CHARMM (Brooks B R. et al., 1983. J Comp Chem. 4, 187-217) or AMBER (Weiner S J. et al., 1984. J Am Chem. Soc. 106, 765-784).

As used herein, "minimization of energy" means achieving an atomic geometry of a chemical structure via systematic alteration such that any further minor perturbation of the atomic geometry would cause the total energy of the system, as measured by a molecular mechanics force-field, to increase. Minimization and molecular mechanics force fields are well understood in computational chemistry (for example, refer to Burkert U. and Allinger N L., "Molecular Mechanics", ACS Monograph 177, pp. 59-78, American Chemical Society, Washington, D.C. (1982)).

Programs employing "builder" type algorithms include LEGEND (Nishibata Y. and Itai A., 1991. Tetrahedron 47, 8985; available from Molecular Simulations, Burlington, Mass.), LEAPFROG (Tripos Associates, St. Louis, Mo.), CAVEAT (Bartlett, P A. et al., 1989. Special Pub Royal Chem. Soc. 78, 182-196; available from University of California, Berkeley), HOOK (Molecular Simulations, Burlington, Mass.), and LUDI (Bohm H J., 1992. J. Comp Aid Molec Design 6, 61-78; available from Biosym Technologies, San Diego, Calif. See Examples section which follows).

The CAVEAT program suggests possible binding molecules based on desired bond vectors. The HOOK program proposes docking sites by using multiple copies of functional groups in simultaneous searches. LUDI is a program based on fragments rather than on descriptors which proposes somewhat larger fragments as possible matches with a binding pocket and scores its hits based on geometric criteria taken from the Cambridge Structural Database (CSD), the Protein Data Bank (PDB) and on criteria based on binding data. LUDI may be advantageously employed to calculate the inhibition constant of a docked chemical structure. Inhibition constants (Ki values) of compounds in the final docking positions can be evaluated using LUDI software.

During or following rational drug design, docking of an intermediate chemical structure or of the putative inhibitor with the binding pocket may be visualized via structural models, such as three-dimensional models thereof displayed on a computer screen, so as to advantageously allow user intervention during the rational drug design to optimize a chemical structure.

Software programs useful for displaying such three-dimensional structural models, include RIBBONS (Carson, M., 1997. Methods in Enzymology 277, 25), O (Jones, T A. et al., 1991. Acta Crystallogr. A47, 110), DINO (DINO: Visualizing Structural Biology (2001) http://wwwdotdino3ddotorg); and QUANTA, INSIGHT, SYBYL, MACROMODE, ICM, MOLMOL, RASMOL and GRASP (reviewed in Kraulis, J., 1991. Appl Crystallogr. 24, 946).

Other molecular modeling techniques may also be employed in accordance with this invention (for example, refer to: Cohen N C. et al, 1990. "Molecular Modeling Software and Methods for Medicinal Chemistry", J. Med. Chem. 33, 883-894; Navia M. A. and Murcko M. A., 1992. "The Use of Structural Information in Drug Design", Current Opinions in Structural Biology 2, 202-210). For example, where the structures of test compounds are known, a model of the test compound may be superimposed over the model of the structure of the invention. Numerous methods and techniques which are well known in the art can be used for performing this step (for example, refer to: Farmer P. S., "Drug Design", Ariens E J. (ed.), Vol. 10, pp 119-143 (Academic Press, New York, 1980); U.S. Pat. No. 5,331,573; U.S. Pat. No. 5,500, 807; Verlinde C., 1994. Structure 2, 577-587; and Kuntz I D., 1992. Science 257, 1078-108).

The polynucleotides, polypeptides and/or compounds of the present invention, collectively termed agents, can be used to treat a PON-associated disease or condition in a subject in need thereof.

As used herein the phrase "PON-associated disease or condition" refers to a disease or a condition which may be treated by upregulating at least one PON activity in a subject (e.g., phosphotriesterase, phospholipase A2 like activities). Examples of such diseases or conditions include, but are not limited to, hyperlipidemia, atherosclerosis (see U.S. Pat. No. 6,521,226), neurological diseases (e.g., Alzheimer's disease, neurofibromatosis, Huntington's disease, depression, amyotrophic lateral sclerosis, multiple sclerosis, stroke, Parkinson's disease, or multi-infarct dementia, see U.S. Pat. No. 6,573,049), cancer (e.g., caused by carcinogenic lactones, see also U.S. Pat. No. 6,242,186), oxidative stress, sepsis (see U.S. Pat. No. 6,573,370), restenoses and intoxication by agents (i.e., endogenous or exogenous agents) which may be hydrolyzed and thereby inactivated by PONs, such as organophosphate poisoning (see U.S. Pat. Appl. Pub. No. 20020151068).

As used herein the term "treating" refers to preventing, curing, reversing, attenuating, alleviating, minimizing, suppressing or halting the deleterious effects of a PON associated condition or disease.

As used herein the phrase "subject in need thereof" refers to an organism, which may benefit from upregulation in PON activity.

The method is effected by administering to the subject a therapeutically effective amount of the agent of the present invention.

The agent can be provided to the subject per se, or as part of a pharmaceutical composition where it is mixed with a pharmaceutically acceptable carrier.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the compound preparation, which is accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases. One of the ingredients included in the pharmaceutically acceptable carrier can be for example polyethylene glycol (PEG), a biocompatible polymer with a wide range of solubility in both organic and aqueous media (Mutter et al. (1979). Alternatively, the physiologically acceptable carrier may be HDL particles, HDL-like particles, and/or reconstituted HDL particles, to which PON enzymes are linked (see U.S. Pat. Nos. 5,128,318, 5,652,339 and 6,514,523).

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, intraperitoneal, intranasal, or intraocular injections. The preferred route of administration is presently oral.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the invention may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The preparations described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The preparation of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of disease or prolong the survival of the subject being treated.

Determination of a therapeutically effective amount is well within the capability of those skilled in the art.

For any preparation used in the methods of the invention, the therapeutically effective amount or dose can be estimated initially from in vitro assays. For example, a dose can be formulated in animal models (e.g., obese models such as disclosed by Bayli's J Pharmacol Exp Ther. 2003; and models for atherosclerosis such as described by Brousseau J Lipid Res. 1999 40(3):365-75) and such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. [See e.g., Fingl, et al., (1975) "The Pharmacological Basis of Therapeutics", Ch. 1 p. 1].

Depending on the severity and responsiveness of the condition to be treated, dosing can be effected over a short period of time (i.e., several days to several weeks) or until cure is effected or diminution of the disease state is achieved.

The amount of a composition to be administered will, of course, be dependent on the subject being treated, the severity of the affliction, the manner of administration, the judgment of the prescribing physician, etc.

Compositions including the preparation of the present invention formulated in a compatible pharmaceutical carrier may also be prepared, placed in an appropriate container, and labeled for treatment of an indicated condition.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

It will be appreciated that the polypeptides of the present invention can also be expressed from a nucleic acid construct administered to the subject employing any suitable mode of administration, described hereinabove (i.e., in-vivo gene therapy). Alternatively, the nucleic acid construct is introduced into a suitable cell via an appropriate gene delivery vehicle/method (transfection, transduction, homologous recombination, etc.) and an expression system as needed and then the modified cells are expanded in culture and returned to the individual (i.e., ex-vivo gene therapy).

As mentioned hereinabove, to enable cellular expression of the polynucleotides of the present invention, the nucleic acid construct of the present invention includes at least one cis acting regulatory element, such as a promoter.

Preferably, the promoter utilized by the nucleic acid construct of the present invention is active in the specific cell population transformed. Examples of cell type-specific and/or tissue-specific promoters include promoters such as albumin that is liver specific [Pinkert et al., (1987) Genes Dev. 1:268-277], lymphoid specific promoters [Calame et al., (1988) Adv. Immunol. 43:235-275]; in particular promoters of T-cell receptors [Winoto et al., (1989) EMBO J. 8:729-733] and immunoglobulins; [Banerji et al. (1983) Cell 33729-740], neuron-specific promoters such as the neurofilament promoter [Byrne et al. (1989) Proc. Natl. Acad. Sci. USA 86:5473-5477], pancreas-specific promoters [Edlunch et al. (1985) Science 230:912-916] or mammary gland-specific promoters such as the milk whey promoter (U.S. Pat. No. 4,873,316 and European Application Publication No. 264, 166). The nucleic acid construct of the present invention can further include an enhancer, which can be adjacent or distant to the promoter sequence and can function in up regulating the transcription therefrom.

The nucleic acid construct of the present invention preferably further includes an appropriate selectable marker and/or an origin of replication. Preferably, the nucleic acid construct utilized is a shuttle vector, which can propagate both in E. coli (wherein the construct comprises an appropriate selectable marker and origin of replication) and be compatible for propagation in cells, or integration in a gene and a tissue of choice. The construct according to the present invention can be, for example, a plasmid, a bacmid, a phagemid, a cosmid, a phage, a virus or an artificial chromosome.

Examples of suitable constructs include, but are not limited to, pcDNA3, pcDNA3.1 (+/−), pGL3, PzeoSV2 (+/−), pDisplay, pEF/myc/cyto, pCMV/myc/cyto each of which is commercially available from Invitrogen Co. (wwwdotinvitrogendotcom). Examples of retroviral vector and packaging systems are those sold by Clontech, San Diego, Calif., including Retro-X vectors pLNCX and pLXSN, which permit cloning into multiple cloning sites and the trasgene is transcribed from CMV promoter. Vectors derived from Mo-MuLV are also included such as pBabe, where the transgene will be transcribed from the 5'LTR promoter.

Currently preferred in vivo nucleic acid transfer techniques include transfection with viral or non-viral constructs, such as adenovirus, lentivirus, Herpes simplex I virus, or adeno-associated virus (AAV) and lipid-based systems. Useful lipids for lipid-mediated transfer of the gene are, for example, DOTMA, DOPE, and DC-Chol [Tonkinson et al., Cancer Investigation, 14(1): 54-65 (1996)]. The most preferred constructs for use in gene therapy are viruses, most preferably adenoviruses, AAV, lentiviruses, or retroviruses. A viral construct such as a retroviral construct includes at least one transcriptional promoter/enhancer or locus-defining element(s), or other elements that control gene expression by other means such as alternate splicing, nuclear RNA export, or post-translational modification of messenger. Such vector constructs also include a packaging signal, long terminal repeats (LTRs) or portions thereof, and positive and negative strand primer binding sites appropriate to the virus used, unless it is already present in the viral construct. In addition, such a construct typically includes a signal sequence for secretion of the peptide from a host cell in which it is placed. Preferably the signal sequence for this purpose is a mammalian signal sequence or the signal sequence of the polypeptide variants of the present invention. Optionally, the construct may also include a signal that directs polyadenylation, as well as one or more restriction sites and a translation termination sequence. By way of example, such constructs will typically include a 5' LTR, a tRNA binding site, a packaging signal, an origin of second-strand DNA synthesis, and a 3' LTR or a portion thereof. Other vectors can be used that are non-viral, such as cationic lipids, polylysine, and dendrimers.

Due to their hydrolytic activities (e.g., lacton and lipid hydrolysis), agents of the present invention may also be used to coat the surface of medical devices, such as for the treatment of artery narrowing caused by fatty deposits (plaque) on the walls of the arteries. Such a modality of treatment combines mechanical and pharmacological solutions. Also such coating is desired whenever the activity of the device is hampered by the accumulation of biomaterial therein or bioincompatibility, leading to foci formation and inflammation (e.g., in-stent restenosis).

As used herein the phrase "a medical device" refers to a device having surfaces which contact human or animal bodily tissue and/or fluids in the course of its operation. Examples of biomedical devices include, but are not limited to, extracorporeal devices for use in surgery such as blood oxygenators, blood pumps, blood sensors, tubing used to carry blood and the like which contact blood which is then returned to the subject; endoprostheses which are implanted in blood contact in a human or animal body such as vascular grafts, stents, pacemaker leads, heart valves, and the like that are implanted in blood vessels or in the heart; and devices for temporary intravascular use such as catheters, guide wires, and the like which are placed into the blood vessels or the heart for purposes of monitoring or repair.

Specific examples of medical devices which can be used in accordance with the present invention, include, but are not limited to, vascular grafts, aortic grafts, arterial, venous, or vascular tubing, vascular stents, dialysis membranes, tubing or connectors, blood oxygenator tubing or membranes, ultrafiltration membranes, intra-aortic balloons, blood bags, catheters, sutures, soft or hard tissue prostheses, synthetic prostheses, prosthetic heart valves, tissue adhesives, cardiac pacemaker leads, artificial organs, endotracheal tubes, lenses for the eye such as contact or intraocular lenses, blood handling equipment, apheresis equipment, diagnostic and monitoring catheters and sensors, biosensors, dental devices, drug delivery systems, or bodily implants of any kind A number of approaches are known in the art for attaching proteins to the surface of a biomedical device. These approaches typically include the use of coupling agents such as glutaraldehyde, cyanogens bromide, p-benzoquinone, succinic anhydrides, carbodiimides, diisocyanates, ethyl chloroformate, dipyridyl disulphide, epichlorohydrin, azides, among others, which serve as attachment vehicles for coupling of biomolecules to substrate surfaces. For example, covalent attachment of biomolecules using water soluble carbodiimides is described by Hoffman et al., "Covalent Binding of Biomolecules to Radiation-Grafted Hydrogels on Inert Polymer Surfaces," Trans. Am. Soc. Artif. Intern. Organs, 18, 10-18 (1972); and Ito et al., "Materials for Enhancing Cell Adhesion by Immobilization of Cell-Adhesive Peptide," J. Biomed. Mat. Res., 25, 1325-1337 (1991). U.S. Pat. No. 6,617,142 discloses methods for forming a coating of immobilized biomolecule on a surface of a medical device to impart improved biocompatibility for contacting tissue and bodily fluids.

Agents of the present invention may be immobilized to the surface of the medical device or released therefrom, either constitutively or upon induction.

To improve therapeutic efficacy, treatment with the agents of the present invention can be combined with pre-established clinical modalities. Thus, for example, treatment of organophosphate poisoning using the agents of the present invention can be combined with the administration of carbamates, antimuscarnics, reactivators and anticonvulsants.

As mentioned hereinabove, the agents of the present invention can be used for decontamination and detoxification of PON-susceptible toxic agents. Thus, for example, stockpiles of toxic agents (e.g., organophosphates, pesticides and volatile organic compounds) can be hydrolyzed using the agents of the present invention [DeFrank (1991) Applications of Enzyme Biotechnology ed. J W Kelly, T O Baldwin p: 165-80, Mazur (1946) J. Biol. Chem. 164:271-89]. Such treatments may be often optimized by UV-ozonation [Kearney (1986) J. Agric. Food Chem. 34:702-6]. Transgenic organisms (e.g., bacteria) expressing PONs of the present invention can be grown on OP toxins, for bioremediation of contaminated regions [Walker (2002) Biotechnol. Bioeng. 78:715-21; Shimazu (2001) Biotechnol. Bioeng. 76:318-24; Munnecke (1974) Appl. Microbiol. 28: 212-17]. These PONs are preferably cell-surface expressed to avoid substrate diffusion through the cell wall or membrane [Hong (1998) Bioremediation J. 2:145-57; Richins (1997) Nat. Biotechnol. 15:984-87; Kaneva (1998) Biotechnol. Prog. 14:275-78; Kim (2002) Biotechnol. Prog. 18:429-36; Zhang (1999) Biotechnol. Bioeng. 64:221-31; Kim (1997) Biotech. Lett. 19:1067-71 Mulchandani (1999) Biotechnol. Bioeng. 63:216-23; Wang (2002) Appl. Environ. Microbiol. 68:1684-89]. To improve water solubility of purified enzymes, micro-emulsions to solubilize and concentrate the hydrophobic compounds. PONs can also be incorporated in fire fighting foams, which can effectively decontaminate large surface without solvents and toxic solutions. Toxic vapors may be hydrolyzed using solid lyophilized PONs in gas phase bioreactors [Russell (1994) Chemtech 24:23-31; Komives (1994) Biotechnol. Bioeng. 43:946-59; Lejeune (1998) Nature 395:27-28; Lejeune (1999) Biotechnol. Bioeng. 62:659-65; Cheng (1998) Ann. NY Acad. Sci. 864:253-58].

Immobilized agents of the present invention are also of valuable use in detoxification and as protective barriers [see Russell (2003) Annu. Rev. Biomed. 5:1-27 and references therein]. For example such agents can be adsorped in protective clothing, however, measures are taken to employ effective immobilization methods which allow for the preparation of immobilized enzymes which retain most activity, high operational stability in its working environment and high storage stability. Methods of immobilization include the attachment of the enzyme on glass-beads via an azide-coupling method, adsorption onto trityl agarose, covalent attachment using glutaraldehyde onto nylon supports, immobilization of bacterially expressed enzymes onto cotton. Recent advances in materials synthesis using enzymes allows the preparation of a variety of bioplastics (e.g., polyurethanes and foams thereof, sol-gel, silicone) and enzyme-polymer composites for use as reactive monoliths, foams, fibers, wipes, and coatings. These polymers involve the incorporation (usually covalent) of the enzyme directly into the polymer. The enzyme may participate in the reaction and via the reactive functionalities on the enzyme surface, form multiple covalent attachments with the polymer. This ensures retention and stability of the polymeric material.

The agents of the present invention may also be incorporated in cleaning solutions (such as for cleaning pesticide-treated foods). These enzyme-based detergents also known as 'green chemicals' may find a wide range of applications in laundry, dishwashing, textile and other such industries. Cleaning compositions of the present invention include the active agents of the present invention as well as cleaning adjunct materials, preferably compatible with the enzyme action. The term "cleaning adjunct materials", as used herein, refers to a liquid, solid or gaseous material selected for the particular type of cleaning composition desired and the form of the product (e.g., liquid; granule; powder; bar; paste; spray; tablet; gel; foam composition), which materials are also preferably compatible with the hydrolytic enzyme used in the composition. Granular compositions can also be in "compact" form and the liquid compositions can also be in a "concentrated" form.

The specific selection of cleaning adjunct materials are readily made by considering the surface, item or fabric to be cleaned, and the desired form of the composition for the cleaning conditions during use (e.g., through the wash detergent use). The term "compatible", as used herein, means the cleaning composition materials do not reduce the hydrolytic activity of the enzyme to such an extent that the enzyme is not effective as desired during normal use situations. Examples of suitable cleaning adjunct materials include, but are not limited to, surfactants, builders, bleaches, bleach activators, bleach catalysts, other enzymes, enzyme stabilizing systems, chelants, optical brighteners, soil release polymers, dye transfer agents, dispersants, suds suppressors, dyes, perfumes, colorants, filler salts, hydrotropes, photoactivators, fluorescers, fabric conditioners, hydrolyzable surfactants, preservatives, anti-oxidants, anti-shrinkage agents, anti-wrinkle agents, germicides, fungicides, color speckles, silvercare, anti-tarnish and/or anti-corrosion agents, alkalinity sources, solubilizing agents, carriers, processing aids, pigments and pH control agents as described in U.S. Pat. Nos. 5,705,464, 5,710,115, 5,698,504, 5,695,679, 5,686,014, 5,646,101 and 6,610,642. Specific cleaning composition materials are exemplified in detail hereinafter.

If the cleaning adjunct materials are not compatible with the enzyme(s) in the cleaning compositions, then suitable methods of keeping the cleaning adjunct materials and the enzyme(s) separate (not in contact with each other) until combination of the two components is appropriate can be used. Suitable methods can be any method known in the art, such as gelcaps, encapsulation, tablets, physical separation, etc.

Preferably an effective amount of one or more enzymes described above are included in compositions useful for cleaning a variety of surfaces in need of toxic agent removal. Such cleaning compositions include detergent compositions for cleaning hard surfaces, unlimited in form (e.g., liquid and granular); detergent compositions for cleaning fabrics, unlimited in form (e.g., granular, liquid and bar formulations); and dishwashing compositions (unlimited in form and including both granular and liquid automatic dishwashing).

As used herein, "effective amount of enzyme" refers to the quantity of enzymes described hereinbefore necessary to achieve the enzymatic activity necessary in the specific cleaning composition. Such effective amounts are readily ascertained by one of ordinary skill in the art and is based on many factors, such as the particular enzyme used, the cleaning application, the specific composition of the cleaning composition, and whether a liquid or dry (e.g., granular, bar) composition is required, and the like. Preferably the cleaning compositions comprise from about 0.0001%, preferably from about 0.001%, more preferably from about 0.01% by weight of the cleaning compositions of one or more enzymes of the present invention, to about 10%, preferably to about 1%, more preferably to about 0.1%. Also preferably the enzyme of the present invention is present in the compositions in an amount sufficient to provide a ratio of mg of active enzyme per 100 grams of composition to ppm theoretical Available $O_2$ from any peroxyacid in the wash liquor, referred to herein as the Enzyme to Bleach ratio (E/B ratio), ranging from about 1:1 to about 20:1. Several examples of various cleaning compositions wherein the enzymes of the present invention may be employed are discussed in further detail below. Also, the cleaning compositions may include from about 1% to about 99.9% by weight of the composition of the cleaning adjunct materials.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W.H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Cloning and Expression of Wild-Type PON1 Genes in *E. Coli*

Materials and Experimental Procedures
Cloning of PON1 Genes—

The plasmid pGex-6p-2 containing the hPON1 gene ((Reddy et al., 2001) kindly provided by Srinivasa T. Reddy, UCLA) was used as a template for PCR amplification with a back primer (pET20-hPON1-bc; Table 1, below) that introduces an NcoI restriction site at the ATG initiation codon, and a forward primer (pET20-hPON1-fo, Table 1, below) annealing downstream to the NotI site. The resulting fragment was digested and cloned into pET20b and pET32b (Novagen,) using the NcoI and NotI sites. For cloning into pET43b, pET43-hPON1-bc (Table 1, below) was used as a back primer annealing downstream to the ATG initiation codon and appending an SpeI restriction. For cloning to pMAL (NEB), a back primer appending an EcoRI site (pMAL-hPON1-bc, Table 1, below), and a forward primer (pMAL-hPON1-fo, Table 1, below) annealing to the hPON1 gene upstream to the stop codon and appending an additional stop codon and a pstI site, were used.

The genes for mouse PON1 (mPON1, GenBank Accession No. NM_011134) and Rat PON1 (RatPON1, GenBank Accession No. XM_342639) were directly amplified by PCR from liver cDNA (CLONTECH) with a back primer pET32-mPON1-bc and pET32-RatPON1(+8)-bc (appending the first 8 amino acids from the mPON1 gene sequence, see Table 1, below), respectively, to introduce an NcoI restriction site at the ATG initiation codon, and forward primers pET32-mPON1-fo and pET32-RatPON1-fo (Table 1, below) to introduce a NotI restriction site downstream to a stop codon.

The gene for Rabbit PON1 (RabPON1, GenBank Accession No. AF220943) was cloned from rabbit cDNA. The total mRNA of a fresh liver of a Rabbit (New-Zealand) was extracted using an RNeasy kit (Beit Haemek) and used as a template for the RT reaction with hexamer random primer and oligo dT (Superscript II, Stratagene). The rabbit PON1 gene was amplified from this cDNA with a back primer (pET32-RabPON1-bc, Table 1) introducing an NcoI site and a forward primer (pET32-RabPON1-fo, Table 1) with a NotI site downstream to the stop codon. The resulting DNA fragments were digested and cloned into pET32b(+) vector (containing Trx and an His tag as a fusion protein) to generate the pET32b-hPON1, pET32b-mPON1, pET32b-RatPON1 and pET32b-RabPON1 constructs.

TABLE 1

| pET20-hPON1-bc | SEQ ID NO: 1 | 5 CGACGAAA CCATGGCGAAGCTGATTGCG 3 |
| --- | --- | --- |
| pET20-hPON1-fo | SEQ ID NO: 2 | 5 CCGGGAGCTGCATGTGTCAGAGG 3 |

TABLE 1-continued

| pET43-hPON1-bc | SEQ ID NO: 3 | 5'TCAATCCG ACTAGTGGTTCTGGTATGGCGA AGCTGATTGCG3' |
| --- | --- | --- |
| PMAL-hPON1-bc | SEQ ID NO: 4 | 5'CTGTCAAG GAATTCATGGCGAAGCTGATTG CG3' |
| PMAL-hPON1-fo | SEQ ID NO: 5 | 5'GTCCCGGG CTGCAGTTATTAGAGCTCACAG TAAAGA3' |
| pET32-mPON1-bc | SEQ ID NO: 6 | 5'CGACAAGG CCATGGCGAAGCTGCTAGCACT CACC3' |
| pET32-RatPON1(+8)-bc | SEQ ID NO: 7 | 5'CGACAAGG CCATGGCGAAGCTGCTAGCACT CACCCTCGTGGGA CTGGTGTTGGCACTTTACAAG3' |
| pET32-mPON1-fo | SEQ ID NO: 8 | 5'GCTCGAGT GCGGCCGCTTACAGATCACAGT AAAGAGCTTTGTGG3' |
| pET32-RatPON1-fo | SEQ ID NO: 9 | 5'GCTCGAGT GCGGCCGCTTACAGGTAACAAC AAAGAGCTCTGTGG3' |
| Hexamer-primer | SEQ ID NO: 10 | 5'NNNNNN3' |
| Oligo dT | SEQ ID NO: 11 | 5' T(20)VN 3' |
| pET32-RabPON1-bc | SEQ ID NO: 12 | 5'CGACAAGG CCATGGCTAAACTGACAGCGCT C3' |
| pET32-RabPON1-fo | SEQ ID NO: 13 | 5'GCTCGAGT GCGGCCGCTTAATTGGCCTGTG AGAGCTCACAG3' |
| pET32-Seq-bc | SEQ ID NO: 14 | 5'CGCGGTTCTGGTATGAAAGAAACCGC3' |
| T7-term-Fo | SEQ ID NO: 15 | 5'CCCGTTTAGAGGCCCCAAGGGG3' |
| Nes-shuf-fo | SEQ ID NO: 16 | 5'-GGCAGCCAACTCAGCTTCC-3' |
| Nes-shuf-bc | SEQ ID NO: 17 | 5'-CGAACGCCAGCACATGG-3' |

Results

Initial attempts to express recombinant PON1 were effected in *E. coli* using the human gene (GenBank Accession No. NM_000446). The gene was sub-cloned into different vectors to express the protein under different promoters (i.e., T7 or tac) and fused to different proteins [bacterial signal peptide, thioredoxin (trx), Nus (Novagen), glutathione S-transferase (GST) or maltose binding protein (MBP)]. Different *E. coli* strains—BL21, BL21 (DE3), Origami B (DE3) (Novagen), RIL (DE3) (Stratagene), were used at different growth temperatures (i.e., 20-37° C.) and under different induction conditions (i.e., 0-1 mM IPTG).

Paraoxonase activity in the crude cell lysates served as a test for the amount of active hPON1. Although, under many conditions, large amounts of full size protein could be detected in the form of inclusion bodies, none of the above-described constructs and conditions produced detectable amounts of active hPON1. However, expression of the rabbit PON1 fused to thioredoxin (Trx-rPON1; FIG. 2) and under the T7 promoter (pET32 vector) in Origami B (DE3) cells resulted in very low paraoxonase activity (FIG. 2a). As is shown in FIG. 2b, thioredoxin was the only tag capable to solubilize rabbit PON1 when fused thereto. The ability of thioredoxin to partially solubilize rabbit PON1 was is in accordance with a recently published assessment of fusion proteins (Hammarstrom et al., 2002).

Example 2

Directed Evolution of Soluble PON1 Variants

Once conditions, under which high amounts of PON1 were expressed to form inclusion bodies in equilibrium with low amount of soluble and active PON1, were at hand (see Example 1, above), these served as a starting point for the directed evolution of highly soluble recombinant PON1 mutants.

Family DNA Shuffling—

The PON1 genes, hPON1, mPON1, RatPON1 and RabPON1 were shuffled using established protocols (Abecassis et al., 2000; Crameri et al., 1998; Stemmer, 1994). A forward primer (T7-term-Fo, Table 1, above) and a reverse primer (pET32-Seq-bc, Table 1, above) were used to individually amplify the various PON1 genes from the respective pET32b (+) plasmid, using ExTaq (Takara). Equal amounts of the four DNA fragments were purified, mixed together and subjected to DNase I digestion (Bovine pancrease, Sigma). A 50 μl digestion contained ~10 μg of DNA and 0.1 unit of DnaseI in 0.1 M Tris-HCl (pH 7.5) containing 10 mM manganese chloride. Following 3.5, 5 and 7 minutes at 20° C., aliquots of 17 μl were removed into 5 μl of 0.25 M EDTA and immediately heated to 90° C. for 10 minutes. The digest was separated on 2% agarose gel and fragments from 50-125 bp were extracted and purified using QIAEX II gel extraction kit (QIAGEN). Fragments were reassembled in a 50 μl reaction containing ~0.5 μg of DNA, dNTPs (0.2 mM each) and 2.5 units of ExTaq polymerase (Takara). Cycling was according to the following protocol (Abecassis et al., 2000): 94° C., 2 min; 35 cycles of (94° C., 30 seconds; 65° C., 90 seconds; 62° C., 90 seconds; 59° C., 90 seconds; 56° C., 90 seconds; 53° C., 90 seconds; 50° C., 90 seconds; 47° C., 90 seconds; 44° C., 90 seconds; 41° C., 90 seconds; 72° C., 2 minutes); 72° C., 7 minutes; and 15° C. for 5-10 hours.

To amplify the full-length genes, 0.01 μl of the reassembly reaction mixture was used as a template for a nested PCR reaction using forward and reverse primers (Nes-shuf-fo and Nes-shuf-bc respectively, Table 1, above). The assembled and PCR-amplified library was cloned to pET32b(+) vector using the NcoI/NotI sites and transformed to DH5α cells. >5×10$^4$ individual colonies were combined, grown and the plasmid DNA comprising this first generation (G1) library extracted with a maxiprep (Nucleobond AX).

Screening Procedures (Esterase Activity Assay and Paraoxonase Activity Assay)—

The G1 library, abotained as described hereinabove, was transformed to origami B (DE3) cells and plated on LB agar plates supplemented with Amp (100 μg/ml), Kanamycin (15 μg/ml) and 1 mM CaCl$_2$. Colonies were grown overnight (O/N) at 37° C., replicated with velvet cloth and incubated at 37° C. for another 9 hours. The plates were screened for esterase activity by covering them with a layer soft agar (0.5%) in activity buffer (50 mM Tris-HCl pH 8, 1 mM CaCl$_2$) supplemented with 0.3 mM 2-naphtylacetate and 1.3 mg/ml of Fast Red (Sigma) (Khalameyzer et al., 1999; Ziomek et al., 1990). Colonies that turned bright red were picked from the replica plate into 500 μl of LB media with Amp (100 μg/ml), Kanamycin (15 μg/ml) and 1 mM CaCl$_2$, in a 96 deep-well plate, and grown O/N in a shaking incubator at 30° C. The following operations were performed in 96-well plates using a Precesion2000 liquid handling robot linked to a microtitre plate reader (Bio-Tek). 50 μl of the O/N culture were removed to a new microtiter plate and kept at 4° C. and the remaining volume spun down (3220 g for 10 min). The cell pellet was resuspended in 300 μl of Bug-buster (Novagen) supplemented with 1 mM CaCl$_2$ and allowed to shake for 15 min at room temperature. The plates were spun down at 3220 g for 15 min and 50-100 μl aliquots of lysates were re-plated. 100 μl of paraoxon in activity buffer (to a final concentration of 0.25 mM) were added to 100 μl lysate, and p-nitrophenol release was monitored at 405 nm. Esterase activity was measured by adding 150 μl of 2-naphtylacetate (to a final concentration of 0.25 mM) to 50 μl of lysate, and the release of 2-naphthol was monitored at 320 nm. About 20 of the best clones according to kinetic assays were spread and grown on agar plates as above. Three isolated colonies were picked from each clone to LB media and grown O/N at 30° C. The culture was lysed and enzymatic activity was measured as above. Plasmid DNA was extracted from the highest activity clones and used as a template for PCR amplification and reshuffling using the same protocol applied to prepare the G1 library.

Results

The present inventors used a directed evolution and screening approaches to generate soluble PON1 which retains catalytic function with both carboxy-esters and paraoxon.

DNA Shuffling—

DNA shuffling of families of homologues genes has proven a powerful technique for the directed evolution of enzymes with specific functions (Abecassis et al., 2000; Crameri et al., 1998; Joern et al., 2002). This technique generates genetic diversity by recombination, thereby combining mutations from preselected functional genes. Such libraries are usually generated by random fragmentation of a pool of related genes, followed by reassembly of the fragments in a self-priming polymerase reaction (Stemmer, 1994).

For these reasons, four different PON1 genes (human, mouse, rat and rabbit) were cloned and shuffled to generate a gene library (G1 library) that was used for screening for functional PON1 expression. The library was generated using the procedure of Stemmer et al (Stemmer, 1994) with minor modifications (Abecassis et al., 2000) and analyzed by DNA sequencing.

Ten randomly chosen clones were analyzed and found to contain full-length open reading frames with no deletions insertions or stop codons. The distribution of the individual parental genes in the G1 library was close to even (mouse: 36.2%, rat: 18%, human: 19.1%, rabbit: 26.7%). In average, a crossover every 78.3 bp (13.6 crossovers per gene), was identified (see FIG. 1). The high number of crossovers and nearly even parental gene distribution in the library allowed for efficient screen of the sequence space of the four parental genes (Crameri et al., 1998).

Directed Evolution of Soluble and Active PON1 Variants—

The G1 library was recloned to an expression vector and transformed to Origami B (DE3) cells. Screening was first performed on agar colonies for esterase activity using 2-naphtylacetate and an azo dye (e.g., Fast Red) that reacts with the released naphthol to generate a red insoluble product (Khalameyzer et al., 1999; Ziomek et al., 1990) (FIG. 6). Positive clones were picked from a replica plate and grown for expression. Cells were lysed and then assayed spectrophotometrically for the hydrolysis of paraoxon as well as 2-naphtylacetate. Colony screening of ~10$^4$ different colonies generated ~500 colonies in the first screen. Out of these 500 colonies, about 50 clones with significantly improved paraoxonase and esterase activity (relative to wild-type Rab-PON1) were observed in the second screen.

The ratio of esterase activity relative to the paraoxonase activity (i.e., 588 in the wild-type hPON1 purified from serum and ~250 for all the various directly-evolved PON1 variants; Table 2, below) was used as a marker for selecting clones that maintained the catalytic properties and specificities of wild-type PON1 but had increased amounts of soluble, active protein. The twenty best clones were sub-cloned and assayed to verify their activity. Enzymatic activity and SDS-PAGE analysis both indicated an increase in solubility of the PON1 with the best clones from the first generation (G1A5, G1C4) exhibiting a 3-6 fold increase in soluble protein (FIGS. 2a-b). Plasmid DNA isolated from the 20 best clones was used as template for PCR amplification of the active PON1 genes and DNA re-shuffling. The resulting gene-library (G2) was cloned and screened as above.

Screening of the second-round library (G2) generated at least 20 new clones with an increase in enzymatic activity of up to 3 fold relative to the best clone from the G1 library (G1A5). The best clone from the G2 library (G2D6) exhibited over 16-fold increase in activity relative to RabPON1. Analysis of the crude lysates by SDS-PAGE indicated that the improved activity resulted from improved solubility of the PON1 variants and not a change in specific activity (FIGS. 2a-b, Table 2, below). The amount of soluble active PON1 protein purified of the G2D6 and G2E6 clones exceeded 14 mg per liter of cell culture (Table 2, below).

Materials and Experimental Procedures

Expression and Purification of the Directly-Evolved PON1 Variants.

Origam B (DE3) cells were transformed with plasmid DNA isolated from selected variants. Single colonies were used to inoculate 5 ml of LB media supplemented with Amp (100 μg/ml), Kanamycin (15 μg/ml) and Calcium chloride (1 mM) and the resulting cultures were grown O/N at 30° C. Cells were harvested by centrifugation and resuspended in 60 ml of activity buffer supplemented with 1 μl of Pepstatin A, 0.1 mM DTT and 0.03% of n-dodecyl-β-D-maltopyranoside ($C_{12}$-maltoside). The cells were disrupted by sonication and the suspension was gently shaken at room temperature for 2 hours. Cell debris was removed by centrifugation and ammonium sulfate was added to 50% saturation (w/v). The resulting precipitate was dissolved in activity buffer and dialysed against the same buffer. Ni-NTA resin (5 ml; Qiagen) was added to the lysate and the mixture gently shaken at 4° C. for three hours and then loaded on a column. The resin was rinsed with activity buffer containing increasing concentrations of imidazole (10-25 mM) and the enzyme eluted at 125 mM of imidazole. Fractions with the highest paraoxonase activity were pooled together, chromatographed on a High Trap Q column with a linear gradient of 26-33% of buffer B (20 mM Tris Hcl pH8, 1 mM $CaCl_2$, 0.03% maltoside and 1M NaCl) in buffer A (i.e., same as B without NaCl). Fractions with the highest paraoxonase activity were analyzed for purity on 12% SDS gel, pooled, dialysed against buffer A and concentrated.

For purification of rPON1 (G3H8 and G3C9; with no affinity tags) from the third round of evolution, dialysed cell

TABLE 2

| Clone/ SEQ ID NO: | $k_{cat}$ (PheAc) $sec^{-1}$ | $K_M$ (PheAc) mM | $k_{cat}$ (Paraoxon) $sec^{-1}$ | $K_M$ (Paraoxon) mM | Ratio of $k_{cat}/K_M$ PheAc/Paraoxon | Yield of purified enzyme (mg/L culture) |
|---|---|---|---|---|---|---|
| G1A5/25 | 833 | 0.39 | 1.16 | 0.085 | 157.9 | 2.2 |
| G1C4/26 | 552 | 0.54 | 0.54 | 0.12 | 227.1 | 2.7 |
| G1C4-20 | 238 | 0.87 | 0.25 | 0.27 | 297.3 | 5 |
| G2D6/27 | 562 | 0.32 | 0.98 | 0.10 | 179.2 | 14.4 |
| G2E6/28 | 965 | 0.43 | 0.87 | 0.089 | 229.7 | 20 |
| G3H8/29 | 1018 | 0.32 | 1.2 | 0.088 | 233.9 | 11.8 |
| G3C9/55 | 789 | 0.33 | 1.1 | 0.094 | 204.3 | 12.6 |
| hPON1[a] (w.t.)/24 | 1236 | 0.42 | 3 | 0.54 | 535 | 0 |

A third round of shuffling yielded the G3 library but its screening indicated no further increase in expression. The G2 library was further cloned into a truncated pET32 vector in which the fusion protein (thioredoxin) and the linker peptide carrying the His and S-tags were all deleted, leaving the intact, 355 amino acids, PON1 protein without any additions (rPON1; FIG. 7c). Screening of this library revealed similar activity levels as the library of the thioredoxin-fused PON1 from the second round of evolution, allowing the identification of at least 20 clones of highly soluble rPON1. Two of these clones (G3H8 and G3C9; FIGS. 2a-b and 3) were expressed and purified to homogeneity with high yield (~12 mg per liter culture).

Example 3

Characterization of Directly Evolved PON1 Variants

Sequence analysis of the directly evolved PON1 variants generated as described above was effected as is described herein below.

lysates after ammonium sulfate precipitation were applied to a Hitrap Q column (Pharmacia) and the protein was eluted as above. Active fractions were pooled dialysed and loaded to ceramic Hydroxyapetite type 1 column (Biorad) using Biologic low-pressure chromatography system (Biorad). The protein was eluted with 0-200 mM potassium phosphate gradient in buffer A. Active fractions were pooled, dialysed against buffer A supplemented with 0.2 M NaCl, concentrated and loaded to a size exclusion column (Hi load superdex 200 26/60, pharmacia). rPON1 was eluted at ~99 kDa (calibrated by molecular weight markers). The paraoxonase active fractions were analyzed for purity on 12% SDS gel, pooled and concentrated. All various purified PON1 variants were stored for over two months at 4° C. with no apparent loss in activity.

Enzyme Kinetics—

Enzyme kinetic rates were measured with 0.005-1.4 μM purified PON1 and 0.01-4 μM PON3. Activity buffer at pH 8 was used with paraoxon, DEPCyC, phenyl acetate, 2Naphtyl acetate (2NA) and dihydrocoumarin; as substrates, and Hepes buffer at pH 7.3 with p-nitrophenyl acetate and L-homocysteine thiolactone (L-Hcy). In general, a range a substrate concentration was applied from $0.3 \times K_M$ up to $(2-3) \times K_M$. Product formation was monitored in 2000 reaction volumes using 96-well microtitre plates, at 405 nm for p-nitrophenol ($\epsilon$=9100 M$^{-1}$), 408 nm for CyC ($\epsilon$=21500 M$^{-1}$), 270 nm for phenol ($\epsilon$=430 M$^{-1}$) and the hydrolysis product of dihydrocoumarin ($\epsilon$=430 M$^{-1}$), and 320 nm for 2-naphthol ($\epsilon$=860 M$^{-1}$). L-Hyc formation was monitored by detecting the free thiol group with Ellman's reagent (5,5-dithio-bis-2-nitrobenzoic acid) at 412 nm ($\epsilon$=7000 M$^{-1}$ for 5-thio-2-nitrobenzoic acid). Kinetic parameters were determined by fitting the data directly to the Michaelis-Menten model: $v_o = k_{cat}[E]_0[S]_0/([S]_0 + K_M)$ using Kaleidograph. Inhibition constants were determined by fitting the data to a competitive inhibition model: $v_o = V_{max}[S]_0/([S]_0 + K_M(1+[I]/K_i))$.

Results

Sequence Analysis—

The sequences of the selected clones revealed that, as early as the first round of evolution, convergence to the RabPON1 gene has occurred with relatively small contributions from the three other parental genes (FIG. 5). This is not surprising given that the wild-type RabPON1 was the only wild-type PON1 that expressed soluble in *E. coli* at a measurable amount.

In all selected variants, position 192 is a lysine as in the rabbit wild-type sequence. This position is either an arginine or an Glutamine in the human R/Q PON1 isoenzymes of which the R form exhibits ~8-fold higher catalytic activity [Li (2000) Pharmacogenetics 10: 767-779]. Lysine is probably equivalent to arginine hence the resemblance of the rate parameters of the new variants to the R form of the human PON1.

Most of the mutations in the different clones analyzed (with respect to RabPON1) did not seem essential to solubility as they did not appear in all the highly-soluble variants.

Eight conserved mutations were identified, in all the selected variants located in only two regions, residues 126-142, and 301-343. The mutations in the first region are: I126T, M130L, K137S, L142V, and in the second region: A301G, A320V, M341L, V343I. Most of these mutations were fixed already at the first round of evolution (I126T, M130L, K137S, L142V, A320V, M341L, V343I; FIG. 5). Interestingly, none of the 8 conserved mutations included a drastic change. One mutation involved a change from a hydrophobic to a polar residue (I126T) and another the reverse change (A320V). But most of the mutations were in fact, from one hydrophobic amino acid into another (M130L, L142V, M341L, V343I).

The convergence of the newly-evolved PON1s towards the RabPON1 sequence may be driven by the higher stability of the wild-type RabPON1 protein (certainly with respect to hPON1) and its higher affinity to calcium. PON1s bind two calcium ions. One calcium ion is bound with higher affinity and is required for maintaining the structure; the second binds with lower affinity and is thought to be involved in catalysis (Kuo and La Du, 1998). The affinity for the first calcium is ~7 fold higher in RabPON1 relative to hPON1 ($K_d$=0.05 µM and 0.36 µM, receptively). The concentration of calcium ions in *E. coli* is rather low (0.3 µM) and does not exceed 0.7 µM even in the presence of high calcium concentrations in the medium (Jones et al., 1999). In the absence of calcium, hPON1 irreversibly aggregates (Kuo and La Du, 1995). The higher affinity of RabPON1 and the soluble variants that evolved from it, may have allowed them to bind calcium at sub-micromolar concentrations and stabilize the structure to prevent aggregation in the *E. coli* cytoplasm.

Kinetic Analysis—

Selected variants of the trx-rPON1 (FIG. 7a) from the first and second round of directed evolution (G1A5, G1C4, G2D6 and G2E6) and variants of rPON1 (FIG. 7c) from the third round of evolution (G3C9, G3H8), were purified to homogeneity as determined by SDS PAGE (FIG. 3).

Kinetic analysis of different trx-rPON1 variants from the first and second round of evolution, with both phenyl acetate and paraoxon hydrolysis, indicated that the kinetic parameters were not significantly changed between one round to another. Variants isolated from the third round of evolution in which the enzyme was expressed without a fusion protein or any other tag (rPON1) gave similar kinetic parameters to those observed with the trx-rPON1 variants from the first and second rounds of evolution (Table 2, above, FIG. 4). It appears therefore, that the thioredoxin and tags to which the enzyme was fused in the first and second rounds did not alter its catalytic properties. Further, the kinetic parameters of the various newly evolved PON1 variants are similar to those measured with hPON1 purified from sera, although some differences were notable [e.g., the $K_M$ of the directly-evolved PON1s (0.085-0.12 mM) was significantly lower than that of hPON1 (0.54 mM)]. It should be noted, however, that the sequences of the directly-evolved PON1s appeared to be most similar to RabPON1 and not hPON1 (FIG. 5).

The kinetic parameters for RabPON1 are not reported in the literature, but comparison of the human and rabbit PON1s indicated similar substrate specificities and a very close specific activity towards phenyl acetate (Josse et al., 1999; Kuo and La Du, 1995). Such similarity is also observed between the directly-evolved PON1 derivatives from the various generations and of different constructs (trx-rPON1 vs. rPON1, for example) and hPON1 purified from sera.

These results indicate that, following the selection pressure for a simultaneous increase in both paraoxonase and esterase activity, the evolutionary process was directed primarily towards increased solubility, and the specific activity and other catalytic properties of PON1 were not significantly altered. In each of the three rounds of the evolutionary process, variants have been identified in which the ratio of paraoxonase vs. esterase activity was significantly different than wild-type (data not shown).

The two mutated regions in the directly-evolved PON1s (amino acid 126-142, and 301-343; FIG. 5) are presumably involved in the hydrophobic packing of PON1 and its correct folding in *E. coli*. A recent paper described the oligomeric state of detergent-solubilized hPON1 purified from sera (Josse et al., 2002). The work highlighted the role of detergent in determining the oligomeric state of hPON1 and suggested that, in addition to the hydrophobic N-terminal leader sequence (Sorenson et al., 1999), exposed hydrophobic surfaces of hPON1 are involved in oligomerisation and aggregation of hPON1, and its incorporation to HDL or to nonionic detergent micelles. These presumed hydrophobic surfaces may also lead to the aggregation of wild-type PON1s when expressed in *E. coli*. Mutations in these solvent-exposed hydrophobic surfaces may prevent misfolding and formation of high-order aggregates. These mutations, being quite subtle in their nature (see above), have probably induced minor changes in other structures and functional features of PON1 as manifested in the very similar kinetic parameters relative to wild-type PON1. In addition, analysis by gel filtration of the oligomerization state of rPON1 (G3H8, G3C9) in the presence of $C_{12}$-maltoside (0.6 mM) reveled that the protein is mostly present as a dimer, although trimers and higher aggregates could also be observed. This result is not dissimilar to the equilibrium between monomers and dimers observed with hPON1 solubilized by nonionic detergents including $C_{12}$-maltoside (Josse et al., 2002).

All wild-type PON1 posses a conserved, hydrophobic, 20 amino acid leader sequence at their N-termini. This sequence, which is not excised and is part of the mature protein, is directly involved in the binding of PON1s to HDL phospholipids (Sorenson et al., 1999). A dramatic decrease was observed upon deletion of the leader sequence of hPON1 (56 fold drop in $k_{cat}/K_M$; (Sorenson et al., 1999)). Therefore a newly-evolved clone (G1C4) without its N-terminal leader sequence was constructed (G1C4-20 N-ter amino acids; FIG. 7b). The expression levels and solubility of this clone were not decreased, and the kinetic analysis indicated only a 4-fold decrease in its catalytic activity (in terms of $k_{cat}/K_M$) for both paraoxon and phenyl acetate hydrolysis (Table 2, above). The different effect of the leader sequence on C4 vs. hPON1 could be due to differences between hPON1 and RabPON1 (no data is available regarding the effect of the leader sequence on wild-type RabPON1) and to the increased solubility of the newly-evolved PON1s. In any case, the present results suggest that the leader sequence is not directly involved in forming the active site of PON1s, nor in determining the protein's conformation. Rather, deletion of the leader sequence in PON1 affects catalysis indirectly, probably via a change in its oligomeric state or solubilization.

0.1-10 mM the L-Hyc formation was monitored by detecting the free thiol group with Ellman's reagent (5,5-dithio-bis-2-nitrobenzoic acid) at 412 nm ($\epsilon$=7000 $M^{-1}$ for 5-thio-2-nitrobenzoic acid). The competitive inhibitor 2-hydroxyquinoline was used at concentrations between 0-0.25 mM and used to inhibit Phenyl acetate, Paraoxon and L-HcyT hydrlysis at fixed substrates concentration (0.2 mM for Phenyl acetate, 0.25 mM for Paraoxon and 1.5 mM for L-HcyT). Kinetic parameters were determined by fitting the data directly to the Michaelis-Menten model: $V_o = k_{cat}[E]_0[S]_0/([S]_0+K_M)$ using Kaleidograph. Inhibition constants were determined by fitting the data to a competitive inhibition model: $V_o = V_{max}[S]_0/([S]_0+K_M(1+[I]/K_i))$.

Results

Recently it has been reported that PON1 can hydrolyze L-HcyT, which is a major risk factor in atherosclerosis [Jakubowski (2000) J. Biol. Chem. 275:3957-3962; Davies (1996) Nat. Genet. 14:334-336]. For this reason, the ability of trx-rRabPON1 and the newly evolved variants to hydrolyze L-HcyT was addressed (i.e., G1A5 and G3H8]. As is shown in FIGS. 8a-b and in Table 3, below, the $K_M$ measured for L-HcyT hydrolysis (~19 mM) was in good agreement with the $K_M$ of serum HuPON1 [23 mM, Jakubowski (2000) Supra]. These results establish the ability of the newly evolved variants to catalyze the hydrolysis of multiple substrates.

TABLE 3

| Variant[a]/ SEQ ID NO: | 2-Naphthyl acetate | | | Dihydrocoumarin | | | L-HcyT |
|---|---|---|---|---|---|---|---|
| | $k_{cat}$ (sec$^{-1}$) | $K_M$ (mM) | $k_{cat}/K_M$ ($M^{-1}$ sec$^{-1}$) | $k_{cat}$ (sec$^{-1}$) | $K_M$ (mM) | $k_{cat}/K_M$ ($M^{-1}$ sec$^{-1}$) | $k_{cat}/K_M$ ($M^{-1}$ sec$^{-1}$) |
| G1A5[a]/25 | 14 | 0.08 | 1.7 * 10$^5$ | 295 | 0.12 | 2.5 * 10$^6$ | 12.2 |
| G3H8[b]/29 | 20 | 0.11 | 1.8 * 10$^5$ | 234 | 0.076 | 3.1 * 10$^6$ | 11.6 |

[a]G1A5 was expressed fused to thioredoxin through S- and His-peptide linkers.
[b]G3H8 was expressed as the unmodified 355 aa PON1 protein without the fusion tags or protein.

It is generally assumed that two out of the three cysteine residues of PON1s (Cys 42 and Cys 353) form a disulphide bond, and that formation of this bond is crucial for the correct folding and activity of rPON1 (Kuo and La Du, 1995). The formation of disulfide bonds is often hindered by the reducing environments of E. coli cytoplasm. Therefore the Origami B (DE3) bacterial strain was used in which the reduction by thioredoxin and glutathione is impaired and disulfide bond formation is therefore facilitated (Bessette et al., 1999).

The results presented herein also indicate that glycosilation of PON1 is not contributing or affecting its enzymatic function. This conclusion stems from the fact that the newly-evolved PON1s that were expressed in E. coli where no glycosylation occurs, posses kinetic parameters that are very close to wild-type PON1s (see above and Table 2). This is in agreement with the findings that mutagenesis at two putative glycosylation sites of hPON1 (N252 and N323) had no effect on its catalytic function (Josse et al., 1999).

Example 4

Homocysteine Thiolactonase Activity of rPON1 and Exclusion of Multiple Sites of Hydrolytic Activity Materials and Experimental Procedures
Enzyme Kinetics for L-HcyT Hydrlysis—
Rates for L-HcyT hydrlysis were measured with 1.4 µM purified PON1 in a Hepes buffer at pH 7.3 supplemented with 1 mM of $CaCl_2$. The L-HcyT concentration used was between To test whether all these activities are mediated by a single catalytic site, the competitive inhibitor, 2-hydroxyquinoline, was used on clone G3H8 [Billecke (2000) Drug Metab. Dispos. 28:1335-1342]. Despite the vast differences in $k_{cat}$ and $K_M$ values, the inhibition constants for phenyl-acetate, paraxon and L-HcyT hydrolysis were found to be 3-11 µM (see Table 4, below and FIGS. 9a-b). These Values are in accordance with an inhibition constant of ~5 µM which was measured for hydrolysis of phenylacetate by serum huPON1 [Billecke (2000) Supra]. The close similarity of the inhibition constants serves as a strong indication that all three substrates are hydrolyzed at the same active site.

TABLE 4

| Substrate | $k_{cat}/K_M$ ($M^{-1}$ sec$^{-1}$) | Inhibition constant ($K_i$) µM |
|---|---|---|
| Phenyl Acetate | 3.2 * 10$^6$ | 11 ± 1.0 (~5)[a] |
| Paraoxon | 1.4 * 10$^4$ | 3 ± 0.06 |
| L-Homocysteinthiolactone | 11.6 | 4.2 ± 0.2 |

[a]$K_i$ for 2-hydroxyquinoline inhibition of phenyl acetate hydrolysis by HuPON1 purified from serum[11].

Example 5

Recombinant Expression and Direct Evolution of PON3

Relative to PON1, little is known about PON3. Because of low amounts in the serum (i.e., ~50-fold lower than PON1), PON3 was only recently purified and characterized [Draganov (2000) J. Biol. Chem. 275:33435-33442; Reddy (2001) Arterioscler. Thromb. Vasc. Biol. 21:542-547] and it was not expressed in heterologous expression systems. The specific kinetic parameters of serum PON3, have not been determined, though relative activities of RabPON3 are available [Draganov (2000) supra]. For these reasons, recopmbinant PON# of various organisms was expressed in a bacterial expression system.

Materials and Experimental Procedures
Cloning of PON3 Genes—

The plasmid pGex-6p-2 containing the HuPON3 (GenBank Accession No. NM_000940) gene (Reddy et al., 2001) was provided by Srinivasa T. (Reddy, UCLA). This gene was used as a template for PCR amplification with a back primer (pET32-hPON3-bc, Table 5, below) and a forward primer (pGex-seq-fo, Table 5, below). The gene for MoPON3 was amplified from mouse liver cDNA (Clontech) using back primer (pET32-mPON3-bc, Table 5, below) and a forward primer (pET32-mPON3-fo, Table 5, below). RabPON3 (GenBank Accession No. AF220944) was amplified from fresh liver of New Zealand rabbits using back primer (pET32-RabPON3-bc, Table 5, below) and a forward primer (pET32-RabPON3-fo, Table 5, below). All genes were cloned into PET32b(+) (Novagen). Primers used for amplifications are listed in Table 5 below.

TABLE 5

| Primer | SEQ ID NO: | Sequence |
|---|---|---|
| pGex-Seq-fo | 18 | 5CCGGGAGCTGCATGTGTCAGAGG 3 |
| pET32-hPON3-bc | 19 | 5CGACAAGGCCATGGGGAAGCTCGTGGC3 |
| pET32-mPON3-fo | 20 | 5GCTCGAGTGCGGCCGCTTACAGATCACAGTAAAGAGCTTTGTGG3 |
| pET32-mPON3-bc | 21 | 5CGACAAGGCCATGGGGCACCTCGTGGC3 |
| pET32-RabPON3-fo | 22 | 5GCTCGAGTGCGGCCGCTTATTAGAGTTCACAGTACAAGGCTTTCTGG3 |
| pET32-RabPON3-fo | 23 | 5CGACAAGGCCATGGCGAAGCTCCTGCTGC3 |

Construction of PON3 Libraries by DNA Shuffling—
see Example 2, above.
Screening Procedures—
see Example 2, above.
Characterization of the Evolved PON3 Variants Including Purification and Kinetic Analysis—
see Example 3, above.

Results
Recombinant Expression and Activities of PON3—

The present inventors were able to express reasonable levels (4-6 mg/lit) of soluble and active PON3 genes when fused to thioredoxin. Serum-purified and *E. coli* expressed RabPON3s (SEQ ID NO: 41) show the same pattern of specificity with the lactone substrate, dihydrocoumarin, and the ester substrates phenyl and naphtyl acetate (see Table 6, below).

TABLE 6

| Substrate | Trx-reRabPON3 $k_{cat}/K_M$ ($M^{-1}sec^{-1}$) | Ratio to PA for trx-rRabPON3 | Ratio to Phenyl acetate for RabPON3 (Draganov et al)[14] |
|---|---|---|---|
| Phenyl Acetate | 278.8 | 1 | 1 |
| 2-Naphthyl acetate | 3128 | 11.2 | 4.6 |
| Dihydrocoumarin | 67901 | 243.5 | 220 |
| PNPA[a] | 331 | 1.2 | — |
| Paraoxon | 0.73 | 0.0026 | — |
| L-Hcy[b] | 0.09 | 0.0003 | — |

[a]PNPA—p-nitrophenyl acetate.
[b]L-HcyT—L-Homocysteinethiolactone.

Interestingly, very weak paraoxonase activity was observed with both mouse and rabbit PON3 (SEQ ID NOs: 42 and 41, respectively). Activity was very low (i.e., <0.1% of that of PON1) and exhibited a prolonged lag (~30 min) in onset (i.e., hysteresis). These findings indicate that the enzymatic properties of RabPON3 are not significantly altered on fusion to thioredoxin and expression in *E. coli*, and the detailed kinetic parameters obtained herein (see Table 7 below) are in general relevant to wild-type PON3s.

Directed Evolution of PON3 Variants—

Wild-type PON3s exhibit 100- to 1,000-fold lower rates of ester and phosphotriester hydrolysis than PON1, although lactonase activities of the two enzymes are similar [Draganov (2000) supra, Reddy (2001) supra]. Their sequences exhibit 65% similarity at the amino acid level. In order to determine how far the two enzymes had diverged and whether, under directed selection pressure, they might re-converge to exhibit, similar, if not identical, phenotypes, PON3 genes were subjected to directed evolution through DNA shuffling. Following three rounds of shuffling and screening of wild-type PON3 genes, a number of clones were obtained with increased rates of both ester and phosphotriester hydrolysis. Comparison of selected variants from three rounds of evolution (see Table 7, below) indicated that the evolutionary process was directed primarily toward an increase in the catalytic efficiency of PON3.

TABLE 7

| | Paraxon hydrolysis | | | 2NA hydrolysis | | |
|---|---|---|---|---|---|---|
| Variant*/SEQ ID NO: | $K_{cat}$, $S^{-1}$ | $K_M$, mM | $K_{cat}/K_M^§$, $M^{-1}$ $S^{-1}$ | $K_{cat}$, $S^{-1}$ | $K_M$, mM | $K_{cat}/K_M^§$, $M^{-1}$ $S^{-1}$ |
| RabPON3/41,30 | 0.001 | 1.3 | 0.73 (1) | 0.66 | 0.211 | $3.1 \cdot 10^3$ (1) |
| MoPON3/42,32 | 0.0008 | 1.4 | 0.58 | 2.12 | 0.5 | $4.2 \cdot 10^3$ |
| G1A7/43,49 | 0.007 | 2.5 | 2.9 (4) | 1.9 | 0.16 | $1.2 \cdot 10^4$ (3.7) |
| G1B11/44,50 | 0.009 | 1.1 | 7.6 (10.4) | 2 | 0.18 | $1.1 \cdot 10^4$ (3.5) |
| G2C2/45,51 | 0.036 | 0.8 | 45 (62) | 18.8 | 0.26 | $7.2 \cdot 10^4$ (23) |
| G3A5/46,52 | 0.04 | 0.51 | 78.3 (107) | ND | ND | $3.5 \cdot 10^4$ (11) |

TABLE 7-continued

|  | Paraxon hydrolysis | | | 2NA hydrolysis | | |
|---|---|---|---|---|---|---|
| Variant*/SEQ ID NO: | $K_{cat}$, $S^{-1}$ | $K_M$, mM | $K_{cat}/K_M^§$, $M^{-1}$ $S^{-1}$ | $K_{cat}$, $S^{-1}$ | $K_M$, mM | $K_{cat}/K_M^§$, $M^{-1}$ $S^{-1}$ |
| G3G3/47,53 | 0.11 | 0.75 | 156.6 (215) | 26.25 | 0.65 | $4.0 \cdot 10^4$ (13) |
| G3H9/48,54 | 0.14 | 0.8 | 175 (240) | ND | ND | $3.5 \cdot 10^4$ (11) |

*All variants described above are trx-rPON3 variants, expressed fused to thioredoxin by S and 6xHis tags.
ND—not determined.
§Noted in parenthesis is the fold improvement relative to trx-RabPON3.

As seen in Table 7, above, following the first round of evolution, a mild improvement in catalytic efficiency was observed (i.e., variants G1A7 and G1B11). Following the second round of evolution, one clone was isolated (G2C2) that exhibited 62- and 23-fold higher activity for paraxon and 2NA hydrolysis, respectively as compared to wild type Rab-PON3. Following the third round of evolution, three clones were isolated (i.e., G3A5, G3G3 and G3H9), which exhibited an overall improvement of up to 240-fold in paraoxonase activity. Thus, although wild-type PON3s exhibit almost no paraoxonase activity, shuffled variants of the same genes exhibit paraoxonase activity which is only 60 fold lower than that of PON1. However, no further improvement in 2NA activity was observed with these clones (see FIG. 10 and Table 7 above). A 4- to 7-fold increase in the expression level of PON3s was also observed following three rounds of evolution (see Table 8, below). Like PON1, the newly evolved PON3 could be expressed and purified, by adding a C-terminal 6x His tag (rPON3 variant G3H9), without the thioredoxin fusion protein (and its catalytic parameters were similar to those of trx-rPON3.

type PON3 (see FIG. 10). Thus, the activity toward p-nitrophenylacetate co-evolved with that of paraxon, whereas all the other substrates showed a much milder improvement. It is appreciated that this does not indicate the existence of two catalytic sites or subsites, rather the common feature of p-nitrophenylacetate and paraxon is the p-nitrophenol-leaving group. The co-evolution of the two substrates suggests that hydrolysis of both carboxy- and phospho-esters occur by means of the same mechanism and at the same site.

Sequence analysis of the selected rPON3 variants indicates that the parental genes are evenly represented in variants of the first round of evolution (FIG. 11b). Alignment of variants from the second and third rounds of evolution revealed that, although the sequence similarity between the selected clones is very low, the RabPON3 gene is mildly over-represented relative to the HuPON3 and MoPON3 genes. These subtle patterns of convergence in the sequences of the selected PON3 are in contrast to the clear convergence of the PON1 newly evolved variants (see FIG. 5 and FIG. 11a).

TABLE 8

| Clone[a,b]/ SEQ ID NO: | PNPA[c] $k_{cat}/K_M$ ($M^{-1}sec^{-1}$) | Dihydrocoumarin[c] $k_{cat}/K_M$ ($M^{-1}sec^{-1}$) | PA[c] $k_{cat}/K_M$ ($M^{-1}sec^{-1}$) | L-Hcy[c] $k_{cat}/K_M$ ($M^{-1}sec^{-1}$) | Yield[c] (mg/L) |
|---|---|---|---|---|---|
| RabPON3/ 30, 41 | $3.3 * 10^2$ | $6.8 * 10^4$ | $2.8 * 10^2$ | 0.09 | 5.84 |
| MPON3/32, 42 | $1.3 * 10^2$ | $7.1 * 10^4$ | $3.5 * 10^2$ | 0.16 | 3.45 |
| G1A7/ 43, 49 | $4.2 * 10^3$ (12.6) | $2.5 * 10^5$ (3.6) | $3.4 * 10^2$ (1.2) | 0.15 (1.7) | 28.8 (4.9) |
| G1B11/44, 50 | $1.1 * 10^3$ (3.5) | $1.3 * 10^5$ (1.9) | $1.3 * 10^2$ (0.5) | 0.08 (0.9) | 20.8 (3.6) |
| G2C2/ 45, 51 | $4.2 * 10^4$ (126) | $6.9 * 10^5$ (10.1) | $1.1 * 10^3$ (3.9) | 0.54 (6.0) | 28.2 (4.8) |
| G3A5/ 46, 52 | $3.8 * 10^4$ (116) | $4.0 * 10^5$ (5.8) | $2.1 * 10^3$ (7.5) | 0.86 (9.5) | 20.3 (3.5) |
| G3G3/ 47, 53 | $1.0 * 10^4$ (30.7) | $2.0 * 10^5$ (2.9) | $5.5 * 10^2$ (2.0) | 0.48 (5.3) | 21.5 (3.7) |
| G3H9/ 48, 54 | $7.5 * 10^4$ (227) | $1.3 * 10^6$ (19.2) | $3.6 * 10^3$ (12.9) | 1.3 (14.4) | 37.8 (6.5) |

[a]All PON3 proteins were expressed fused to thioredoxin through S- and His-linker peptides.
[b]G1, G2 and G3 designate clones isolated after the first, second and third round of evolution, respectively.
[c]The numbers in parentheses show the fold improvement relative to trx-RabPON3.

Kinetic parameters for other ester and lactone substrates (Table 8, above) revealed that the improvements in the catalytic efficiency can be divided into two groups. For the first group, which included 2NA, phenylacetate, dihydrocoumarin and L-HcyT, the increase in $K_{cat}/K_M$ values for the third-generation variants was 2- to 20-fold relative to the wild-type, trx-rRabPON3. The second group included, paraxon and p-nitrophenylacetate, for which the third-generation variants exhibited $K_{cat}/K_M$ values up to 240-fold higher than wild- Example 5

Newly Evolved OP-Selective rPON1 Variants rPON1 variants presented in Example 3 above, were used as the starting point for evolution of PON1 variants with improved paraoxonase or esterase activity.
Experimental Procedures
Mutagenesis—
Error-prone PCR libraries were derived from highly soluble rePON1 variant G3C9 gene using wobble-base PCR essentially as described [Zaccolo (1996) J. Mol. Biol. 255: 589-603]. Briefly, the reG3C9 gene was PCR-amplified from a plasmid template using standard conditions, except that the nucleotide analog 6-(2-deoxy-d-ribofuranosyl)-3,4-dihydro-8H-pyrimidino-[4,5-c][1,2]oxazin-7-one-triphosphate (dPTP) was added at either ⅛ (25 μM) or 1/16 (12.5 μM) the concentration of the other four dNTPs (200 μM). In a separate reaction, 8-oxo-2'-deoxoguanosine (8-oxo-dGTP) was added at 200 μM. PCRs were performed for either 5 or 5, 10 and 15 cycles with dPTP and 8-oxo-dGTP, respectively, resulting in 5 different libraries. The PCR-amplified libraries were recloned into pET32-tr and plasmids comprising libraries were prepared as described above. The average number of synonymous mutations per gene was 5-10 for the dPTP and 3-8 for the 8-oxo-dGTP libraries, respectively.

Synthesis of 7-O-Diethylphosphoryl-(3-Cyano-7-Hydroxycuomarin) (DEPCyC)—

Triethylamine (0.6 ml, 4.3 mmol) was added to a suspension of 3-cyano-7-hydroxycoumarin (Indofine, N.J.; 562 mg, 3 mmol) in dichloromethane (50 ml) containing diethylphosphorochloridate (0.61 ml, 4.2 mmol). The mixture was stirred for 3 h at room temperature, by which time the insoluble 3-cyano-7-hydroxycoumarin had almost completely disappeared. TLC on silica (solvent: 5% methanol in dichloromethane) indicated the disappearance of the fluorescent starting material (Rf<0.1) and a non-fluorescent product with Rf≈0.7. The reaction mixture was diluted with dichloromethane (100 ml) and extracted twice with 0.5N HCl, once with 0.1M NaHCO$_3$ and finally with brine acidified with HCl. The reaction mixture was dried over Na$_2$SO$_4$, the organic solvent evaporated, and the product purified by chromatography on silica using the same solvent system as for TLC. Recrystallization in dichloromethane-ether gave a white crystalline solid (650 mg; 68% yield). $^1$H NMR (CDCl$_3$): 8.22 (s, 1H), 7.57 (d, J=8 Hz, 1H), 7.27 (m, 1H), 7.25 (d, J=5.5 Hz), 4.28 (m, 4H), 1.36 (m, 6H).

Results

Gene libraries of the highly soluble rPON1 variant, G3C9, were prepared by random mutagenesis using the wobble-base PCR method with either dPTP or 8-oxo-dGTP nucleoside analogs [Zaccolo (1996) J. Mol. Biol. 255:589-603]. The number of mutations per gene was adjusted by varying the concentration of dNTP analogs and the number of PCR cycles. Five libraries were generated: two dPTP libraries with 98% transitions, an average of 5-14 mutations per gene, and 20% to 6% residual activity in the pools of genes, respectively; and three 8-oxo-dGTP libraries with an average of 85% transversions, 3-10 mutations per gene, and 13% to 7% residual activity. In addition to the plate screen for 2NA hydrolysis described above, the libraries were directly screened on agar plates, negating the use of replication, for the hydrolysis of a newly synthesized fluorogenic OP substrate, DEPCyC [see FIG. 25]. DEPCyC is a close homologue of the insecticide, coumaphos, previously used for the directed evolution of a bacterial phosphotriesterase [Harcourt (2002) Lett. Appl. Microbiol. 34:263-268; Yang (2003) Protein Eng. 16:135-145]. The substrate exhibits higher fluorescence at a more convenient wavelength (408 nm). Screening of ~10$^3$ to 10$^4$ colonies from each library with 2NA yielded variants with mildly improved activity against OP substrates. The best variants were re-shuffled and screened directly with DEPCyC, yielding a highly improved variant, reG3C9.49 that carried four mutations: G19R, S193P, N287D and V346A. The V346A mutation appeared in other improved variant, suggesting its primary role in the enhancement of DEPCyC-hydrolyzing activity.

The first generation 8-oxo-dGTP libraries were also screened directly with DEPCyC to yield another highly improved variant, reG3C9.10, which contained two mutations, L69V and E218D. The two clones were purified and analyzed as described in FIGS. 12a-b and in Table 9, below.

TABLE 9

| | DEPCyC hydrolysis$^§$ | | | Phenylacetate hydrolysis | | | Selectivity factor $K_{cat}/K_M$ |
|---|---|---|---|---|---|---|---|
| Variant*/SEQ ID NO: | $K_{cat}$, S$^{-1}$ | $K_M$, mM | $K_{cat}/K_M$, M$^{-1}$ S$^{-1}$ | $K_{cat}$, S$^{-1}$ | $K_M$, mM | $K_{cat}/K_M$, M$^{-1}$ S$^{-1}$ | (DEPCyC)/ $K_{cat}/K_M$(PA) |
| G3C9/55,56 | 0.8 | 0.07 | 1.1 · 10$^4$ | 789 | 0.33 | 2.4 · 10$^6$ | 0.0046 |
| G3C9.10/62,63 | 25.7 | 0.05 | 4.8 · 10$^5$ | 39.6 | 0.76 | 5.2 · 10$^4$ | 9.2 |
| G3C9.49/64,65 | 28.1 | 0.08 | 3.6 · 10$^5$ | 12.4 | 0.3 | 4.1 · 10$^4$ | 8.8 |

*All rPON1 variants above include the unmodified 355-aa PON1 protein without any additions.
$^§$see FIG. 12.

The mutations affected the specific activity toward DEPCyC and phenylacetate, whereas the expression level of the two selected variants was not altered. Both variants exhibited a ~40 fold increase in catalytic proficiency ($K_{cat}/K_M$) toward DEPCyC compared with wild-type PON1 and its recombinant variant G3C, and a simultaneous 50-fold reduction in catalytic proficiency toward phenylacetate. The change in catalytic efficiencies, resulted primarily from changes in Kcat values for both substrates. Both variants showed a similarly reduced activity with other esters (e.g., 2NA) and mildly improved activity with another OP substrate (paraxon).

Thus, in contrast to wild type PON1 which is essentially an esterase with very weak phosphotriesterase activity, the directly evolved variants were converted into a phosphotriesterase with weak esterase activity. Noteworthy are the subtle nature of mutations, which led to the shift in specificity and the fact that mutations at two different locations (i.e., V346A in rG3C9.49 vs. L69V in E218D in rG3C9.10) produce the same shift.

Example 6

Crystallization and Structure Elucidation of PON1

Previous attempts to determine the structure of PON1 relied on limited amounts of serum-purified proteins and led to the crystallization of a protein that co-purified with it [A. Fokine et al., Acta Crystallogr D Biol Crystallogr 59, 2083 (2003)]. Human PON1 is rather unstable, and tends to aggregate in the absence of detergents [D. Josse et al., J Biol Chem 277, 33386 (2002)]. For these reasons, soluble recombinant PON1 variants generated according to the teachings of the present invention (see Examples 1-3 above) were used for performing detailed evolutionary, mechanistic and structural studies of PON enzymes.

Materials and Experimental Procedures

Expression and Purification of Native rePON1-G2E6 and its SeMet Derivative— rePON1-G2E6 was expressed in fusion with thioredoxin (Trx) and purified essentially as described above. During the course of the purification and crystallization attempts it was noticed that during storage, the linker between the Trx and rePON1 was spontaneously cleaved and the crystals were comprised of intact rePON1. The origins of this cleavage are still under investigation. It was observed in all rePON1 variants, and could even be mediated by PON1 itself. Subsequent crystallizations were set up with the cleaved and purified rePON1 as described below. Following purification of the Trx fusion by Ni-NTA and ion exchange, the protein was incubated at 25° C. for ten days. The cleavage was monitored by 10% SDS gel and mass spectrometry. The cleaved protein was concentrated and applied to HiLoad 26/60/Superdex 200 (preparative grade, Pharmacia). Fractions from the main peak were analyzed by 10% SDS gel, and enzymatic activity, pooled, and concentrated to 10 mg/ml. Sodium azide was added to a concentration of 0.02%. Mass spectrometry indicated a mass of 40223±201 Da. N-terminal Edman sequencing gave the following sequence: $H_2N$-DDDKAM. Both data are consistent with cleavage of the linker 5 amino acids (expected mass spec 40108 Da) before the methionine residue that comprised PON 1's first amino acid.

The SeMet labeled rePON1-G2E6 was obtained as follows: pET 32b plasmid containing rePON1-G2E6 (see Example 1) was freshly transformed to B834(DE3) cells and plated on an LB agar plates supplemented with Ampicilin. Colonies from three agar plates were scraped and rinsed (by resuspension and centrifugation) with M9 salt solution supplemented with 2 mM $MgSO_4$, 0.4% Glucose, 25 µg/ml $FeSO_4$, 40 µg/ml of each of the 20 natural amino acid except L-methionine, 40 µg/ml of Seleno-L-Methionine, 1 µg/ml of vitamins (Riboflavin, Niacinamide, Pyridoxine monohydrochloride and Thiamine) and 100 µg/ml of Ampicilin. Typically, 1 L of M9 minimal media with the above supplements was inoculated with 5 ml of rinsed *E. coli* colonies and grown at 30° C. to $OD^{600\,nm}$ of 0.7. Cultures were then transferred to 20° C. and IPTG added to 0.5 mM. Growth was continued for another 36 hours at 20° C. after which, cells were harvested, lysed and purified as above. Mass spectrometry indicated the incorporation of six SeMets per rePON1 including the Trx tag. Purification, cleavage of the Trx fusion, and isolation of rePON1 were performed as above.

Crystallization, Data Collection and Structure Refinement—

Crystallization: The rePON1 crystals were grown using the crystallization Douglas Instruments robot IMPAX 1-5 microbatch method. Native crystals grew in 3 days from an optimization grid varying the protein concentration from 1.1 to 4.5 mg/ml and the mother liquor (20% PEG 3350, 0.2M $NaH_2PO_4$) from 50 to 62.5% concentration. The drops consisted of 0.3 µL protein and 0.3 µL mother liquor. The crystals were cryoprotected with a gradient of 5%-15% glycerol. The SeMet protein crystals were grown in an optimization grid, varying the protein concentration from 1.1 to 5.5 mg/ml and the mother liquor (0.17M $NH_4Ac$, 0.085M citrate buffer pH 5.6, 25.5% PEG 4000, 15% glycerol) from 25 to 45% concentration.

Data collection: 3 X-ray datasets were collected from the SeMet protein crystal at 100K at Se peak wavelength (0.9794 Å) in order to increase the redundancy and accuracy of the Se anomalous signal while monitoring the extent of radiation damage. A data set of the native crystal was collected at a wavelength of 0.9796 Å. Data were collected on beamline ID14-4 at the European Synchrotron Radiation Facility (ESRF) and processed with XDS [Kabsch (1993)]. Data collection statistics are given in Table 10, below.

Molecular replacement (MR): Although PON1 bears no sequence similarity to any other protein sequence, it was suggested that it may have a 6-beta propeller conformation. As a consequence, we attempted to solve its structure by MR using the structure of 3-carboxy-cis, cis-muconate lactonizing enzyme (PDB-code 1jof) as a search template. A weak but still significant MR peak was found by the maximum likelihood program PHASER [Storoni (2004)]. Although this did not result in structure solution, it did help in selecting the correct space group ($P4_32_12$).

Structure solution and refinement: 3 Se sites were located on the basis of the anomalous difference using SHELXD after local scaling using XPREP [Uson (1999)]. SHELXE confirmed the correct space group and solvent content. Good experimental SIRAS (single isomorphous replacement anomalous scattering) phases were obtained using the program SHARP [Fortelle (1997)] while refining 3 Se sites against the 2.2 Å native and 2.6 Å Se SAD data, resulting in an overall figure of merit (FOM) of 0.11/0.06 for the acentric/centric reflections respectively. The isomorphous difference phasing power was very low (0.22 overall) due to the lack of isomorphism between the native and SeMet data sets, however, the anomalous phasing power for the SeMet SAD data set was good to at least 4 Å (0.74 overall). Phases were improved by applying solvent-flipping density modification using SOLOMON [Abrahams (1996)] as directed by SHARP using a 63% solvent content giving an overall FOM of 0.88. An automated tracing program ARP/wARP [Perrakis (1999)], using native amplitudes to 2.2 Å, coupled with experimental phase-restraints resulted in an automatic tracing of ca. 95% of the chain. Manual model completion was performed using program O [Jones (1999)] iterated with refinement using REFMAC [Murshudov (1999)]. The refinement and model statistics are listed in Table 10, below.

Results rPON1 variants exhibiting enzymatic properties essentially identical to those of wild-type (wt) PON1, and similar biological activities in inhibiting LDL oxidation and mediating macrophage cholesterol efflux were used for crystallization.

An interesting correlation was observed between solubility and degree of evolution towards bacterial expression, and the tendency to crystallize. Variants from the 1$^{st}$ round of evolution (e.g., variants G1A5 and G1C4, see Example 1-4, above) aggregated, and none crystallized. The 2$^{nd}$-generation variants (obtained by shuffling of the 1$^{st}$ generation variants and screening for highest expression levels) did not aggregate, and at least one (G2E6) gave stable and well diffracting crystals. rPON1-G2E6 exhibits 91% homology to wt rabbit PON1 with the vast majority of variations deriving from human, mouse, or rat wt PON1. Rabbit and human PON1s are also highly homologous in sequence (86%) and function. Sequence variations between rPON1-G2E6 and rabbit and human PON1 are in regions that do not affect their active sites and overall structures (see FIGS. 13-14*a-b*.).

Table 14, below, lists amino acid changes in G2E6 relative to Rabbit PON1.

TABLE 14

| Group | Mutations[a,b] | Origin[c,d] | Location and nature[e] |
|---|---|---|---|
| I | T126, L130, S138, V143, G301, V320, L341, I343 | wild type Human, Mouse, | hydrophobic core; conserved residues |

TABLE 14-continued

| Group | Mutations[a,b] | Origin[c,d] | Location and nature[e] |
|---|---|---|---|
| | | Rat, PON1c | among all soluble PON variants. |
| II | M12, K93, E94, A96, S98, E101, I103, N105, L107, I109, I121, E149, V261, S263, D265, F293, A296, E297, E313, D354. | wild type Human, Mouse, Rat, PON1c | protein surface; non-conserved between different soluble PON1 variants. |
| III | R19, D123, R260 | Mutation[d] | protein surface |
| Group | Mutations[a,b] | Origin[c,d] | Location and nature[e] |
| I | T126, L130, S138, V143, G301, V320, L341, I343 | wild type Human, Mouse, Rat, PON1c | hydrophobic core; conserved residues among all soluble PON variants. |
| II | M12, K93, E94, A96, S98, E101, I103, N105, L107, I109, I121, E149, V261, S263, D265, F293, A296, E297, E313, D354. | wild type Human, Mouse, Rat, PON1c | protein surface; non-conserved between different soluble PON1 variants. |
| III | R19, D123, R260 | Mutation[d] | protein surface |

[a]The rePON1-G2E6 sequence was aligned to the Rabbit PON1 protein sequence using ClustaWl. Amino acid identities are to rePON1-G2E6 sequence.
[b]positions highlighted in red were also found to be mutated in the directed evolution of PON1 for catalytic specialization (see Table 2 and article text for additional information).
[c]Positions identical to Human, Mouse and Rat PON1 sequence.
[d]Mutations that occurred during the shuffling process.
[e]The precise locations of these amino acids on PON1's structure are shown in FIG. 14a-b.

The refined 2.2 Å crystal structure of rPON1 (R-factor 18.5%; R-free 21.7%) contains one molecule per asymmetric unit. It was solved by single isomorphous replacement anomalous scattering (SIRAS) from data collected on crystals of the native protein and the selenomethionine (SeMet) protein at 2.6 Å resolution (Table 10, below). The structure shows all residues except N-terminal residues 1-15 and a surface loop (72-79). Two calcium atoms, a phosphate ion, and 115 water molecules are also seen.

TABLE 10

Part A: Data collection

| | Native[a] | SeMet protein[b] |
|---|---|---|
| Wavelength (Å) | 0.9796 | 0.9794 |
| Unit cell (Å) | 98.44, 139.17 | 98.49, 139.56 |
| Space group | $P4_32_12$ | $P4_32_12$ |
| Resolution range (Å) | 20-2.2 | 30-2.6 |
| Number of unique reflections | 35,312 | 39,473 |
| Completeness (%)[c] | 99.7 (97.9) | 97.8 (97.7) |
| $I/\sigma(I)^c$ | 12.7 (2.7) | 13.7 (4.2) |
| $R_{sym}(I)$ (%)[c] | 8.6 (66.1) | 10.4 (51.0) |

Part B: Refinement and model statistics[d]

| | |
|---|---|
| Resolution range (Å) | 20-2.2 |
| Number of reflections | 33,505 |
| R-factor: work, free (%) | 18.5, 21.7 |
| Average B-factors (Å$^2$) | 347.6 |
| RMSD from ideal values: | |
| Bond length (Å) | 0.028 |
| Bond angle (°) | 2.02 |
| Dihedral angles (°) | 28.7 |
| Improper torsion angles (°) | 2.06 |
| Estimated coordinate error: | |
| Low resolution cutoff (Å) | 5.0 |
| ESD from Luzzati plot (Å) | 0.32 |
| ESD from SIGMAA (Å) | 0.34 |
| Ramachandran outliers (%)[e] | 3.9 |

[a]The structure was determined for rePON1 variant G2E6 (sequence is given in FIG. 13). rePON1-G2E6 was expressed and purified in fusion with thioredoxin (via a linker containing a 6His tag) [A. Aharoni et al., Proc. Natl. Acad. Sci. USA 101, 482 (2004)]. The Trx tag was cleaved, leaving rePON1's intact sequence plus 4 amino acids from the linker peptide. The purified protein was crystallized using the Douglas Instruments robot IMPAX 1-5 micro-batch method.
[b]The SeMet rePON1-G2E6 was expressed, purified and crystallized as above, but from a different mother liquor. Details for the native and SeMet protein are provided in the Supplementary experimental section.
[c]Data for the outer shell given in parentheses.

The Overall Architecture of PON1—

PON1 adopts the fold of a 6-bladed β-propeller, with each blade containing 4 strands (FIGS. 15a-b). The 'velcro' closure characteristic of this fold is between the fourth strand of blade 6 (6D) coming from the N-terminus, and the third strand of blade 6 (6C) that comprises the C-terminus of the protein. This consensus interaction [Z. Jawad, M. Paoli, Structure 10, 447 (2002)] is complemented by a disulphide bridge between Cys42 (strand 6D) and Cys353 (strand 6C). This covalent closure of the N- and C-termini is rarely seen in β-propellers with more than four blades, but is conserved throughout the PON family (see below).

Two calcium ions, 7.4 Å apart, were seen in the central tunnel of the propeller: one at the top (Ca-1) and one in the central section (Ca-2). Ca-2 is most probably a 'structural calcium' whose dissociation leads to irreversible denaturation [C. L. Kuo, B. N. La Du, Drug Metab Dispos 26, 653 (1998)]. It appears to be ligated to three protein residues (the carboxylate oxygens of Asp54 and Asp169 and the backbone carbonyl of Ile117) and three water molecules (FIG. 16).

Ca-1 is assigned as the 'catalytic calcium' [Kuo (1998) Supra]. It appears to interact with five protein residues (the side-chain oxygens of Asn224, Asn270, Asn168, Asp269 and Glu53), 2.2-2.5 Å away.

Two other potential ligands are a water molecule (2.5 Å away in the direction of Ca-2), and one of the oxygens of a phosphate ion (see FIG. 17). PON1's two calcium ions exhibit markedly different affinities [C. L. Kuo, B. N. La Du, Drug Metab Dispos 23, 935 (1995)]. Ca-1's ligation is more extensive than Ca-2's. However, two of Ca-1's ligating residues (Asn224, Asp269) exhibited distorted dihedral angles. This, and the higher solvent accessibility of Ca-1, indicate that Ca-2 is the higher affinity calcium.

As is shown in FIGS. 15a-b, PON1's structure resembles Loligo Volgaris DFPase [Scharff (2001) Supra]. Both are 6-bladed propellers with two calcium atoms in their central tunnel. They also share functional homology, since both exhibit phosphotriesterase activity, although PON1 is primarily an esterase or lactonase. However, there is no clear sequence homology between them (BLAST E-score>>3.6) although more sensitive algorithms indicate weak but significant similarity [A. Fokine et al., Acta Crystallogr D Biol Crystallogr 59, 2083 (2003)]. This is not surprising: low sequence homology is a distinct characteristic of β-propellers [H. Jakubowski, J Biol Chem 275, 3957 (2000)]. DFPase, for example, exhibits no sequence homology to other 6-blade β-propellers [E. I. Scharff, J. Koepke, G. Fritzsch, C. Lucke, H. Ruterjans, Structure 9, 493 (2001)]. Closer inspection reveals that PON1 and DFPase differ significantly in their overall architecture, active-site structure and mechanism. Most distinctly, PON1 possesses a unique addition in the form of an active-site canopy defined by helices H2 and H3 and the loops connecting them to the β-propeller scaffold. This addition provides PON with an uncharacteristically closed active site as β-propellers, including DFPase, generally exhibit uncovered active sites defined only by loops that connect the β-strands. This addition seems to play a critical role in PON 1's function, both in defining the active-site architecture and sequestering it from solvent, and in anchoring PON1 to the HDL particle. It is notable that the LDL receptor which, like PON1, is involved in prevention of atherosclerosis and in cholesterol efflux or homeostasis, contains a 6-bladed β-propeller domain [G. Rudenko et al., Science 298, 2353 (2002); H. Jeon et al., Nature Struct Biology 8, 499 (2001)].

Detergent-solubilized PON1 forms dimers and higher oligomers [D. Josse et al., J Biol Chem 277, 33386 (2002)], but there is only one molecule per asymmetric unit, and very few contacts between symmetry-related molecules. It could be that crystallization favours a monomeric form. But it seems more likely that oligomerization of PON1 is a consequence of its anchoring to detergent micelles in a mode similar to its anchoring to HDL.

PON1 expressed in animal cells is glycosylated [D. I. Draganov, B. N. La Du, Nau Schm Arch Pharmacol (2003)]. Glycosylation is not essential for the hydrolytic activities of PONs [A. Aharoni et al., Proc. Natl. Acad. Sci. USA 101, 482 (2004); D. Josse et al., Biochemistry 38, 2816 (1999)] but may be important in increasing their solubility and stability, or in preventing non-specific binding to cell membranes, as proposed for other HDL-associated enzymes [A. Jonas, Biochim Biophys Acta-Mol Cell Biol Lipids 1529, 245 (2000)]. There are four potential N-glycosylation sites on PON1 (NX(S/T) sites). Two (Asn227 and Asn270) are in the central tunnel of the propeller, and are largely inaccessible to solvent. Asn253 and Asn324 are located on surface loops, and are most probably, as previously proposed [D. Josse et al., Biochemistry 38, 2816 (1999)], PON1's glycosylation sites.

Site-directed mutagenesis is routinely used to identify residues in active site residues. This approach suffers, however, from a well-recognized drawback. Loss of activity does not necessarily indicate direct involvement of a particular amino acid in the protein's function since mutations often disrupt the overall structure. Indeed, whereas certain residues identified by site-directed mutagenesis as being essential for PON1's activity [D. Josse et al., Biochemistry 38, 2816 (1999); D. Josse et al., J Appl Toxicol 21, S7 (2001); D. Josse, W. H. Xie, P. Masson, L. M. Schopfer, O. Lockridge, Chem. Biol. Interact. 120, 79 (1999)] are related to its active site (e.g., Glu53 that ligates Ca-1, His115 and His134), others are not (e.g., Glu54 that ligates the structural calcium (Ca-2) and Trp281 that is far from the active site). In contrast, mutations identified following directed evolution towards a modified function are inevitably relevant to activity, and involve residues located within, or in the vicinity of, the active site. Indeed, the amino acids identified by the directed evolution process described above led to the unambiguous identification of PON1's active site, and provided key insights as to how the substrate selectivity of the PON family members evolved in nature.

As is mentioned herein above (see Example 5), the newly-evolved PON1 variants clearly define a set of amino acids the alteration of which dramatically shifts PON1's reactivity and substrate selectivity (see Table 11, below).

TABLE 11

| | | | Esterase activity[e] | |
|---|---|---|---|---|
| Variant[a] | Phosphotriesterase activity[b,c] | Lactonase activity[d] | short chain ester | long chain esters |
| rPON1 (wt-like activity) | $3.5 * 10^3$ | $1.4 * 10^2$ | $3.0 * 10^4$ | $1.7 * 10^2$ |
| Directly-evolved variants with 'specialized' substrate selectivities | | | | |
| ID/SEQ ID NO: Mutations[f] | | | | |
| 7PC/ 66, 67    V346A | $1.3 * 10^4$ (3.7)[b] | $5.0 * 10^1$ (0.36) | $1.4 * 10^3$ (0.05) | $1.4 * 10^1$ (0.08) |
| 4PC/ 68, 69    L69V, S193P, V346A | $5.7 * 10^4$ (16.3) | 0.9 (0.006) | $4.4 * 10^2$ (0.015) | n.d |
| 1HT/ 70, 71    I291L, T332A, G339E | $6.0 * 10^2$ (0.17) | $3.0 * 10^3$ (25.9) | $8.6 * 10^3$ (0.3) | n.d. |
| 2AC/ 72, 73    F292S, V346M V30A, E249K | $1.1 * 10^2$ (0.03) | 6.4 (0.04) | $6.0 * 10^5$ (20) | $7.0 * 10^2$ (4.1) |
| 7HY/ 74, 75    F292V, Y293D, I109M | $4.1 * 10^1$ (0.01) | 4.1 (0.03) | $1.2 * 10^5$ (4.0) | $8.0 * 10^3$ (47) |
| 4HY/ 76, 77    I74L, F292L K84Q, I343M | $5.3 * 10^1$ (0.015) | 5.9 (0.04) | $5.2 * 10^4$ (1.7) | $6.5 * 10^3$ (38) |

[a]rPON1 variant G3C9 was used as the starting point for directed evolution. It exhibits a sequence almost identical to those of wt rabbit PON1 and rPON1 variant G2E6, whose 3D-structure was determined (91% homology; FIG. 13), and the same enzymatic parameters.
[b]All activities were determined at 0.1 mM substrate, and are expressed as μmoles of product released per minute per mg enzyme. In parentheses are the activities of the new variants relative to wt PON1's activity for the same substrate.
[c]Phosphotriesterase activity was screened, and subsequently quantified, with the fluorogenic OP substrate, 7-O-diethylphosphoryl-3-cyano-7-hydroxycoumarin as described [A. Aharoni et al., Proc. Natl. Acad. Sci. USA 101, 482 (2004)].
[d]Libraries were initially screened with 2NA, and positive clones picked from replica plates and grown in 96-well plates as described [A. Aharoni et al., Proc. Natl. Acad. Sci. USA 101, 482 (2004)]. The crude cell lysates and purified proteins were assayed for hydrolysis of γ-butyrothiolactone using DTNB (5,5-dithio-bis-2-nitrobenzoic acid) for detection of product (absorbance at 412 nm).
[e]Esterase activity was screened with the fluorogenic substrate, 7-acetoxycoumarin (for short-chain esterase activity) or with 2-naphthyl octanoate (for long-chain esterase activity) using fast red for the detection of 2-naphthol [A. Aharoni et al., Proc. Natl. Acad. Sci. USA 101, 482 (2004)]. Colonies exhibiting the highest activity were grown in 96-well plates, and the crude cell lysate assayed spectrophotometrically at 365 nm, for hydrolysis of 7-acetoxycoumarin, and at 320 nm with 2-naphthyl laurate. The activity of the variants described above was determined with the same substrates and assays.
[f]Mutations are given in relation to the sequence of the wt-like variant G3C9. In bold are positions found to be mutated in all the highest-activity variants for a given substrate. Typically, the same mutations could be individually identified in the sequence of selected variants from the 1st and 2nd rounds of evolution, and appear together in the 3rd generation variants. Mutations that appear in only one selected variant, but not in others selected for the same substrate, and/or do not appear in the 1st and 2nd round of evolution, are noted in regular print.

Directed Evolution of an Array of Specialized Variants Reveals the Location and Structure of PON1's Active Site—

These shifts involve not only an increase of 16-46-fold in activity towards the substrate for which each particular variant was evolved, but also a drastic decrease in activity on substrates which had not been selected for (6-167-fold). Overall, shifts in substrate selectivity of up to 4,600-fold were observed (e.g., variant 7HY that exhibits, relative to wt PON1, 46-fold higher long-chain esterase activity and 100-fold lower phosphotriesterase activity). Some of the new variants, which were all derived from PON1, represent substrate and reaction selectivities that are closer to PON2 or PON3. For example, variants 2AC and 1HT exhibit ~20-fold higher esterase and lactonase activity relative to PON1 and 5-30-fold weaker phosphotriesterase activity.

The positions identified by directed evolution all appear in the same region at the top of the β-propeller and thereby clearly mark the entrance to and walls of PON1's active site (FIGS. 18a-b). The Cα and phenyl side-chain of Phe292, the entire side-chain of Ile291, and the carbonyl oxygens of both these residues, all line the cavity. At the bottom of the cavity lies the methyl side chain of Thr332. The phenyl ring of Phe293 is part of the active-site perimeter. All these residues seem to affect the esterase and lactonase activities of PON1. Another subset of residues was identified in the variants specialized for OP hydrolysis.

The side-chains of Leu69 and Val346, and Cα and the side-chain methylene of Ser193, are part of the active-site walls, as are the side-chain methylenes of Lys192. In human PON1, this position is normally arginine, but a commonly observed polymorphism to glutamine (192Q) results in ~10-fold decrease in paraoxonase activity and higher susceptibility to atherosclerosis [D. I. Draganov, B. N. La Du, Nau Schm Arch Pharmacol (2003)]. Given the drastic effects that changes in other active-site residues have on PON1's substrate selectivity, the human 192Q variant may indeed exhibit significantly reduced activities with PON1's physiological substrates, resulting in increased susceptibility to atherosclerosis.

Other residues lining the cavity, which did not mutate during directed evolution, include the side chains of Met196, Phe222, and Leu240, and Glu53 (the carboxylate of which interacts with Ca-1 at the bottom of the cavity). The perimeter is defined by several residues that are ~15-20 Å from the deepest point of the cavity, including Tyr190, His 197, Phe293 and Tyr294. The top of the active site is partly covered, e.g., by the phenyl ring of Phe347 and the backbones of Lys70 and Tyr71. The latter form the end of a loop that is disordered and hence not seen in the structure. This loop may be part of an active-site lid, since mutations in residue 74 were also observed that led to changes in substrate selectivity (e.g., variant 4HY, Table 11).

The Catalytic Mechanism of PON1—

At the very bottom of the active-site cavity just described, lies the upper calcium (Ca-1), and a phosphate ion which was present in the mother liquor (FIG. 18b). One of the phosphate's oxygens is only 2.2 Å from Ca-1. This phosphate ion may be bound in a mode similar to the intermediates in the hydrolytic reactions catalyzed by PON. One of its negatively-charged oxygens, that closest to Ca-1, may mimic the oxyanionic moiety of these intermediates stabilized by the positively-charged calcium. This type of 'oxyanion hole' is seen in secreted phospholipases A2 (PLA2s) [K. Sekar et al., Biochemistry 36, 3104 (1997)] and has also been suggested for DFPase. Two other phosphate oxygens may be mimicking the attacking hydroxyl ion and the oxygen of the alkoxy or phenoxy leaving groups of ester and lactone substrates.

To help elucidate PON 1's mechanism, the pH-rate profile thereof was determined with two typical substrates: an ester (2-naphthyl acetate, 2NA, FIG. 19) and a phosphotriester (paraoxon). Both profiles exhibit a bell-shaped curve. The minor basic shoulder fits a pKa of 9.8 (paraoxon) or 9.0 (2NA), probably reflecting the deprotonation of a basic side-chain that affects the active site but is not directly involved in catalysis. The fully pronounced acidic shoulder, with a pKa of ~7.1, may be ascribed to a His imidazole involved in a base-catalyzed, rate-determining step. In hydrolytic enzymes, His often serves as a base, deprotonating a water molecule and generating the attacking hydroxide ion that produces hydrolysis. In secreted PLA2, the attacking hydroxide is generated by a His-Asp dyad, in which the imidazole acts as a base to deprotonate a water molecule, and the Asp carboxylate increases the imidazole's basicity via a proton-shuttle mechanism. The closest His nitrogen in PLA2 is 6.3 Å from the catalytic calcium, and two water molecules are involved: one attacking the substrate (after deprotonation), and another 'catalytic water' that mediates between the attacking water and the His base [Sekar (1997) Supra]. The DFPase active site also contains a His-Glu dyad with a His nitrogen 7.2 Å from the catalytic calcium [Scharff (2001) Supra].

Interestingly PON1 adopted a similar mechanism—namely a His-Glu/Asp dyad acting as base on a two-water-molecule cascade. PON1's active site contains a His-Glu/Asp dyad (Asp183, His184), with the Asp183 carboxylate oxygen apparently H-bonded to one of His184's nitrogens. However, His184's nitrogens are 10.8 Å and 12 Å from Ca-1, and the His184Asn mutant of human PON1 is active [Josse (1999) Supra]. Another such dyad in PON1's active site is His285-Asp269. Yet Asp269 ligates Ca-1, and His285 is ~8 Å from Ca-1 and ~5 Å from the nearest phosphate oxygen. A His-His dyad was identified near both Ca-1 and the phosphate ion (FIG. 20-21). It is suggested that His115 (the closer nitrogen of which is only 4.1 Å from Ca-1) acts as a general-base to deprotonate a single water molecule and generate the attacking hydroxide, while His 134 acts in a proton shuttle mechanism to increase His 115's basicity. His134 appears to make a second H-bond to Ser139-Oγ that may stabilize the dyad and further increase its basicity. Interestingly, His115 adopts distorted dihedral angles—a phenomenon observed in catalytic residues of many enzymes. In strong support of the proposed mechanism are the His115Gln mutation, that resulted in a dramatic decrease (~2×10$^4$ fold) in activity, and His134Gln, that resulted in a milder, yet significant decrease (6-150 fold; Table 12, below).

TABLE 12

| Variant | Phenyl acetate[a] (Units) (fold decrease) | Paraoxon[a] (Units) (fold decrease) |
|---|---|---|
| WT | 1.5 * 10$^6$ (1) | 3.8 * 10$^3$ (1) |
| H134Q | 9.5 * 10$^3$ (154) | 6.1 * 10$^2$ (6.2) |
| H115Q | 42 (35,100) | 0.22 (17,270) |
| C283A | 8.7 * 10$^5$ (1.7) | 1.9 * 10$^3$ (2) |
| C283S[b] | | |

[a]Activities for phenyl acetate and paraoxon hydrolyses were determined at 0.2 mM and 0.1 mM, respectively, and are given in units (μmoles product/minute/mg enzyme). The decrease in activity of the mutants relative to 'wt' rPON1-G2E6 are given in parenthesis.
[b]The C283S mutant did not express in E. coli, neither as soluble protein nor in inclusion bodies. It is presumably misfolded and proteolytically digested.

It will be appreciated that, the mechanism proposed above has not been observed before, although its key elements are seen in DFPase and PLA2. Catalysis of both C—O and P—O hydrolyses at one site is unusual but not unprecedented [Bencharit, C. L. Morton, Y. Xue, P. M. Potter, M. R. Redinbo, Nature Struct Biol 10, 349 (2003); C. B. Millard, O. Lockridge, C. A. Broomfield, Biochemistry 37, 237 (1998)]. The structure, the directed evolution results, the pH-rate profiles, and previous biochemical data (see Draganov and Examples 1-5) show that both these activities take place at the same site. At this stage, however, a possibility remains that certain PON1 activities (e.g., as homocysteine thiolactonase) make use of a different subset of residues of this site, including His285, whose side chain also points towards both the center of the cavity and the phosphate ion. In addition, nucleophilic catalysis by His115 cannot yet be ruled out, although there is currently no evidence to support catalysis via an acyl- or phosphoryl-enzyme intermediate.

The 3D-structure does provide a hint regarding the origins of PON1's remarkably wide substrate range. The transition states, intermediates and leaving groups of the various substrates (phenoxy, alkoxy, etc.) are obviously very different. Yet hydrophobicity is common to all of PON1's effective substrates. The hydrophobicity and depth of PON 1's active site explain this preference, and account for the fact that PON1's substrates, whether poor or effective, generally exhibit similar $K_M$ values (0.1-0.5 mM) but dramatically different $k_{cat}$ values. Homocysteine thiolactone is perhaps the only poor PON substrate with a notably high $K_M$ (~20 mM) (8, 13). It is also the only charged substrate. Thus, PON1's multi-specificity is driven primarily by non-specific hydrophobic forces, as observed with other enzymes that possess deep hydrophobic active sites [e.g., acetylcholinesterase; H. M. Greenblatt, H. Dvir, I. Silman, J. L. Sussman, *J Mol Neurosci* 20, 369 (2003)]. The mutations that led to up to 4,600-fold changes in PON1's substrate selectivity also affect the $k_{cat}$ values, whereas $K_M$ values remain essentially unchanged. Yet the structure makes it clear that the active-site chemistry of these mutants is identical to the wt. The results presented herein thus indicate that, poor as well as effective substrates, bind at the active site with similar affinity; yet the mode of binding differs, as the poor substrates are inadequately positioned relative to Ca-1 and to the catalytic base. The mutations reshape the active site walls and perimeter, thereby improving the positioning of certain substrates (and of their respective catalytic intermediates and transition states) and worsening that of others. As discussed below, reshaping of the active site walls is also the driving force behind the divergence of various PON sub-families.

Structural and Evolutionary Analysis of the PON Family Members—

The 3D structure of PON1 provides key insights as to how the substrate and reaction selectivity of different PONs is determined, and how they diverged towards different activities. Further insights are provided into the possible effects of various SNPs on PON's activity and stability.

The key elements of the PON catalytic site are highly conserved; these include the residues that ligate Ca-1, neighboring residues that are in H-bond contact with the latter, and the catalytic histidines (see FIG. 22). The different PON sub-families therefore diverged while maintaining their overall active-site structure and catalytic machinery. However, their substrate and reaction selectivities changed dramatically. The present results show how PONs readily adopt new selectivities. PON1 variants evolved in the laboratory show patterns reminiscent of PON2 or PON3 (e.g., variants 1HT and 2AC, with high lactonase and esterase activity and low phosphotriesterase activity). These results define a set of sixteen residues that comprise the walls and perimeter of the PON active site, and thereby govern substrate selectivity (Table 13, below).

TABLE 13

| Sub-family | | | | Newly-evolved PON1s | |
|---|---|---|---|---|---|
| Position | PON1 | PON2 | PON3 | Residue | Selectivity |
| 69 | L | L | L | V/I | PTE[a] |
| 74[b] | I | L | M | L/M | lactonase/esterase |
| 75[b] | K/M | K/H | P | | |
| 76[b] | S | S | N/A | | |
| 78[b] | N/D | A | A | | |
| 190 | Y | F/I | L/V/F | | |
| 192 | K/R | K/M | S/A/V | | human R/Q SNP |
| 193 | S | Y/F | F/L | P | PTE[a] |
| 196 | M | M/T | M | | |
| 222 | F | S | S | | |
| 240 | L | I | V | | |
| 291 | I | L/V | L | L | lactonase |
| 292 | F | F/Y | L | L/V/S | esterase |
| 293 | F/Y | V/Y/I | N/I | D | lipase-like[c] |
| 332 | T | S | S/T | A | lactonase |
| 346 | V | L/V | I/V | A | PTE[a] |

[a]PTE = phosphotriesterase. Note that the PTE activity of these mutants is much higher than that of wt PON1 which is the best PTE amongst all PONs (Table 11).
[b]Residues 74-79 belong to the selectivity-determining residues which differ between the PON subfamilies (FIG. 22) but are conserved within them. These residues are part of a mobile loop, which also contains residue 74, is not seen in the structure but is part of the active site.
[c]Lipase-like activity refers to esters of long-chain carboxylic acids (Table 11).

Variants exhibiting patterns of activities that have not yet been identified in natural PONs, carry mutations at the same positions, but to amino acids other than those observed in wt PONs (e.g., 4PC, with higher phosphotriesterase activity than wt PON1 and dramatically lower esterase activity; Table 13, above). At some stage in evolution, changes in the selectivity-determining residues (Table 13, above) led to divergence of the individual PON sub-families, each of which is highly conserved with respect to these residues. It may be that each of the sub-families evolved, and is evolutionarily preserved, for a different substrate of key physiological importance, yet the identities of these substrates remain obscure.

There are also residues outside the active site that vary from one subfamily to another, yet are conserved within each family. Most seem to be related to the β-propeller scaffold, but some may be linked to function. A clear example is Asn253, which is one of the two presumed glycosylation sites of PON1, and thus is within an NX(S/T) consensus sequence. This site is abolished in PON2 and PON3 due to a change in the third position, from Thr to Asn or Asp (FIG. 22). Other residues, or clusters of residues, appear to be specific for each sub-family (e.g., in the region of 20-50). These may be linked to non-hydrolytic roles of PONs, in particular in relation to atherosclerosis, and to their localization (e.g., PON1 and PON3 are exclusively localized in the liver and HDL, whereas PON2 is found in many tissues).

As is the case for the catalytic machinery, the residues maintaining the hydrophobic core of the β-propeller, its central tunnel, the two calciums, and the 'velcro' closure, are also highly conserved (FIG. 22). Residue 55 falls into this category (Leu/Ile in all PONs, Leu in PON1s) except for the human polymorphism of Met55. Residue 55's conservation is clear, given its neighboring residues (Glu53 and Asp54 that ligate Ca-1 and Ca-2), and its role in packing the propeller's central tunnel at the interface between blade 1 and 6. A mutation of Leu to Met may significantly affect PON 1's stability and account for the lower enzymatic activity [I. Leviev, S. Deakin, R. W. James, J Lipid Res 42, 528 (2001).]. Cys284 (strand 5B) is another example. It is in a highly conserved stretch (283-287) that includes active-site His 285. It is packed against four highly-conserved residues from the adjacent strands: Leu267 and Val268 (strand 5A) and Leu305 and the methylenes of Glu303's side-chain (strand 5C).

Mutation of Cys284 is, therefore, likely to destabilize the core structure, thus indirectly affecting function. Although mutation of Cys284 has no significant effect on PON1's hydrolytic activity [R. C. Sorenson et al., Proc Natl Acad Sci USA 92, 7187 (1995)], Cys284 mutants of rPON1 were found to be poorly expressed and relatively unstable (Table 12, above). As the 3D structure reveals that Cys284 has no solvent accessibility, this residue is less likely to serve in alternative functions of PON1 related to atherosclerosis [M. Aviram et al., Arterioscler Thromb Vasc Biol 18, 1617 (1998)].

Some remote PON family members, found in bacteria and fungi, exhibit functional and, presumably, structural resemblance to mammalian PONs [M. Kobayashi, M. Shinohara, C. Sakoh, M. Kataoka, S. Shimizu, Proc Natl Acad Sci USA 95, 12787 (1998)]. Nature has also recruited the PON scaffold for completely different tasks. An interesting example is the C. elegans MEC-6 protein, shown to be part of the degenerin channel that mediates mechanotransduction [D. S. Chelur et al., Nature 420, 669 (2002).]. The present analysis, based on the PON1 structure, suggests that MEC-6 maintains the key structural elements of PON (most notably, the Cys42-Cys353 disulphide bridge, and two of the three residues that ligate the structural calcium). The hydrolytic site, however, including the residues that ligate Ca-1 and the His-dyad, were mutated away.

PON1s Structure Suggests a Mode of Anchoring of PON1 to HDL—

PON1 and PON3 are synthesized in the liver, and secreted into the blood, where they specifically associate with HDL. HDL mediates reverse transport of cholesterol from peripheral cells and limits LDL oxidation by the activity of HDL-associated enzymes such as platelet-activating factor actetylhydrolase (PAF-AH), PON1 and PON3 [S. Lund-Katz, L. J. Liu, S. T. Thuahnai, M. C. Phillips, Frontiers in Bioscience 8, D1044 (2003); M. Navab et al., Curr Opin Lipidology 9, 449 (1998)]. HDL is a particle of ~10 nm diameter, composed primarily of membrane components (phospholipids, cholesterol and cholesterol esters), and apolipoprotein A-I (apoA-I), the amphipathic helices of which are thought to wrap around the particle's membrane-like bilayer in a belt-wise manner [J. P. Segrest, S. C. Harvey, V. Zannis, Trends Cardiovasc Med 10, 246 (2000)]. Several other proteins are associated with HDL, including lecithin:cholesterol acyl transferase (LCAT) (24), but their mode of binding to HDL is still under investigation. PON1 is the first HDL-associated protein the 3D-structure of which becomes known.

PON1 retains its hydrophobic N-terminus, which resembles a signal peptide, and is thought to be involved in anchoring of PON1 to HDL [R. C. Sorenson et al., Arterioscler Thromb Vasc Biol 19, 2214 (1999)]. Most of the N-terminus is disordered and invisible in the crystal structure, yet the hydrophilic part of it that extends beyond the signal peptide (residues 19-28) adopts a helical structure (H1). The entire sequence of the N-terminus is compatible with a trans-membrane helix, yet following a secondary structure prediction, only residues 7-18 were found to be part of H1 (FIG. 23). Helix H2, adjacent to H1, shows a clear amphipathic nature. Its hydrophobic face points unexpectedly to the solvent, as do several residues from the two loops that connect H2 to the propeller scaffold. Helices H1 and H2 form, therefore, two adjacent hydrophobic patches that clearly provide a potential membrane-binding surface (FIG. 23). The interface with HDL was further defined by a characteristic 'aromatic belt' rich in Trp and Tyr side chains, and a Lys side chain on H1 (38). Notably, the glycosylation sites point away from the interface (FIG. 23).

It has also been suggested that PON1 interacts specifically with apoA-I, and that these interactions modulate its activity [M. N. Oda, J. K. Bielicki, T. Berger, T. M. Forte, Biochemistry 40, 1710 (2001)]. This hypothesis is supported by the striking proximity of PON1's HDL-anchoring region to its active site. In fact, the proposed HDL-anchoring region is part of an active-site lid, and several of the selectivity-determining residues are on amphipathic helix H2 and on the loops linked to H1 (FIG. 23). If the postulated mode of HDL-anchoring is correct, it may support the notion of interfacial activation, whereby HDL-anchoring modifies PON1's active site. This mode is present in both lipases [K. Sekar et al., Biochemistry 36, 3104 (1997)] and LCAT [A. Jonas, Biochim Biophys Acta-Mol Cell Biol Lipids 1529, 245 (2000)] for both of which interfacial activation leads to dramatically higher activity towards lipid substrates. The structure of PON1 presented here should direct further research aimed at elucidating PON1's mode of binding to HDL and its effect on the enzyme's activities, as well as the precise physiological roles of these activities.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

REFERENCES CITED

Abecassis, V., Pompon, D. and Truan, G. (2000) High efficiency family shuffling based on multi-step PCR and in vivo DNA recombination in yeast: statistical and functional analysis of a combinatorial library between human cytochrome P450 1A1 and 1A2. *Nucleic Acids Res,* 28, e88.

Ahmed, Z., Ravandi, A., Maguire, G. F., Emili, A., Draganov, D., La Du, B. N., Kuksis, A. and Connelly, P. W. (2001) Apolipoprotein A-I promotes the formation of phosphatidylcholine core aldehydes that are hydrolyzed by paraoxonase (PON-1) during high density lipoprotein oxidation with a peroxynitrite donor. *Journal of Biological Chemistry,* 276, 24473-24481.

Aviram, M., Rosenblat, M., Bisgaier, C. L., Newton, R. S., Primo-Parmo, S. L. and La Du, B. N. (1998) Paraoxonase inhibits high-density lipoprotein oxidation and preserves its functions. A possible peroxidative role for paraoxonase. *J Clin Invest,* 101, 1581-1590.

Bessette, P., Aslund, F., Beckwith, J. and Georgiou, G. (1999) Efficient folding of proteins with multiple disulfide bonds in the *Escherichia coli* cytoplasm. *Proc Natl Acad Sci USA,* 96, 13703-13708.

Billecke, S., Draganov, D., Counsell, R., Stetson, P., Watson, C., Hsu, C. and La Du, B. N. (2000) Further characterization of human serum paraoxonase (PON1) lactonase activity. *Faseb Journal*, 14, 74.

Billeclke, S., Draganov, D., Counsell, R., Stetson, P., Watson, C. and La Du, B. N. (2000) Human serum paraoxonase (PON1) isozymes Q and R hydrolyze lactones and cyclic carbonate esters. *Drug Metabolism and Disposition*, 28, 1335-1342.

Brushia, R. J., Forte, T. M., Oda, M. N., La Du, B. and Bielicki, J. K. (2001) Baculovirus-mediated expression and purification of human serum paraoxonase 1A. *J Lipid Res*, 42, 951-958.

Crameri, A., Raillard, S. A., Bermudez, E. and Stemmer, W. P. (1998) DNA shuffling of a family of genes from diverse species accelerates directed evolution. *Nature*, 391, 288-291.

Davies, H. G., Richter, R. J., Keifer, M., Broomfield, C. A., Sowalla, J. and Furlong, C. E. (1996) The effect of the human serum paraoxonase polymorphism is reversed with diazoxon, soman and sarin. *Nat Genet*, 14, 334-336.

Georgiou, G. (2000) Analysis of large libraries of protein mutants using flow cytometry. *Adv Protein Chem*, 55, 293-315.

Griffiths, A. D. and Tawfik, D. S. (2000) Man-made enzymes—from design to in vitro compartmentalisation. *Curr Opin Biotechnol*, 11, 338-353.

Hammarstrom, M., Hellgren, N., van Den Berg, S., Berglund, H. and Hard, T. (2002) Rapid screening for improved solubility of small human proteins produced as fusion proteins in *Escherichia coli. Protein Sci*, 11, 313-321.

Jakubowski, H. (2000) Calcium-dependent human serum homocysteine thiolactone hydrolase. A protective mechanism against protein N-homocysteinylation. *J Biol Chem*, 275, 3957-3962.

Joern, J. M., Meinhold, P. and Arnold, F. H. (2002) Analysis of shuffled gene libraries. *J Mol Biol*, 316, 643-656.

Jones, H. E., Holland, I. B., Baker, H. L. and Campbell, A. K. (1999) Slow changes in cytosolic free Ca2+ in *Escherichia coli* highlight two putative influx mechanisms in response to changes in extracellular calcium. *Cell Calcium*, 25, 265-274.

Josse, D., Ebel, C., Stroebel, D., Fontaine, A., Borges, F., Echalier, A., Baud, D., Renault, F., le Maire, M., Chabrieres, E. and Masson, P. (2002) Oligomeric states of the detergent-solubilized human serum paraoxonase (PON1). *Journal of Biological Chemistry*, 277, 33386-33397.

Josse, D., Xie, W. H., Renault, F., Rochu, D., Schopfer, L. M., Masson, P. and Lockridge, O. (1999) Identification of residues essential for human paraoxonase (PON1) arylesterase/organophosphatase activities. *Biochemistry*, 38, 2816-2825.

Khalameyzer, V., Fischer, I., Bornscheuer, U. and Altenbuchner, J. (1999) Screening, nucleotide sequence, and biochemical characterization of an esterase from *Pseudomonas fluorescens* with high activity towards lactones. *Appl Environ Microbiol*, 65, 477-482.

Kuo, C. L. and La Du, B. N. (1995) Comparison of purified human and rabbit serum paraoxonases. *Drug Metab Dispos*, 23, 935-944.

Kuo, C. L. and La Du, B. N. (1998) Calcium binding by human and rabbit serum paraoxonases. Structural stability and enzymatic activity. *Drug Metab Dispos*, 26, 653-660.

Mackness, M. I., Mackness, B., Durrington, P. N., Connelly, P. W. and Hegele, R. A. (1996) Paraoxonase: biochemistry, genetics and relationship to plasma lipoproteins. *Curr Opin Lipidol*, 7, 69-76.

Marathe, G., Zimmerman, G. and McIntyre, T. (2002) PAF acetylhydrolase, and not paraoxonase-1, is the oxidized phospholipid hydrolase of high density lipoprotein particles. *J Biol Chem*, In Press.

Maxwell, K. L., Mittermaier, A. K., Forman-Kay, J. D. and Davidson, A. R. (1999) A simple in vivo assay for increased protein solubility. *Protein Sci*, 8, 1908-1911.

Petrounia, I. P. and Arnold, F. H. (2000) Designed evolution of enzymatic properties. *Curr Opin Biotechnol*, 11, 325-330.

Reddy, S. T., Wadleigh, D. J., Grijalva, V., Ng, C., Hama, S., Gangopadhyay, A., Shih, D. M., Lusis, A. J., Navab, M. and Fogelman, A. M. (2001) Human paraoxonase-3 is an HDL-associated enzyme with biological activity similar to paraoxonase-1 protein but is not regulated by oxidized lipids. *Arteriosclerosis Thrombosis and Vascular Biology*, 21, 542-547.

Rodrigo, L., Mackness, B., Durrington, P. N., Hernandez, A. and Mackness, M. I. (2001) Hydrolysis of platelet-activating factor by human serum paraoxonase. *Biochemical Journal*, 354, 1-7.

Shih, D. M., Gu, L. J., Xia, Y. R., Navab, M., Li, W. F., Hama, S., Castellani, L. W., Furlong, C. E., Costa, L. G., Fogelman, A. M. and Lusis, A. J. (1998) Mice lacking serum paraoxonase are susceptible to organophosphate toxicity and atherosclerosis. *Nature*, 394, 284-287.

Smolen, A., Eckerson, H., Gan, K., Hailat, N. and La Du, B. (1991) Characteristics of the genetically determined allozymic forms of human serum paraoxonase/arylesterase. *Drug Metab Dispos*, 19, 107-112.

Sorenson, R. C., Bisgaier, C. L., Aviram, M., Hsu, C., Billecke, S, and La Du, B. N. (1999) Human serum paraoxonase/arylesterase's retained hydrophobic N-terminal leader sequence associates with HDLs by binding phospholipids—Apolipoprotein A-I stabilizes activity. *Arteriosclerosis Thrombosis and Vascular Biology*, 19, 2214-2225.

Stemmer, W. P. (1994) DNA shuffling by random fragmentation and reassembly: in vitro recombination for molecular evolution. *Proc Natl Acad Sci USA*, 91, 10747-10751.

Sun, L., Petrounia, I. P., Yagasaki, M., Bandara, G. and Arnold, F. H. (2001) Expression and stabilization of galactose oxidase in *Escherichia coli* by directed evolution. *Protein Eng*, 14, 699-704.

Waldo, G. S. (2003) Genetic screens and directed evolution for protein solubility. *Curr Opin Chem biol*, 7, 33-38.

Waldo, G. S., Standish, B. M., Berendzen, J. and Terwilliger, T. C. (1999) Rapid protein-folding assay using green fluorescent protein. *Nat Biotechnol*, 17, 691-695.

Yang, J. K., Park, M. S., Waldo, G. S, and Suh, S. W. (2003) Directed evolution approach to a structural genomics project: Rv2002 from Mycobacteriumtuberculosis. *Proc Natl Acad Sci USA*, 100, 455-460.

Ziomek, C. A., Lepire, M. L. and Tones, I. (1990) A highly fluorescent simultaneous azo dye technique for demonstration of nonspecific alkaline phosphatase activity. *J Histochem Cytochem*, 38, 437-442.

Kabsch, W. *J. Appl. Cryst.* 26, 795-800, (1993).

Storoni, L. C., McCoy, A. J. and Read, R., *Acta Crystallog. D* (in press).

Uson, I. And Sheldrick, G. M., *Curr. Opin. Struct. Biol.*, 9, 643-648 (1999).

Fortelle, E. and Bricogne, G., *Methods Enzymol.*, 276, 472-494 (1997).

Abrahams, J. P. and Leslie, A. G., *Acta Crystallog. D.*, 52, 30-42 (1996).

Perrakis, A., Morris, R. and Lamzin, V. S., *Nature Struct. Biol.*, 6, 458-463 (1999).

Jones, T. A., Zou, J.-Y., Cowan, S. W. and Kjeldgaard, M., *Acta Crystallogr. A.*, 47, 110-119 (1991).

Murshudov, G. N., Vagin, A. A., Lebedev, A., Wilson, K. S, and Dodson, E. J., *Acta Crystallogr. D.*, 55, 247-255 (1999).

---

What is claimed is:

1. An isolated mutated serum paraoxonase (PON1) enzyme polypeptide comprising an amino acid sequence having at least 95% sequence identity to SEQ ID NO: 56, said mutated PON1 enzyme being soluble and catalytically active when expressed in *E. coli* bacteria and having a phosphotriester hydrolytic activity and phosphotriesterase substrate specificity, wherein said phosphotriesterase substrate specificity, expressed as $k_{cat}/K_M$ ratio for paraoxon hydrolysis, is greater than the $k_{cat}/K_M$ ratio for paraoxon hydrolysis of wild type human PON1, when assayed under the same assay conditions.

2. The isolated mutated serum paraoxonase enzyme polypeptide of claim 1, wherein at least 50% of the mutated paraoxonase enzyme polypeptide does not precipitate into inclusion bodies when expressed in bacteria.

3. A pharmaceutical composition comprising a therapeutically effective amount of the isolated mutated serum paraoxonase enzyme polypeptide of claim 1.

4. A method of treating or preventing a PON-related disease or condition, the method is effected by administering to a subject in need a therapeutically effective amount of the isolated mutated serum paraoxonase enzyme polypeptide of claim 1.

5. The method of claim 4, wherein the disease or condition is selected from the group consisting of hyperlipidemia, atherosclerosis, neurological disease, cancer and organophosphate poisoning.

6. The method of claim 5, wherein said neurological disease is selected from the group consisting of Alzheimer's disease, neurofibromatosis, Huntington's disease, depression, amyotrophic lateral sclerosis, multiple sclerosis, stroke, Parkinson's disease, and multi-infarct dementia.

* * * * *

SEQUENCE LISTING

```
<160> NUMBER OF SEQ ID NOS: 89

<210> SEQ ID NO 1
<211> LENGTH: 28
<212> TYPE: DNA
<213> ORGANISM: Artificial sequence
<220> FEATURE:
<223> OTHER INFORMATION: Single strand DNA oligonucleotide

<400> SEQUENCE: 1
cgacgaaacc atggcgaagc tgattgcg                                          28

<210> SEQ ID NO 2
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 2
ccgggagctg catgtgtcag agg                                               23

<210> SEQ ID NO 3
<211> LENGTH: 41
<212> TYPE: DNA
<213> ORGANISM: Artificial sequence
<220> FEATURE:
<223> OTHER INFORMATION: Single strand DNA oligonucleotide

<400> SEQUENCE: 3
tcaatccgac tagtggttct ggtatggcga agctgattgc g                           41

<210> SEQ ID NO 4
<211> LENGTH: 32
<212> TYPE: DNA
<213> ORGANISM: Artificial sequence
<220> FEATURE:
<223> OTHER INFORMATION: Single strand DNA oligonucleotide

<400> SEQUENCE: 4
ctgtcaagga attcatggcg aagctgattg cg                                     32

<210> SEQ ID NO 5
<211> LENGTH: 36
<212> TYPE: DNA
<213> ORGANISM: Artificial sequence
<220> FEATURE:
<223> OTHER INFORMATION: Single strand DNA oligonucleotide

<400> SEQUENCE: 5
gtcccgggct gcagttatta gagctcacag taaaga                                 36

<210> SEQ ID NO 6
<211> LENGTH: 34
<212> TYPE: DNA
<213> ORGANISM: Artificial sequence
<220> FEATURE:
<223> OTHER INFORMATION: Single strand DNA oligonucleotide

<400> SEQUENCE: 6
```

```
cgacaaggcc atggcgaagc tgctagcact cacc                                34
```

<210> SEQ ID NO 7
<211> LENGTH: 64
<212> TYPE: DNA
<213> ORGANISM: Artificial sequence
<220> FEATURE:
<223> OTHER INFORMATION: Single strand DNA oligonucleotide

<400> SEQUENCE: 7

```
cgacaaggcc atggcgaagc tgctagcact caccctcgtg ggactggtgt tggcacttta    60
caag                                                                 64
```

<210> SEQ ID NO 8
<211> LENGTH: 44
<212> TYPE: DNA
<213> ORGANISM: Artificial sequence
<220> FEATURE:
<223> OTHER INFORMATION: Single strand DNA oligonucleotide

<400> SEQUENCE: 8

```
gctcgagtgc ggccgcttac agatcacagt aaagagcttt gtgg                     44
```

<210> SEQ ID NO 9
<211> LENGTH: 44
<212> TYPE: DNA
<213> ORGANISM: Artificial sequence
<220> FEATURE:
<223> OTHER INFORMATION: Single strand DNA oligonucleotide

<400> SEQUENCE: 9

```
gctcgagtgc ggccgcttac aggtaacaac aaagagctct gtgg                     44
```

<210> SEQ ID NO 10
<211> LENGTH: 6
<212> TYPE: DNA
<213> ORGANISM: Artificial sequence
<220> FEATURE:
<223> OTHER INFORMATION: Random hexamers
<220> FEATURE:
<221> NAME/KEY: misc_feature
<222> LOCATION: (1)..(6)
<223> OTHER INFORMATION: n is a, c, g, or t

<400> SEQUENCE: 10

```
nnnnnn                                                                6
```

<210> SEQ ID NO 11
<211> LENGTH: 22
<212> TYPE: DNA
<213> ORGANISM: Artificial sequence
<220> FEATURE:
<223> OTHER INFORMATION: Oligo dT
<220> FEATURE:
<221> NAME/KEY: misc_feature
<222> LOCATION: (22)..(22)
<223> OTHER INFORMATION: n is a, c, g, or t

<400> SEQUENCE: 11

```
tttttttttt tttttttttt vn                                             22
```

<210> SEQ ID NO 12
<211> LENGTH: 31
<212> TYPE: DNA
<213> ORGANISM: Artificial sequence
<220> FEATURE:

```
<223> OTHER INFORMATION: Single strand DNA oligonucleotide

<400> SEQUENCE: 12
cgacaaggcc atggctaaac tgacagcgct c                              31

<210> SEQ ID NO 13
<211> LENGTH: 41
<212> TYPE: DNA
<213> ORGANISM: Artificial sequence
<220> FEATURE:
<223> OTHER INFORMATION: Single strand DNA oligonucleotide

<400> SEQUENCE: 13
gctcgagtgc ggccgcttaa ttggcctgtg agagctcaca g                   41

<210> SEQ ID NO 14
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 14
cgcggttctg gtatgaaaga aaccgc                                    26

<210> SEQ ID NO 15
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 15
cccgtttaga ggccccaagg gg                                        22

<210> SEQ ID NO 16
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 16
ggcagccaac tcagcttcc                                            19

<210> SEQ ID NO 17
<211> LENGTH: 17
<212> TYPE: DNA
<213> ORGANISM: Artificial sequence
<220> FEATURE:
<223> OTHER INFORMATION: Single strand DNA oligonucleotide

<400> SEQUENCE: 17
cgaacgccag cacatgg                                              17

<210> SEQ ID NO 18
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 18
ccgggagctg catgtgtcag agg                                       23
```

```
<210> SEQ ID NO 19
<211> LENGTH: 27
<212> TYPE: DNA
<213> ORGANISM: Artificial sequence
<220> FEATURE:
<223> OTHER INFORMATION: Single strand DNA oligonucleotide

<400> SEQUENCE: 19
cgacaaggcc atggggaagc tcgtggc                                    27

<210> SEQ ID NO 20
<211> LENGTH: 44
<212> TYPE: DNA
<213> ORGANISM: Artificial sequence
<220> FEATURE:
<223> OTHER INFORMATION: Single strand DNA oligonucleotide

<400> SEQUENCE: 20
gctcgagtgc ggccgcttac agatcacagt aaagagcttt gtgg                 44

<210> SEQ ID NO 21
<211> LENGTH: 27
<212> TYPE: DNA
<213> ORGANISM: Artificial sequence
<220> FEATURE:
<223> OTHER INFORMATION: Single strand DNA oligonucleotide

<400> SEQUENCE: 21
cgacaaggcc atggggcacc tcgtggc                                    27

<210> SEQ ID NO 22
<211> LENGTH: 47
<212> TYPE: DNA
<213> ORGANISM: Artificial sequence
<220> FEATURE:
<223> OTHER INFORMATION: Single strand DNA oligonucleotide

<400> SEQUENCE: 22
gctcgagtgc ggccgcttat tagagttcac agtacaaggc tttctgg              47

<210> SEQ ID NO 23
<211> LENGTH: 29
<212> TYPE: DNA
<213> ORGANISM: Artificial sequence
<220> FEATURE:
<223> OTHER INFORMATION: Single strand DNA oligonucleotide

<400> SEQUENCE: 23
cgacaaggcc atggcgaagc tcctgctgc                                  29

<210> SEQ ID NO 24
<211> LENGTH: 1065
<212> TYPE: DNA
<213> ORGANISM: Homo sapiens

<400> SEQUENCE: 24
atggcgaagc tgattgcgct caccctcttg gggatgggac tggcactctt caggaaccac    60
cagtcttctt accaaacacg acttaatgct ctccgagagg tacaacccgt agaacttcct   120
aactgtaatt tagttaaagg aatcgaaact ggctctgaag acttggagat actgcctaat   180
ggactggctt tcattagctc tggattaaag tatcctggaa taaagagctt caaccccaac   240
agtcctggaa aaatacttct gatggacctg aatgaagaag atccaacagt gttggaattg   300
gggatcactg aagtaaaatt tgatgtatct tcatttaacc ctcatgggat tagcacattc   360
```

| | |
|---|---|
| acagatgaag ataatgccat gtacctcctg gtggtgaacc atccagatgc caagtccaca | 420 |
| gtggagttgt ttaaatttca agaagaagaa aaatcgcttt tgcatctaaa aaccatcaga | 480 |
| cataaacttc tgcctaattt gaatgatatt gttgctgtgg gacctgagca cttttatggc | 540 |
| acaaatgatc actattttct tgaccectac ttacaatcct gggagatgta tttgggttta | 600 |
| gcgtggtcgt atgttgtcta ctatagtcca agtgaagttc gagtggtggc agaaggattt | 660 |
| gattttgcta atggaatcaa catttcaccc gatggcaagt atgtctatat agctgagttg | 720 |
| ctggctcata agattcatgt gtatgaaaag catgctaatt ggactttaac tccattgaag | 780 |
| tcccttgact ttaatacect cgtggataac atatctgtgg atcctgagac aggagacctt | 840 |
| tgggttggat gccatcccaa tggcatgaaa atcttcttct atgactcaga gaatcctcct | 900 |
| gcatcagagg tgcttcgaat ccagaacatt ctaacagaag aacctaaagt gacacaggtt | 960 |
| tatgcagaaa atggcacagt gttgcaaggc agtacagttg cctctgtgta caagggaaa | 1020 |
| ctgctgattg gcacagtgtt tcacaaagct ctttactgtg agctc | 1065 |

<210> SEQ ID NO 25
<211> LENGTH: 1065
<212> TYPE: DNA
<213> ORGANISM: Artificial sequence
<220> FEATURE:
<223> OTHER INFORMATION: In vitro evolved PON variant G1A5

<400> SEQUENCE: 25

| | |
|---|---|
| atggctaaac tgacagcgct cacgctcttg gggctgggat tggcactctt cgatggacag | 60 |
| aagtcttctt tccaaacacg atttaatgtt caccgtgaag taactccagt ggaacttcct | 120 |
| aactgtaatt tagttaaagg gattgacaat ggttctgaag acttggaaat actgcccaat | 180 |
| ggactggctt tcatcagctc cggattaaaa tatcctggaa taatgagctt tgaccctgat | 240 |
| aagtctggaa agatacttct aatggacctg aatgaggaag acccagtagt gttggaactg | 300 |
| ggcattactg gaaatacatt ggatatatct tcatttaacc ctcatgggat tagcacattc | 360 |
| atagatgaag ataacactgt gtacctactg gtggtaaacc atccagactc ctcgtccact | 420 |
| gtggaggtat ttaaatttca agaaaaagaa aaatcacttt tgcatctgaa aaccatcaga | 480 |
| cacaagcttc tgcctagtgt gaatgacatt gtcgctgtgg gacctgaaca cttttatgct | 540 |
| accaatgatc actattttat tgaccettac ttaaaatcct gggaaatgca tttgggatta | 600 |
| gcgtggtcat ttgttactta ttatagtccc aatgatgttc gagtagtggc agaaggattt | 660 |
| gattttgcta acggaatcaa catctcacca gacggcaagt atgtctatat agctgaactg | 720 |
| ctggctcata agatccatgt gtatgaaaag cacgctaatt ggactttaac tccattgaag | 780 |
| tccctcgact ttaacactct tgtggacaac atatccgtgg atcctgtgac aggggacctt | 840 |
| tgggttggtt gtcatcccaa tggcatgcga atcttctact atgacccaga gaatcctccc | 900 |
| ggctcagagg tgcttcgaat ccagaacatt ttatccaaag agcccaaagt gacagtggtt | 960 |
| tatgcagaga atggtaccgt cctgcaaggc accacggtcg cctctgtgta caagggaaaa | 1020 |
| ctgctgattg gcactgtgtt ccacaaagct ctttactgtg agctc | 1065 |

<210> SEQ ID NO 26
<211> LENGTH: 1065
<212> TYPE: DNA
<213> ORGANISM: Artificial sequence
<220> FEATURE:
<223> OTHER INFORMATION: In vitro evolved PON variant G1C4

<400> SEQUENCE: 26

```
atggcgaagc tgctagcact caccctcgtg ggactgggat tggcactctt cgatggacag    60
aagtcttctt tccaaacacg atttaatgtt caccgtgaag taacgccagt agaacttcct   120
aactgtaatt tagttaaagg aatcgagacg ggtgctgaag acttagagat tctgcctaat   180
ggactggctt tcatcagctc cggattaaaa tatcctggaa taatgagctt tgaccctgat   240
aagtctggaa agatacttct aatggacctg aatgaggaag acccagtagt gttggaactg   300
ggcattactg gaagtacatt tgatttatct tcatttaacc ctcatgggat tagtacattc   360
acagatgaag ataacactgt gtacctactg gtggtaaacc atccagactc ctcgtccact   420
gtggaggtat ttaaatttca agaaaaagaa aaatcacttt tgcatctgaa aaccatcaga   480
cacaagcttc tgcctagtgt gaatgacatt gtcgctgtgg acctgaaca cttttatgct   540 accaatgatc actattttat tgacccttac ttaaaatcct gggaaatgca tttgggatta   600
gcgtggtcat ttgttactta ttatagtccc aatgatgttc gagtagtggc agaaggattt   660
gattttgcta acggaatcaa catctcacca gacggcaagt atgtctatat agctgaattg   720
ctggctcaca gattcacgt gtatgaaaag cacgctaatt ggactttaac tccattgaag   780
tccctcgact ttaacactct tgtggacaac atatccgtgg atcctgtgac agggaccttt   840
tgggttggtt gtcatcccaa tggcatgcga atcttctact atgacccaaa gaatcctcct   900
gcatcagagg tgcttcgaat ccaggacatt ttatccgaag accccaaaat aactgtagtt   960
tatgcagaga atggtaccgt cctgcaaggc accacggtcg cctctgtgta caagggaaa  1020 ctgctgattg gcacagtgtt tcacaaagct ctttactgtg atctg                 1065

<210> SEQ ID NO 27
<211> LENGTH: 1065
<212> TYPE: DNA
<213> ORGANISM: Artificial sequence
<220> FEATURE:
<223> OTHER INFORMATION: In vitro evolved PON variant G2D6

<400> SEQUENCE: 27
atggctaaac tgacagcgct cacgctcttg gggctgggat tggcactctt cgatagacag    60
aagtcttctt tccaaacacg atttaatgtt caccgtgaag taactccagt ggaacttcct   120
aactgtaatt tagttaaagg gattgacaat ggttctgaag acttggaaat actgcccaat   180
ggactggctt tcatcagctc cggattaaaa tatcctggaa taatgagctt tgaccctgat   240
aagtctggaa agatacttct aatggacctg aatgaggaag acccagtagt gttggaactg   300
ggcattactg gaagtacatt tgatttatct tcatttaacc ctcatgggat tagcacattc   360
acagatgaag ataacactgt gtacctactg gtagtaaacc atccagactc ctcgtccact   420
gtggaggtat ttaaatttca agaaaaggag agatcacttt tgcatctgaa aaccatcaga   480
cacaagcttc tgcctagtgt gaatgacatt gtcgctgtgg acctgagag cttctatgcc   540 acaaatgatc actattttgc tgacccttac ttaaaatcct gggaaatgca tttgggatta   600
gcgtggtcat ttgttactta ttatagtccc aatgatgttc gagtagtggc agaaggattt   660
gattttgcta acggaatcaa catctcaccc gatggcaagt atgtctatat agctgaactg   720
ctggctcata gatccatgt gtatgaaaag cacgctaatt ggactttaac tccattgaag   780
tccctcgact ttaacactct tgtggataac atctctgtgg atcctgtgac agggaccctc   840
tgggtgggat gccatcccaa tggcatgcga atcttctact atgacccaga gaatcctccc   900
ggctcagagg tacttcgaat ccaggacatt ttatccaaag agcccaaagt gacagtggtt   960
```

```
tatgcagaaa atggcactgt gttacagggc agcacggtgg ccgctgtgta caaagggaaa   1020
ctgctgattg gcactgtgtt ccacaaagct ctttactgtg atctg                  1065

<210> SEQ ID NO 28
<211> LENGTH: 1065
<212> TYPE: DNA
<213> ORGANISM: Artificial sequence
<220> FEATURE:
<223> OTHER INFORMATION: In vitro evolved PON variant G2E6

<400> SEQUENCE: 28
atggctaagc tgacagcgct caccctcttg gggatgggac tggcactctt cgataggcag     60
aagtcttctt tccaaacacg atttaatgtt caccgtgaag taacgccagt agaacttcct    120
aactgtaatt tagttaaagg gattgacaat ggttctgaag acttggaaat actgcccaat    180
ggactggctt tcatcagctc cggattaaaa tatcctggaa taatgagctt tgaccctgat    240
aagtctggaa agatacttct aatggacctg aatgagaagg agccagcagt gtcagagtta    300
gaaattatag gaaatacatt ggatatatct tcatttaacc ctcatgggat tagcacattc    360
atagatgatg ataacactgt gtacctactg gtggtaaacc atccaggctc ctcgtccact    420
gtggaggtat ttaaatttca agaagaagaa aaatcgcttt tgcatctgaa aaccatcaga    480
cacaagcttc tgcctagtgt gaatgacatt gtcgctgtgg acctgaaca cttttatgct    540 accaatgatc actattttat tgacccttac ttaaaatcct gggaaatgca tttgggatta    600
gcgtggtcat ttgttactta ttatagtccc aatgatgttc gagtagtggc agaaggattt    660
gattttgcta acggaatcaa catctcacca gacggcaagt atgtctatat agctgaactg    720
ctggctcata gatccatgt gtatgaaaag cacgctaatt ggactttaac gccattgagg    780
gtcctcagct tgacaccct tgtggataac atatccgtgg atcctgtgac aggggacctt    840
tgggttggtt gtcatcccaa cggaatgagg atcttttct atgacgcaga gaatcctccc    900
ggctcagagg tgcttcgaat ccaggacatt ttatccgaag agcccaaagt gacagtggtt    960
tatgcagaaa atggcactgt gttacagggc agcacggtgg ccgctgtgta caaagggaaa   1020
ctgctgattg gcacagtgtt tcacaaagct ctttactgtg atctg                  1065

<210> SEQ ID NO 29
<211> LENGTH: 1065
<212> TYPE: DNA
<213> ORGANISM: Artificial sequence
<220> FEATURE:
<223> OTHER INFORMATION: In vitro evolved PON variant G3H8

<400> SEQUENCE: 29
atggctaaac tgacagcgcc cacgctcttg gggctgggat tggcactctt cgatagacag     60
aagtcttctt tccaaacacg atttaatgtt caccgtgaag taactccagt ggaacttcct    120
aactgtaatt tagttaaagg gattgacaat ggttctgaag acttggaaat actgcccaat    180
ggactggctt tcatcagctc cggattaaaa tatcctggaa taatgagctt tgaccctgat    240
aagtctggaa agatacttct aatggacctg aatgaggaag acccagtagt gttggaactg    300
ggcattactg gaagtacatt tgattttatct tcatttaacc ctcatgggat tagcacattc    360
acagatgaag ataacactgt gtacctactg gtagtaaacc atccagactc ctcgtccact    420
gtggaggtat ttaaatttca agaaaaggag agatcacttt tgcatctgaa aaccatcaga    480
cacaagcttc tgcctagtgt gaatgacatt gtcgctgtgg acctgagag cttttatgcc    540 acaaatgatc actattttgc tgacccttac ttaaaatcct gggaaatgca tttgggatta    600
```

```
gcgtggtcat ttgttactta ttatagtccc aatgatgttc gagtagtggc agaaggattt      660
gattttgcta acggaatcaa catctcaccc gatggcaagt atgtctatat agctgaactg      720
ctggctcata agatccatgt gtatgaaaag cacgccaatt ggactttaac tccattgaag      780
tccctcgact ttaacactct tgtggataac atctctgtgg atcctgtgac aggggacctc      840
tgggtgggat gccatcccaa tggcatgcga atcttctact atgacccaga gaatcctccc      900
ggctcagagg tacttcgaat ccaggacatt ttatccaaag agcccaaagt gacagtggtt      960
tatgcagaaa atggcactgt gttacagggc agcacggtgg ccgctgtgta caaagggaaa     1020
ctgctgattg gcactgtgtt ccacaaagct ctttactgtg atctg                     1065

<210> SEQ ID NO 30
<211> LENGTH: 1062
<212> TYPE: DNA
<213> ORGANISM: Oryctolagus cuniculus

<400> SEQUENCE: 30
atggcgaagc tcctgctgct gaccctgctg ggggccagcc tcgccttcgt cggggagagg       60
ttgctggcgt ttagaaacag ctttggtgca gttcaagaac tggagccagt agaaccccag      120
aactgtgtcc ttattgaggg actcgaaaat ggctcggaag atattgatat acttcctagt      180
gggctggctt ttatctccag tggattaaaa tatccaggca tgccaaactt tgcaccagat      240
gagccaggaa aaatcttctt gatagatatg aatgagaaga cccaagagc acaagagctg      300 gaaatcagca atggatttga aaagaatca ttcaatccac atgggatcag cactttcatt      360
gataaagacc atactgtgta tctttatgtt gtgaatcatc cccacatgaa gtctactgtg      420
gagatattta aatttgagga acaacaacgc tctcttgtac acctgaaaac tataaaacat      480
gaacttctca agagtgtgaa taacattgtg gttcttggac cggaacagtt ctacgccacc      540
agagaccact attttaccaa ctatgtctta gcacttcttg atgttttt ggatcttcac      600 tggacttccg ttctttttcta cagccccaaa gaggtcaaag tggtggccaa aggattcagt      660
tctgccaatg ggatcacagt ctcactagat aagaagtatg tctatgttgc tgatgccaca      720
gctaagaatg tgcatgtaat ggaaaaacat gacaactggg atttaactga actgaaggta      780
atacacttgg acaccttagt ggataattg tctgttgatc ctgccacggg agatatcttg      840
gcaggatgcc atcctaatgg catgaagctt ctgaactata accctgagga tcctccagga      900
tcagaagtac ttcgtatcca gaatgttttg tctgagaagc ccagggtgag caccgtgtac      960
accaatgacg ctctgtgct tcagggctcc accgtggctt ctgtgtacca agggaagatt     1020
ctcataggca ctatattca caaaactctg tattgtgtgc tc                        1062

<210> SEQ ID NO 31
<211> LENGTH: 1062
<212> TYPE: DNA
<213> ORGANISM: Homo sapiens

<400> SEQUENCE: 31
atggggaagc tcgtggcgct ggtcctgctg ggggtcggcc tgtccttagt cggggagatg       60
ttcctggcgt ttagagaaag ggtgaatgcc tctcgagaag tggagccagt agaacctgaa      120
aactgccacc ttattgagga acttgaaagt ggctctgaag atattgatat acttcctagt      180
gggctggctt ttatctccag tggattaaaa tatccaggca tgccaaactt tgcgccagat      240
gaaccaggaa aaatcttctt gatggatctg aatgaacaaa cccaagggc acaagcacta      300
```

```
gaaatcagtg gtggatttga caaagaatta tttaatccac atgggatcag tattttcatc    360
gacaaagaca atactgtgta tctttatgtt gtgaatcatc cccacatgaa gtccactgtg    420
gagatattta aatttgagga acaacaacgt tctctggtat acctgaaaac tataaaacat    480
gaacttctca aaagtgtgaa tgacattgtg gttcttggac cagaacagtt ctatgccacc    540
agagaccact attttaccaa ctccctcctg tcatttttg agatgatctt ggatcttcgc     600
tggacttatg ttcttttcta cagcccaagg gaggttaaag tggtggccaa aggattttgt    660
agtgccaatg ggatcacagt ctcagcagac cagaagtatg tctatgtagc tgatgtagca    720
gctaagaaca ttcacataat ggaaaaacat gataactggg atttaactca actgaaggtg    780
atacagttgg gcaccttagt ggataacctg actgtcgatc ctgccacagg agacattttg    840
gcaggatgcc atcctaatcc tatgaagcta ctgaactata accctgagga ccctccagga    900
tcagaagtac ttcgcatcca gaatgttttg tctgagaagc ccagggtgag caccgtgtat    960
gccaacaatg gctctgtgct tcagggcacc tctgtggctt ctgtgtacca tgggaaaatt   1020
ctcataggca ccgtatttca caaaactctg tactgtgagc tc                      1062
```

<210> SEQ ID NO 32
<211> LENGTH: 1062
<212> TYPE: DNA
<213> ORGANISM: Mus musculus
<220> FEATURE:
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (56)..(56)
<223> OTHER INFORMATION: n is a, c, g, or t

<400> SEQUENCE: 32

```
atggggcacc tcgtggcgct gcccttgctg ggagcctgtc tggccttaat angggnaagg     60
ctgctgaatt ttagagaacg agttagtaca actcgagaaa taaaggccac agaaccacaa    120
aactgccacc tgattgaggg cctcgagaat ggctctgaag atattgatat acttcctagc    180
gggctggctt ttatctccac tggattaaaa tatccgggca tgccagcgtt tgcaccggac    240
aaaccaggaa gaatctttct gatggatctg aatgagcaaa cccagaggc gcaagcactg    300 gaaatcagtg gtgggcttga ccaggagtca ctaaatcctc acgggatcag cactttcatc    360
gacaaagaca acactgctta tctttatgtc gtgaatcacc ccaacatgga ctccactgtg    420
gagatattta agtttgaaga acaacaacgc tctctcatcc acctgaaaac tctaaaacat    480
gaacttctca agagtgtgaa tgacattgtg gttcttgggc cagagcagtt ctatgccaca    540
agagaccatt actttaccag ttatttcttg gtacttctgg agatgatctt ggaccctcac    600
tggacttccg tcgttttcta cagcccaaaa gaggtcaaag ttgtgcccca aggattcagt    660
tctgccaacg gaatcacagt ctcactagac cagaagtttg tctatgtagc tgatgtaaca    720
gctaagaaca ttcacataat ggaaaaacat gataattggg atttaactcc agtgaaggtc    780
attcagctgg ggaccttagt ggataacctg accgttgctc cagccacggg agatattttg    840
gcaggctgcc accctaaccc catgaagctg ttgatctata atcctgaggg ccctccagga    900
tcagaagtac tacgcatcca ggactctttg tcagataagc ccagggtgag cacactgtat    960
gcgaacaacg gctctgtgct tcagggcagc accgtggctt ctgtgtatca taagagaatg   1020
ctcataggta ctatatttca caaagctctg tactgtgacc tc                      1062
```

-continued

<210> SEQ ID NO 33
<211> LENGTH: 1065
<212> TYPE: DNA
<213> ORGANISM: Oryctolagus cuniculus

<400> SEQUENCE: 33

| | | |
|---|---|---|
| atggctaaac tgacagcgct cacgctcttg gggctgggat tggcactctt cgatggacag | 60 |
| aagtcttctt tccaaacacg atttaatgtt caccgtgaag taactccagt ggaacttcct | 120 |
| aactgtaatt tagttaaagg gattgacaat ggttctgaag acttggaaat actgcccaat | 180 |
| ggactggctt tcatcagctc cggattaaaa tatcctggaa taatgagctt tgaccctgat | 240 |
| aagtctggaa agatacttct aatggacctg aatgaggaag acccagtagt gttggaactg | 300 |
| ggcattactg aagtacatt tgatttatct tcatttaacc ctcatgggat tagcacattc | 360 |
| acagatgaag ataatatcgt ctacctgatg gtggtgaacc atccagattc aaagtccaca | 420 |
| gtggagttgt ttaaattcca agaaaaagaa aaatcacttt tgcatctgaa accatcaga | 480 |
| cacaagcttc tgcctagtgt gaatgacatt gtcgctgtgg gacctgaaca cttttatgct | 540 |
| accaatgatc actatttat tgacccttac ttaaaatcct gggaaatgca tttgggatta | 600 |
| gcgtggtcat tgttactta ttatagtccc aatgatgttc gagtagtggc agaaggattt | 660 |
| gattttgcta acggaatcaa catctcacca gacggcaagt atgtctatat agctgaactg | 720 |
| ctggctcata gatccatgt gtatgaaaag cacgctaatt ggactttaac tccattgaag | 780 |
| tccctcgact ttaacactct tgtggacaac atatccgtgg atcctgtgac aggggacctt | 840 |
| tgggttggtt gtcatcccaa tggcatgcga atcttctact atgacccaaa gaatcctcct | 900 |
| gcatcagagg tgcttcgaat ccaggacatt ttatccaaag agcccaaagt gacagtggct | 960 |
| tatgcagaaa atggcactgt gttacagggc agcacggtgg ccgctgtgta caaagggaaa | 1020 |
| atgctggttg gcaccgtgtt ccacaaagct ctctactgtg agctc | 1065 |

<210> SEQ ID NO 34
<211> LENGTH: 1065
<212> TYPE: DNA
<213> ORGANISM: Mus musculus

<400> SEQUENCE: 34

| | | |
|---|---|---|
| atggcgaagc tgctagcact caccctcgtg ggactggtgt tggcacttta caagaaccat | 60 |
| cggtcttcct atcaaacaag attaaatgct ttccgtgaag taacgccagt agaacttcct | 120 |
| aactgtaatt tagttaaagg aatcgagacg ggtgctgaag acttagagat tctgcctaat | 180 |
| ggactaactt tctttagcac tgggctaaag tatcctggaa taaaaagttt cgatcccagt | 240 |
| aagcctggaa aaatacttct gatggacttg aacaagaagg agccagcagt gtcagagtta | 300 |
| gaaattatag gaaatacatt ggatatatct tcatttaacc ctcatgggat tagtacattc | 360 |
| acagatgaag ataacactgt gtacctactg gtggtaaacc atccagactc ctcgtccact | 420 |
| gtggaggtat ttaaatttca agaagaggaa agatcactct tgcatctgaa accatcaca | 480 |
| catgaacttc tgcctagcat caacgatata gctgctattg gacctgagag cttttatgcc | 540 |
| acaaatgatc actatttggc tgacccatac ttacggtcct gggaaatgta cttgggtctg | 600 |
| tcgtggtcca tgttgtttta ctacagtcca gataaagtcc aggtggtagc agaagggttt | 660 |
| gatttcgcga atggcattgg catttccctt gatggcaagt atgtctatat agctgaattg | 720 |
| ctggctcaca gattcatgt gtatgaaaag catgctaatt ggactttaac accattgaag | 780 |
| gtcctcaact ttgacacct tgtggataac atctctgtgg atcctgtgac aggggacctc | 840 |

| | |
|---|---|
| tgggtgggat gccatcccaa cggaatgagg atcttttttct atgacgcaga gaatcctccc | 900 |
| ggctcagagg tgcttcgaat ccagaacatt ttatccgaag accccaaaat aactgtagtt | 960 |
| tatgcagaga atggtaccgt cctgcaaggc accacggtcg cctctgtgta caaagggaaa | 1020 |
| ctgctgattg cactgtgtt ccacaaagct ctttactgtg atctg | 1065 |

<210> SEQ ID NO 35
<211> LENGTH: 1068
<212> TYPE: DNA
<213> ORGANISM: Rattus norvegicus

<400> SEQUENCE: 35

| | |
|---|---|
| atggcgaaac tgctagggct caccctcgtg ggactggtgt tggcactttta caagaaccat | 60 |
| cggtcttcct atcaaacaag attaaatgct ttccgtgaag taacaccggt agatcttcct | 120 |
| aactgtactt tagttaaagg aatcgaagcg ggtgctgaag acttagagat tctgcctaat | 180 |
| ggactaactt tctttagcac agggttaaag tatcctggaa taaaaagttt cgatcccagt | 240 |
| aagcctggaa aaatacttct gatggacttg aatgagaagg agccagcagt gtcagaatta | 300 |
| gcaattatgg gaaatacgtt ggatatgtct tcatttaacc ctcatgggat tagcacattc | 360 |
| atagatgaag ataacactgt gtacctactg gtggtaagcc acccagactc ctcgtccacc | 420 |
| gtggaggtgt ttaaatttca agaagaggaa agatcacttt tgcatctgaa accatcacc | 480 |
| catgaacttc tgcctagcat caacgatata gctgctgttg acctgagag cttctatgcc | 540 |
| acaaatgatc actattttgc tgacccatac ttacggtcct gggaaatgta cttgggcctg | 600 |
| tcatggtcca atgttgtata ctacagtcca gataaagtcc gagtggtagc agatggattt | 660 |
| gatttcgcta atggcattgg catttccctt gatggcaagt atgtctatat cgctgaattg | 720 |
| ctggctcaca gattcacgt gtatgaaaag catgctaatt ggactttaac gccattgaag | 780 |
| gtcctcagct ttgacaccct tgtggataac atctctgtgg atcctgtgac aggggacctc | 840 |
| tgggttggat gccatcccaa tgggatgagg attttttttct atgactcgga gaatcctcct | 900 |
| ggctcagagg tgcttcggat ccagagcatt ttatccgaag accccaaagt aactgtagtt | 960 |
| tatgcagaga atggcacggt gttgcaaggt acgacagtcg ctgctgtgta caaaggaaaa | 1020 |
| ctgctgattg aacggtgtt ccacagagct ctttgttgtg acctgtga | 1068 |

<210> SEQ ID NO 36
<211> LENGTH: 355
<212> TYPE: PRT
<213> ORGANISM: Homo sapiens

<400> SEQUENCE: 36

Met Ala Lys Leu Ile Ala Leu Thr Leu Leu Gly Met Gly Leu Ala Leu
1               5                   10                  15

Phe Arg Asn His Gln Ser Ser Tyr Gln Thr Arg Leu Asn Ala Leu Arg
                20                  25                  30

Glu Val Gln Pro Val Glu Leu Pro Asn Cys Asn Leu Val Lys Gly Ile
            35                  40                  45

Glu Thr Gly Ser Glu Asp Leu Glu Ile Leu Pro Asn Gly Leu Ala Phe
        50                  55                  60

Ile Ser Ser Gly Leu Lys Tyr Pro Gly Ile Lys Ser Phe Asn Pro Asn
65                  70                  75                  80

Ser Pro Gly Lys Ile Leu Leu Met Asp Leu Asn Glu Glu Asp Pro Thr
                85                  90                  95

Val Leu Glu Leu Gly Ile Thr Gly Ser Lys Phe Asp Val Ser Ser Phe

Asn Pro His Gly Ile Ser Thr Phe Thr Asp Glu Asp Asn Ala Met Tyr
              115                 120                 125

Leu Leu Val Val Asn His Pro Asp Ala Lys Ser Thr Val Glu Leu Phe
    130                 135                 140

Lys Phe Gln Glu Glu Lys Ser Leu Leu His Leu Lys Thr Ile Arg
145                 150                 155                 160

His Lys Leu Leu Pro Asn Leu Asn Asp Ile Val Ala Val Gly Pro Glu
                165                 170                 175

His Phe Tyr Gly Thr Asn Asp His Tyr Phe Leu Asp Pro Tyr Leu Gln
            180                 185                 190

Ser Trp Glu Met Tyr Leu Gly Leu Ala Trp Ser Tyr Val Val Tyr Tyr
        195                 200                 205

Ser Pro Ser Glu Val Arg Val Ala Glu Gly Phe Asp Phe Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asn Thr Leu Val Asp Asn Ile Ser
            260                 265                 270

Val Asp Pro Glu Thr Gly Asp Leu Trp Val Gly Cys His Pro Asn Gly
        275                 280                 285

Met Lys Ile Phe Phe Tyr Asp Ser Glu Asn Pro Pro Ala Ser Glu Val
    290                 295                 300

Leu Arg Ile Gln Asn Ile Leu Thr Glu Glu Pro Lys Val Thr Gln Val
305                 310                 315                 320

Tyr Ala Glu Asn Gly Thr Val Leu Gln Gly Ser Thr Val Ala Ser Val
                325                 330                 335

Tyr Lys Gly Lys Leu Leu Ile Gly Thr Val Phe His Lys Ala Leu Tyr
            340                 345                 350

Cys Glu Leu
        355

<210> SEQ ID NO 37
<211> LENGTH: 355
<212> TYPE: PRT
<213> ORGANISM: Oryctolagus cuniculus

<400> SEQUENCE: 37

Met Ala Lys Leu Thr Ala Leu Thr Leu Leu Gly Leu Gly Leu Ala Leu
1               5                   10                  15

Phe Asp Gly Gln Lys Ser Ser Phe Gln Thr Arg Phe Asn Val His Arg
            20                  25                  30

Glu Val Thr Pro Val Glu Leu Pro Asn Cys Asn Leu Val Lys Gly Ile
        35                  40                  45

Asp Asn Gly Ser Glu Asp Leu Glu Ile Leu Pro Asn Gly Leu Ala Phe
    50                  55                  60

Ile Ser Ser Gly Leu Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Ser Thr Phe Asp Leu Ser Ser Phe
            100                 105                 110

Asn Pro His Gly Ile Ser Thr Phe Thr Asp Glu Asp Asn Ile Val Tyr
            115                 120                 125

Leu Met Val Val Asn His Pro Asp Ser Lys Ser Thr Val Glu Leu Phe
        130                 135                 140

Lys Phe Gln Glu Lys Glu Lys Ser Leu Leu His Leu Lys Thr Ile Arg
145                 150                 155                 160

His Lys Leu Leu Pro Ser Val Asn Asp Ile Ala Val Gly Pro Glu
                165                 170                 175

His Phe Tyr Ala Thr Asn Asp His Tyr Phe Ile Asp Pro Tyr Leu Lys
                180                 185                 190

Ser Trp Glu Met His Leu Gly Leu Ala Trp Ser Phe Val Thr Tyr Tyr
                195                 200                 205

Ser Pro Asn Asp Val Arg Val Val Ala Glu Gly Phe Asp Phe Ala Asn
            210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asn Thr Leu Val Asp Asn Ile Ser
            260                 265                 270

Val Asp Pro Val Thr Gly Asp Leu Trp Val Gly Cys His Pro Asn Gly
    275                 280                 285

Met Arg Ile Phe Tyr Tyr Asp Pro Lys Asn Pro Pro Ala Ser Glu Val
        290                 295                 300

Leu Arg Ile Gln Asp Ile Leu Ser Lys Glu Pro Lys Val Thr Val Ala
305                 310                 315                 320

Tyr Ala Glu Asn Gly Thr Val Leu Gln Gly Ser Thr Val Ala Ala Val
                325                 330                 335

Tyr Lys Gly Lys Met Leu Val Gly Thr Val Phe His Lys Ala Leu Tyr
                340                 345                 350

Cys Glu Leu
        355

<210> SEQ ID NO 38
<211> LENGTH: 355
<212> TYPE: PRT
<213> ORGANISM: Mus musculus

<400> SEQUENCE: 38

Met Ala Lys Leu Leu Ala Leu Thr Leu Val Gly Leu Val Leu Ala Leu
1               5                   10                  15

Tyr Lys Asn His Arg Ser Ser Tyr Gln Thr Arg Leu Asn Ala Phe Arg
                20                  25                  30

Glu Val Thr Pro Val Glu Leu Pro Asn Cys Asn Leu Val Lys Gly Ile
            35                  40                  45

Glu Thr Gly Ala Glu Asp Leu Glu Ile Leu Pro Asn Gly Leu Thr Phe
        50                  55                  60

Phe Ser Thr Gly Leu Lys Tyr Pro Gly Ile Lys Ser Phe Asp Pro Ser
65                  70                  75                  80

Lys Pro Gly Lys Ile Leu Leu Met Asp Leu Asn Lys Lys Glu Pro Ala
                85                  90                  95

Val Ser Glu Leu Glu Ile Ile Gly Asn Thr Leu Asp Ile Ser Ser Phe
            100                 105                 110

Asn Pro His Gly Ile Ser Thr Phe Thr Asp Glu Asp Asn Thr Val Tyr
            115                 120                 125

```
Leu Leu Val Val Asn His Pro Asp Ser Ser Thr Val Glu Val Phe
        130                 135                 140

Lys Phe Gln Glu Glu Arg Ser Leu Leu His Leu Lys Thr Ile Thr
145                 150                 155                 160

His Glu Leu Leu Pro Ser Ile Asn Asp Ile Ala Ala Ile Gly Pro Glu
                165                 170                 175

Ser Phe Tyr Ala Thr Asn Asp His Tyr Leu Ala Asp Pro Tyr Leu Arg
            180                 185                 190

Ser Trp Glu Met Tyr Leu Gly Leu Ser Trp Ser Asn Val Val Tyr Tyr
                195                 200                 205

Ser Pro Asp Lys Val Gln Val Val Ala Glu Gly Phe Asp Phe Ala Asn
        210                 215                 220

Gly Ile Gly Ile Ser Leu Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Val Leu Asn Phe Asp Thr Leu Val Asp Asn Ile Ser
        260                 265                 270

Val Asp Pro Val Thr Gly Asp Leu Trp Val Gly Cys His Pro Asn Gly
    275                 280                 285

Met Arg Ile Phe Phe Tyr Asp Ala Glu Asn Pro Pro Gly Ser Glu Val
290                 295                 300

Leu Arg Ile Gln Asn Ile Leu Ser Glu Asp Pro Lys Ile Thr Val Val
305                 310                 315                 320

Tyr Ala Glu Asn Gly Thr Val Leu Gln Gly Thr Thr Val Ala Ser Val
                325                 330                 335

Tyr Lys Gly Lys Leu Leu Ile Gly Thr Val Phe His Lys Ala Leu Tyr
            340                 345                 350

Cys Asp Leu
        355

<210> SEQ ID NO 39
<211> LENGTH: 355
<212> TYPE: PRT
<213> ORGANISM: Rattus norvegicus

<400> SEQUENCE: 39

Met Ala Lys Leu Leu Gly Leu Thr Leu Val Gly Val Leu Ala Leu
1               5                   10                  15

Tyr Lys Asn His Arg Ser Ser Tyr Gln Thr Arg Leu Asn Ala Phe Arg
                20                  25                  30

Glu Val Thr Pro Val Asp Leu Pro Asn Cys Thr Leu Val Lys Gly Ile
            35                  40                  45

Glu Ala Gly Ala Glu Asp Leu Glu Ile Leu Pro Asn Gly Leu Thr Phe
50                  55                  60

Phe Ser Thr Gly Leu Lys Tyr Pro Gly Ile Lys Ser Phe Asp Pro Ser
65                  70                  75                  80

Lys Pro Gly Lys Ile Leu Leu Met Asp Leu Asn Glu Lys Glu Pro Ala
                85                  90                  95

Val Ser Glu Leu Ala Ile Met Gly Asn Thr Leu Asp Met Ser Ser Phe
            100                 105                 110

Asn Pro His Gly Ile Ser Thr Phe Ile Asp Glu Asp Asn Thr Val Tyr
        115                 120                 125

Leu Leu Val Val Ser His Pro Asp Ser Ser Thr Val Glu Val Phe
```

```
                    130                 135                 140
Lys Phe Gln Glu Glu Arg Ser Leu Leu His Leu Lys Thr Ile Thr
145                 150                 155                 160

His Glu Leu Leu Pro Ser Ile Asn Asp Ile Ala Ala Val Gly Pro Glu
                165                 170                 175

Ser Phe Tyr Ala Thr Asn Asp His Tyr Phe Ala Asp Pro Tyr Leu Arg
                180                 185                 190

Ser Trp Glu Met Tyr Leu Gly Leu Ser Trp Ser Asn Val Val Tyr Tyr
                195                 200                 205

Ser Pro Asp Lys Val Arg Val Val Ala Asp Gly Phe Asp Phe Ala Asn
210                 215                 220

Gly Ile Gly Ile Ser Leu Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Val Leu Ser Phe Asp Thr Leu Val Asp Asn Ile Ser
                260                 265                 270

Val Asp Pro Val Thr Gly Asp Leu Trp Val Gly Cys His Pro Asn Gly
                275                 280                 285

Met Arg Ile Phe Phe Tyr Asp Ser Glu Asn Pro Pro Gly Ser Glu Val
                290                 295                 300

Leu Arg Ile Gln Ser Ile Leu Ser Glu Asp Pro Lys Val Thr Val Val
305                 310                 315                 320

Tyr Ala Glu Asn Gly Thr Val Leu Gln Gly Thr Thr Val Ala Ala Val
                325                 330                 335

Tyr Lys Gly Lys Leu Leu Ile Gly Thr Val Phe His Arg Ala Leu Cys
                340                 345                 350

Cys Asp Leu
        355

<210> SEQ ID NO 40
<211> LENGTH: 354
<212> TYPE: PRT
<213> ORGANISM: Homo sapiens

<400> SEQUENCE: 40

Met Gly Lys Leu Val Ala Leu Val Leu Leu Gly Val Gly Leu Ser Leu
1               5                   10                  15

Val Gly Glu Met Phe Leu Ala Phe Arg Glu Arg Val Asn Ala Ser Arg
                20                  25                  30

Glu Val Glu Pro Val Glu Pro Glu Asn Cys His Leu Ile Glu Glu Leu
                35                  40                  45

Glu Ser Gly Ser Glu Asp Ile Asp Ile Leu Pro Ser Gly Leu Ala Phe
50                  55                  60

Ile Ser Ser Gly Leu Lys Tyr Pro Gly Met Pro Asn Phe Ala Pro Asp
65                  70                  75                  80

Glu Pro Gly Lys Ile Phe Leu Met Asp Leu Asn Glu Gln Asn Pro Arg
                85                  90                  95

Ala Gln Ala Leu Glu Ile Ser Gly Gly Phe Asp Lys Glu Leu Phe Asn
                100                 105                 110

Pro His Gly Ile Ser Ile Phe Ile Asp Lys Asp Asn Thr Val Tyr Leu
                115                 120                 125

Tyr Val Val Asn His Pro His Met Lys Ser Thr Val Glu Ile Phe Lys
                130                 135                 140
```

```
Phe Glu Glu Gln Gln Arg Ser Leu Val Tyr Leu Lys Thr Ile Lys His
145                 150                 155                 160

Glu Leu Leu Lys Ser Val Asn Asp Ile Val Leu Gly Pro Glu Gln
            165                 170                 175

Phe Tyr Ala Thr Arg Asp His Tyr Phe Thr Asn Ser Leu Leu Ser Phe
            180                 185                 190

Phe Glu Met Ile Leu Asp Leu Arg Trp Thr Tyr Val Leu Phe Tyr Ser
            195                 200                 205

Pro Arg Glu Val Lys Val Val Ala Lys Gly Phe Cys Ser Ala Asn Gly
    210                 215                 220

Ile Thr Val Ser Ala Asp Gln Lys Tyr Val Tyr Val Ala Asp Val Ala
225                 230                 235                 240

Ala Lys Asn Ile His Ile Met Glu Lys His Asp Asn Trp Asp Leu Thr
                245                 250                 255

Gln Leu Lys Val Ile Gln Leu Gly Thr Leu Val Asp Asn Leu Thr Val
            260                 265                 270

Asp Pro Ala Thr Gly Asp Ile Leu Ala Gly Cys His Pro Asn Pro Met
    275                 280                 285

Lys Leu Leu Asn Tyr Asn Pro Glu Asp Pro Pro Gly Ser Glu Val Leu
    290                 295                 300

Arg Ile Gln Asn Val Leu Ser Glu Lys Pro Arg Val Ser Thr Val Tyr
305                 310                 315                 320

Ala Asn Asn Gly Ser Val Leu Gln Gly Thr Ser Val Ala Ser Val Tyr
                325                 330                 335

His Gly Lys Ile Leu Ile Gly Thr Val Phe His Lys Thr Leu Tyr Cys
            340                 345                 350

Glu Leu

<210> SEQ ID NO 41
<211> LENGTH: 354
<212> TYPE: PRT
<213> ORGANISM: Oryctolagus cuniculus

<400> SEQUENCE: 41

Met Ala Lys Leu Leu Leu Leu Thr Leu Leu Gly Ala Ser Leu Ala Phe
1               5                   10                  15

Val Gly Glu Arg Leu Leu Ala Phe Arg Asn Ser Phe Gly Ala Val Gln
            20                  25                  30

Glu Leu Glu Pro Val Glu Pro Gln Asn Cys Val Leu Ile Glu Gly Leu
        35                  40                  45

Glu Asn Gly Ser Glu Asp Ile Asp Ile Leu Pro Ser Gly Leu Ala Phe
    50                  55                  60

Ile Ser Ser Gly Leu Lys Tyr Pro Gly Met Pro Asn Phe Ala Pro Asp
65                  70                  75                  80

Glu Pro Gly Lys Ile Phe Leu Ile Asp Met Asn Glu Lys Asn Pro Arg
                85                  90                  95

Ala Gln Glu Leu Glu Ile Ser Asn Gly Phe Glu Lys Glu Ser Phe Asn
            100                 105                 110

Pro His Gly Ile Ser Thr Phe Ile Asp Lys Asp His Thr Val Tyr Leu
        115                 120                 125

Tyr Val Val Asn His Pro His Met Lys Ser Thr Val Glu Ile Phe Lys
    130                 135                 140

Phe Glu Glu Gln Gln Arg Ser Leu Val His Leu Lys Thr Ile Lys His
145                 150                 155                 160
```

```
Glu Leu Leu Lys Ser Val Asn Asn Ile Val Val Gly Pro Glu Gln
                165                 170                 175

Phe Tyr Ala Thr Arg Asp His Tyr Phe Thr Asn Tyr Val Leu Ala Leu
            180                 185                 190

Leu Glu Met Phe Leu Asp Leu His Trp Thr Ser Val Leu Phe Tyr Ser
        195                 200                 205

Pro Lys Glu Val Lys Val Val Ala Lys Gly Phe Ser Ser Ala Asn Gly
    210                 215                 220

Ile Thr Val Ser Leu Asp Lys Lys Tyr Val Tyr Val Ala Asp Ala Thr
225                 230                 235                 240

Ala Lys Asn Val His Val Met Glu Lys His Asp Asn Trp Asp Leu Thr
                245                 250                 255

Glu Leu Lys Val Ile His Leu Asp Thr Leu Val Asp Asn Leu Ser Val
            260                 265                 270

Asp Pro Ala Thr Gly Asp Ile Leu Ala Gly Cys His Pro Asn Gly Met
        275                 280                 285

Lys Leu Leu Asn Tyr Asn Pro Glu Asp Pro Gly Ser Glu Val Leu
    290                 295                 300

Arg Ile Gln Asn Val Leu Ser Glu Lys Pro Arg Val Ser Thr Val Tyr
305                 310                 315                 320

Thr Asn Asp Gly Ser Val Leu Gln Ser Thr Val Ala Ser Val Tyr
                325                 330                 335

Gln Gly Lys Ile Leu Ile Gly Thr Ile Phe His Lys Thr Leu Tyr Cys
            340                 345                 350

Val Leu

<210> SEQ ID NO 42
<211> LENGTH: 354
<212> TYPE: PRT
<213> ORGANISM: Mus musculus
<220> FEATURE:
<221> NAME/KEY: misc_feature
<222> LOCATION: (18)..(19)
<223> OTHER INFORMATION: Xaa can be any naturally occurring amino acid

<400> SEQUENCE: 42

Met Gly His Leu Val Ala Leu Pro Leu Gly Ala Cys Leu Ala Leu
1               5                   10                  15

Ile Xaa Xaa Arg Leu Leu Asn Phe Arg Glu Arg Val Ser Thr Thr Arg
            20                  25                  30

Glu Ile Lys Ala Thr Glu Pro Gln Asn Cys His Leu Ile Glu Gly Leu
        35                  40                  45

Glu Asn Gly Ser Glu Asp Ile Asp Ile Leu Pro Ser Gly Leu Ala Phe
    50                  55                  60

Ile Ser Thr Gly Leu Lys Tyr Pro Gly Met Pro Ala Phe Ala Pro Asp
65                  70                  75                  80

Lys Pro Gly Arg Ile Phe Leu Met Asp Leu Asn Glu Gln Asn Pro Glu
                85                  90                  95

Ala Gln Ala Leu Glu Ile Ser Gly Gly Leu Asp Gln Glu Ser Leu Asn
            100                 105                 110

Pro His Gly Ile Ser Thr Phe Ile Asp Lys Asp Asn Thr Ala Tyr Leu
        115                 120                 125

Tyr Val Val Asn His Pro Asn Met Asp Ser Thr Val Glu Ile Phe Lys
    130                 135                 140

Phe Glu Glu Gln Gln Arg Ser Leu Ile His Leu Lys Thr Leu Lys His
145                 150                 155                 160
```

```
Glu Leu Leu Lys Ser Val Asn Asp Ile Val Val Leu Gly Pro Glu Gln
            165                 170                 175
Phe Tyr Ala Thr Arg Asp His Tyr Phe Thr Ser Tyr Phe Leu Val Leu
        180                 185                 190
Leu Glu Met Ile Leu Asp Pro His Trp Thr Ser Val Val Phe Tyr Ser
    195                 200                 205
Pro Lys Glu Val Lys Val Ala Gln Gly Phe Ser Ser Ala Asn Gly
210                 215                 220
Ile Thr Val Ser Leu Asp Gln Lys Phe Val Tyr Val Ala Asp Val Thr
225                 230                 235                 240
Ala Lys Asn Ile His Ile Met Glu Lys His Asp Asn Trp Asp Leu Thr
            245                 250                 255
Pro Val Lys Val Ile Gln Leu Gly Thr Leu Val Asp Asn Leu Thr Val
        260                 265                 270
Ala Pro Ala Thr Gly Asp Ile Leu Ala Gly Cys His Pro Asn Pro Met
    275                 280                 285
Lys Leu Leu Ile Tyr Asn Pro Glu Gly Pro Gly Ser Glu Val Leu
290                 295                 300
Arg Ile Gln Asp Ser Leu Ser Asp Lys Pro Arg Val Ser Thr Leu Tyr
305                 310                 315                 320
Ala Asn Asn Gly Ser Val Leu Gln Gly Ser Thr Val Ala Ser Val Tyr
            325                 330                 335
His Lys Arg Met Leu Ile Gly Thr Ile Phe His Lys Ala Leu Tyr Cys
        340                 345                 350
Asp Leu
```

<210> SEQ ID NO 43
<211> LENGTH: 1062
<212> TYPE: DNA
<213> ORGANISM: Artificial sequence
<220> FEATURE:
<223> OTHER INFORMATION: In vitro evolved PON variant G1A7

<400> SEQUENCE: 43

```
atggcgaagc tcctgctgct gaccctgctg ggggtcggcc tgtccttagt cggggagagg      60
ttgctggcgt ttagaaacag ctttggtgca gttcaagaac tggagccagt agaaccgcaa     120
aactgccacc tgattgaggg cctcgagaat ggctcgaagg atattgatat acttcctagc     180
gggctggctt ttatctccag tggattaaaa tatccaggca tgccagcgtt tgcaccggac     240
aaaccaggaa gaatctttct gatggatctg aatgagcaaa acccagaggc gcaagcactg     300
gaaatcagtg gtgggcttga ccaggagtca ctaaatcctc acgggatcag cactttcatc     360
gacaaagaca gcactgctta tctttatgtc gtgaatcacc caacatggac tccactgtg      420
gagatattta aatttgagga caacaacgt tctctggtac acatgaaaac tataaaacat      480
gaacttctca gagtgtgaa taacattgtg gttcttggac cggaacagtt ctacgccacc      540
agagaccact attttaccaa ctccctcctg tcattttttg agatgatctt ggaccctcac      600
tggacttccg tcgttttcta cagcccaagg gaggttaaag tggtggccaa aggattcagt      660
tctgccaacg gaatcacagt ctcactagat aagaagtatg tctatgttgc tgatgccaca      720
gctaagaatg tgcatgtaat ggaaaaacat gataactggg atttaactga actgaaggta      780
atacacttgg acaccttagt ggataacttg accgttgatc cagccacggg agatattttg      840
gcaggctgcc accctaaccc catgaagctg ttgatctata accctgagga tcctccaggg      900
```

```
tcagaagtac tacgcatcca ggactctttg tcagataagc ccagggtgag cacactgtat    960
gcgaacaacg gctccgtgct tcagggcacc tctgtggctt ctgtgtacca cggaaaaatt   1020
ctcataggca ctatatttca caaaactctg tactgtgacc tc                      1062

<210> SEQ ID NO 44
<211> LENGTH: 1062
<212> TYPE: DNA
<213> ORGANISM: Artificial sequence
<220> FEATURE:
<223> OTHER INFORMATION: In vitro evolved PON variant G1B11

<400> SEQUENCE: 44
atggcgaagc tcctgctgct gaccctgctg ggagcctgtc tggccttaat aggggaaagg     60
ctgctgaatt ttagagaacg agttagtaca actcgagaaa taaaggccac agaaccacaa    120
aactgccacc tgattgaggg cctcgagaat ggctctgaag atattgatat acttcctagc    180
gggctggctt ttatctccag tggattaaaa tatccaggca tgccaaactt tgcaccagat    240
gaaccaggaa aaatcttctt gatagatatg aatgaacaaa cccaaggggc acaagcacta    300
gaaatcagtg gtggatttga caagaatta tttaatccac atgggatcag cactttcatt    360
gataaagacc atactgtgta tctttatgtt gtgaatcacc ccaacatgga ctccactgtg    420
gagatattta gtttgaaga caacaacac tctctcatcc acctgaaaac tctaaaacat    480
gaacttctca agagtgtgaa tgacattgtg gttcttggac cggaacagtt ctacgccacc    540
agagaccact attttaccaa ctatgtctta gcacttctga gatgttttt ggatcttcgc    600 tggacttccg ttcttttcta cagccccaaa gaggtcaaag tggtggccaa aggattcagt    660
tctgccaatg ggatcacagt ctcactagat aagaagtatg tctatgttgc tgatgccaca    720
gctaagaatg tgcatgtaat ggaaaaacat gacaactggg atttaactga actgaaggtg    780
atacagttgg gcaccttagt ggataacctg actgtcgatc ctgccacagg acacattttg    840
gcaggatgcc atcctaatcc tatgaagctg ttgatctata ccctgaggga ccctccagga    900
tcagaagtac ttcgcatcca ggatgttttg tctgagaagc ccagggtgag caccgtgtat    960
gcgaacaacg gctctgtgct tcagggctcc accgtggctt ctgtgtacca agggaagatt   1020
ctcataggca ctatatttca caaaactctg tattgtgtac tc                      1062

<210> SEQ ID NO 45
<211> LENGTH: 1062
<212> TYPE: DNA
<213> ORGANISM: Artificial sequence
<220> FEATURE:
<223> OTHER INFORMATION: In vitro evolved PON variant G2C2

<400> SEQUENCE: 45
atggcgaagc tcctgctgct gaccctgctg ggggtcggcc tgtccttagt cggggagagg     60
ttgctggcgt ttagaaacag ctttggtgct gttcaagaac tggagccagt agaaccccag    120
aactgtgtcc ttattgaggg actcgaaaat ggctcggaag atattgatat acttcctagc    180
gggctggctt ttatctccac tggattaaaa tatccaggca tgccaaactt tgcaccagat    240
gagccaggaa aaatcttctt gatggatctg aatgaacaaa cccaaggggc acaggcacta    300
gaaatcagtg gtggatttga caagaatta tttaatccac atgggatcag cactttcatt    360
gataaagaca atactgtgta tctttatgtt gtgaatcatc cccacatgga gtccactgtg    420
gagatattta aatttgagga acaacaacac tctctcatcc acctgaaaac tataaaacat    480
gaacttctca aaagtgtgaa tgacattgtg gttcttggac cggaacagtt ctacgccacc    540
```

```
agagaccact attttaccaa ctatgtctta gcacgtcttg agatgatctt ggatcttcgc      600
tggacttatg ttcttttcta cagcccaagg gaggttaaag tggtggccaa aggattcagt      660
tctgccaatg ggatcacagt ctcactagat aagaagtatg tctatgttgc tgatgccaca      720
gctaagaatg tgcatgtaat ggaaaaacat gacaactggg atttaactca actgaaggtg      780
atacagttgg gcaccttagt ggataatttg tctgttgatc ctgccacggg agatatcttg      840
gcaggatgcc atcctaatcc tatgaagcta ctgaactata ccctgagga ccctccagga      900 tcagaagtac ttcgcatcca gaatgttttg tctgagaagc cagggtgag caccgtgtac       960 accaatgacg gctctgtgct tcagggcacc tctgtggctt ctgtgtatca agggaagatt     1020
ctcataggca ctatatttca caaagctctg cactgtgacc tc                        1062

<210> SEQ ID NO 46
<211> LENGTH: 1062
<212> TYPE: DNA
<213> ORGANISM: Artificial sequence
<220> FEATURE:
<223> OTHER INFORMATION: In vitro evolved PON variant G3A5

<400> SEQUENCE: 46
atgggcgaac tcctgctgct gaccctgctg ggggccagcc tcgccttcgt cggggagatg       60
ttcctggcgt ttagagaaag ggtgaatgcc ctcgagaag tggagccagt agaaccccag       120
aactgtgtcc ttattgaggg actcgaaaat ggctcggaag atattgatat acttcctaat      180
gggctggctt ttatctccag tggattaaaa tatccaggca tgccaaactt tgcaccagat      240
gaaccaggaa aaatcttctt gatggatctg aatgaacaaa cccaagagc acaagagctg       300 gaaatcagca tggatttga aaagaatca ttcaatccac atgggatcag cactttcatc        360
gacaaagacc atactgtgta tctttatgtt gtgaatcacc ccaacatgga ctccactgtg      420
gagatattta aatttgagga cgacaacgt tctcttgtgc acctgaaaac tataaaacat       480
gaacttctca aaagtgtgaa tgacattgtg gttcttggac cggaacagtt ctatgccacc      540
agagaccgct attttaccaa ctatgtctta gcacttcttg agatgatttt ggatcctcac      600
tggacttccg tcgtttctca cagcccaaaa gaggtcaaag ttgtggccca aggattcagt      660
tctgccaacg gaatcacagt ctcactagat aagaagtatg tctatgttgc tgatgccaca      720
gctaaaaatg tgcatgtaat ggaaaaacat gacaactggg atttaactcc agtgaaggtc      780
attcagctgg gaaccttagt ggataatttg tctgttgatc ctgccacggg agatatcttg      840
gcaggatgcc atcctaatcc tatgaagcta ctgaactata ccctgagga ccctccagga      900 tcagaagtac ttcgcatccg gaatgttttg tctgagaagc cagggtgag caccgtgtac       960 accaatgacg gctctgtgct tcagggcacc tctgtggctt ctgtgtatca agggaagatt     1020
ctcataggca ctatatttca caaaactctg tattgtgacc tc                         1062

<210> SEQ ID NO 47
<211> LENGTH: 1062
<212> TYPE: DNA
<213> ORGANISM: Artificial sequence
<220> FEATURE:
<223> OTHER INFORMATION: In vitro evolved PON variant G3G3

<400> SEQUENCE: 47
atggcgaagc tcctgctgct gaccctgctg ggggccagcc tcgccttcgt cggggagagg       60
ttgctggcgt ttagagacag ctttggtgca gttcaagaac tggagccagt agaaccccag      120
```

| | |
|---|---|
| aactgtgtcc ttattgaggg actcgaaaat ggctcggaag atattgatat acttcctagt | 180 |
| gggctggctt ttatctccag tggattaaaa tatccaggca tgccaaactt tgcaccagat | 240 |
| gaaccaggaa aaatcttctt gatagatatg aatgagaaga acccaagagc acaggcacta | 300 |
| gaaatcagtg gtggatttga caaagaatca ttcaatccac atgggatcag cactttcatt | 360 |
| gataaagacc atactgtgta tctttatgtt gtgaatcacc ccaacatgga ctccactgtg | 420 |
| gaggtattta aatttgagga acaacaacac tctctcatcc acctgaaaac tataaaacat | 480 |
| gaacttctca aaagtgtgaa tgacattgtg gttcttggac cggaacagtt ctacgccacc | 540 |
| agagaccact attttaccaa ctccctcctg tcattttttg atgatgatct ggatcttcgc | 600 |
| tggacttccg ttcttttcta cagcccaagg gaggttaaag tggtggccaa aggattcagt | 660 |
| tctgccaatg ggatcacagt ctcactagat aaaaagtatg tctatgtagc tgatgtagca | 720 |
| gctaagaaca ttcacataat ggaaaaacat gacaactggg atttaactga actgaaggta | 780 |
| atacacttgg acaccttagt ggataacctg accgttgatc cagccacggg agatattttg | 840 |
| gcaggatgcc atcctaatcc tatgaagcta ctgaactata accctgagga ccctccagga | 900 |
| tcagaagtac tccgtatcca gaatgttttg tctgagaagc ccagggtgag caccgtgtac | 960 |
| gccaacaatg gctctgtgct tcagggcacc tccgtggctt ctgtgtacca cgggaagatt | 1020 |
| ctcataggca ctatatttca caaaactctg tactgtgacc tc | 1062 |

<210> SEQ ID NO 48
<211> LENGTH: 1062
<212> TYPE: DNA
<213> ORGANISM: Artificial sequence
<220> FEATURE:
<223> OTHER INFORMATION: In vitro evolved PON variant G3H9

<400> SEQUENCE: 48

| | |
|---|---|
| atggcgaagc tcctgctgct gaccctgctg ggggtcggcc tgtccttagt cggggagagg | 60 |
| ttgctggcgt ttagaaacag cttcggtgca gttcaagaac tggagtcagt agaaccccag | 120 |
| aactgtgtcc ttattgaggg actcgaaaat ggttcggaag atattgatat acttcctagc | 180 |
| gggctggctt ttatctccag tggattaaaa tatccaggca tgccaaactt tgcaccagat | 240 |
| gaaccaggaa aaatcttctt gatagatatg aatgagaaga acccaagagc acaagagctg | 300 |
| aaaatcagca tggatttga aaagaatca ttcaatccac atgggatcag cactttcatt | 360 |
| gataaagacc atactgtgta tctttatgtt gtgaatcacc ccaacatgga ttccactgtg | 420 |
| gagatattta aatttgagga acaacaacgc tctcttgtac acctgaaaac tataaaacat | 480 |
| gaacttctca aaagtgtgaa tgacattgtg gttcttggac cggaacagtt ctatgccacc | 540 |
| agagaccact attttaccaa ctccctcctg tcattttttg atgatgatct ggatcttcgc | 600 |
| tggacttccg tcgttttcta cagcccaaaa gaggtcaaag tggtggccaa aggattcagt | 660 |
| tctgccaacg gaatcacagt ctcactagat aagaagtatg tctatgttgc tgatgccacg | 720 |
| gctaagaatg tgcatgtaat ggaaaaacat gacaactggg atttaactcc agtgaaggtc | 780 |
| attcagctgg gaaccttagt ggataacttg actgttgatc ctgccacggg agatattttg | 840 |
| gcaggctgcc accctaaccc catgaagcta ctgaactata accctgagga ccctccagga | 900 |
| tcagaagtac ttcgcatcca gaatgttttg tctgagaagc ccagggtgag caccgtgtac | 960 |
| accaatgacg gctctgtgct tcagggcacc tctgtggctt ctgtgtacca agggaagatt | 1020 |
| ctcataggca ctatatttca caaagctctg tactgtgacc tc | 1062 |

```
<210> SEQ ID NO 49
<211> LENGTH: 354
<212> TYPE: PRT
<213> ORGANISM: Artificial sequence
<220> FEATURE:
<223> OTHER INFORMATION: In vitro evolved PON variant G1A7

<400> SEQUENCE: 49

Met Ala Lys Leu Leu Leu Thr Leu Leu Gly Val Gly Leu Ser Leu
1               5                   10                  15

Val Gly Glu Arg Leu Leu Ala Phe Arg Asn Ser Phe Gly Ala Val Gln
            20                  25                  30

Glu Leu Glu Pro Val Glu Pro Gln Asn Cys His Leu Ile Glu Gly Leu
        35                  40                  45

Glu Asn Gly Ser Glu Asp Ile Asp Ile Leu Pro Ser Gly Leu Ala Phe
    50                  55                  60

Ile Ser Ser Gly Leu Lys Tyr Pro Gly Met Pro Ala Phe Ala Pro Asp
65                  70                  75                  80

Lys Pro Gly Arg Ile Phe Leu Met Asp Leu Asn Glu Gln Asn Pro Glu
                85                  90                  95

Ala Gln Ala Leu Glu Ile Ser Gly Gly Leu Asp Gln Glu Ser Leu Asn
            100                 105                 110

Pro His Gly Ile Ser Thr Phe Ile Asp Lys Asp Ser Thr Ala Tyr Leu
        115                 120                 125

Tyr Val Val Asn His Pro Asn Met Asp Ser Thr Val Glu Ile Phe Lys
    130                 135                 140

Phe Glu Glu Gln Gln Arg Ser Leu Val His Met Lys Thr Ile Lys His
145                 150                 155                 160

Glu Leu Leu Lys Ser Val Asn Asn Ile Val Val Leu Gly Pro Glu Gln
                165                 170                 175

Phe Tyr Ala Thr Arg Asp His Tyr Phe Thr Asn Ser Leu Leu Ser Phe
            180                 185                 190

Phe Glu Met Ile Leu Asp Pro His Trp Thr Ser Val Val Phe Tyr Ser
        195                 200                 205

Pro Arg Glu Val Lys Val Ala Lys Gly Phe Ser Ser Ala Asn Gly
    210                 215                 220

Ile Thr Val Ser Leu Asp Lys Lys Tyr Val Tyr Val Ala Asp Ala Thr
225                 230                 235                 240

Ala Lys Asn Val His Val Met Glu Lys His Asp Asn Trp Asp Leu Thr
                245                 250                 255

Glu Leu Lys Val Ile His Leu Asp Thr Leu Val Asp Asn Leu Thr Val
            260                 265                 270

Asp Pro Ala Thr Gly Asp Ile Leu Ala Gly Cys His Pro Asn Pro Met
        275                 280                 285

Lys Leu Leu Ile Tyr Asn Pro Glu Asp Pro Pro Gly Ser Glu Val Leu
    290                 295                 300

Arg Ile Gln Asp Ser Leu Ser Asp Lys Pro Arg Val Ser Thr Leu Tyr
305                 310                 315                 320

Ala Asn Asn Gly Ser Val Leu Gln Gly Thr Ser Val Ala Ser Val Tyr
                325                 330                 335

His Gly Lys Ile Leu Ile Gly Thr Ile Phe His Lys Thr Leu Tyr Cys
            340                 345                 350

Asp Leu

<210> SEQ ID NO 50
```

<211> LENGTH: 354
<212> TYPE: PRT
<213> ORGANISM: Artificial sequence
<220> FEATURE:
<223> OTHER INFORMATION: In vitro evolved PON variant G1B11

<400> SEQUENCE: 50

```
Met Ala Lys Leu Leu Leu Thr Leu Leu Gly Ala Cys Leu Ala Leu
1               5                   10                  15

Ile Gly Glu Arg Leu Leu Asn Phe Arg Glu Arg Val Ser Thr Thr Arg
            20                  25                  30

Glu Ile Lys Ala Thr Glu Pro Gln Asn Cys His Leu Ile Glu Gly Leu
        35                  40                  45

Glu Asn Gly Ser Glu Asp Ile Asp Ile Leu Pro Ser Gly Leu Ala Phe
    50                  55                  60

Ile Ser Ser Gly Leu Lys Tyr Pro Gly Met Pro Asn Phe Ala Pro Asp
65                  70                  75                  80

Glu Pro Gly Lys Ile Phe Leu Ile Asp Met Asn Glu Gln Asn Pro Arg
                85                  90                  95

Ala Gln Ala Leu Glu Ile Ser Gly Gly Phe Asp Lys Glu Leu Phe Asn
            100                 105                 110

Pro His Gly Ile Ser Thr Phe Ile Asp Lys Asp His Thr Val Tyr Leu
        115                 120                 125

Tyr Val Val Asn His Pro Asn Met Asp Ser Thr Val Glu Ile Phe Lys
130                 135                 140

Phe Glu Glu Gln Gln His Ser Leu Ile His Leu Lys Thr Leu Lys His
145                 150                 155                 160

Glu Leu Leu Lys Ser Val Asn Asp Ile Val Val Leu Gly Pro Glu Gln
                165                 170                 175

Phe Tyr Ala Thr Arg Asp His Tyr Phe Thr Asn Tyr Val Leu Ala Leu
            180                 185                 190

Leu Lys Met Phe Leu Asp Leu Arg Trp Thr Ser Val Leu Phe Tyr Ser
        195                 200                 205

Pro Lys Glu Val Lys Val Val Ala Lys Gly Phe Ser Ser Ala Asn Gly
    210                 215                 220

Ile Thr Val Ser Leu Asp Lys Lys Tyr Val Tyr Val Ala Asp Ala Thr
225                 230                 235                 240

Ala Lys Asn Val His Val Met Glu Lys His Asp Asn Trp Asp Leu Thr
                245                 250                 255

Glu Leu Lys Val Ile Gln Leu Gly Thr Leu Val Asp Asn Leu Thr Val
            260                 265                 270

Asp Pro Ala Thr Gly Asp Ile Leu Ala Gly Cys His Pro Asn Pro Met
        275                 280                 285

Lys Leu Leu Ile Tyr Asn Pro Glu Asp Pro Pro Gly Ser Glu Val Leu
    290                 295                 300

Arg Ile Gln Asp Val Leu Ser Glu Lys Pro Arg Val Ser Thr Val Tyr
305                 310                 315                 320

Ala Asn Asn Gly Ser Val Leu Gln Gly Ser Thr Val Ala Ser Val Tyr
                325                 330                 335

Gln Gly Lys Ile Leu Ile Gly Thr Ile Phe His Lys Thr Leu Tyr Cys
            340                 345                 350

Val Leu
```

<210> SEQ ID NO 51
<211> LENGTH: 354

```
<212> TYPE: PRT
<213> ORGANISM: Artificial sequence
<220> FEATURE:
<223> OTHER INFORMATION: In vitro evolved PON variant G2C2

<400> SEQUENCE: 51

Met Ala Lys Leu Leu Leu Thr Leu Gly Val Gly Leu Ser Leu
1               5                   10                  15

Val Gly Glu Arg Leu Leu Ala Phe Arg Asn Ser Phe Gly Ala Val Gln
            20                  25                  30

Glu Leu Glu Pro Val Glu Pro Gln Asn Cys Val Leu Ile Glu Gly Leu
        35                  40                  45

Glu Asn Gly Ser Glu Asp Ile Asp Ile Leu Pro Ser Gly Leu Ala Phe
    50                  55                  60

Ile Ser Thr Gly Leu Lys Tyr Pro Gly Met Pro Asn Phe Ala Pro Asp
65                  70                  75                  80

Glu Pro Gly Lys Ile Phe Leu Met Asp Leu Asn Glu Gln Asn Pro Arg
                85                  90                  95

Ala Gln Ala Leu Glu Ile Ser Gly Gly Phe Asp Lys Glu Leu Phe Asn
            100                 105                 110

Pro His Gly Ile Ser Thr Phe Ile Asp Lys Asp Asn Thr Val Tyr Leu
        115                 120                 125

Tyr Val Val Asn His Pro His Met Glu Ser Thr Val Glu Ile Phe Lys
130                 135                 140

Phe Glu Glu Gln Gln His Ser Leu Ile His Leu Lys Thr Ile Lys His
145                 150                 155                 160

Glu Leu Leu Lys Ser Val Asn Asp Ile Val Val Leu Gly Pro Glu Gln
                165                 170                 175

Phe Tyr Ala Thr Arg Asp His Tyr Phe Thr Asn Tyr Val Leu Ala Arg
            180                 185                 190

Leu Glu Met Ile Leu Asp Leu Arg Trp Thr Tyr Val Leu Phe Tyr Ser
        195                 200                 205

Pro Arg Glu Val Lys Val Val Ala Lys Gly Phe Ser Ser Ala Asn Gly
210                 215                 220

Ile Thr Val Ser Leu Asp Lys Lys Tyr Val Tyr Val Ala Asp Ala Thr
225                 230                 235                 240

Ala Lys Asn Val His Val Met Glu Lys His Asp Asn Trp Asp Leu Thr
                245                 250                 255

Gln Leu Lys Val Ile Gln Leu Gly Thr Leu Val Asp Asn Leu Ser Val
            260                 265                 270

Asp Pro Ala Thr Gly Asp Ile Leu Ala Gly Cys His Pro Asn Pro Met
        275                 280                 285

Lys Leu Leu Asn Tyr Asn Pro Glu Asp Pro Pro Gly Ser Glu Val Leu
    290                 295                 300

Arg Ile Gln Asn Val Leu Ser Glu Lys Pro Arg Val Ser Thr Val Tyr
305                 310                 315                 320

Thr Asn Asp Gly Ser Val Leu Gln Gly Thr Ser Val Ala Ser Val Tyr
                325                 330                 335

Gln Gly Lys Ile Leu Ile Gly Thr Ile Phe His Lys Ala Leu His Cys
            340                 345                 350

Asp Leu

<210> SEQ ID NO 52
<211> LENGTH: 354
<212> TYPE: PRT
```

<213> ORGANISM: Artificial sequence
<220> FEATURE:
<223> OTHER INFORMATION: In vitro evolved PON variant G3A5

<400> SEQUENCE: 52

```
Met Gly Glu Leu Leu Leu Thr Leu Leu Gly Ala Ser Leu Ala Phe
1               5                   10                  15

Val Gly Glu Met Phe Leu Ala Phe Arg Glu Arg Val Asn Ala Ser Arg
            20                  25                  30

Glu Val Glu Pro Val Glu Pro Gln Asn Cys Val Leu Ile Glu Gly Leu
            35                  40                  45

Glu Asn Gly Ser Glu Asp Ile Asp Ile Leu Pro Asn Gly Leu Ala Phe
50                  55                  60

Ile Ser Ser Gly Leu Lys Tyr Pro Gly Met Pro Asn Phe Ala Pro Asp
65                  70                  75                  80

Glu Pro Gly Lys Ile Phe Leu Met Asp Leu Asn Glu Gln Asn Pro Arg
                85                  90                  95

Ala Gln Glu Leu Glu Ile Ser Asn Gly Phe Glu Lys Glu Ser Phe Asn
            100                 105                 110

Pro His Gly Ile Ser Thr Phe Ile Asp Lys Asp His Thr Val Tyr Leu
            115                 120                 125

Tyr Val Val Asn His Pro Asn Met Asp Ser Thr Val Glu Ile Phe Lys
130                 135                 140

Phe Glu Glu Arg Gln Arg Ser Leu Val His Leu Lys Thr Ile Lys His
145                 150                 155                 160

Glu Leu Leu Lys Ser Val Asn Asp Ile Val Leu Gly Pro Glu Gln
                165                 170                 175

Phe Tyr Ala Thr Arg Asp Arg Tyr Phe Thr Asn Tyr Val Leu Ala Leu
            180                 185                 190

Leu Glu Met Ile Leu Asp Pro His Trp Thr Ser Val Phe Tyr Ser
            195                 200                 205

Pro Lys Glu Val Lys Val Ala Gln Gly Phe Ser Ser Ala Asn Gly
            210                 215                 220

Ile Thr Val Ser Leu Asp Lys Lys Tyr Val Tyr Val Ala Asp Ala Thr
225                 230                 235                 240

Ala Lys Asn Val His Val Met Glu Lys His Asp Asn Trp Asp Leu Thr
            245                 250                 255

Pro Val Lys Val Ile Gln Leu Gly Thr Leu Val Asp Asn Leu Ser Val
            260                 265                 270

Asp Pro Ala Thr Gly Asp Ile Leu Ala Gly Cys His Pro Asn Pro Met
            275                 280                 285

Lys Leu Leu Asn Tyr Asn Pro Glu Asp Pro Pro Gly Ser Glu Val Leu
            290                 295                 300

Arg Ile Arg Asn Val Leu Ser Glu Lys Pro Arg Val Ser Thr Val Tyr
305                 310                 315                 320

Thr Asn Asp Gly Ser Val Leu Gln Gly Thr Val Ala Ser Val Tyr
                325                 330                 335

Gln Gly Lys Ile Leu Ile Gly Thr Ile Phe His Lys Thr Leu Tyr Cys
            340                 345                 350

Asp Leu
```

<210> SEQ ID NO 53
<211> LENGTH: 354
<212> TYPE: PRT
<213> ORGANISM: Artificial sequence
<220> FEATURE:
<223> OTHER INFORMATION: In vitro evolved PON variant G3G3

<400> SEQUENCE: 53

Met Ala Lys Leu Leu Leu Thr Leu Gly Ala Ser Leu Ala Phe
1               5                   10                  15

Val Gly Glu Arg Leu Leu Ala Phe Arg Asp Ser Phe Gly Ala Val Gln
            20                  25                  30

Glu Leu Glu Pro Val Glu Pro Gln Asn Cys Val Leu Ile Glu Gly Leu
        35                  40                  45

Glu Asn Gly Ser Glu Asp Ile Asp Ile Leu Pro Ser Gly Leu Ala Phe
    50                  55                  60

Ile Ser Ser Gly Leu Lys Tyr Pro Gly Met Pro Asn Phe Ala Pro Asp
65                  70                  75                  80

Glu Pro Gly Lys Ile Phe Leu Ile Asp Met Asn Glu Lys Asn Pro Arg
                85                  90                  95

Ala Gln Ala Leu Glu Ile Ser Gly Gly Phe Asp Lys Glu Ser Phe Asn
            100                 105                 110

Pro His Gly Ile Ser Thr Phe Ile Asp Lys Asp His Thr Val Tyr Leu
        115                 120                 125

Tyr Val Val Asn His Pro Asn Met Asp Ser Thr Val Glu Val Phe Lys
    130                 135                 140

Phe Glu Glu Gln Gln His Ser Leu Ile His Leu Lys Thr Ile Lys His
145                 150                 155                 160

Glu Leu Leu Lys Ser Val Asn Asp Ile Val Val Leu Gly Pro Glu Gln
                165                 170                 175

Phe Tyr Ala Thr Arg Asp His Tyr Phe Thr Asn Ser Leu Leu Ser Phe
            180                 185                 190

Phe Glu Met Ile Leu Asp Leu Arg Trp Thr Ser Val Leu Phe Tyr Ser
        195                 200                 205

Pro Arg Glu Val Lys Val Ala Lys Gly Phe Ser Ser Ala Asn Gly
    210                 215                 220

Ile Thr Val Ser Leu Asp Lys Lys Tyr Val Tyr Val Ala Asp Val Ala
225                 230                 235                 240

Ala Lys Asn Ile His Ile Met Glu Lys His Asp Asn Trp Asp Leu Thr
                245                 250                 255

Glu Leu Lys Val Ile His Leu Asp Thr Leu Val Asp Asn Leu Thr Val
            260                 265                 270

Asp Pro Ala Thr Gly Asp Ile Leu Ala Gly Cys His Pro Asn Pro Met
        275                 280                 285

Lys Leu Leu Asn Tyr Asn Pro Glu Asp Pro Pro Gly Ser Glu Val Leu
    290                 295                 300

Arg Ile Gln Asn Val Leu Ser Glu Lys Pro Arg Val Ser Thr Val Tyr
305                 310                 315                 320

Ala Asn Asn Gly Ser Val Leu Gln Gly Thr Ser Val Ala Ser Val Tyr
                325                 330                 335

His Gly Lys Ile Leu Ile Gly Thr Ile Phe His Lys Thr Leu Tyr Cys
            340                 345                 350

Asp Leu

<210> SEQ ID NO 54
<211> LENGTH: 354
<212> TYPE: PRT
<213> ORGANISM: Artificial sequence
<220> FEATURE:

<223> OTHER INFORMATION: In vitro evolved PON variant G3H9

<400> SEQUENCE: 54

Met Ala Lys Leu Leu Leu Thr Leu Leu Gly Val Gly Leu Ser Leu
1               5                   10                  15

Val Gly Glu Arg Leu Leu Ala Phe Arg Asn Ser Phe Gly Ala Val Gln
            20                  25                  30

Glu Leu Glu Ser Val Glu Pro Gln Asn Cys Val Leu Ile Glu Gly Leu
        35                  40                  45

Glu Asn Gly Ser Glu Asp Ile Asp Ile Leu Pro Ser Gly Leu Ala Phe
    50                  55                  60

Ile Ser Ser Gly Leu Lys Tyr Pro Gly Met Pro Asn Phe Ala Pro Asp
65                  70                  75                  80

Glu Pro Gly Lys Ile Phe Leu Ile Asp Met Asn Glu Lys Asn Pro Arg
                85                  90                  95

Ala Gln Glu Leu Lys Ile Ser Asn Gly Phe Glu Lys Glu Ser Phe Asn
            100                 105                 110

Pro His Gly Ile Ser Thr Phe Ile Asp Lys Asp His Thr Val Tyr Leu
        115                 120                 125

Tyr Val Val Asn His Pro Asn Met Asp Ser Thr Val Glu Ile Phe Lys
130                 135                 140

Phe Glu Glu Gln Gln Arg Ser Leu Val His Leu Lys Thr Ile Lys His
145                 150                 155                 160

Glu Leu Leu Lys Ser Val Asn Asp Ile Val Val Leu Gly Pro Glu Gln
                165                 170                 175

Phe Tyr Ala Thr Arg Asp His Tyr Phe Thr Asn Ser Leu Leu Ser Phe
            180                 185                 190

Phe Glu Met Ile Leu Asp Leu Arg Trp Thr Ser Val Val Phe Tyr Ser
        195                 200                 205

Pro Lys Glu Val Lys Val Val Ala Lys Gly Phe Ser Ser Ala Asn Gly
    210                 215                 220

Ile Thr Val Ser Leu Asp Lys Lys Tyr Val Tyr Val Ala Asp Ala Thr
225                 230                 235                 240

Ala Lys Asn Val His Val Met Glu Lys His Asp Asn Trp Asp Leu Thr
                245                 250                 255

Pro Val Lys Val Ile Gln Leu Gly Thr Leu Val Asp Asn Leu Thr Val
            260                 265                 270

Asp Pro Ala Thr Gly Asp Ile Leu Ala Gly Cys His Pro Asn Pro Met
        275                 280                 285

Lys Leu Leu Asn Tyr Asn Pro Glu Asp Pro Pro Gly Ser Glu Val Leu
    290                 295                 300

Arg Ile Gln Asn Val Leu Ser Glu Lys Pro Arg Val Ser Thr Val Tyr
305                 310                 315                 320

Thr Asn Asp Gly Ser Val Leu Gln Gly Thr Ser Val Ala Ser Val Tyr
                325                 330                 335

Gln Gly Lys Ile Leu Ile Gly Thr Ile Phe His Lys Ala Leu Tyr Cys
            340                 345                 350

Asp Leu

<210> SEQ ID NO 55
<211> LENGTH: 1065
<212> TYPE: DNA
<213> ORGANISM: Artificial sequence
<220> FEATURE:
<223> OTHER INFORMATION: In vitro evolved PON variant G3C9

<400> SEQUENCE: 55

```
atggctaaac tgacagcgct cacactcttg gggctgggat tggcactctt cgatggacag      60
aagtcttctt tccaaacacg atttaatgtt caccgtgaag taactccagt ggaacttcct     120
aactgtaatt tagttaaagg ggttgacaat ggttctgaag acttggaaat actgcccaat     180
ggactggctt tcatcagctc cggattaaag tatcctggaa taatgagctt tgaccctgat     240
aagtctggaa agatacttct aatggacctg aatgaggaag acccagtagt gttggaactg     300
ggcattactg gaaatacatt ggatatatct tcatttaacc ctcatgggat tagcacattc     360
acagatgaag ataacactgt gtacctactg gtggtaaacc atccagactc ctcgtccacc     420
gtggaggtgt ttaaatttca agaagaagaa aaatcacttt tgcatctgaa aaccatcaga     480
cacaagcttc tgcctagtgt gaatgacatt gtcgctgtgg acctgaaca cttttatgcc      540
acaaatgatc actatttgc tgaccctta ctaaaatcct gggaaatgca tttgggatta       600
gcgtggtcat ttgttactta ttatagtccc aatgatgttc gagtagtggc agaaggattt     660
gattttgcta acggaatcaa catctcacca gacggcaagt atgtctatat agctgagttg     720
ctggctcata agatccatgt gtatgaaaag cacgctaatt ggactttaac tccattgaag     780
tccctcgact ttgacaccct tgtggataac atctctgtgg atcctgtgac aggggacctc     840
tgggtgggat gccatcccaa cggaatgcga atcttctact atgacccaaa gaatcctccc     900
ggctcagagg tgcttcgaat ccaggacatt ttatccgaag agcccaaagt gacagtggtt     960
tatgcagaaa atggcactgt gttacagggc agcacggtgg ccgctgtgta caaagggaaa    1020
ctgctgattg gcacagtgtt tcacaaagct ctttactgtg agctg                    1065
```

<210> SEQ ID NO 56
<211> LENGTH: 355
<212> TYPE: PRT
<213> ORGANISM: Artificial sequence
<220> FEATURE:
<223> OTHER INFORMATION: In vitro evolved PON variant G3C9

<400> SEQUENCE: 56

```
Met Ala Lys Leu Thr Ala Leu Thr Leu Leu Gly Leu Gly Leu Ala Leu
  1               5                  10                  15

Phe Asp Gly Gln Lys Ser Ser Phe Gln Thr Arg Phe Asn Val His Arg
                 20                  25                  30

Glu Val Thr Pro Val Glu Leu Pro Asn Cys Asn Leu Val Lys Gly Val
             35                  40                  45

Asp Asn Gly Ser Glu Asp Leu Glu Ile Leu Pro Asn Gly Leu Ala Phe
         50                  55                  60

Ile Ser Ser Gly Leu Lys Tyr Pro Gly Ile Met Ser Phe Asp Pro Asp
 65                  70                  75                  80

Lys Ser Gly Lys Ile Leu Leu Met Asp Leu Asn Glu Glu Asp Pro Val
                 85                  90                  95

Val Leu Glu Leu Gly Ile Thr Gly Asn Thr Leu Asp Ile Ser Ser Phe
            100                 105                 110

Asn Pro His Gly Ile Ser Thr Phe Thr Asp Glu Asp Asn Thr Val Tyr
        115                 120                 125

Leu Leu Val Val Asn His Pro Asp Ser Ser Thr Val Glu Val Phe
    130                 135                 140

Lys Phe Gln Glu Glu Glu Lys Ser Leu Leu His Leu Lys Thr Ile Arg
145                 150                 155                 160
```

His Lys Leu Leu Pro Ser Val Asn Asp Ile Val Ala Val Gly Pro Glu
            165                 170                 175

His Phe Tyr Ala Thr Asn Asp His Tyr Phe Ala Asp Pro Tyr Leu Lys
        180                 185                 190

Ser Trp Glu Met His Leu Gly Leu Ala Trp Ser Phe Val Thr Tyr Tyr
    195                 200                 205

Ser Pro Asn Asp Val Arg Val Ala Glu Gly Phe Asp Phe Ala Asn
210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
            245                 250                 255

Thr Pro Leu Lys Ser Leu Asp Phe Asp Thr Leu Val Asp Asn Ile Ser
        260                 265                 270

Val Asp Pro Val Thr Gly Asp Leu Trp Val Gly Cys His Pro Asn Gly
    275                 280                 285

Met Arg Ile Phe Tyr Tyr Asp Pro Lys Asn Pro Pro Gly Ser Glu Val
290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Thr Val Ala Ala Val
            325                 330                 335

Tyr Lys Gly Lys Leu Leu Ile Gly Thr Val Phe His Lys Ala Leu Tyr
        340                 345                 350

Cys Glu Leu
    355

<210> SEQ ID NO 57
<211> LENGTH: 355
<212> TYPE: PRT
<213> ORGANISM: Artificial sequence
<220> FEATURE:
<223> OTHER INFORMATION: In vitro evolved PON variant G1A5

<400> SEQUENCE: 57

Met Ala Lys Leu Thr Ala Leu Thr Leu Leu Gly Leu Gly Leu Ala Leu
1               5                   10                  15

Phe Asp Gly Gln Lys Ser Ser Phe Gln Thr Arg Phe Asn Val His Arg
            20                  25                  30

Glu Val Thr Pro Val Glu Leu Pro Asn Cys Asn Leu Val Lys Gly Ile
        35                  40                  45

Asp Asn Gly Ser Glu Asp Leu Glu Ile Leu Pro Asn Gly Leu Ala Phe
    50                  55                  60

Ile Ser Ser Gly Leu Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
            85                  90                  95

Val Leu Glu Leu Gly Ile Thr Gly Asn Thr Leu Asp Ile Ser Ser Phe
        100                 105                 110

Asn Pro His Gly Ile Ser Thr Phe Ile Asp Glu Asp Asn Thr Val Tyr
    115                 120                 125

Leu Leu Val Val Asn His Pro Asp Ser Ser Ser Thr Val Glu Val Phe
130                 135                 140

Lys Phe Gln Glu Lys Glu Lys Ser Leu Leu His Leu Lys Thr Ile Arg
145                 150                 155                 160

His Lys Leu Leu Pro Ser Val Asn Asp Ile Val Ala Val Gly Pro Glu
            165                 170                 175

His Phe Tyr Ala Thr Asn Asp His Tyr Phe Ile Asp Pro Tyr Leu Lys
            180                 185                 190

Ser Trp Glu Met His Leu Gly Leu Ala Trp Ser Phe Val Thr Tyr Tyr
            195                 200                 205

Ser Pro Asn Asp Val Arg Val Ala Glu Gly Phe Asp Phe Ala Asn
            210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
            245                 250                 255

Thr Pro Leu Lys Ser Leu Asp Phe Asn Thr Leu Val Asp Asn Ile Ser
            260                 265                 270

Val Asp Pro Val Thr Gly Asp Leu Trp Val Gly Cys His Pro Asn Gly
            275                 280                 285

Met Arg Ile Phe Tyr Tyr Asp Pro Glu Asn Pro Pro Gly Ser Glu Val
            290                 295                 300

Leu Arg Ile Gln Asn Ile Leu Ser Lys Glu Pro Lys Val Thr Val Val
305                 310                 315                 320

Tyr Ala Glu Asn Gly Thr Val Leu Gln Gly Thr Thr Val Ala Ser Val
            325                 330                 335

Tyr Lys Gly Lys Leu Leu Ile Gly Thr Val Phe His Lys Ala Leu Tyr
            340                 345                 350

Cys Glu Leu
        355

<210> SEQ ID NO 58
<211> LENGTH: 355
<212> TYPE: PRT
<213> ORGANISM: Artificial sequence
<220> FEATURE:
<223> OTHER INFORMATION: In vitro evolved PON variant G1C4

<400> SEQUENCE: 58

Met Ala Lys Leu Leu Ala Leu Thr Leu Val Gly Leu Gly Leu Ala Leu
1               5                   10                  15

Phe Asp Gly Gln Lys Ser Ser Phe Gln Thr Arg Phe Asn Val His Arg
            20                  25                  30

Glu Val Thr Pro Val Glu Leu Pro Asn Cys Asn Leu Val Lys Gly Ile
            35                  40                  45

Glu Thr Gly Ala Glu Asp Leu Glu Ile Leu Pro Asn Gly Leu Ala Phe
50                  55                  60

Ile Ser Ser Gly Leu Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
            85                  90                  95

Val Leu Glu Leu Gly Ile Thr Gly Ser Thr Phe Asp Leu Ser Ser Phe
            100                 105                 110

Asn Pro His Gly Ile Ser Thr Phe Thr Asp Glu Asp Asn Thr Val Tyr
            115                 120                 125

Leu Leu Val Val Asn His Pro Asp Ser Ser Ser Thr Val Glu Val Phe
130                 135                 140

Lys Phe Gln Glu Lys Glu Lys Ser Leu Leu His Leu Lys Thr Ile Arg
145                 150                 155                 160

```
His Lys Leu Leu Pro Ser Val Asn Asp Ile Val Ala Val Gly Pro Glu
            165                 170                 175

His Phe Tyr Ala Thr Asn Asp His Tyr Phe Ile Asp Pro Tyr Leu Lys
        180                 185                 190

Ser Trp Glu Met His Leu Gly Leu Ala Trp Ser Phe Val Thr Tyr Tyr
        195                 200                 205

Ser Pro Asn Asp Val Arg Val Ala Glu Gly Phe Asp Phe Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asn Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Phe Tyr Tyr Asp Pro Lys Asn Pro Pro Ala Ser Glu Val
        290                 295                 300

Leu Arg Ile Gln Asp Ile Leu Ser Glu Asp Pro Lys Ile Thr Val Val
305                 310                 315                 320

Tyr Ala Glu Asn Gly Thr Val Leu Gln Gly Thr Thr Val Ala Ser Val
                325                 330                 335

Tyr Lys Gly Lys Leu Leu Ile Gly Thr Val Phe His Lys Ala Leu Tyr
            340                 345                 350

Cys Asp Leu
        355

<210> SEQ ID NO 59
<211> LENGTH: 355
<212> TYPE: PRT
<213> ORGANISM: Artificial sequence
<220> FEATURE:
<223> OTHER INFORMATION: In vitro evolved PON variant G2D6

<400> SEQUENCE: 59

Met Ala Lys Leu Thr Ala Leu Thr Leu Leu Gly Leu Gly Leu Ala Leu
1               5                   10                  15

Phe Asp Arg Gln Lys Ser Ser Phe Gln Thr Arg Phe Asn Val His Arg
            20                  25                  30

Glu Val Thr Pro Val Glu Leu Pro Asn Cys Asn Leu Val Lys Gly Ile
        35                  40                  45

Asp Asn Gly Ser Glu Asp Leu Glu Ile Leu Pro Asn Gly Leu Ala Phe
    50                  55                  60

Ile Ser Ser Gly Leu Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Ser Thr Phe Asp Leu Ser Ser Phe
            100                 105                 110

Asn Pro His Gly Ile Ser Thr Phe Thr Asp Glu Asp Asn Thr Val Tyr
        115                 120                 125

Leu Leu Val Val Asn His Pro Asp Ser Ser Ser Thr Val Glu Val Phe
    130                 135                 140

Lys Phe Gln Glu Lys Glu Arg Ser Leu Leu His Leu Lys Thr Ile Arg
145                 150                 155                 160
```

```
His Lys Leu Leu Pro Ser Val Asn Asp Ile Val Ala Val Gly Pro Glu
                165                 170                 175
Ser Phe Tyr Ala Thr Asn Asp His Tyr Phe Ala Asp Pro Tyr Leu Lys
            180                 185                 190
Ser Trp Glu Met His Leu Gly Leu Ala Trp Ser Phe Val Thr Tyr Tyr
        195                 200                 205
Ser Pro Asn Asp Val Arg Val Ala Glu Gly Phe Asp Phe Ala Asn
    210                 215                 220
Gly Ile Asn Ile Ser Pro Asp Gly Lys Tyr Val Tyr Ile Ala Glu Leu
225                 230                 235                 240
Leu Ala His Lys Ile His Val Tyr Glu Lys His Ala Asn Trp Thr Leu
                245                 250                 255
Thr Pro Leu Lys Ser Leu Asp Phe Asn Thr Leu Val Asp Asn Ile Ser
            260                 265                 270
Val Asp Pro Val Thr Gly Asp Leu Trp Val Gly Cys His Pro Asn Gly
        275                 280                 285
Met Arg Ile Phe Tyr Tyr Asp Pro Glu Asn Pro Pro Gly Ser Glu Val
    290                 295                 300
Leu Arg Ile Gln Asp Ile Leu Ser Lys Glu Pro Lys Val Thr Val Val
305                 310                 315                 320
Tyr Ala Glu Asn Gly Thr Val Leu Gln Gly Ser Thr Val Ala Ala Val
                325                 330                 335
Tyr Lys Gly Lys Leu Leu Ile Gly Thr Val Phe His Lys Ala Leu Tyr
            340                 345                 350
Cys Asp Leu
        355

<210> SEQ ID NO 60
<211> LENGTH: 355
<212> TYPE: PRT
<213> ORGANISM: Artificial sequence
<220> FEATURE:
<223> OTHER INFORMATION: In vitro evolved PON variant G2E6

<400> SEQUENCE: 60

Met Ala Lys Leu Thr Ala Leu Thr Leu Leu Gly Met Gly Leu Ala Leu
1               5                   10                  15
Phe Asp Arg Gln Lys Ser Ser Phe Gln Thr Arg Phe Asn Val His Arg
            20                  25                  30
Glu Val Thr Pro Val Glu Leu Pro Asn Cys Asn Leu Val Lys Gly Ile
        35                  40                  45
Asp Asn Gly Ser Glu Asp Leu Glu Ile Leu Pro Asn Gly Leu Ala Phe
    50                  55                  60
Ile Ser Ser Gly Leu Lys Tyr Pro Gly Ile Met Ser Phe Asp Pro Asp
65                  70                  75                  80
Lys Ser Gly Lys Ile Leu Leu Met Asp Leu Asn Glu Lys Glu Pro Ala
                85                  90                  95
Val Ser Glu Leu Glu Ile Ile Gly Asn Thr Leu Asp Ile Ser Ser Phe
            100                 105                 110
Asn Pro His Gly Ile Ser Thr Phe Ile Asp Asp Asn Thr Val Tyr
        115                 120                 125
Leu Leu Val Val Asn His Pro Gly Ser Ser Ser Thr Val Glu Val Phe
    130                 135                 140
Lys Phe Gln Glu Glu Glu Lys Ser Leu Leu His Leu Lys Thr Ile Arg
145                 150                 155                 160
```

```
His Lys Leu Leu Pro Ser Val Asn Asp Ile Val Ala Val Gly Pro Glu
            165                 170                 175

His Phe Tyr Ala Thr Asn Asp His Tyr Phe Ile Asp Pro Tyr Leu Lys
            180                 185                 190

Ser Trp Glu Met His Leu Gly Leu Ala Trp Ser Phe Val Thr Tyr Tyr
            195                 200                 205

Ser Pro Asn Asp Val Arg Val Ala Glu Gly Phe Asp Phe Ala Asn
            210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Arg Val Leu Ser Phe Asp Thr Leu Val Asp Asn Ile Ser
            260                 265                 270

Val Asp Pro Val Thr Gly Asp Leu Trp Val Gly Cys His Pro Asn Gly
            275                 280                 285

Met Arg Ile Phe Phe Tyr Asp Ala Glu Asn Pro Pro Gly Ser Glu Val
            290                 295                 300

Leu Arg Ile Gln Asp Ile Leu Ser Glu Pro Lys Val Thr Val Val
305                 310                 315                 320

Tyr Ala Glu Asn Gly Thr Val Leu Gln Gly Ser Thr Val Ala Ala Val
                325                 330                 335

Tyr Lys Gly Lys Leu Leu Ile Gly Thr Val Phe His Lys Ala Leu Tyr
            340                 345                 350

Cys Asp Leu
        355

<210> SEQ ID NO 61
<211> LENGTH: 355
<212> TYPE: PRT
<213> ORGANISM: Artificial sequence
<220> FEATURE:
<223> OTHER INFORMATION: In vitro evolved PON variant G3H8

<400> SEQUENCE: 61

Met Ala Lys Leu Thr Ala Pro Thr Leu Leu Gly Leu Gly Leu Ala Leu
1               5                   10                  15

Phe Asp Arg Gln Lys Ser Ser Phe Gln Thr Arg Phe Asn Val His Arg
            20                  25                  30

Glu Val Thr Pro Val Glu Leu Pro Asn Cys Asn Leu Val Lys Gly Ile
            35                  40                  45

Asp Asn Gly Ser Glu Asp Leu Glu Ile Leu Pro Asn Gly Leu Ala Phe
50                  55                  60

Ile Ser Ser Gly Leu Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Ser Thr Phe Asp Leu Ser Ser Phe
            100                 105                 110

Asn Pro His Gly Ile Ser Thr Phe Thr Asp Glu Asp Asn Thr Val Tyr
            115                 120                 125

Leu Leu Val Val Asn His Pro Asp Ser Ser Ser Thr Val Glu Val Phe
130                 135                 140

Lys Phe Gln Glu Lys Glu Arg Ser Leu Leu His Leu Lys Thr Ile Arg
145                 150                 155                 160
```

```
His Lys Leu Leu Pro Ser Val Asn Asp Ile Val Ala Val Gly Pro Glu
            165                 170                 175
Ser Phe Tyr Ala Thr Asn Asp His Tyr Phe Ala Asp Pro Tyr Leu Lys
        180                 185                 190
Ser Trp Glu Met His Leu Gly Leu Ala Trp Ser Phe Val Thr Tyr Tyr
    195                 200                 205
Ser Pro Asn Asp Val Arg Val Ala Glu Gly Phe Asp Phe Ala Asn
    210                 215                 220
Gly Ile Asn Ile Ser Pro Asp Gly Lys Tyr Val Tyr Ile Ala Glu Leu
225                 230                 235                 240
Leu Ala His Lys Ile His Val Tyr Glu Lys His Ala Asn Trp Thr Leu
                245                 250                 255
Thr Pro Leu Lys Ser Leu Asp Phe Asn Thr Leu Val Asp Asn Ile Ser
            260                 265                 270
Val Asp Pro Val Thr Gly Asp Leu Trp Val Gly Cys His Pro Asn Gly
        275                 280                 285
Met Arg Ile Phe Tyr Tyr Asp Pro Glu Asn Pro Gly Ser Glu Val
    290                 295                 300
Leu Arg Ile Gln Asp Ile Leu Ser Lys Glu Pro Lys Val Thr Val Val
305                 310                 315                 320
Tyr Ala Glu Asn Gly Thr Val Leu Gln Gly Ser Thr Val Ala Ala Val
                325                 330                 335
Tyr Lys Gly Lys Leu Leu Ile Gly Thr Val Phe His Lys Ala Leu Tyr
            340                 345                 350
Cys Asp Leu
        355

<210> SEQ ID NO 62
<211> LENGTH: 1065
<212> TYPE: DNA
<213> ORGANISM: Artificial sequence
<220> FEATURE:
<223> OTHER INFORMATION: In vitro evolved PON variant G3C9.10

<400> SEQUENCE: 62
atggctaaac tgacagcgct cacactcttg gggctgggat tggcactctt cgatggacag      60
aagtcttctt tccaaacacg atttaatgtt caccgtgaag taactccagt ggaacttcct     120
aactgtaatt tagttaaagg ggttgacaat ggttctgaag acttggaaat actgcccaat     180
ggactggctt tcatcagctc cggagtaaag tatcctggaa taatgagctt gaccctgat      240 aagtctggaa agatacttct aatggacctg aatgaggaag acccagtagt gttggaactg     300
ggcattactg gaaatacatt ggatatatct tcatttaacc ctcatgggat tagcacattc     360
acggatgaag ataacactgt gtacctactg gtggtaaacc atccagactc ctcgtccacc     420
gtggaggtgt ttaaatttca agaagaagaa aaatcacttt tgcatctgaa accatcaga      480 cacaagcttc tgcctagtgt gaatgacatt gtcgctgtgg acctgaaca cttttatgcc      540 acaaatgatc actattttgc tgacccttac ttaaaatcct gggaaatgca tttgggatta     600
gcgtggtcat tgttacttta ttatagcccc aatgatgttc gagtagtggc agacggattt     660
gattttgcta acggaatcaa catctcacca gacggcaagt atgtctatat agctgagttg     720
ctggctcata gatccatgt gtatgaaaag cacgctaatt ggactttaac tccattgaag     780
tccctcgact tgacaccct tgtggataac atctctgtgg atcctgtgac agggacctc      840 tgggtgggat gccatcccaa cggaatgcga atcttctact atgacccaaa gaatcctccc     900
```

-continued

```
ggctcagagg tgcttcgaat ccaggacatt ttatccgaag agcccaaagt gacagtggtt      960
tatgcagaaa atggcactgt gttacagggc agcacggtgg ccgctgtgta caaagggaaa     1020
ctgctgattg gcacagtgtt tcacaaagct ctttactgtg agctg                     1065
```

<210> SEQ ID NO 63
<211> LENGTH: 355
<212> TYPE: PRT
<213> ORGANISM: Artificial sequence
<220> FEATURE:
<223> OTHER INFORMATION: In vitro evolved PON variant G3C9.10

<400> SEQUENCE: 63

```
Met Ala Lys Leu Thr Ala Leu Thr Leu Leu Gly Leu Gly Leu Ala Leu
1               5                   10                  15

Phe Asp Gly Gln Lys Ser Ser Phe Gln Thr Arg Phe Asn Val His Arg
                20                  25                  30

Glu Val Thr Pro Val Glu Leu Pro Asn Cys Asn Leu Val Lys Gly Val
            35                  40                  45

Asp Asn Gly Ser Glu Asp Leu Glu Ile Leu Pro Asn Gly Leu Ala Phe
        50                  55                  60

Ile Ser Ser Gly Val Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro His Gly Ile Ser Thr Phe Thr Asp Glu Asp Asn Thr Val Tyr
        115                 120                 125

Leu Leu Val Val Asn His Pro Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Asp Gly Phe Asp Phe Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Phe Tyr Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Thr Val Ala Ala Val
                325                 330                 335
```

Tyr Lys Gly Lys Leu Leu Ile Gly Thr Val Phe His Lys Ala Leu Tyr
            340                 345                 350

Cys Glu Leu
        355

<210> SEQ ID NO 64
<211> LENGTH: 1065
<212> TYPE: DNA
<213> ORGANISM: Artificial sequence
<220> FEATURE:
<223> OTHER INFORMATION: In vitro evolved PON variant G3C9.49

<400> SEQUENCE: 64

```
atggctaaac tgacagcgct cacactcttg gggctgggat tggcactctt cgatagacag      60
aagtcttctt tccaaacacg atttaatgtt caccgtgaag taactccagt ggaacttcct     120
aactgtaatt tagttaaagg ggttgacaat ggttctgaag acttggaaat actgcccaat     180
ggactggctt tcatcagctc cggattaaag tatcctggaa taatgagctt tgaccctgat     240
aagtctggaa agatacttct aatggacctg aatgaggaag acccagtagt gttggaactg     300
ggcattactg gaaatacatt ggatatatct tcatttaacc ctcatgggat tagcacattc     360
acagacgaag ataacactgt gtatctactg gtggtaaacc atccagactc ctcgtccacc     420
gtggaggtgt ttaaatttca agaagaagaa aaatcacttt tgcatctgaa accatcaga     480
cacaagcttc tgcctagtgt gaatgacatt gtcgctgtgg acctgaaca cttttatgcc     540
acaaatgatc actattttgc tgaccttac ttaaaaccct gggaaatgca tttgggatta     600
gcgtggtcat tgttactta ctatagtccc aatgatgttc gagtagtggc agaaggattt     660
gattttgcta acggaatcaa catctcacca gacggcaagt atgtctatat agctgagttg     720
ctggctcata gatccatgt gtatgaaaag cacgctaatt ggactttaac tccattgaag     780
tccctcgact ttgacaccct tgtggataac atctctgtgg atcctgtgac agggacctc     840
tgggtgggat gccatcccga cggaatgcga atcttctact atgacccaaa gaatcctccc     900
ggctcagagg tgcttcgaat ccaggacatt ttatccgaag agcccaaagt gacagtggtg     960
tatgcagaaa atggcactgt gttacagggc agcacggtgg ccgctgtgta caaagggaaa    1020
ctgctgattg gcacagcgtt tcacaaagct ctttactgtg agctg                    1065
```

<210> SEQ ID NO 65
<211> LENGTH: 355
<212> TYPE: PRT
<213> ORGANISM: Artificial sequence
<220> FEATURE:
<223> OTHER INFORMATION: In vitro evolved PON variant G3C9.49

<400> SEQUENCE: 65

Met Ala Lys Leu Thr Ala Leu Thr Leu Leu Gly Leu Gly Leu Ala Leu
1               5                   10                  15

Phe Asp Arg Gln Lys Ser Ser Phe Gln Thr Arg Phe Asn Val His Arg
                20                  25                  30

Glu Val Thr Pro Val Glu Leu Pro Asn Cys Asn Leu Val Lys Gly Val
            35                  40                  45

Asp Asn Gly Ser Glu Asp Leu Glu Ile Leu Pro Asn Gly Leu Ala Phe
        50                  55                  60

Ile Ser Ser Gly Leu Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

```
Val Leu Glu Leu Gly Ile Thr Gly Asn Thr Leu Asp Ile Ser Ser Phe
            100                 105                 110

Asn Pro His Gly Ile Ser Thr Phe Thr Asp Glu Asp Asn Thr Val Tyr
            115                 120                 125

Leu Leu Val Val Asn His Pro Asp Ser Ser Thr Val Glu Val Phe
130                 135                 140

Lys Phe Gln Glu Glu Lys Ser Leu Leu His Leu Lys Thr Ile Arg
145                 150                 155                 160

His Lys Leu Leu Pro Ser Val Asn Asp Ile Ala Val Gly Pro Glu
                165                 170                 175

His Phe Tyr Ala Thr Asn Asp His Tyr Phe Ala Asp Pro Tyr Leu Lys
            180                 185                 190

Pro Trp Glu Met His Leu Gly Leu Ala Trp Ser Phe Thr Tyr Tyr
            195                 200                 205

Ser Pro Asn Asp Val Arg Val Val Ala Glu Gly Phe Asp Phe Ala Asn
210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asp Gly
            275                 280                 285

Met Arg Ile Phe Tyr Tyr Asp Pro Lys Asn Pro Pro Gly Ser Glu Val
            290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Thr Val Ala Ala Val
                325                 330                 335

Tyr Lys Gly Lys Leu Leu Ile Gly Thr Ala Phe His Lys Ala Leu Tyr
            340                 345                 350

Cys Glu Leu
        355

<210> SEQ ID NO 66
<211> LENGTH: 1065
<212> TYPE: DNA
<213> ORGANISM: Artificial sequence
<220> FEATURE:
<223> OTHER INFORMATION: In vitro evolved PON variant 7PC

<400> SEQUENCE: 66
atggctaaac tgacagcgct cacactcttg gggctgggat tggcactctt cgatggacag      60
aagtcttctt ccaaacacg atttaatgtt caccgtgaag taactccagt ggaacttcct     120
aactgtaatt tagttaaagg ggtcgacaat ggttctgaag acttggaaat actgcccaat     180
ggactggctt tcatcagctc cggattaaag tatcctggaa taatgagctt tgaccctgat     240
aagtctggaa agatacttct aatggacctg aatgaggaag acccagtagt gttggaactg     300
ggcattactg gaaatacatt ggatatatct tcatttaacc ctcatgggat tagcacattc     360
acagatgaag ataacactgt gtacctactg gtggtaaacc atccagactc ctcgtccacc     420
gtggaggtgt ttaaatttca agaagaagaa aaatcacttt tgcatctgaa aaccatcaga     480
cacaagcttc tgcctagtgt gaatgacatt gtcgctgtgg gacctgaaca ctttatgcc     540
```

```
acaaatgatc actattttgc tgacccttac ttaaaatcct gggaaatgca tttgggatta    600
gcgtggtcat ttgttactta ttatagtccc aatgatgttc gagtagtggc agaaggattt    660
gattttgcta acggaatcaa catctcacca gacggcaagt atgtctatat agctgagttg    720
ctggctcata agatccatgt gtatgaaaag cacgctaatt ggactttaac tccattgaag    780
tccctcgact ttgacaccct tgtggataac atctctgtgg atcctgtgac aggggacctc    840
tgggtgggat gccatcccaa cggaatgcga atcttctact atgacccaaa gaatcctccc    900
ggctcagagg tgcttcgaat ccaggacatt ttatccgaag agcccaaagt gacagtggtt    960
tatgcagaaa atggcactgt gttacagggc agcacggtgg ccgctgtgta caagggaaa    1020 ctgctgattg gcacagtgtt tcacaaagct ctttactgtg agctg                   1065
```

<210> SEQ ID NO 67
<211> LENGTH: 355
<212> TYPE: PRT
<213> ORGANISM: Artificial sequence
<220> FEATURE:
<223> OTHER INFORMATION: In vitro evolved PON variant 7PC

<400> SEQUENCE: 67

```
Met Ala Lys Leu Thr Ala Leu Thr Leu Leu Gly Leu Gly Leu Ala Leu
1               5                   10                  15

Phe Asp Gly Gln Lys Ser Ser Phe Gln Thr Arg Phe Asn Val His Arg
            20                  25                  30

Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Leu Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro His Gly Ile Ser Thr Phe Thr Asp Glu Asp Asn Thr Val Tyr
        115                 120                 125

Leu Leu Val Val Asn His Pro Asp Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Phe Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270
```

```
Val Asp Pro Val Thr Gly Asp Leu Trp Val Gly Cys His Pro Asn Gly
        275                 280                 285

Met Arg Ile Phe Tyr Tyr Asp Pro Lys Asn Pro Pro Gly Ser Glu Val
        290                 295                 300

Leu Arg Ile Gln Asp Ile Leu Ser Glu Pro Lys Val Thr Val Val
305                 310                 315                 320

Tyr Ala Glu Asn Gly Thr Val Leu Gln Gly Ser Thr Val Ala Ala Val
                325                 330                 335

Tyr Lys Gly Lys Leu Leu Ile Gly Thr Ala Phe His Lys Ala Leu Tyr
        340                 345                 350

Cys Glu Leu
        355

<210> SEQ ID NO 68
<211> LENGTH: 1065
<212> TYPE: DNA
<213> ORGANISM: Artificial sequence
<220> FEATURE:
<223> OTHER INFORMATION: In vitro evolved PON variant 4PC

<400> SEQUENCE: 68
atggctaaac tgacagcgct cacactcttg gggctgggat tggcactctt cgatggacag      60
aagtcttctt tccaaacacg atttaatgtt caccgtgaag taactccagt ggaacttcct     120
aactgtaatt tagttaaagg ggttgacaat ggttctgaag acttggaaat actgcccaat     180
ggactggctt tcatcagctc cggagtaaag tatcctggaa taatgagctt tgaccctgat     240
aagtctggaa agatacttct aatggacctg aatgaggaag acccagtagt gttggaactg     300
ggcattactg gaaatacatt ggatatatct tcatttaacc ctcatgggat tagcacattc     360
acagatgaag ataacactgt gtacctactg gtggtaaacc atccagactc ctcgtccacc     420
gtggaggtgt ttaaatttca agaagaagaa aaatcacttt tgcatctgaa accatcaga     480 cacaagcttc tgcctagtgt gaatgacatt gtcgctgtgg gacctgaaca cttttatgcc     540
acaaatgatc actattttgc tgacccttac ttaaaaccct gggaaatgca tttgggatta     600
gcgtggtcat ttgttactta ttatagtccc aatgatgttc gagtagtggc agaaggattt     660
gattttgcta acggaatcaa catctcacca gacggcaagt atgtctatat agctgagttg     720
ctggctcata gatccatgt gtatgaaaag cacgctaatt ggactttaac tccattgaag     780
tccctcgact tgacaccct tgtggataac atttctgtgg atcctgtgac aggggacctc     840
tgggtgggat gccatcccaa cggaatgcga atcttctact atgacccaaa gaatcctccc     900
ggctcagagg tgcttcgaat ccaggacatt ttatccgaag agcccaaagt gacagtggtt     960
tatgcagaaa atggcactgt gttacagggc agcacggtgg ccgctgtgta caagggaaa    1020 ctgctgattg gcacagcgtt tcacaaagct ctttactgtg agctg                   1065

<210> SEQ ID NO 69
<211> LENGTH: 355
<212> TYPE: PRT
<213> ORGANISM: Artificial sequence
<220> FEATURE:
<223> OTHER INFORMATION: In vitro evolved PON variant 4PC

<400> SEQUENCE: 69

Met Ala Lys Leu Thr Ala Leu Thr Leu Leu Gly Leu Gly Leu Ala Leu
1               5                   10                  15

Phe Asp Gly Gln Lys Ser Ser Phe Gln Thr Arg Phe Asn Val His Arg
```

```
                20                  25                  30
Glu Val Thr Pro Val Glu Leu Pro Asn Cys Asn Leu Val Lys Gly Val
            35                  40                  45
Asp Asn Gly Ser Glu Asp Leu Glu Ile Leu Pro Asn Gly Leu Ala Phe
        50                  55                  60
Ile Ser Ser Gly Val Lys Tyr Pro Gly Ile Met Ser Phe Asp Pro Asp
65                  70                  75                  80
Lys Ser Gly Lys Ile Leu Leu Met Asp Leu Asn Glu Glu Asp Pro Val
                85                  90                  95
Val Leu Glu Leu Gly Ile Thr Gly Asn Thr Leu Asp Ile Ser Ser Phe
            100                 105                 110
Asn Pro His Gly Ile Ser Thr Phe Thr Asp Glu Asp Asn Thr Val Tyr
        115                 120                 125
Leu Leu Val Val Asn His Pro Asp Ser Ser Thr Val Glu Val Phe
    130                 135                 140
Lys Phe Gln Glu Glu Glu Lys Ser Leu Leu His Leu Lys Thr Ile Arg
145                 150                 155                 160
His Lys Leu Leu Pro Ser Val Asn Asp Ile Val Ala Val Gly Pro Glu
                165                 170                 175
His Phe Tyr Ala Thr Asn Asp His Tyr Phe Ala Asp Pro Tyr Leu Lys
            180                 185                 190
Pro Trp Glu Met His Leu Gly Leu Ala Trp Ser Phe Val Thr Tyr Tyr
        195                 200                 205
Ser Pro Asn Asp Val Arg Val Val Ala Glu Gly Phe Asp Phe Ala Asn
    210                 215                 220
Gly Ile Asn Ile Ser Pro Asp Gly Lys Tyr Val Tyr Ile Ala Glu Leu
225                 230                 235                 240
Leu Ala His Lys Ile His Val Tyr Glu Lys His Ala Asn Trp Thr Leu
                245                 250                 255
Thr Pro Leu Lys Ser Leu Asp Phe Asp Thr Leu Val Asp Asn Ile Ser
            260                 265                 270
Val Asp Pro Val Thr Gly Asp Leu Trp Val Gly Cys His Pro Asn Gly
        275                 280                 285
Met Arg Ile Phe Tyr Tyr Asp Pro Lys Asn Pro Pro Gly Ser Glu Val
    290                 295                 300
Leu Arg Ile Gln Asp Ile Leu Ser Glu Glu Pro Lys Val Thr Val Val
305                 310                 315                 320
Tyr Ala Glu Asn Gly Thr Val Leu Gln Gly Ser Thr Val Ala Ala Val
                325                 330                 335
Tyr Lys Gly Lys Leu Leu Ile Gly Thr Ala Phe His Lys Ala Leu Tyr
            340                 345                 350
Cys Glu Leu
        355

<210> SEQ ID NO 70
<211> LENGTH: 1065
<212> TYPE: DNA
<213> ORGANISM: Artificial sequence
<220> FEATURE:
<223> OTHER INFORMATION: In vitro evolved PON variant 1HT

<400> SEQUENCE: 70
atggctaaac tgacagcgct cacactcttg gggctgggat tggcactctt cgatggacag      60
aagtcttctt tccaaacacg atttaatgtt caccgtgaag taactccagt ggaacttcct     120
```

```
aactgtaatt tagttaaagg ggttgacaat ggttctgaag acttggaaat actgcccaat      180
ggactggctt tcatcagctc cggattaaag tatcctggaa taatgagctt tgaccctgat      240
aagtctggaa agatacttct aatggacctg aatgaggaag acccagtagt gttggaactg      300
ggcattactg gaaatacatt ggatatatct tcatttaacc ctcatgggat tagcacattc      360
acagatgaag ataacactgt gtacctactg gtggtaaacc atccagactc ctcgtccacc      420
gtggaggtgt ttaaatttca agaagaagaa aaatcacttt tgcatctgaa accatcaga       480 cacaagcttc tgcctagtgt gaatgacatt gtcgctgtgg gacctgaaca cttttatgcc      540
acaaatgatc actattttgc tgacccttac ttaaaatcct gggaaatgca tttgggatta      600
gcgtggtcat tgttacttta ttatagtccc aatgatgttc gagtagtggc agaaggattt      660
gattttgcta acggaatcaa catctcacca gacggcaagt atgtctatat agctgagttg      720
ctggctcata agatccatgt gtatgaaaag cacgctaatt ggactttaac tccattgaag      780
tccctcgact ttgacaccct tgtggataac atctctgtgg atcctgtgac aggggacctc      840
tgggtgggat gccatcccaa cggaatgcga ctcttctact atgacccaaa gaatcctccc      900
ggctcagagg tgcttcgaat ccaggacatt ttatccgaag agcccaaagt gacagtggtt      960
tatgcagaaa atggcactgt gttacagggc agcgcggtgg ccgctgtgta caagagaaa     1020 ctgctgattg gcacagtgtt tcacaaagct ctttactgtg agctg                     1065
```

<210> SEQ ID NO 71
<211> LENGTH: 355
<212> TYPE: PRT
<213> ORGANISM: Artificial sequence
<220> FEATURE:
<223> OTHER INFORMATION: In vitro evolved PON variant 1HT

<400> SEQUENCE: 71

```
Met Ala Lys Leu Thr Ala Leu Thr Leu Leu Gly Leu Gly Leu Ala Leu
1               5                   10                  15

Phe Asp Gly Gln Lys Ser Ser Phe Gln Thr Arg Phe Asn Val His Arg
            20                  25                  30

Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Leu Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro His Gly Ile Ser Thr Phe Thr Asp Glu Asp Asn Thr Val Tyr
        115                 120                 125

Leu Leu Val Val Asn His Pro Asp Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
```

```
                195                 200                 205
Ser Pro Asn Asp Val Arg Val Val Ala Glu Gly Phe Asp Phe Ala Asn
    210                 215                 220
Gly Ile Asn Ile Ser Pro Asp Gly Lys Tyr Val Tyr Ile Ala Glu Leu
225                 230                 235                 240
Leu Ala His Lys Ile His Val Tyr Glu Lys His Ala Asn Trp Thr Leu
                245                 250                 255
Thr Pro Leu Lys Ser Leu Asp Phe Asp Thr Leu Val Asp Asn Ile Ser
            260                 265                 270
Val Asp Pro Val Thr Gly Asp Leu Trp Val Gly Cys His Pro Asn Gly
        275                 280                 285
Met Arg Leu Phe Tyr Tyr Asp Pro Lys Asn Pro Pro Gly Ser Glu Val
    290                 295                 300
Leu Arg Ile Gln Asp Ile Leu Ser Glu Pro Lys Val Thr Val Val
305                 310                 315                 320
Tyr Ala Glu Asn Gly Thr Val Leu Gln Gly Ser Ala Val Ala Ala Val
                325                 330                 335
Tyr Lys Glu Lys Leu Leu Ile Gly Thr Val Phe His Lys Ala Leu Tyr
            340                 345                 350
Cys Glu Leu
        355

<210> SEQ ID NO 72
<211> LENGTH: 1065
<212> TYPE: DNA
<213> ORGANISM: Artificial sequence
<220> FEATURE:
<223> OTHER INFORMATION: In vitro evolved PON variant 2AC

<400> SEQUENCE: 72
atggctaaac tgacagcgct cacactcttg gggctgggat tggcactctt cgatggacag      60
aagtcttctt tccaaacacg atttaatgct caccgtgaag taactccagt ggaacttcct     120
aactgtaatt tagttaaagg ggttgacaat ggttctgaag acttggaaat actgcccaat     180
ggactggctt tcatcagctc cggattaaag tatcctggaa taatgagctt tgaccctgat     240
aagtctggaa agatacttct aatggacctg aatgaggaag acccagtagt gttggaactg     300
ggcattactg gaaatacatt ggatatatct tcatttaacc ctcatgggat tagcacattc     360
acagatgaag ataacactgt gtacctactg gtggtaaacc atccagactc ctcgtccacc     420
gtggaggtgt ttaaatttca agaagaagaa aaatcacttt tgcatctgaa accatcaga      480
cacaagcttc tgcctagtgt gaatgacatt gtcgctgtgg gacctgaaca ctttatgcc      540
acaaatgatc actattttgc tgaccttac ttaaaatcct gggaaatgca tttgggatta      600
gcgtggtcat ttgttactta ttatagtccc aatgatgttc gagtagtggc agaaggattt      660
gattttgcta acggaatcaa catctcacca gacggcaagt atgtctatat agctgagttg      720
ctggctcata gatccatgt gtataaaaag cacgctaatt ggactttaac tccattgaag     780
tccctcgact ttgacaccct tgtggataac atctctgtgg atcctgtgac aggggacctc     840
tgggtgggat gccatcccaa cggaatgcga atctcctact atgacccaaa gaatcctccc     900
ggctcagagg tgcttcgaat ccaggacatt ttatccgaag agcccaaagt gacagtggtt     960
tatgcagaaa atggcactgt gttacagggc agcacggtgg ccgctgtgta caagggaaa    1020
ctgctgattg gcacaatgtt tcacaaagct ctttactgtg agctg                    1065
```

```
<210> SEQ ID NO 73
<211> LENGTH: 355
<212> TYPE: PRT
<213> ORGANISM: Artificial sequence
<220> FEATURE:
<223> OTHER INFORMATION: In vitro evolved PON variant 2AC

<400> SEQUENCE: 73

Met Ala Lys Leu Thr Ala Leu Thr Leu Leu Gly Leu Gly Leu Ala Leu
1               5                   10                  15

Phe Asp Gly Gln Lys Ser Ser Phe Gln Thr Arg Phe Asn Ala His Arg
                20                  25                  30

Glu Val Thr Pro Val Glu Leu Pro Asn Cys Asn Leu Val Lys Gly Val
            35                  40                  45

Asp Asn Gly Ser Glu Asp Leu Glu Ile Leu Pro Asn Gly Leu Ala Phe
        50                  55                  60

Ile Ser Ser Gly Leu Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro His Gly Ile Ser Thr Phe Thr Asp Glu Asp Asn Thr Val Tyr
        115                 120                 125

Leu Leu Val Val Asn His Pro Asp Ser Ser Ser Thr Val Glu Val Phe
130                 135                 140

Lys Phe Gln Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Phe Ala Asn
210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Lys Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Ser Tyr Tyr Asp Pro Lys Asn Pro Pro Gly Ser Glu Val
290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Thr Val Ala Ala Val
                325                 330                 335

Tyr Lys Gly Lys Leu Leu Ile Gly Thr Ala Phe His Lys Ala Leu Tyr
            340                 345                 350

Cys Glu Leu
        355
```

<210> SEQ ID NO 74
<211> LENGTH: 1065
<212> TYPE: DNA
<213> ORGANISM: Artificial sequence
<220> FEATURE:
<223> OTHER INFORMATION: In vitro evolved PON variant 7HY

<400> SEQUENCE: 74

```
atggctaaac tgacagcgct cacactcttg gggctgggat tggcactctt cgatggacag    60
aagtcttctt tccaaacacg atttaatgtt caccgtgaag taactccagt ggaacttcct   120
aactgtaatt tagttaaagg ggttgacaat ggttctgaag acttggaaat actgcccaat   180
ggactggctt tcatcagctc cggattaaag tatcctggaa taatgagctt tgaccctgat   240
aagtctggaa agatacttct aatggacctg aatgaggaag acccagtagt gttggaactg   300
ggcattactg gaaatacatt ggatatgtct tcatttaacc ctcatgggat tagcacattc   360
acagatgaag ataacactgt gtacctactg gtggtaaacc atccagactc ctcgtccacc   420
gtggaggtgt ttaaatttca agaagaagaa aaatcacttt tgcatctgaa aaccatcaga   480
cacaagcttc tgcctagtgt gaatgacatt gtcgctgtgg acctgaaca cttttatgcc   540
acaaatgatc actattttgc tgacccttac ttaaaatcct gggaaatgca tttgggatta   600
gcgtggtcat ttgttactta ttatagtccc aatgatgttc gagtagtggc agaaggattt   660
gattttgcta acggaatcaa catctcacca gacggcaagt atgtctatat agctgagttg   720
ctggctcata gatccatgt gtatgaaaag cacgctaatt ggactttaac tccattgaag   780
tccctcgact ttgacaccct tgtggataac atctctgtgg atcctgtgac aggggacctc   840
tgggtgggat gccatcccaa cggaatgcga atcgtcgact atgacccaaa gaatcctccc   900
ggctcagagg tgcttcgaat ccaggacatt ttatccgaag agcccaaagt gacagtggtt   960
tatgcagaaa atggcactgt gttacagggc agcacggtgg ccgctgtgta caagggaaa  1020
ctgctgattg gcacagtgtt tcacaaagct ctttactgtg agctg              1065
```

<210> SEQ ID NO 75
<211> LENGTH: 355
<212> TYPE: PRT
<213> ORGANISM: Artificial sequence
<220> FEATURE:
<223> OTHER INFORMATION: In vitro evolved PON variant 7HY

<400> SEQUENCE: 75

```
Met Ala Lys Leu Thr Ala Leu Thr Leu Leu Gly Leu Gly Leu Ala Leu
1               5                  10                  15

Phe Asp Gly Gln Lys Ser Ser Phe Gln Thr Arg Phe Asn Val His Arg
            20                  25                  30

Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Leu Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Met Ser Ser Phe
            100                 105                 110

Asn Pro His Gly Ile Ser Thr Phe Thr Asp Glu Asp Asn Thr Val Tyr
        115                 120                 125
```

```
Leu Leu Val Val Asn His Pro Asp Ser Ser Thr Val Glu Val Phe
    130                 135                 140

Lys Phe Gln Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Phe Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Val Asp Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Thr Val Ala Ala Val
                325                 330                 335

Tyr Lys Gly Lys Leu Leu Ile Gly Thr Val Phe His Lys Ala Leu Tyr
            340                 345                 350

Cys Glu Leu
        355

<210> SEQ ID NO 76
<211> LENGTH: 1065
<212> TYPE: DNA
<213> ORGANISM: Artificial sequence
<220> FEATURE:
<223> OTHER INFORMATION: In vitro evolved PON variant 4HY

<400> SEQUENCE: 76
atggctaaac tgacagcgct cacactcttg gggctgggat tggcactctt cgatggacag      60
aagtcttctt tccaaacacg atttaatgtt caccgtgaag taactccagt ggaacttcct     120
aactgtaatt tagttaaagg ggttgacaat ggttctgaag acttggaaat actgcccaat     180
ggactggctt tcatcagctc cggattaaag tatcctggac taatgagctt tgaccctgat     240
aagtctggac agatacttct aatggacctg aatgaggaag acccagtagt gttggaactg     300
ggcattactg gaaatacatt ggatatatct tcatttaacc ctcatgggat tagcacattc     360
acagatgaag ataacactgt gtacctactg gtggtaaacc atccagactc ctcgtccacc     420
gtggaggtgt ttaaatttca agaagaagaa aaatcacttt tgcatctgaa aaccatcaga     480
cacaagcttt tgcctagtgt gaatgacatt gtcgctgtgg gacctgaaca cttttatgcc     540
acaaatgatc actattttgc tgacccttac ttaaaatcct gggaaatgca tttgggatta     600
gcgtggtcat ttgttactta ttatagtccc aatgatgttc gagtagtggc agaaggattt     660
gattttgcta acggaatcaa catctcacca gacggcaagt atgtctatat agctgagttg     720
```

```
ctggctcata agatccatgt gtatgaaaag cacgctaatt ggactttaac tccattgaag    780
tccctcgact ttgacaccct tgtggataac atctctgtgg atcctgtgac aggggacctc    840
tgggtgggat gccatcccaa cggaatgcga atcctctact atgacccaaa gaatcctccc    900
ggctcagagg tgcttcgaat ccaggacatt ttatccgaag agcccaaagt gacagtggtt    960
tatgcagaaa atggcactgt gttacagggc agcacggtgg ccgctgtgta caaagggaaa   1020
ctgctgatgg gcacagtgtt tcacaaagct ctttactgtg agctg                   1065
```

<210> SEQ ID NO 77
<211> LENGTH: 355
<212> TYPE: PRT
<213> ORGANISM: Artificial sequence
<220> FEATURE:
<223> OTHER INFORMATION: In vitro evolved PON variant 4HY

<400> SEQUENCE: 77

```
Met Ala Lys Leu Thr Ala Leu Thr Leu Leu Gly Leu Gly Leu Ala Leu
1               5                   10                  15

Phe Asp Gly Gln Lys Ser Ser Phe Gln Thr Arg Phe Asn Val His Arg
            20                  25                  30

Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Leu Lys Tyr Pro Gly Leu Met Ser Phe Asp Pro Asp
65                  70                  75                  80

Lys Ser Gly Gln Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro His Gly Ile Ser Thr Phe Thr Asp Glu Asp Asn Thr Val Tyr
        115                 120                 125

Leu Leu Val Val Asn His Pro Asp Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Phe Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Leu Tyr Tyr Asp Pro Lys Asn Pro Pro Gly Ser Glu Val
    290                 295                 300
```

```
Leu Arg Ile Gln Asp Ile Leu Ser Glu Glu Pro Lys Val Thr Val
305                 310                 315                 320

Tyr Ala Glu Asn Gly Thr Val Leu Gln Gly Ser Thr Val Ala Ala Val
                325                 330                 335

Tyr Lys Gly Lys Leu Leu Met Gly Thr Val Phe His Lys Ala Leu Tyr
            340                 345                 350

Cys Glu Leu
    355

<210> SEQ ID NO 78
<211> LENGTH: 1065
<212> TYPE: DNA
<213> ORGANISM: Artificial sequence
<220> FEATURE:
<223> OTHER INFORMATION: In vitro evolved PON variant G1A9

<400> SEQUENCE: 78
atggctaaac tgacagcgct cacgctcttg gggctgggat tggcactctt cgatggacag      60
aagtcttctt tccaaacacg atttaatgtt caccgtgaag taactccagt ggaacttcct     120
aactgtaatt tagttaaagg gattgacaat ggttctgaag acttggaaat actgcctaat     180
ggactggctt tcattagctc tggattaaaa tatcctggaa taatgagctt tgaccctgat     240
aagtctggaa agatacttct aatggacctg aatgaggaag acccagtagt gttggaactg     300
ggcattactg gaagtacatt tgatttatct tcatttaacc ctcatgggat tagcacattc     360
acagatgaag ataatatcgt ctacctgatg gtggtgaacc atccagattc aaagtccaca     420
gtggaggtat ttaaatttca agaagaagaa aaatcgcttt gcatctaaa aactatcaga      480 cataaacttc tgcctaattt gaatgatatt gttgctgtgg accctgaaca cttttatgct     540
accaatgatc actattttct tgacccctac ttacgatcct gggaaatgta cttgggtctg     600
tcgtggtcca atgttgttta ctacagtcca gataaagtcc aggtggtagc agaagggttt     660
gatttcgcta tggaatcaa catttcaccc gatggcaagt atgtctatat agctgagttg     720
ctggctcata gattcatgt gtatgaaaag catgctaatt ggactttaac gccattgaag     780
gtcctcagct ttgacaccct tgtgataac atctctgtgg atcctgtgac aggggacctc     840
tgggtgggat gccatcccaa cggaatgagg atcttttct atgacgcaga gaatcctccc     900
ggctcagagg tgcttcgaat ccaggacatt ttatccaaag agcccaaagt gacagtggtt     960
tatgcagaaa atggcactgt gttgcaaggc agtacagttg cctctgtgta caagggaaa    1020 ctgctgattg gcaccgtgtt ccacaaagct ctttactgtg agctc                   1065

<210> SEQ ID NO 79
<211> LENGTH: 1065
<212> TYPE: DNA
<213> ORGANISM: Artificial sequence
<220> FEATURE:
<223> OTHER INFORMATION: In vitro evolved PON variant G2D4

<400> SEQUENCE: 79
atggctaaac tgacagcgct cacgctcttg gggctgggat tggcactctt cgatagacag      60
aagtcttctt tccaaacacg atttaatgtt caccgtgaag taactccagt ggaacttcct     120
aactgtaatt tagttaaagg gattgacaat ggttctgaag acttggaaat actgcccaat     180
ggactggctt tcatcagctc cggattaaaa tatcctggaa taatgagctt tgaccctgat     240
aagtctggaa agatacttct aatggacctg aatgaggaag acccagtagt gttggaactg     300
ggcattcctg gaagtacatt tgatttatct tcatttaacc ctcatgggat tagcacattc     360
```

```
acagatgaag ataatatcgt ctacctgatg gtggtgaacc atccagattc aaagtccaca      420
gtggagttgt ttaaattcca agaagaggaa agatcacttt tgcatctgaa aaccatcacc      480
catgagcttc tgcctagtgt gaatgacatt gtcgctgtgg gacctgagag cttctatgct      540
accaatgatc actattttat tgacccttac ttaaaatcct gggaaatgta cttgggtctg      600
tcgtggtcca atgttgttta ctacagtcca gataaagtcc aggtggtggc agaaggattt      660
gattttgcta acggaatcaa catttcaccc gatggcaagt atgtctatat agctgaactg      720
ctggctcata agatccatgt gtatgaaaag cacgctaatt ggactttaac gccattgaag      780
gtcctcaact ttgacaccct tgtggataac atctctgtgg atcctgtgac aggggacctc      840
tgggtgggat gccatcccaa cggaatgagg atcttttct atgacgcaga gaatcctccc      900
ggctcagagg tgcttcgaat ccaggacatt ttatccaaag agcccaaagt gacagtggtt      960
tatgcagaaa atggcactgt gttgcaaggc agcacggtcg cctctgtgta caagggaaaa     1020
ctgctgattg gcactgtgtt ccacaaagct ctttactgtg atctg                     1065

<210> SEQ ID NO 80
<211> LENGTH: 1065
<212> TYPE: DNA
<213> ORGANISM: Artificial sequence
<220> FEATURE:
<223> OTHER INFORMATION: In vitro evolved PON variant G3H10

<400> SEQUENCE: 80
atggctaaac tgacagcgcc cacgctcttg gggctgggat tggcactctt cgatagacag       60
aagtcttctt tccaaacacg atttaatgtt caccgtgaag taactccagt ggaacttcct      120
aactgtaatt tagttaaagg gattgacaat ggttctgaag acttggaaat actgcccaat      180
ggactggctt tcatcagctc cggattaaaa tatcctggaa taatgagctt tgaccctgat      240
aagtctggaa agatacttct aatggacctg aatgaggaag acccagtagt gttggaactg      300
ggcattactg gaagtacatt tgatttatct tcatttaacc ctcatgggat tagcacattc      360
acagatgaag ataacactgt gtacctactg gtagtaaacc atccagactc ctcgtccact      420
gtggaggtat ttaaatttca agaaaaggag agatcacttt tgcatctgaa aaccatcaga      480
cacaagcttc tgcctagtgt gaatgacatt gtcgctgtgg gacctgagag ctttatgcc      540 acaaatgatc actattttgc tgaccctctac ttaaaatcct gggaaatgca tttgggatta      600
gcgtggtcat ttgttactta ttatagtccc aatgatgttc gagtagtggc agaaggattt      660
gattttgcta acggaatcaa catctcaccc gatggcaagt atgtctatat agctgaactg      720
ctggctcata agatccatgt gtatgaaaag cacgctaatt ggactttaac tccattgaag      780
tccctcgact ttaacactct tgtggataac atctctgtgg atcctgtgac aggggacctc      840
tgggtgggat gccatcccaa tggcatgcga atcttctact atgacccaga gaatcctccc      900
ggctcagagg tacttcgaat ccaggacatt ttatccaaag agcccaaagt gacagtggtt      960
tatgcagaaa atggcactgt gttacagggc agcacggtgg ccgctgtgta caagggaaaa     1020
ctgctgattg gcactgtgtt ccacaaagct ctttactgtg atctg                     1065

<210> SEQ ID NO 81
<211> LENGTH: 1062
<212> TYPE: DNA
<213> ORGANISM: Artificial sequence
<220> FEATURE:
<223> OTHER INFORMATION: In vitro evolved PON variant G1E10
<220> FEATURE:
```

<221> NAME/KEY: misc_feature
<222> LOCATION: (427)..(427)
<223> OTHER INFORMATION: n is a, c, g, or t

<400> SEQUENCE: 81

```
atggcgaagc tcctgctgct gaccctgctg ggggtcggcc tgtccttagt cggggagatg    60
ttcctggcgt ttagagaaag ggtgaatgcc tctcgagaac tggagccagt agaacccag    120
aactgtgtcc ttattgaggg actcgaaaat ggctcggaag atattgatat acttcctagc   180
gggctggctt ttatctccac tggattaaaa tatccaggca tgccaaactt tgcaccagat   240
gagccaggaa aaatcttctt gatggatctg aatgagcaaa acccagaggc gcaagcactg   300
gaaatcagtg gtgggcttga ccaggagtca ctaaatcctc acgggatcag cactttcatc   360
gacaaagaca atactgtgta tctttatgtt gtgaatcacc ccaacatgga ctccactgtg   420
gagatantta aatttgagga acaacaacgc tctcttgtac acctgaaaac tataaaacat   480
gaacttctca agagtgtgaa tgacattgtg gttcttgggc cagagcagtt ctatgccacc   540
agagaccact attttaccaa ctccctcctg tcatttttg  agatgatctt ggaccctcac   600
tggacttccg tcgttttcta cagcccaaaa gaggtcaaag ttgtggccca aggattcagt   660
tctgccaacg gaatcacagt ctcagcagac cagaagtatg tctatgtagc tgatgtagca   720
gctaagaaca ttcacataat ggaaaaacat gacaactggg atttaactca actgaaggtg   780
atacagttgg acaccttagt ggataatttg tctgttgatc ctgccacggg agatattttg   840
gcaggatgcc atcctaatcc tatgaagcta ctggactata accctgagga tcctccagga   900
tcagaagtac ttcgtatcca gaatgttttg tctgagaagc ccagggtgag caccgtgtat   960
gccaatgacg gctctgtgct tcagggctcc accgtggctt ctgtgtacca agggaagatt  1020
ctcataggca ctatatttca caaaactctg tattgtgtac tc                     1062
```

<210> SEQ ID NO 82
<211> LENGTH: 1062
<212> TYPE: DNA
<213> ORGANISM: Artificial sequence
<220> FEATURE:
<223> OTHER INFORMATION: In vitro evolved PON variant G1G7
<220> FEATURE:
<221> NAME/KEY: misc_feature
<222> LOCATION: (571)..(571)
<223> OTHER INFORMATION: n is a, c, g, or t

<400> SEQUENCE: 82

```
atggggaagc tcgtggcgct ggtcctgctg ggggtcggcc tgtccttagt cggggagatg    60
ttcctggcgt ttggagaaag ggtgaatgcc tctcgagaag tggagccagt agaacctgaa   120
aactgccacc ttattgaggg cctcgagaat ggctctgaag atattgatat acttcctagc   180
gggctggctt ttatctccac tggattaaaa tatccaggca tgccaaactt tgcgccagat   240
gaaccaggaa aaatcttctt gatagatatg aatgagaaga acccaagagc acaagagctg   300
gaaatcagca atggatttga aaagaatca ttcaatccac atgggatcag cactttcatc    360
gacaaagaca atactgctta tctttatgtc gtgaatcacc ccaacatgga ctccactgtg   420
gagatattta gtttgaaga acaacaacac tctctcatcc acctgaaaac tctaaaacat    480
gaacttctca agagtgtgaa tgacattgtg gttcttggac cggaacagtt ctatgccacc   540
agagaccact attttaccaa ctatgtctta ncacttcttg agatgttttt ggaccctcac   600
tggacttccg tcgttttcta cagcccaaaa gaggtcaaag ttgtggccca aggattcagt   660
tctgccaatg ggatcacagt ctcactagat aagaagtatg tctatgttgc tgatgccaca   720
```

```
gctaagaatg tgcatgtaat ggaaaaacat gataactggg atttaactcc agtgaaggtc      780
attcagctgg gaaccttagt ggataacttg accgttgatc cagccacggg agatattttg      840
gcaggctgcc accctaaccc catgaagcta ctgaactata accctgagga ccctccagga      900
tcagaagtac ttcgcatcca ggactctttg tcagataagc ccagggtgag caccgtgtat      960
gccaacaatg gctctgtgct tcagggctcc accgtggctt ctgtgtacca agggaagatt     1020
ctcataggca ctatatttca caaagctctg tactgtgacc tc                        1062
```

<210> SEQ ID NO 83
<211> LENGTH: 1062
<212> TYPE: DNA
<213> ORGANISM: Artificial sequence
<220> FEATURE:
<223> OTHER INFORMATION: In vitro evolved PON variant G2E11
<220> FEATURE:
<221> NAME/KEY: misc_feature
<222> LOCATION: (775)..(775)
<223> OTHER INFORMATION: n is a, c, g, or t

<400> SEQUENCE: 83

```
atggcgaagc tcctgctgct gaccctgctg ggggccagcc tcgccttcgt cggggagagg       60
ttgctggcgt ttagaaaaag ggtgaatgcc tctcgagaag tggagccagt agaaccaaaa      120
aactgccacc ttattgaggg actcgaaaat ggctcggaag atattgatat acttcctagt      180
gggctggctt ttatctccac tggattaaaa tatccaggca tgccaaactt tgcaccagat      240
gagccaggaa aaatcttctt gatagacatg aatgagaaga cccaagagc acaagagctg       300 gaaatcagca atggatttga aaagaatca ttcaatccac atgggatcag cactttcatc       360
gacaaagacc atactgtgta tctttatgtt gtgaatcacc ccaacatgga ttccactgtg      420
gagatattta aatttgagga caacaacgt tctctggtat acctgaaaac tctaaaacat       480
gaacttctca agagtgtgaa tgacattgtg gttcttggac cggaacagtt ctatgccacc      540
agagaccact attttaccaa ctccctcctg tcatttttg agatgttctt ggatcttcgc       600
tggacttatg ttcttttcta cagcccaaaa gaagtcaaag tggtggccaa aggattcagt      660
tctgccaatg ggatcacagt ctcactagat aagaagtatg tctatgtagc tgatgtagca      720
gctaagaaca ttcacataat ggaaaaacat gacaactggg atttaactga actgnaggta      780
atacacttgg acaccttagt ggataatttg tctgttgatc ctgccacggg agatatcttg      840
gcaggatgcc atcctaatgg catgaagctt ctgaactata accctgagga ccctccagga      900
tcagaagtac ttcgcatcca gaatgttttg tctgagaagc ccagggtgag caccgtgtac      960
accaatgacg gctctgtgct tcagggcacc tctgtggctt ctgtgtacca agggaagatt     1020
ctcataggca ctatatttca caaaactctg tactgtgacc tc                        1062
```

<210> SEQ ID NO 84
<211> LENGTH: 1062
<212> TYPE: DNA
<213> ORGANISM: Artificial sequence
<220> FEATURE:
<223> OTHER INFORMATION: In vitro evolved PON variant G2A7

<400> SEQUENCE: 84

```
atggcgaagc tcgtggcgct ggtcctgctg ggggtcgggc tgtccttagt cggggagatg       60
ttcctggcgt ttagagaaag ggtggatgcc tctcgagaag tggagccagt agaacccag       120 aactgtgtcc ttattgaggg actcgaaaat ggctcggaag atattgatat acttcctagt      180
```

```
gggctggctt ttatctccag tggattaaaa tatccaggca tgccaaactt tgcaccagat        240
gagccaggaa aaatcttctt gatggatctg aatgagaaga acccaagagc acaagagctg        300
gaaatcagca atggatttga aaaagaatca ttcaatccac atgggatcag cactttcatc        360
gacaaagaca cactgctta tctttatgtc gtgaatcacc ccaacatgga ctccactgtg         420
gagatattta aatttgagga caacaacac tctctcatcc acctgaaaac tataaaacat         480
gaacttctca aaagtgtgaa tgacattgtg gttcttggac cggaacagtt ctacgccacc        540
agagaccact attttaccaa ctccctcctg tcattttttg agatgatctt ggatcttcgc        600
tggacttatg ttcttttcta cagccccaaa gaggccaaag tggtggccaa aggattcagt        660
tctgccaatg ggatcacagt ctcactagat aagaagtatg tctatgttgc tgatgccaca        720
gctaagaatg tgcacataat ggaaaaacat gacaactggg atttaactga actgaaggta        780
gtacacttgg acaccttagt ggataacttg accgttgatc cagccacggg agatattttg        840
gcaggctgcc accctaaccc catgaagctg ttgaactata accctgagga ccctccagga        900
tcagaagtac ttcgcatcca gaatgttttg tctgagaagc ccagggtgag caccgtgtac        960
accaatgacg gctctgtgct tcagggcacc tctgtggctt ctgtgtacca agggaagatt       1020
ctcataggca ctatatttca caaaactctg tattgtgtac tt                          1062
```

<210> SEQ ID NO 85
<211> LENGTH: 1062
<212> TYPE: DNA
<213> ORGANISM: Artificial sequence
<220> FEATURE:
<223> OTHER INFORMATION: In vitro evolved PON variant G2F8

<400> SEQUENCE: 85

```
atggcgaagc tcctgctgct gaccctgctg ggggccagcc tcgccttcgt cggggagagg         60
ttgctggcgt ttagagacag ctttggtgca gttcaagaac tggagccagt ggaaccccag        120
aactgtgtcc ttattgaggg actcgaaaat ggctcggaag atattgatat acttcctaat        180
gggctggctt ttatctccag tggattaaaa tatccaggca tgccaaactt tgcaccagat        240
gagccaggaa aaatcttctt gatagatatg aatgagaaga acccaagagc acaagagctg        300
gaaatcagca atggatttga aaaagaatca ttcaatccac atgggatcag cactttcatc        360
gataaagacc atactgtgta tctttatgtt gtgaatcatc cccacatgaa gtccactgtg        420
gagatattta agtttgaaga acaacaacgt tctctggtat acctgaaaac tctaaaacat        480
gaacttctca agagtgtgaa tgacattgtg gttcttggac cggaacagtt ctatgccacc        540
agagaccact attttaccaa ctccctcctg tcattttttg agatgatctt ggatcttcgc        600
tggacttccg ttcttttcta cagcccaagg gaggttaaag tggtggccaa aggattcagt        660
tctgccaatg ggatcacagt ctcactagat aagaagtatg tctatgtagc tgatgtagca        720
gctaagaatg tgcatgtaat ggaaaaacat gataactggg atttaactga actgaaggta        780
atacacttgg acaccttagt ggataacttg accgttgatc cagccacagg agacattttg        840
gcaggatgcc atcctaaccc catgaagcta ctgaactata accctgagga ccctccagga        900
tcagaagtac ttcgcatcca gaatgttttg tctgagaagc ccagggtgag caccgtgtat        960
gccaacaatg gctctgtgct tcagggcacc tctgtggctt ctgtgtacca cgggaaaatt       1020
ctcataggca ctatatttca caaagctctg tactgtgacc tc                          1062
```

<210> SEQ ID NO 86
<211> LENGTH: 1062

```
<212> TYPE: DNA
<213> ORGANISM: Artificial sequence
<220> FEATURE:
<223> OTHER INFORMATION: In vitro evolved PON variant G3C6

<400> SEQUENCE: 86
atggggaagc tcctgctgct gaccctgctg ggggccagcc tcaccttcgt cggggagagg      60
ttgctggcgt ttagaaacag ctttggtgca gttcaagaac tggagccagt agaaccccgg     120
aactgtgtcc ttattgaggg actcgaaaat ggctcggaag atattgatat acttcctagt     180
gggctggctt ttatctccag tggattaaaa tatccaggca tgccaaactt tgcaccagat     240
gagccaggaa aaatcttctt gatagacatg aatgagaaga cccaagagc acaagagctg      300 gaaatcagca atggatttga aaagaatca ttcaatccac atgggatcag cactttcatc      360
gataaagacc atactgtgta tctttatgtc gtgaatcacc ccaacatgga ctccactgtg      420
gagatattta gtttaagga caacaacgc tctcttgtac acctgaaaac tataaaacat       480
gaacttctca aaagtgtgaa tgacattgtg gttcttggac agaacagtt ctatgccacc      540 agagaccact attttaccaa ctccctcctg tcatttttg agatgatctt ggatcttcgc      600
tggacctatg ttcttttcta cagccccaaa gaggtcaaag ttgtggccaa aggattcagt     660
tctgccaacg aatcacagt ctcactagat aagaagtatg tctatgttgc tgatgccaca      720
gctaagaatg tgcatgtaat ggaaaaacat gataactggg atttaactga actgaaggtc      780
attcagctgg aaccttagt ggataacttg actgtcgatc ccgccacagg agacattttg      840
gcaggctgcc accctaaccc catgaagcta ctgaactata accctgagga ccctccagga      900
tcagaagtac ttcgcatcca ggatgttttg tctgagaagc ccagggtgag caccgtgtat      960
gccaatgacg gctctgtgct tcagggcacc tctgtggctt ctgtatacca cgggaaaatt    1020
ctcataggca ctatatttca caaaactctg tactgtgtac tc                        1062

<210> SEQ ID NO 87
<211> LENGTH: 1062
<212> TYPE: DNA
<213> ORGANISM: Artificial sequence
<220> FEATURE:
<223> OTHER INFORMATION: In vitro evolved PON variant G3G5

<400> SEQUENCE: 87
atggcgaagc tcctgctgct gacccggctg ggggccagcc tcgccttcgt cggggagagg      60
ttgctggcgt ttagaaaaag ggtgaatgcc tctcgagaag tggagccagt agaaccccag     120
aactgtgtcc ttattgaggg actcgaaaat ggctcggaag atattgatat acttcctagt     180
gggctggctt ttatctccac tggattaaaa tatccaggca tgccaaactt tgcaccagat     240
gaaccaggaa aaatcttctt gatggatctg aatgaacaaa cccaagagc acaagcacta     300 gaaatcagtg gtggatttga caaagaatta tttaatccac atgggatcag cactttcatt     360
gataaagaca atactgtgta tctttatgtt gtgaatcatc cccacatgaa gtctactgtg      420
gagatattta aatttgagga caacaacgt tctctggtat acctgaaaac tataaaacat       480
gaacttctca aaagtgtgaa tgacattgtg gttcttgggc cggaacagtt ctatgccacc      540
agagaccact attttaccaa ctccctcctg tcatttttg agatgttttt ggatcttcgc      600
tggacttacg ttcttttcta cagcccaagg gaggttaaag tggtggccaa aggattcagt     660
tctgccaatg gatcacagt ctcactagat aagaagtatg tctatgttgc tgatgccacg      720
gctaagaatg tgcatgtaat ggaaaaacat gataactggg atttaactcc actgaaggta      780
```

| | | |
|---|---|---|
| atacacttgg acaccttagt ggataatttg tctgttgatc ctgccacggg agatattttg | 840 |
| gcaggatgcc atcctaatcc catgaagctg ttgaactata accctgagga ccctccagga | 900 |
| tcagaagtac ttcgcatcca gaatgttttg tctgggaagc ccagggtgag caccgtgtat | 960 |
| gccaacaatg gctctgtgct tcagggcacc tctgtggctt ctgtgtacca agggaagatt | 1020 |
| ctcataggca ctatatttca caaaactctg tactgtgagc tc | 1062 |

<210> SEQ ID NO 88
<211> LENGTH: 354
<212> TYPE: PRT
<213> ORGANISM: Homo sapiens

<400> SEQUENCE: 88

```
Met Gly Lys Leu Val Ala Leu Val Leu Leu Gly Val Gly Leu Ser Leu
1               5                   10                  15

Val Gly Glu Met Phe Leu Ala Phe Arg Glu Arg Val Asn Ala Ser Arg
            20                  25                  30

Glu Val Glu Pro Val Glu Pro Glu Asn Cys His Leu Ile Glu Glu Leu
        35                  40                  45

Glu Ser Gly Ser Glu Asp Ile Asp Ile Leu Pro Ser Gly Leu Ala Phe
    50                  55                  60

Ile Ser Ser Gly Leu Lys Tyr Pro Gly Met Pro Asn Phe Ala Pro Asp
65                  70                  75                  80

Glu Pro Gly Lys Ile Phe Leu Met Asp Leu Asn Glu Gln Asn Pro Arg
                85                  90                  95

Ala Gln Ala Leu Glu Ile Ser Gly Gly Phe Asp Lys Glu Leu Phe Asn
            100                 105                 110

Pro His Gly Ile Ser Ile Phe Ile Asp Lys Asp Asn Thr Val Tyr Leu
        115                 120                 125

Tyr Val Val Asn His Pro His Met Lys Ser Thr Val Glu Ile Phe Lys
    130                 135                 140

Phe Glu Glu Gln Gln Arg Ser Leu Val Tyr Leu Lys Thr Ile Lys His
145                 150                 155                 160

Glu Leu Leu Lys Ser Val Asn Asp Ile Val Val Leu Gly Pro Glu Gln
                165                 170                 175

Phe Tyr Ala Thr Arg Asp His Tyr Phe Thr Asn Ser Leu Leu Ser Phe
            180                 185                 190

Phe Glu Met Ile Leu Asp Leu Arg Trp Thr Tyr Val Leu Phe Tyr Ser
        195                 200                 205

Pro Arg Glu Val Lys Val Ala Lys Gly Phe Cys Ser Ala Asn Gly
    210                 215                 220

Ile Thr Val Ser Ala Asp Gln Lys Tyr Val Tyr Val Ala Asp Val Ala
225                 230                 235                 240

Ala Lys Asn Ile His Ile Met Glu Lys His Asp Asn Trp Asp Leu Thr
                245                 250                 255

Gln Leu Lys Val Ile Gln Leu Gly Thr Leu Val Asp Asn Leu Thr Val
            260                 265                 270

Asp Pro Ala Thr Gly Asp Ile Leu Ala Gly Cys His Pro Asn Pro Met
        275                 280                 285

Lys Leu Leu Asn Tyr Asn Pro Glu Asp Pro Pro Gly Ser Glu Val Leu
    290                 295                 300

Arg Ile Gln Asn Val Leu Ser Glu Lys Pro Arg Val Ser Thr Val Tyr
305                 310                 315                 320

Ala Asn Asn Gly Ser Val Leu Gln Gly Thr Ser Val Ala Ser Val Tyr
```

```
                         325             330             335
His Gly Lys Ile Leu Ile Gly Thr Val Phe His Lys Thr Leu Tyr Cys
            340             345             350

Glu Leu

<210> SEQ ID NO 89
<211> LENGTH: 367
<212> TYPE: PRT
<213> ORGANISM: Caenorhabditis elegans

<400> SEQUENCE: 89

Met Leu Val Lys Val Val Leu Phe Gly Leu Leu Gly Val Ser Ile His
1               5                   10                  15

Phe Ile Phe Asn Thr Leu Leu Thr Leu Asp Ile Asn Lys Arg Val Tyr
            20                  25                  30

Asn His Arg Pro Gly Glu Cys Arg Lys Ile Glu Gly Pro Val His Gly
        35                  40                  45

Ser Glu Asp Ile Glu Val Ile Asp Lys Leu Gln Ile Ala Phe Ile Ser
    50                  55                  60

Ser Gly Leu Val Tyr Leu Pro Asn Ser Ala Ser Asp Val Lys Trp Lys
65                  70                  75                  80

Gly Gln Ile Phe Leu Tyr Asp Leu Thr Lys Arg Ser Tyr Lys Ala Glu
                85                  90                  95

Pro Ile Pro Val Leu Asn Leu Glu Asp Val Asp Gly Phe His Pro His
            100                 105                 110

Gly Leu Ser His Trp Ile Leu Asn Asn Arg Thr Val Arg Leu Phe Val
        115                 120                 125

Val Val His Ser Lys Thr Phe Lys His Ser Ile Val Ile Leu Asp Tyr
    130                 135                 140

Asn Ser Ala Lys Arg Glu Leu Asn His Val Lys Thr Ile Arg Gly Glu
145                 150                 155                 160

Lys Phe Val Arg Pro Asn Asp Ile Val Ala Thr Gly Glu Asn Ser Phe
                165                 170                 175

Leu Val Ser Asn Asp Gly Gly Ala Gln Thr Ala Leu Gly Asn Val Trp
            180                 185                 190

Glu Ile Leu Ser Gly Phe Tyr Lys Gly Gly Leu Val Tyr Tyr Asn Gly
        195                 200                 205

Lys Lys Ser Gln Phe Leu Met Glu Asn Asn Ile Ala Asn Gly Ile Ile
    210                 215                 220

Leu Ser Arg Asp Gln Lys Thr Leu Phe Val Ser His Ile Asn Gln Glu
225                 230                 235                 240

Thr Ile Gly Val Tyr Thr Trp Asn Gln Lys Asp Gly Glu Ile Gln Lys
                245                 250                 255

Ile Ser Glu Ile Glu Thr Leu Thr Gly Cys Asp Asn Phe Tyr Val Asp
            260                 265                 270

Thr Gln Asp His Leu Trp Ala Gly Cys His Pro Val Val Lys Asp Ala
        275                 280                 285

Ala Gly His Leu Gly Asn Val Ser Asp Ser Thr Leu Tyr Gly Pro Ser
    290                 295                 300

Gln Val Leu Arg Val Ser Phe Ser Lys Asp Leu Lys Thr Ala Glu Ile
305                 310                 315                 320

Val Glu Val Leu Ala Asp Asp Gly Arg Phe Val Ser Ala Ser Thr Ile
                325                 330                 335

Ala Ile Pro Phe Asp Asp Gly Lys Gln Met Ile Val Gly Thr Val Ala
```

-continued

```
               340                 345                 350
Arg Pro Ala Ile His Cys Asp Ile Asn Val Ser Leu Asn Leu Tyr
        355                 360                 365
```